United States Patent
Otomo et al.

(10) Patent No.: US 9,977,150 B2
(45) Date of Patent: *May 22, 2018

(54) SECOND-ORDER NONLINEAR OPTICAL COMPOUND AND NONLINEAR OPTICAL ELEMENT COMPRISING THE SAME

(71) Applicants: NATIONAL INSTITUTE OF INFORMATION AND COMMUNICATIONS TECHNOLOGY, Tokyo (JP); SUMITOMO ELECTRIC INDUSTRIES, LTD., Osaka (JP); KYUSHU UNIVERSITY, NATIONAL UNIVERSITY CORPORATION, Fukuoka (JP)

(72) Inventors: Akira Otomo, Tokyo (JP); Isao Aoki, Tokyo (JP); Hideki Miki, Tokyo (JP); Hidehisa Tazawa, Kanagawa (JP); Shiyoshi Yokoyama, Fukuoka (JP)

(73) Assignees: NATIONAL INSTITUTE OF INFORMATION AND COMMUNICATIONS TECHNOLOGY, Tokyo (JP); SUMITOMO ELECTRIC INDUSTRIES, LTD., Osaka (JP); KYUSHU UNIVERSITY, NATIONAL UNIVERSITY CORPORATION, Fukuoka (JP)

(*) Notice: Subject to any disclaimer, the term of this patent is extended or adjusted under 35 U.S.C. 154(b) by 0 days. days.

This patent is subject to a terminal disclaimer.

(21) Appl. No.: 15/208,976

(22) Filed: Jul. 13, 2016

(65) Prior Publication Data

US 2016/0318889 A1    Nov. 3, 2016

Related U.S. Application Data

(62) Division of application No. 14/317,192, filed on Jun. 27, 2014, now Pat. No. 9,488,755, which is a division
(Continued)

(30) Foreign Application Priority Data

Aug. 24, 2009  (JP) .................................. 2009-192738
Apr. 30, 2010  (JP) .................................. 2010-104951

(51) Int. Cl.
*G02B 1/04*     (2006.01)
*G02F 1/00*     (2006.01)
*C09B 69/10*    (2006.01)
*C07D 307/68*   (2006.01)
*C07D 409/14*   (2006.01)
(Continued)

(52) U.S. Cl.
CPC ............ *G02B 1/045* (2013.01); *C07C 223/06* (2013.01); *C07D 307/30* (2013.01); *C07D 307/68* (2013.01); *C07D 333/22* (2013.01); *C07D 409/06* (2013.01); *C07D 409/12* (2013.01); *C07D 409/14* (2013.01); *C07D 471/06* (2013.01); *C07F 7/1844* (2013.01); *C07F 7/1856* (2013.01); *C09B 23/0066* (2013.01); *C09B 23/0075* (2013.01); *C09B 69/008* (2013.01); *C09B 69/107* (2013.01); *G02B 1/046* (2013.01); *G02B 6/105* (2013.01); *G02F 1/0063* (2013.01); *G02F 1/3611* (2013.01); *G02F 1/3612* (2013.01); *G02F 1/3614* (2013.01); *G02F 1/3615* (2013.01)

(58) Field of Classification Search
CPC ........ G02B 1/045; G02B 1/046; G02B 6/105; G02F 1/0063; G02F 1/3612; G02F 1/3614; G02F 1/3615; G02F 1/3611; C07D 409/14; C07D 307/68; C07D 409/12; C07D 471/06; C07D 333/22; C07D 409/06; C07D 307/30; C07F 7/1856; C07F 7/1844; C09B 69/107; C09B 23/0066; C09B 69/008; C09B 23/0075; C07C 223/06
See application file for complete search history.

(56) References Cited

U.S. PATENT DOCUMENTS

| | | |
|---|---|---|
| 5,081,101 A | 1/1992 | Evans et al. |
| 5,169,828 A | 12/1992 | Janssens et al. |

(Continued)

FOREIGN PATENT DOCUMENTS

| | | |
|---|---|---|
| AU | 43922/72 | 1/1974 |
| CN | 100400537 | 7/2008 |

(Continued)

OTHER PUBLICATIONS

Ohtomo, A., "Organic electrooptical pigment having new donor structure and its electrooptical properties", 2010, Molecular Electronics and Bioelectronics 21(2):103-104.*

(Continued)

*Primary Examiner* — John M Mauro
(74) *Attorney, Agent, or Firm* — Wenderoth, Lind & Ponack, L.L.P.

(57) ABSTRACT

Problem to Be Solved: to provide a chromophore having a far superior nonlinear optical activity to conventional chromophores and to provide a nonlinear optical element comprising said chromophore.
Solution: a chromophore comprising a donor structure D, a π-conjugated bridge structure B, and an acceptor structure A, the donor structure D comprising an aryl group substituted with a substituted oxy group; and a nonlinear optical element comprising said chromophore.

8 Claims, 1 Drawing Sheet

Related U.S. Application Data of application No. 13/391,948, filed as application No. PCT/JP2010/064216 on Aug. 24, 2010, now Pat. No. 8,846,955.

(51) Int. Cl.

| | | |
|---|---|---|
| C07F 7/18 | (2006.01) | |
| C07D 409/12 | (2006.01) | |
| C07D 333/22 | (2006.01) | |
| C07D 409/06 | (2006.01) | |
| C07D 307/30 | (2006.01) | |
| C07D 471/06 | (2006.01) | |
| G02B 6/10 | (2006.01) | |
| C09B 23/01 | (2006.01) | |
| G02F 1/361 | (2006.01) | |
| C09B 69/00 | (2006.01) | |
| C07C 223/06 | (2006.01) | |

(56) References Cited

U.S. PATENT DOCUMENTS

| | | | |
|---|---|---|---|
| 5,189,134 | A | 2/1993 | Mignani et al. |
| 5,359,072 | A | 10/1994 | Mignani et al. |
| 5,535,048 | A | 7/1996 | Mignani et al. |
| 5,578,416 | A | 11/1996 | Tutt |
| 6,067,186 | A | 5/2000 | Dalton et al. |
| 6,348,992 | B1 | 2/2002 | Zhang et al. |
| 6,361,717 | B1 | 3/2002 | Dalton et al. |
| 6,584,266 | B1 | 6/2003 | He et al. |
| 6,616,865 | B1 | 9/2003 | Zhang et al. |
| 6,652,779 | B1 | 11/2003 | Zhang et al. |
| 7,885,011 | B1 | 2/2011 | Wang et al. |
| 2002/0027220 | A1 | 5/2002 | Wang et al. |
| 2004/0096137 | A1 | 5/2004 | Risser et al. |
| 2006/0079001 | A1 | 4/2006 | Haidekker |
| 2006/0084177 | A1 | 4/2006 | Haidekker et al. |
| 2008/0004415 | A1* | 1/2008 | McGinniss ............ C07C 205/45 528/26 |
| 2010/0310456 | A1 | 12/2010 | Siclovan et al. |
| 2010/0310457 | A1 | 12/2010 | Tan Hehir et al. |
| 2010/0312122 | A1 | 12/2010 | Yazdanfar et al. |
| 2011/0142759 | A1 | 6/2011 | Zhang et al. |

FOREIGN PATENT DOCUMENTS

| | | |
|---|---|---|
| DE | 2345189 | 3/1975 |
| GB | 1165317 | 9/1969 |
| JP | 48-56638 | 8/1973 |
| JP | 63-030853 | 2/1988 |
| JP | 1-179041 | 7/1989 |
| JP | 02-011660 | 1/1990 |
| JP | 2-115827 | 4/1990 |
| JP | 2-142756 | 5/1990 |
| JP | 3-33833 | 2/1991 |
| JP | 2003-033833 | 2/1991 |
| JP | 03-109554 | 5/1991 |
| JP | 4-116640 | 4/1992 |
| JP | 4-226393 | 8/1992 |
| JP | 4-265792 | 9/1992 |
| JP | 8-184866 | 7/1996 |
| JP | 2004-501159 | 1/2004 |
| JP | 2004-243596 | 9/2004 |
| JP | 2006-506688 | 2/2006 |
| JP | 2007-057940 | 3/2007 |
| JP | 2012-528880 | 11/2012 |
| WO | 96/03674 | 2/1996 |
| WO | 2005/072216 | 8/2005 |
| WO | 2005/073697 | 8/2005 |
| WO | 2009/095253 | 8/2009 |
| WO | 2010/141704 | 12/2010 |

OTHER PUBLICATIONS

Tretiak et al., "Electronic screening in second order optical polarizabilities of elongated Donor/Acceptor polyenes", chemical Physics, 1999, vol. 245, pp. 145-163.

Blanchard-Desce et al., "Large quadratic hyperpolarizabilities with donor-acceptor polyenes functionalized with strong donors. Comparison with donor-acceptor diphenylpolyenes", Chemical Physics, 1995, vol. 199, pp. 253-261.

Blanchard-Desce et al., "Intramolecular charge transfer and enhanced quadratic optical non-linearities in push-pull polyenes", Journal of Photochemistry and Photobiology A: Chemistry, 1997, vol. 105, pp. 115-121.

International Search Report dated Nov. 16, 2010 in International (PCT) Application No. PCT/JP2010/064216.

A. Perjessy et al., "Preparation of 3-cyano-4-(R-vinyl)-5,5,-dimethyl-$\Delta^3$-Butenolides and Substituent Effects on Their Infrared Spectra", Collect. Czech. Chem. Commun., 1989, vol. 54, pp. 1666-1674.

A. M. Asiri, "Synthesis and Characterisation of Methine Dyes Derived from Condensation of 4-nitrophenylacetonitrile with Aromatic Aldehydes", Pigment & Resin Technology, 2004, vol. 33, No. 6, pp. 370-374.

M. C. Zerner et al., "Push-Pull Dyes Containing Malononitrile Dimer as Acceptor: Synthesis, Spectroscopy and Quantum Chemical Calculations", Journal of Molecular Structure (Theochem), 2001, vol. 543, pp. 129-146.

English translation of International Preliminary Report on Patentability and Written Opinion dated Mar. 13, 2012 in International (PCT) Application No. PCT/JP2010/064216.

C. Peinado et al., "Solvatochromic and rigidochromic fluorescent probes based on D-π—A diaryl ethylene and butadiene derivatives for UV-curing monitoring", Polymer, 2001, vol. 42, No. 7, pp. 2815-2825.

William E. Truce et al., "Stereoselective Sulfene-Tropone Cycloadditions and Stereospecific Thermolysis of Resulting Adducts", Journal of the American Chemical Society, 1973, vol. 95, No. 13, pp. 4426-4428.

Georg Manecke et al., "Über Synthesen einiger oligomerer substituierter Arylenvinylene", Chem. Ber., 1970, vol. 103, No. 3, pp. 700-707.

A.A. Avetissyan, et al., "Study of Chemical Transformations of 2-Cyano-3-Methyl-4,4-Cyclopentamethylene-2-Butene-4-olides", Chemical Journal of Armenia, 2009, vol. 62, No. 1-2, pp. 183-187 (with English Abstract).

M.M. Buzlanova et al., "Photometric Determination of Nitrostilbenes Using Formamidinesulfinic Acid", Journal of Analytical Chemistry, 1999, vol. 54, No. 11, pp. 1010-1012.

Indubhusan Deb et al., "Morita-Baylis-Hillman Reactions Between Conjugated Nitroalkenes or Nitrodienes and Carbonyl Compounds", Eur. J. Org. Chem., 2009, vol. 24, pp. 4091-4101.

Li et al., "Synthesis, crystal structures, and nonlinear optical properties of three TCF-based chromophores", CrystEngComm, 2009, vol. 11, pp. 589-596.

Kim et al., "Synthesis and properties of nonlinear optical chromophore alkoxy-substituted phenylene as conjugation bridge", Optical Materials, 2007, vol. 29, pp. 1423-1428.

Ju et al., "Synthesis and optical nonlinearity of thermally stable polyimides incorporated with electro-optic chromophores as side chain", Macromolecular Symoposia, 2007, vol. 249/250, pp. 21-28.

You et al., "Pronounced photorefractive effect at wavelength over 1000 nm in monolithic organic materials", Applied Physics Letters, 2005, vol. 86, pp. 151906-1-151906-3.

\* cited by examiner

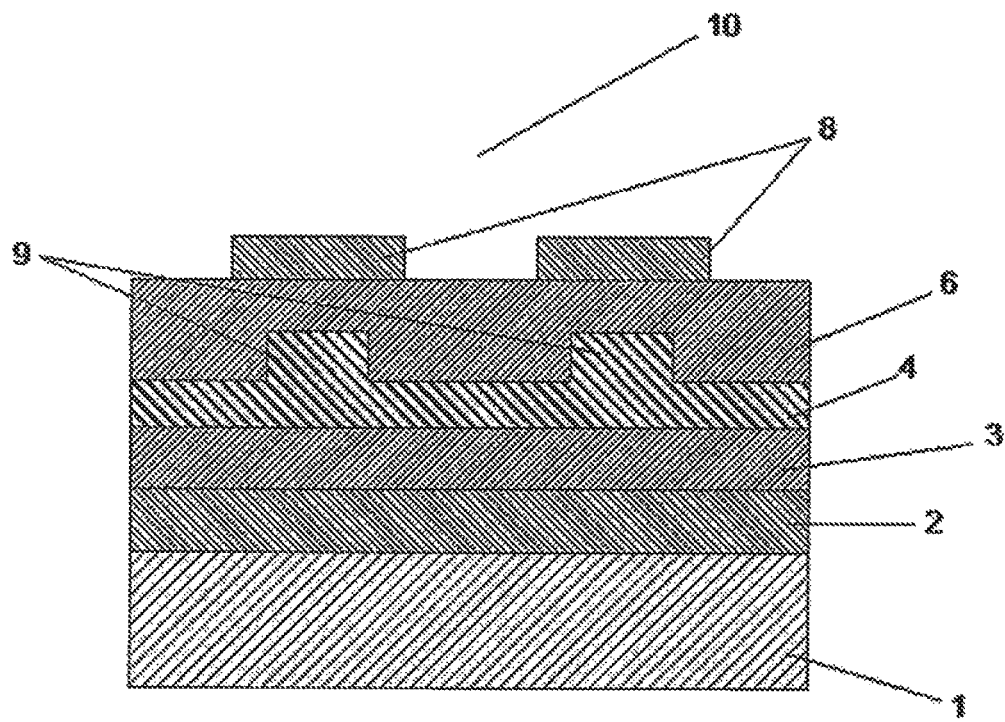

SECOND-ORDER NONLINEAR OPTICAL COMPOUND AND NONLINEAR OPTICAL ELEMENT COMPRISING THE SAME

TECHNICAL FIELD

The present invention relates to a nonlinear optical compound, a nonlinear optical material comprising the nonlinear optical compound, and a nonlinear optical element comprising the nonlinear optical compound.

BACKGROUND ART

Nonlinear optical materials can change the intensity and phase of light in response to an external field such as an electric field and a magnetic field and are therefore practically used as optical control elements in optical communication equipment, laser apparatus, and the like. Inter alia, devices such as optical modulators, optical switches, and optical memories utilize the electrooptic effect of non-linear optical materials.

Conventionally, as nonlinear optical materials, inorganic materials such as lithium niobate and potassium dihydrogen phosphate have been widely used. However, the demands for higher nonlinear optical performance, manufacturing cost reduction, composites with an electronic integrated circuit, and the like have led to increased attention on organic nonlinear optical materials and various investigations into their practical use have been conducted, as described in "Hisenkei Kougaku No Tameno Yuuki Zairyo (Organic Materials for Nonlinear Optics)", edited by the Chemical Society of Japan, KIKAN KAGAKU SOSETSU No. 15 (1992); "Organic Nonlinear Optical Materials", Ch. Bosshard, et al., Gordon and Breach Publishers (1995); and "Joho, Tsushin Yo Hikari Yuuki Zairyo No Saishin Gijutsu (The Newest Technology of Optical Organic Materials for Information and Telecommunication)", supervised by Toshikuni Kaino, CMC Publishing CO., LTD., 2007.

Organic nonlinear optical materials are obtainable by dispersing in or binding to a host material (e.g., a polymeric material) a compound having nonlinear optical activity (hereinafter simply referred to as a "nonlinear optical compound"). A known nonlinear optical compound that exhibits the electrooptic effect is a push-pull π-conjugated compound having an electron donor group (donor structure D) and an electron acceptor group (acceptor structure A), which are present at either end of the molecular structure, as well as a π-conjugated chain (π-conjugated bridge structure B) that connects said groups. For example, U.S. Pat. No. 6,067,186 describes a nonlinear optical compound having a thiophene ring in a π-conjugated bridge structure B, as represented by the following formula:

[Formula 1]

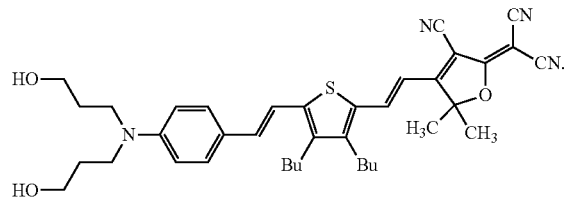

JP 2004-501159 T describes an attempt to improve the performance of a nonlinear optical compound by employing a predetermined group as an acceptor structure A. "Large Electro-optic Activity and Enhanced Thermal Stability from Diarylaminophenyl-Containing High-β Nonlinear Optical Chromophores." Y. J. Cheng, et al., Chem. Mater. Vol. 19, 1154 (2009) also describes an attempt to improve the performance of a nonlinear optical compound by employing a predetermined group as a donor structure D.

SUMMARY OF INVENTION

Technical Problem

In production of an optical element having an optical waveguide made of a nonlinear optical material, orientation processing is sometimes performed on the nonlinear optical compound to produce the second-order nonlinear optical activity of the nonlinear optical material. Generally the method used for orienting a nonlinear optical compound is electric field poling. In electric field poling, an electric field is applied to a nonlinear optical material and, by the Coulomb force between the dipole moment of the nonlinear optical compound and the applied electric field, the nonlinear optical compound is oriented toward the applied electric field direction.

In electric field poling, usually a nonlinear optical material is heated to near the glass transition temperature of its host material so that the molecular motion in the nonlinear optical compound is accelerated, and an electric field is then applied to the material. Therefore, in order to obtain a nonlinear optical element that achieves an excellent nonlinear optical performance, it is necessary to use a nonlinear optical compound that has, besides an excellent nonlinear optical property, heat resistance sufficient to prevent the compound from deteriorating when heated in orientation processing.

Further, because of demands for the high-speed performance of electronic circuits, attempts have been made to increase the rate of signal transmission by connecting electronic circuits with an optical circuit and investigations have been conducted into the use of an electrooptic element made of a nonlinear optical material in electric-optical signal conversion. In this conversion, the temperature of the electronic circuit that operates at a high rate becomes high, and the molecular motion in the nonlinear optical compound thus increases, which might relax the orientation. Therefore the host material is required to have higher glass transition temperature and accordingly the nonlinear optical compound is required to have higher heat resistance.

The present invention has been made in light of the above circumstances, and an object of the present invention is to provide a nonlinear optical compound that can achieve a sufficiently high level of both a nonlinear optical property and heat resistance by utilizing a donor structure D that can improve the nonlinear optical property without significantly deteriorating the heat resistance.

Another object of the present invention is to provide a nonlinear optical material utilizing the nonlinear optical compound and to provide a nonlinear optical element utilizing the nonlinear optical compound.

Another object of the present invention is to provide a chromophore having a far superior nonlinear optical activity to conventional chromophores and to provide a nonlinear optical element comprising said chromophore.

Solution to Problem

The inventors have conducted extensive research to solve the above problems and, as a result, found out that a chromophore comprising a donor structure D, π-conjugated bridge structure B, and an acceptor structure A has a far superior nonlinear optical activity to conventional chromophores when the donor structure D contains a substituted oxyaryl, and thus the present invention has been completed.

That is, the present invention relates to:

<1> a chromophore comprising a donor structure D, a π-conjugated bridge structure B, and an acceptor structure A, the donor structure D comprising an aryl group substituted with a substituted oxy group and the acceptor structure A being free of —SO$_2$—;

<2> the chromophore according to the above <1>, wherein the substituted oxy group is attached to an ortho-carbon atom of the aryl group or to an ortho-carbon atom and the para-carbon atom of the aryl group;

<3> the chromophore according to the above <1> or <2>, wherein the aryl group may be further substituted with an optionally substituted amino group;

<4> the chromophore according to any of the above <1> to <3>, wherein the π-conjugation of the π-conjugated bridge structure B is a carbon-carbon conjugation;

<5> the chromophore according to any of the above <1> to <4>, wherein the chromophore is represented by the formula D-B-A, wherein D represents the donor structure D, B represents the π-conjugated bridge structure B, and A represents the acceptor structure A;

<6> the chromophore according to any of the above <1> to <5>, wherein the donor structure D is represented by the formula D-1:

[Formula 2]

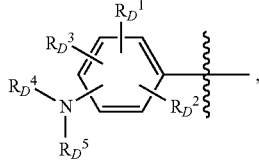
(D-1)

wherein at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom and optionally having a substituent;

<7> the chromophore according to any of the above <1> to <6>, wherein the donor structure D is represented by the formula D-1-1:

[Formula 3]

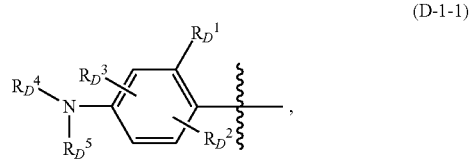
(D-1-1)

wherein $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent); and $R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom and optionally having a substituent;

<8> the chromophore according to any of the above <1> to <6>, wherein the donor structure D is represented by the formula D-1-2:

[Formula 4]

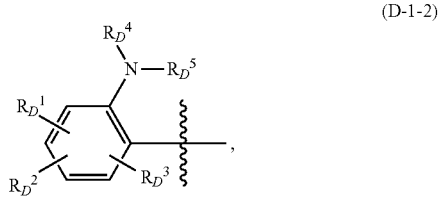
(D-1-2)

wherein at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a saturated heterocyclic ring optionally having a substituent, or $R_D^4$ and $R_D^5$ form, together with the nitrogen atom to which they are attached, with the aryl carbon atom to which said nitrogen atom is attached, and with the aryl carbon atom which is adjacent to said carbon atom, a heterocyclic ring containing the nitrogen atom as a hetero atom and optionally having a substituent;

<9> the chromophore according to any of the above <1>, <2>, <4> and <5>, wherein the donor structure D is represented by the formula D-2:

[Formula 5]

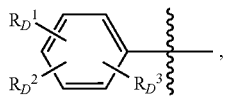

(D-2)

wherein at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

<10> the chromophore according to any of the above <1>, <2>, <4>, <5> and <9>, wherein the donor structure D is represented by the formula D-2-1:

[Formula 6]

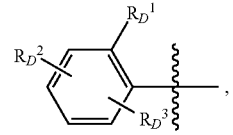

(D-2-1)

wherein $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent; and $R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

<11> the chromophore according to any of the above <1> to <10>, wherein the acceptor structure A is represented by the formula selected from the group consisting of:

[Formula 7]

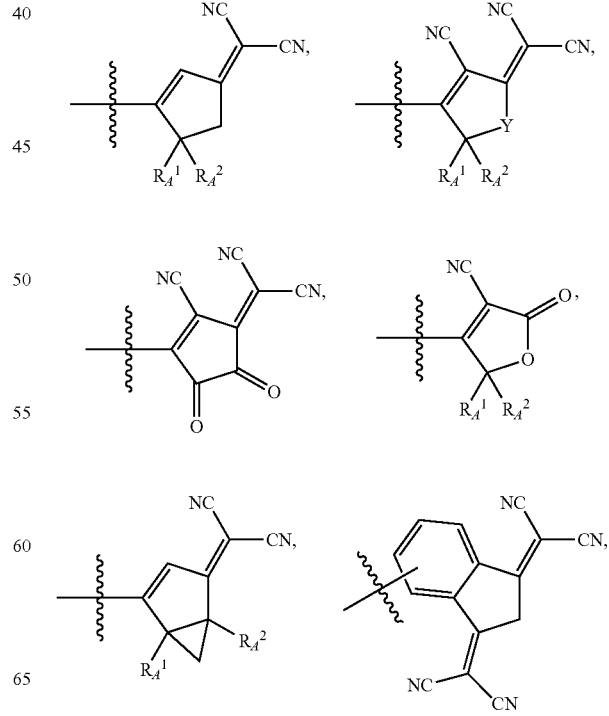

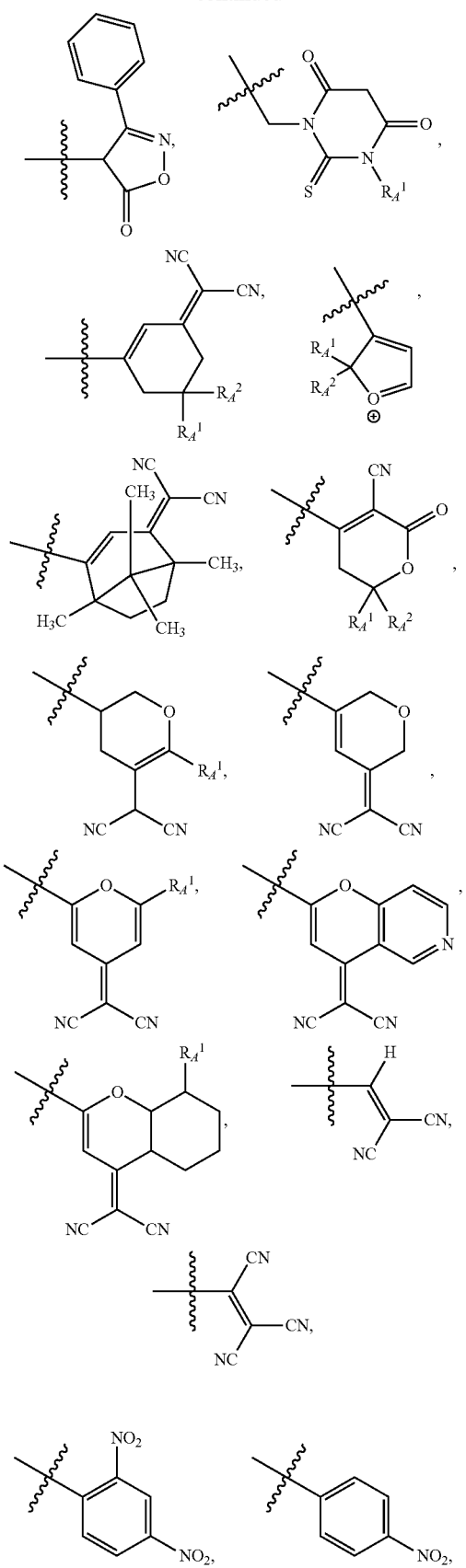

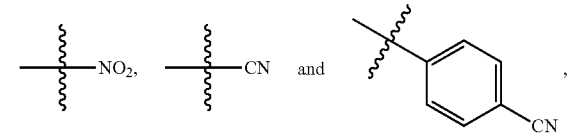

wherein
Y represents —CR$_A^1$R$_A^2$—, —O—, —S—, —SO—, —SiR$_A^1$R$_A^2$—, —NR— (wherein R represents a hydrogen atom or an alkyl group), or —C(=CH$_2$)—; and R$_A^1$ and R$_A^2$ independently represent a hydrogen atom, an alkyl group, an alkenyl group, a cycloalkyl group, a cycloalkenyl group, an alkoxy group, a haloalkyl group, or an aryl group, and R$_A^1$ and R$_A^2$ each may have the same or different substituents, or R$_A^1$ and R$_A^2$ form, together with the carbon atom to which they are attached, a structure that may have a substituent and is represented by the following formula:

[Formula 9]

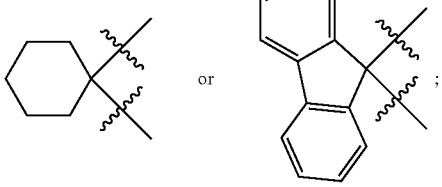

<12> the chromophore according to any of the above <1> to <11>, wherein the carbon-carbon conjugated bridge structure B may have a substituent and is represented by the formula selected from the group consisting of:

[Formula 10]

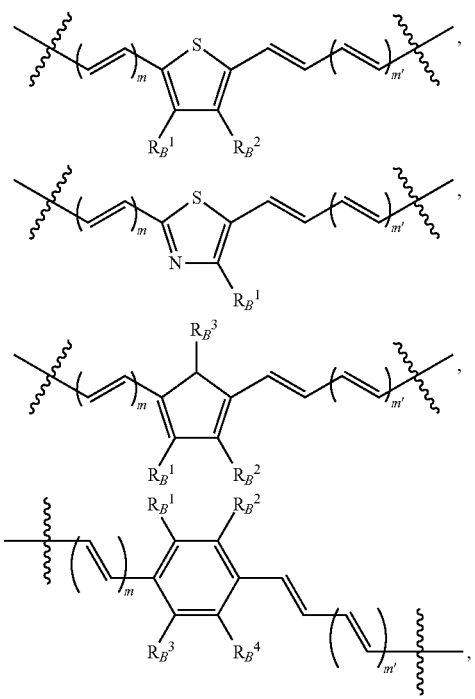

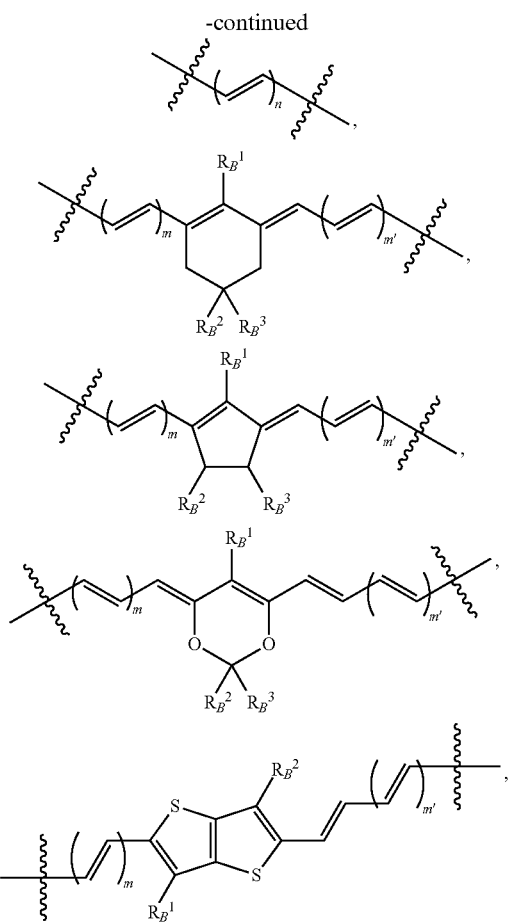

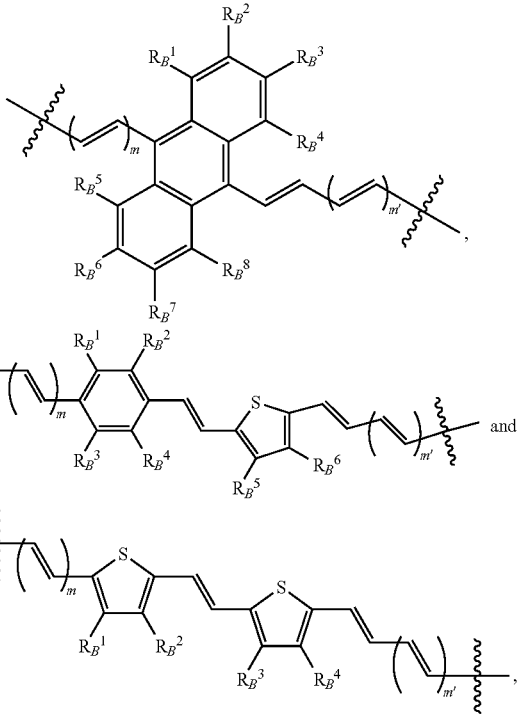

wherein
$R_B^1$ to $R_B^8$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$ to $R_B^8$ each may have the same or different substituents;
n represents an integer of 1 to 5; and
m and m' independently represent an integer of 0 to 3;
<13> the chromophore according to any of the above <1> to <12>, wherein the carbon-carbon conjugated bridge structure B is represented by the formula B-I:

[Formula 13]

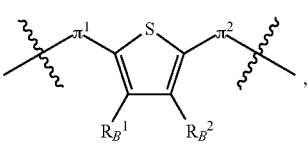

(B-I)

wherein
$\pi^1$ and $\pi^2$ independently represent the same or different carbon-carbon conjugated π-bonds, and $\pi^1$ and $\pi^2$ each may have the same or different substituents; and
$R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$ and $R_B^2$ each may have the same or different substituents;
<14> the chromophore according to any of the above <1> to <6> and <11> to <13>, wherein the chromophore is represented by the formula I-1:

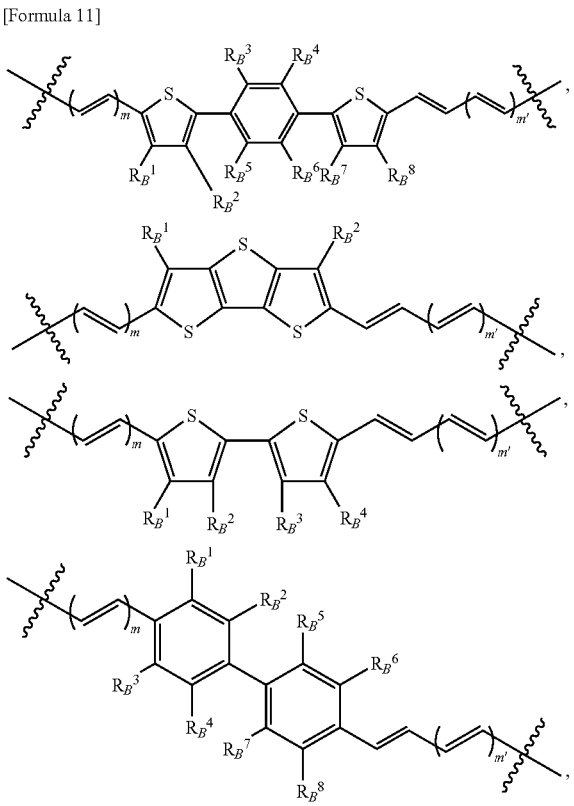

[Formula 14]

(I-1)

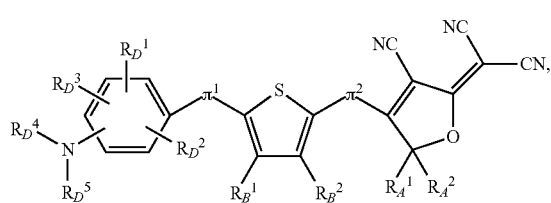

wherein $\pi^1$ and $\pi^2$ independently represent the same or different carbon-carbon conjugated π-bonds, and $\pi^1$ and $\pi^2$ each may have the same or different substituents;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$ and $R_B^2$ independently represent a hydrogen atom, an alkyl group, an alkoxy group, an aryl group, an aralkyl group, an aryloxy group, or an aralkyloxy group, and $R_B^1$ and $R_B^2$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents;

<15> the chromophore according to any of the above <1> to <7> and <11> to <14>, wherein the chromophore is represented by the formula I-1-1:

[Formula 15]

(I-1-1)

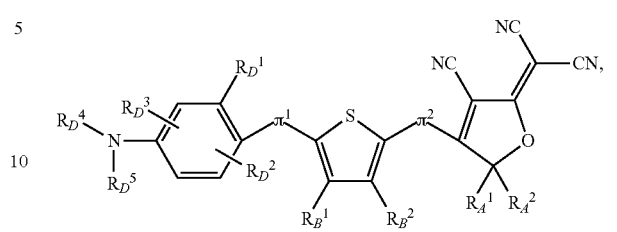

wherein $\pi^1$ and $\pi^2$ independently represent the same or different carbon-carbon conjugated π-bonds, and $\pi^1$ and $\pi^2$ each may have the same or different substituents;

$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$ and $R_B^2$ independently represent a hydrogen atom, an alkyl group, an alkoxy group, an aryl group, an aralkyl group, an aryloxy group, or an aralkyloxy group, and $R_B^1$ and $R_B^2$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents;

<16> the chromophore according to any of the above <1>, <2>, <4>, <5>, <9> and <11> to <13>, wherein the chromophore is represented by the formula I-2:

[Formula 16]

(I-2)

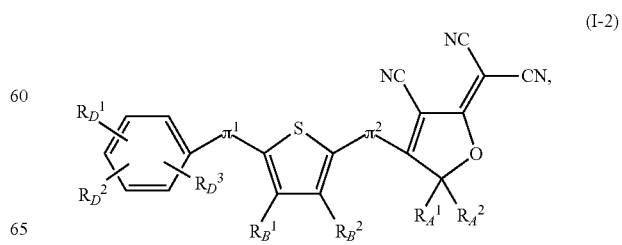

wherein $\pi^1$ and $\pi^2$ independently represent the same or different carbon-carbon conjugated π-bonds, and $\pi^1$ and $\pi^2$ each may have the same or different substituents;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_B^1$ and $R_B^2$ independently represent a hydrogen atom, an alkyl group, an alkoxy group, an aryl group, an aralkyl group, an aryloxy group, or an aralkyloxy group, and $R_B^1$ and $R_B^2$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents;

<17> the chromophore according to any of the above <1> to <12>, wherein the carbon-carbon conjugated bridge structure B is represented by the formula B-II:

[Formula 17]

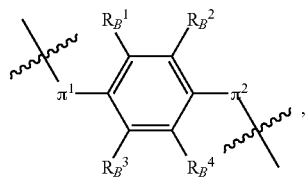

(B-II)

wherein $\pi^1$ and $\pi^2$ independently represent the same or different carbon-carbon conjugated π-bonds, and $\pi^1$ and $\pi^2$ each may have the same or different substituents; and $R_B^1$, $R_B^2$, $R_B^3$, and $R_B^4$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$, $R_B^2$, $R_B^3$, and $R_B^4$ each may have the same or different substituents;

<18> the chromophore according to any of the above <1> to <6>, <11>, <12>, and <17>, wherein the chromophore is represented by the formula II-1:

[Formula 18]

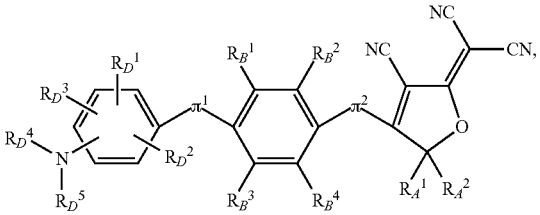

(II-1)

wherein $\pi^1$ and $\pi^2$ independently represent the same or different carbon-carbon conjugated π-bonds, and $\pi^1$ and $\pi^2$ each may have the same or different substituents;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$, $R_B^2$, $R_B^3$, and $R_B^4$ independently represent a hydrogen atom, an alkyl group, an alkoxy group, an aryl group, an aralkyl group, an aryloxy group, or an aralkyloxy group, and $R_B^1$, $R_B^2$, $R_B^3$, and $R_B^4$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents;

<19> the chromophore according to any of the above <1> to <7>, <11>, <12>, <17>, and <18>, wherein the chromophore is represented by the formula II-1-1:

[Formula 19]

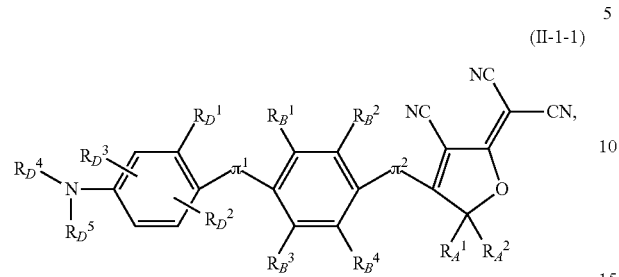

(II-1-1)

wherein

π¹ and π² independently represent the same or different carbon-carbon conjugated π-bonds, and π¹ and π² each may have the same or different substituents;

$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom and optionally having a substituent;

$R_B^1$, $R_B^2$, $R_B^3$, and $R_B^4$ independently represent a hydrogen atom, an alkyl group, an alkoxy group, an aryl group, an aralkyl group, an aryloxy group, or an aralkyloxy group, and $R_B^1$, $R_B^2$, $R_B^3$, and $R_B^4$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents;

<20> the chromophore according to any of the above <1> to <12>, wherein the carbon-carbon conjugated bridge structure B is represented by the formula B-III:

[Formula 20]

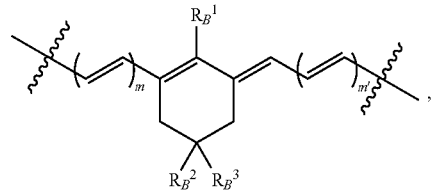

(B-III)

wherein m and m' independently represent an integer of 0 to 3; and $R_B^1$, $R_B^2$, and $R_B^3$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$, $R_B^2$, and $R_B^3$ each may have the same or different substituents;

<21> the chromophore according to any of the above <1> to <6>, <11>, <12>, and <20>, wherein the chromophore is represented by the formula III-1:

[Formula 21]

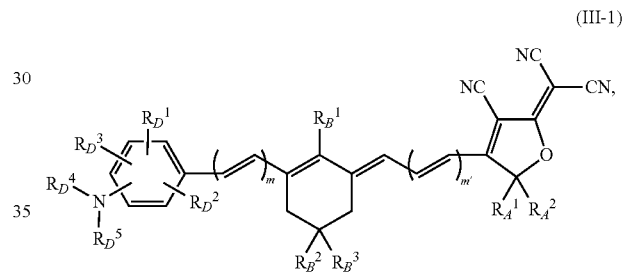

(III-1)

wherein m and m' independently represent an integer of 0 to 3;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D{}^2$ and —$NR_D{}^4R_D{}^5$ and (b) $R_D{}^3$ and —$NR_D{}^4R_D{}^5$ independently form, together with the carbon atoms to which they are attached, a heterocyclic ring containing the nitrogen atom as a hetero atom and optionally having a substituent;

$R_B{}^1$, $R_B{}^2$, and $R_B{}^3$ independently represent a hydrogen atom, an alkyl group, an alkoxy group, an aryl group, an aralkyl group, an aryloxy group, or an aralkyloxy group, and $R_B{}^1$, $R_B{}^2$, and $R_B{}^3$ each may have the same or different substituents; and $R_A{}^1$ and $R_A{}^2$ independently represent a hydrogen atom, an alkyl group, a haloalkyl group, or an aryl group, and $R_A{}^1$ and $R_A{}^2$ each may have the same or different substituents;

<22> the chromophore according to any of the above <1> to <7>, <11>, <12>, <20>, and <21>, wherein the chromophore is represented by the formula III-1-1:

[Formula 22]

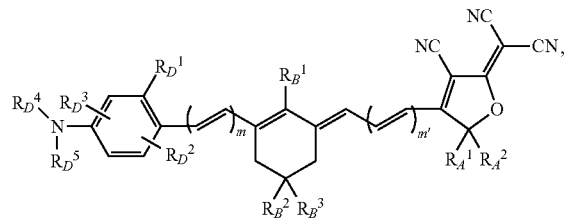

(III-1-1)

wherein m and m' independently represent an integer of 0 to 3;

$R_D{}^1$ represents an alkoxy group, an aryloxy group, an aralkyloxy group, a silyloxy group, an alkenyloxy group, an alkenylcarbonyloxy group, an alkynyloxy group, or a hydroxy group, and $R_D{}^1$ may have a substituent;

$R_D{}^2$ and $R_D{}^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D{}^2$ and $R_D{}^3$ each may have the same or different substituents (when $R_D{}^2$ and $R_D{}^3$ are each attached to adjacent carbon atoms of the aryl of the donor structure D, $R_D{}^2$ and $R_D{}^3$ may form, together with the two adjacent carbon atoms, a ring optionally having a substituent);

$R_D{}^4$ and $R_D{}^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D{}^4$ and $R_D{}^5$ each may have the same or different substituents, or $R_D{}^4$ and $R_D{}^5$ form, together with the nitrogen atom to which they are attached, a heterocyclic ring containing the nitrogen atom as a hetero atom and optionally having a substituent; or (a) $R_D{}^2$ and —$NR_D{}^4R_D{}^5$ and (b) $R_D{}^3$ and —$NR_D{}^4R_D{}^5$ independently form, together with the carbon atoms to which they are attached, a heterocyclic ring containing the nitrogen atom as a hetero atom and optionally having a substituent;

$R_B{}^1$, $R_B{}^2$, and $R_B{}^3$ independently represent a hydrogen atom, an alkyl group, an alkoxy group, an aryl group, an aralkyl group, an aryloxy group, or an aralkyloxy group, and $R_B{}^1$, $R_B{}^2$, and $R_B{}^3$ each may have the same or different substituents; and $R_A{}^1$ and $R_A{}^2$ independently represent a hydrogen atom, an alkyl group, a haloalkyl group, or an aryl group, and $R_A{}^1$ and $R_A{}^2$ each may have the same or different substituents;

<23> the chromophore according to any of the above <1> to <12>, wherein the carbon-carbon conjugated bridge structure B is represented by the formula B-IV:

[Formula 23]

(B-IV)

wherein n represents an integer of 1 to 5;

<24> the chromophore according to any of the above <1> to <6>, <11>, <12>, and <23>, wherein the chromophore is represented by the formula IV-1-a:

[Formula 24]

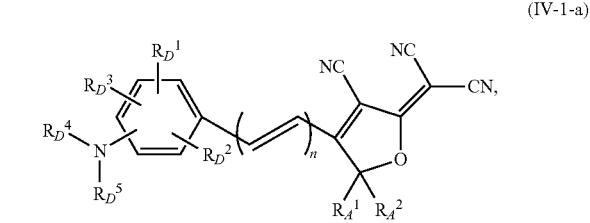

(IV-1-a)

wherein n represents an integer of 1 to 5;

$R_D{}^1$ represents an alkoxy group, an aryloxy group, an aralkyloxy group, a silyloxy group, an alkenyloxy group, an alkenylcarbonyloxy group, an alkynyloxy group, or a hydroxy group, and $R_D{}^1$ may have a substituent;

$R_D{}^2$ and $R_D{}^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D{}^2$ and $R_D{}^3$ each may have the same or different substituents (when $R_D{}^2$ and $R_D{}^3$ are each attached to adjacent carbon atoms of the aryl of the donor structure D, $R_D{}^2$ and $R_D{}^3$ may form, together with the two adjacent carbon atoms, a ring optionally having a substituent);

$R_D{}^4$ and $R_D{}^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D{}^4$ and $R_D{}^5$ each may have the same or different substituents, or $R_D{}^4$ and $R_D{}^5$ form, together with the nitrogen atom to which they are attached, a heterocyclic ring containing the nitrogen atom as a hetero atom and optionally having a substituent; or (a) $R_D{}^2$ and —$NR_D{}^4R_D{}^5$ and (b) $R_D{}^3$ and —$NR_D{}^4R_D{}^5$ independently form, together with the carbon atoms to which they are attached, a heterocyclic ring containing the nitrogen atom as a hetero atom and optionally having a substituent; and $R_A{}^1$ and $R_A{}^2$ independently represent a hydrogen atom, an alkyl group, a haloalkyl group, or an aryl group, and $R_A{}^1$ and $R_A{}^2$ each may have the same or different substituents;

<25> the chromophore according to any of the above <1> to <6>, <11>, <12>, and <23>, wherein the chromophore is represented by the formula IV-1-b:

[Formula 25]

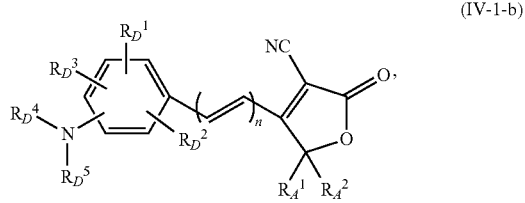

(IV-1-b)

wherein n represents an integer of 1 to 5;

$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent; and $R_A^1$ and $R_A^2$ independently represent a hydrogen atom, an alkyl group, a haloalkyl group, or an aryl group, and $R_A^1$ and $R_A^2$ each may have the same or different substituents;

<26> the chromophore according to any of the above <1>, <2>, <4>, <5>, <9>, <11>, <12> and <23>, wherein the chromophore is represented by the formula IV-2-a:

[Formula 26]

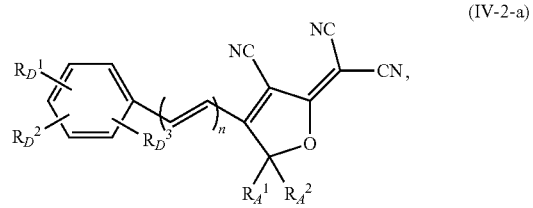

(IV-2-a)

wherein n represents an integer of 1 to 5;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $R_A^1$ and $R_A^2$ independently represent a hydrogen atom, an alkyl group, a haloalkyl group, or an aryl group, and $R_A^1$ and $R_A^2$ each may have the same or different substituents;

<27> the chromophore according to any of the above <1>, <2>, <4>, <5>, <9>, <11>, <12> and <23>, wherein the chromophore is represented by the formula IV-2-b:

[Formula 27]

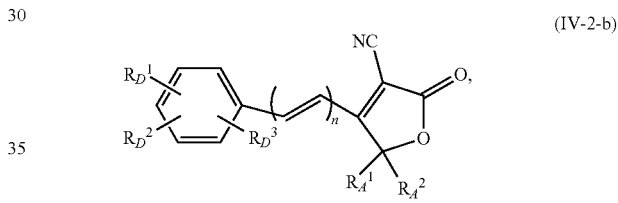

(IV-2-b)

wherein n represents an integer of 1 to 5;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $R_A^1$ and $R_A^2$ independently represent a hydrogen atom, an alkyl group, a haloalkyl group, or an aryl group, and $R_A^1$ and $R_A^2$ each may have the same or different substituents;

<28> the chromophore according to any of the above <6> to <10>, <14> to <16>, <18>, <19>, <21>, <22> and <24> to <27>, wherein $R_D^1$ represents a $C_{1-6}$ alkoxy group, a benzyloxy group, a silyloxy group, a $C_{2-6}$ alkenyloxy group, a $C_{2-6}$ alkenylcarbonyloxy group, a $C_{3-6}$ alkynyloxy group, or a hydroxy group, and $R_D^1$ may have a substituent; and $R_D^2$ and $R_D^3$ independently represent a hydrogen atom, a $C_{1-6}$ alkoxy group, a benzyloxy group, a silyloxy group, a $C_{2-6}$ alkenyloxy group, a $C_{2-6}$ alkenylcarbonyloxy group, a $C_{3-6}$ alkynyloxy group, or a hydroxy group, and $R_D^2$ and $R_D^3$ each may have the same or different substituents;

<29> the chromophore according to any of the above <6> to <8>, <14>, <15>, <18>, <19>, <21>, <22>, <24>, and <25>, wherein $R_D^4$ and $R_D^5$ independently represent an alkyl group, a hydroxyalkyl group, or a silyloxyalkyl group, and $R_D^4$ and $R_D^5$ each may have the same or different substituents;

<30> the chromophore according to any of the above <11>, <14> to <16>, <18>, <19>, <21>, <22>, <24>, <25>, <26>, and <27>, wherein $R_A^1$ and $R_A^2$ independently represent a methyl group, a trifluoromethyl group, or a phenyl group, and $R_A^1$ and $R_A^2$ each may have the same or different substituents;

<31> the chromophore according to any of the above <13> to <19>, wherein $\pi^1$ and $\pi^2$ are each represented by the following formula:

[Formula 28]

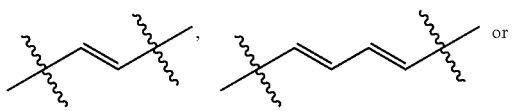

and $\pi^1$ and $\pi^2$ each may have the same or different substituents;

<32> the chromophore according to any of the above <13> to <19>, wherein $\pi^1$ and $\pi^2$ are represented by the following formula:

[Formula 29]

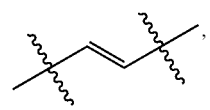

and $\pi^1$ and $\pi^2$ each may have the same or different substituents;

<33> the chromophore according to any of the above <1> to <7>, <11> to <15>, and <28> to <32>, wherein the chromophore is represented by the formula selected from the group consisting of:

[Formula 30]

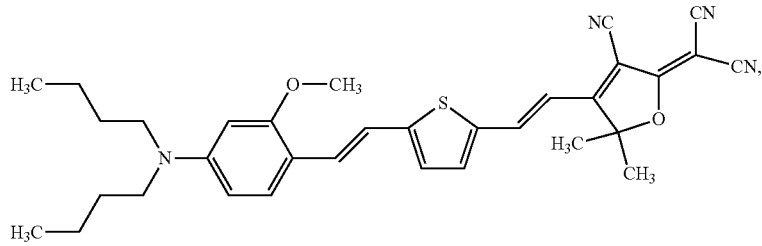

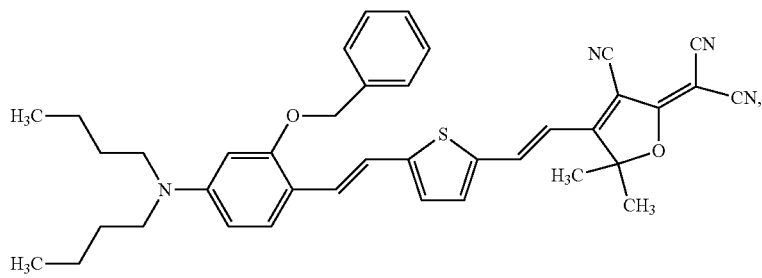

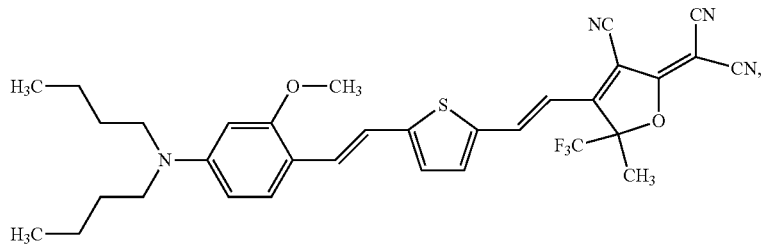

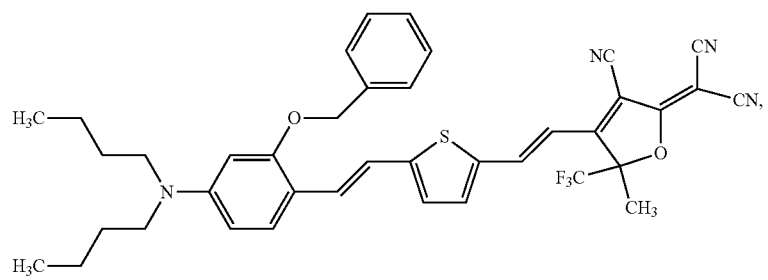
[Formula 31]
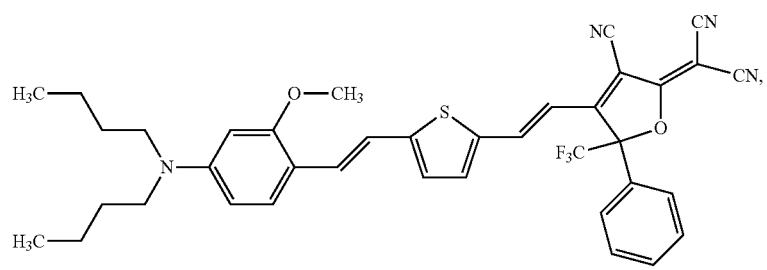
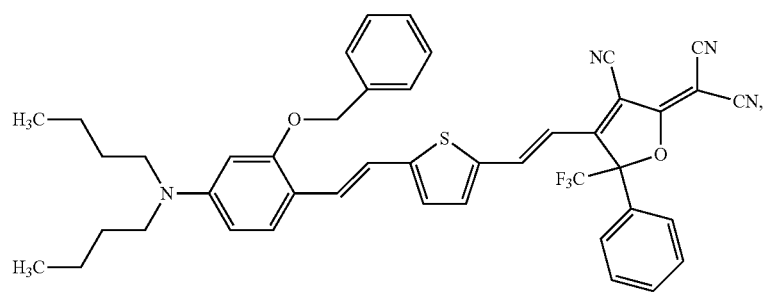
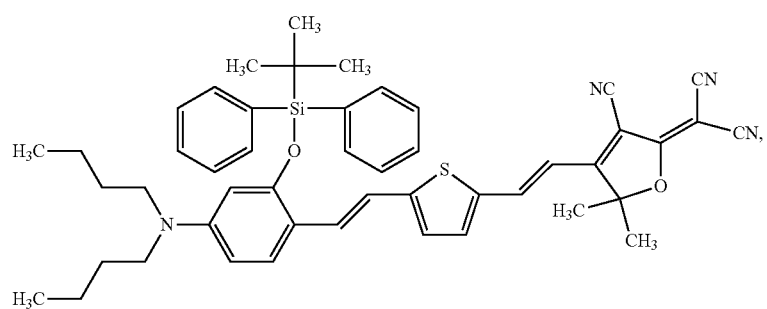
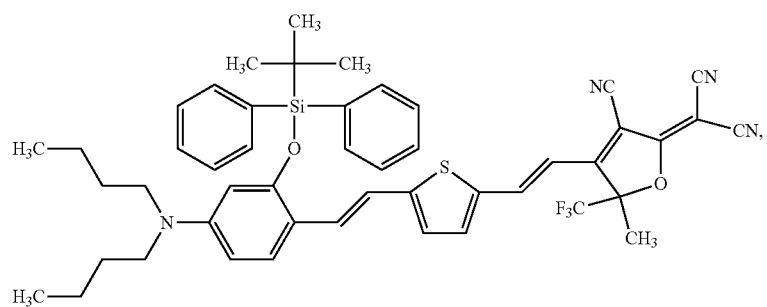

[Formula 32]
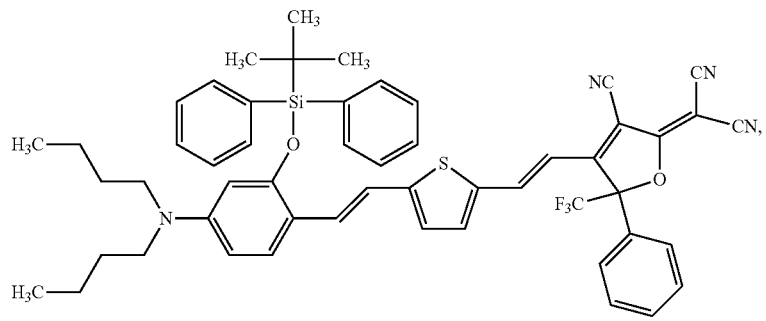
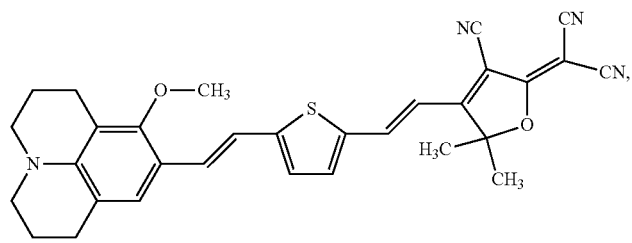
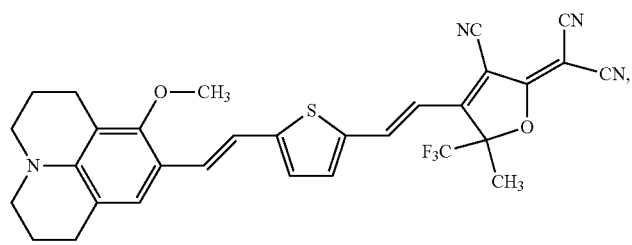
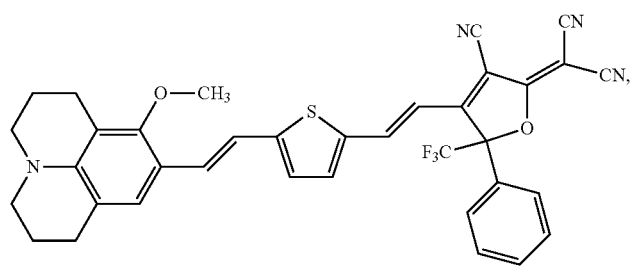
[Formula 33]
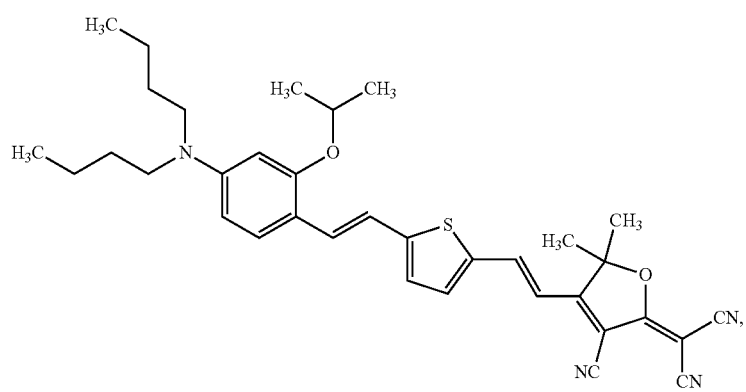

-continued
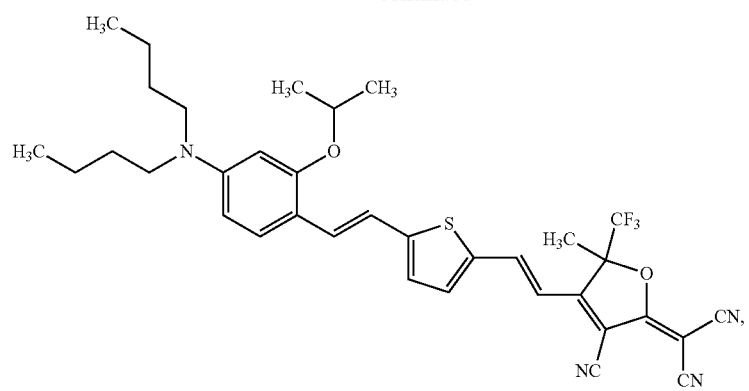
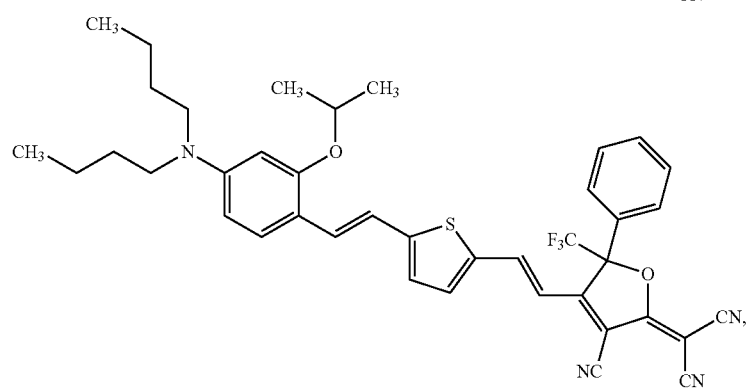
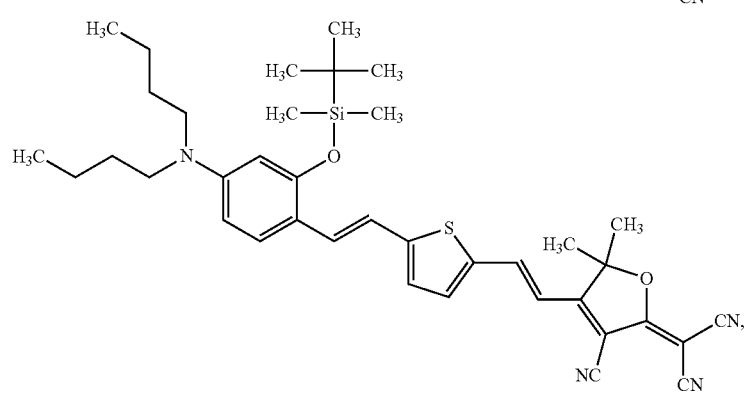
[Formula 34]
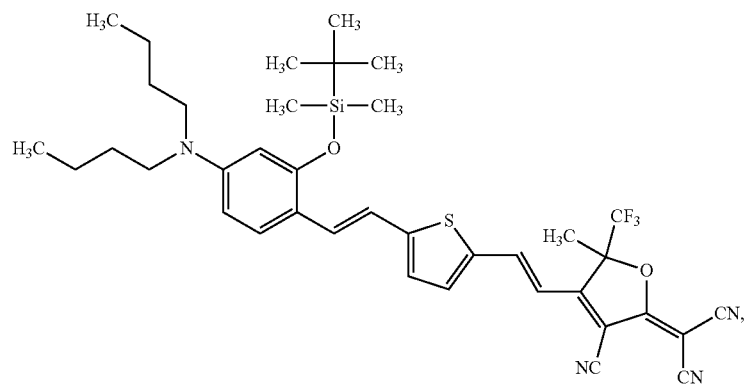

-continued
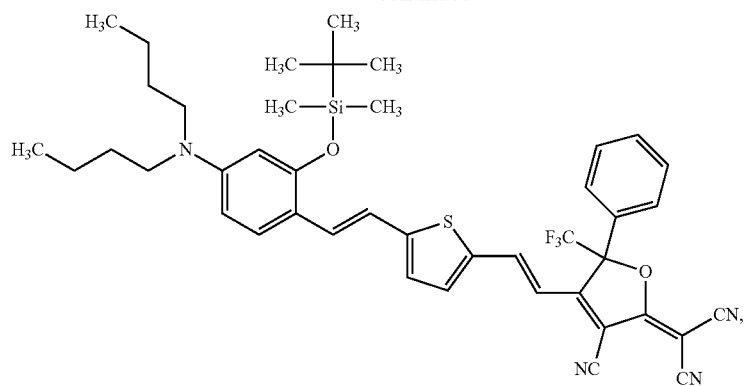
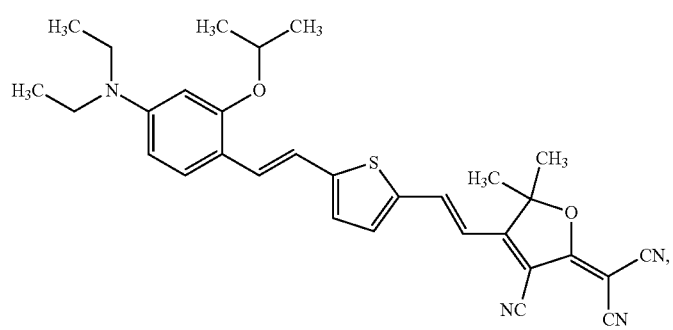
[Formula 35]
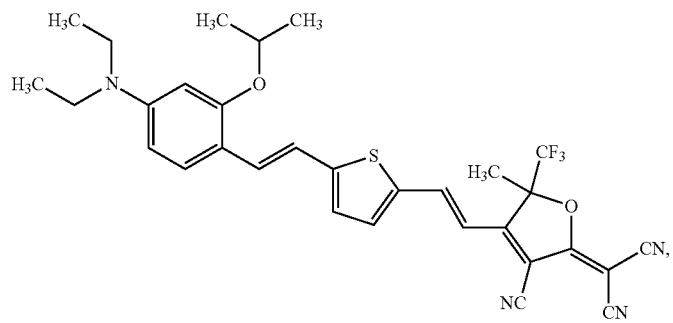
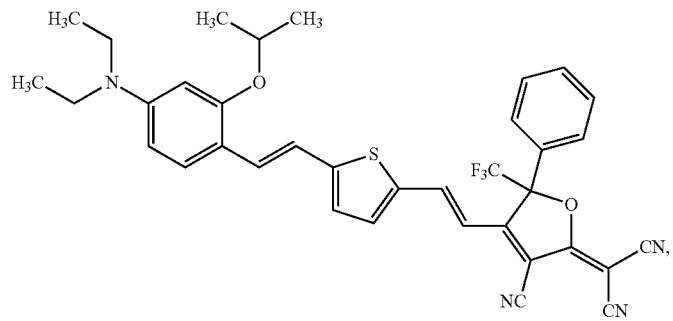

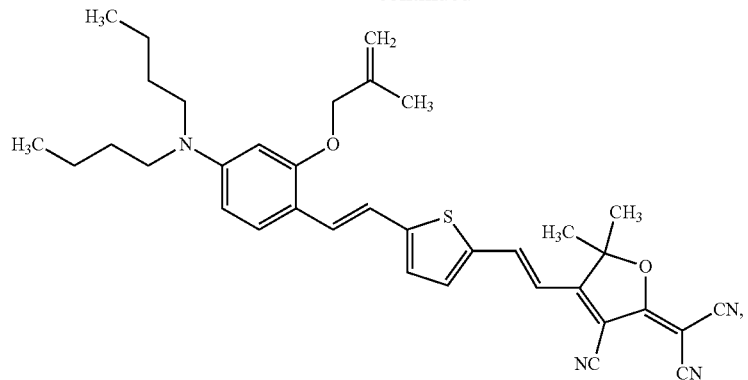
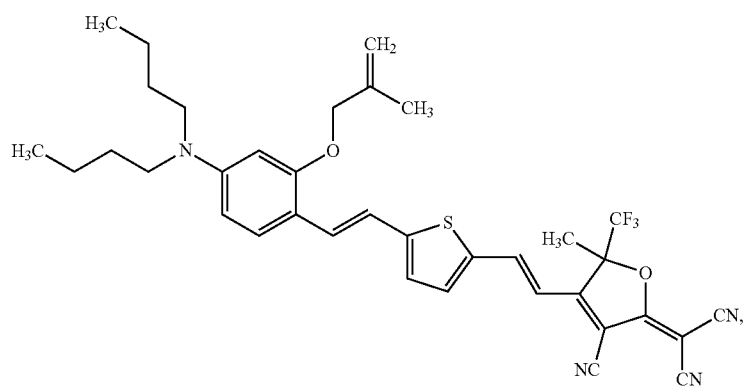
[Formula 36]
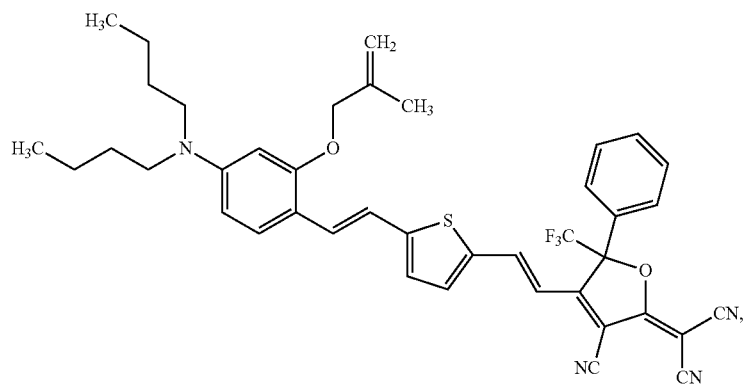
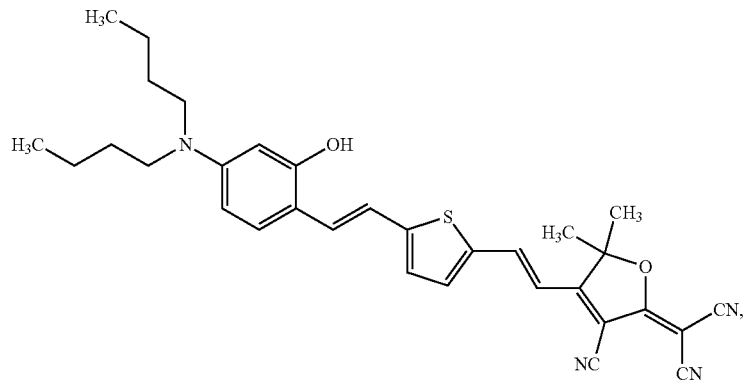

-continued
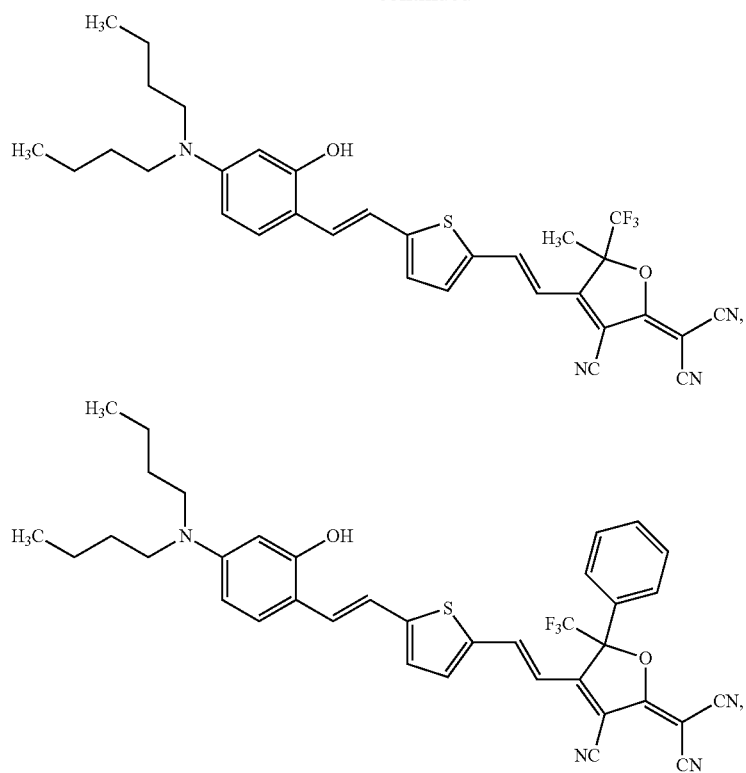
[Formula 37]
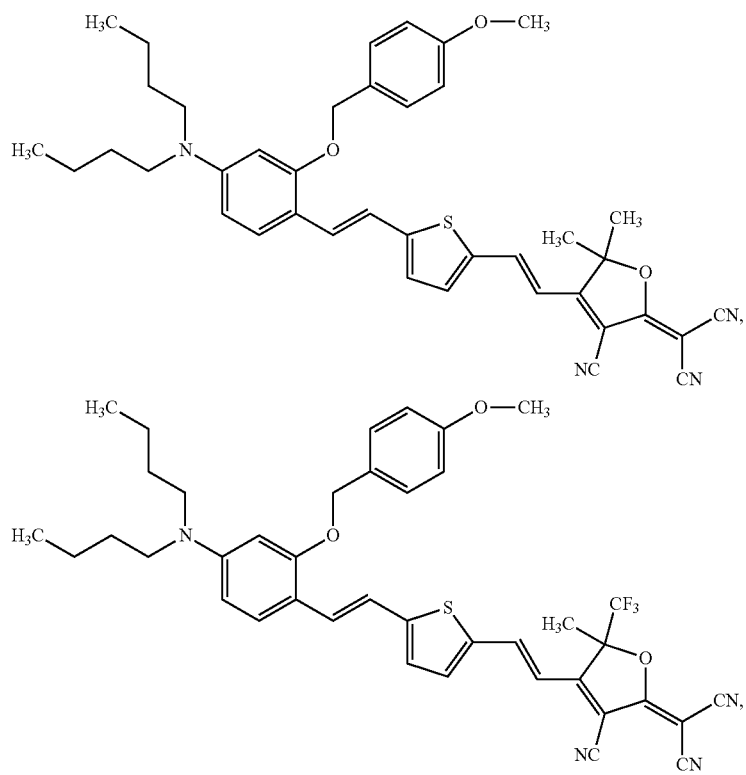

-continued
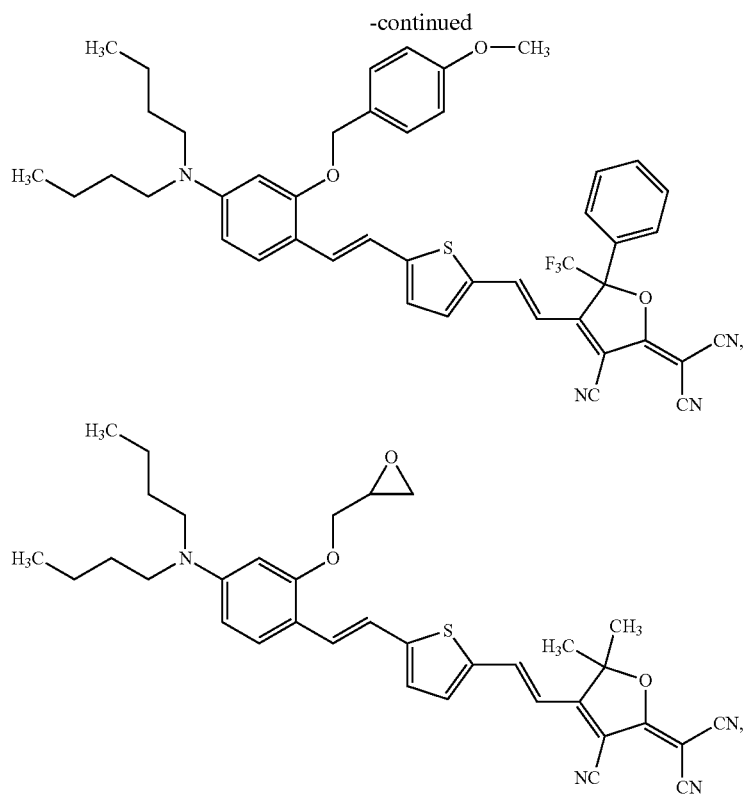
[Formula 38]
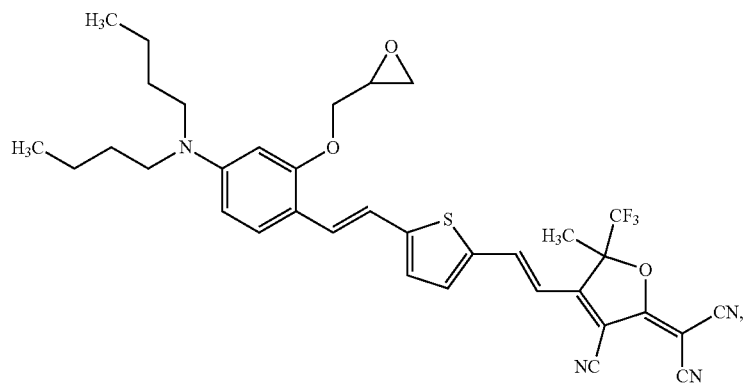
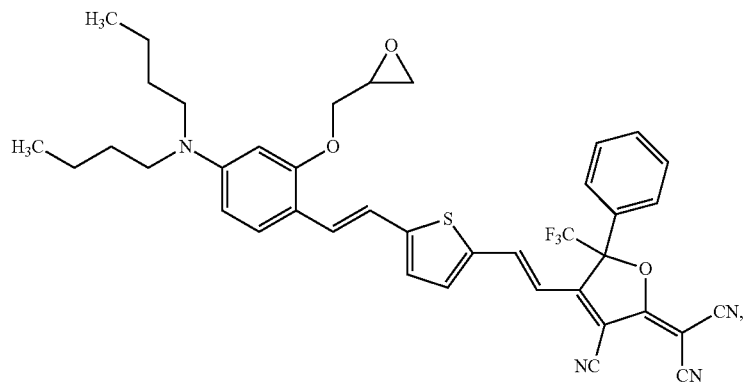

-continued
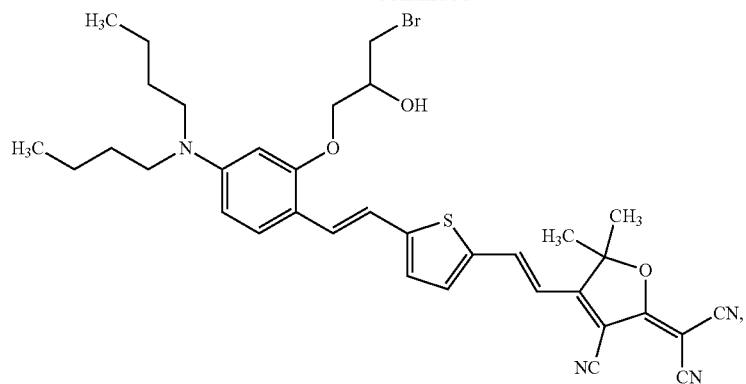
[Formula 39]
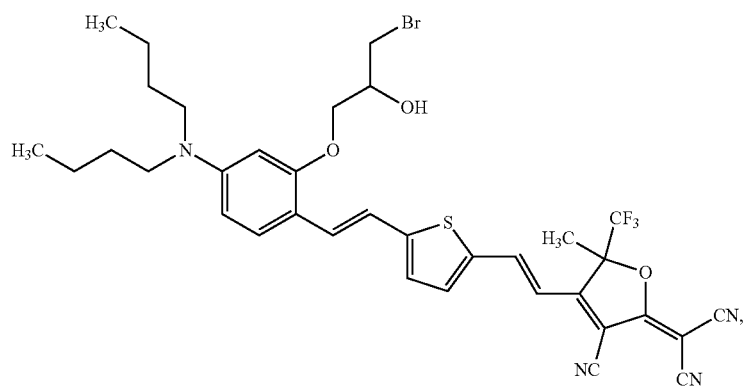
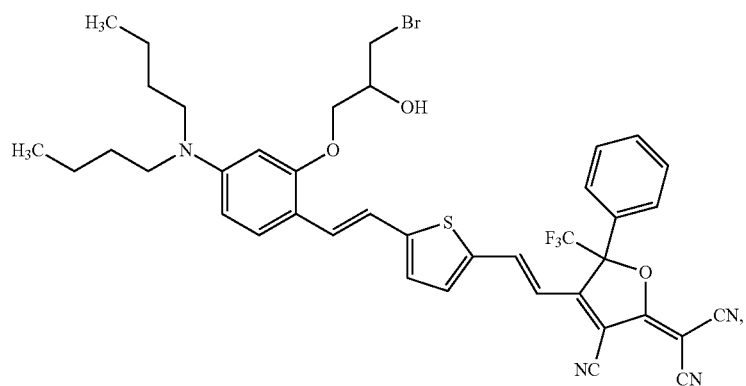
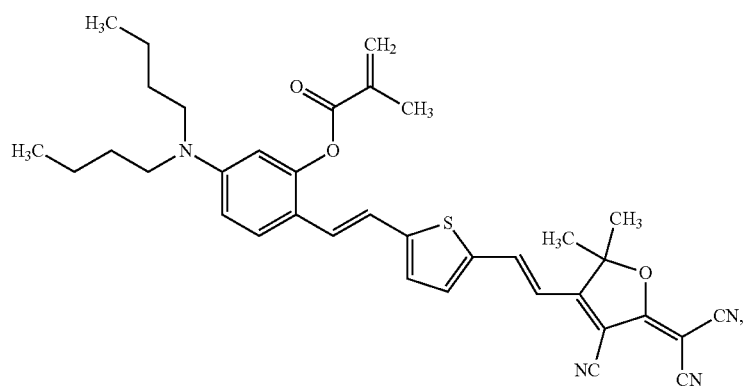

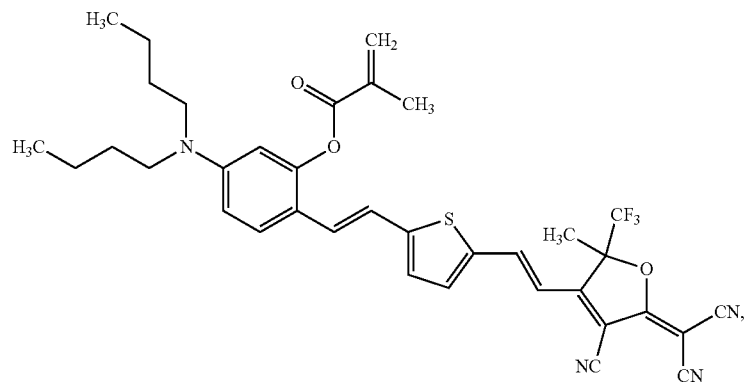
[Formula 40]
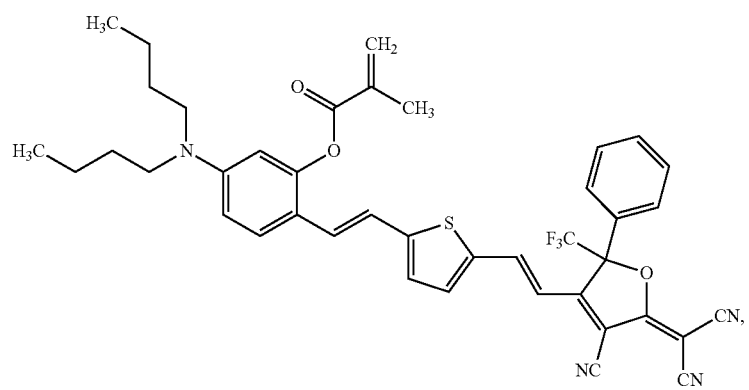
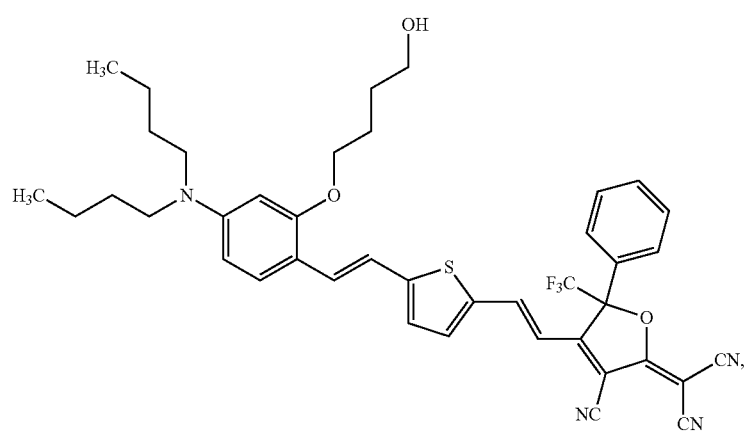
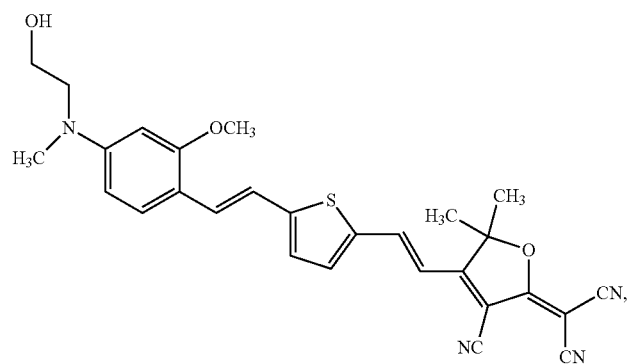

[Formula 41]
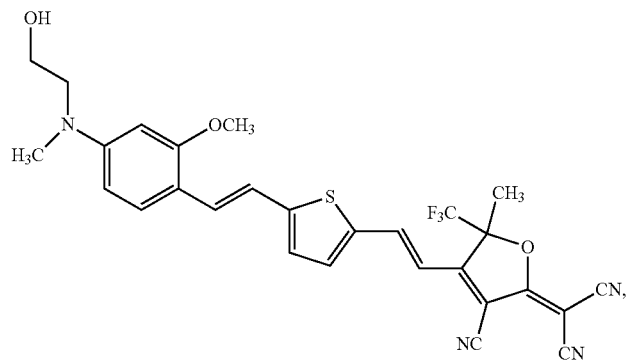
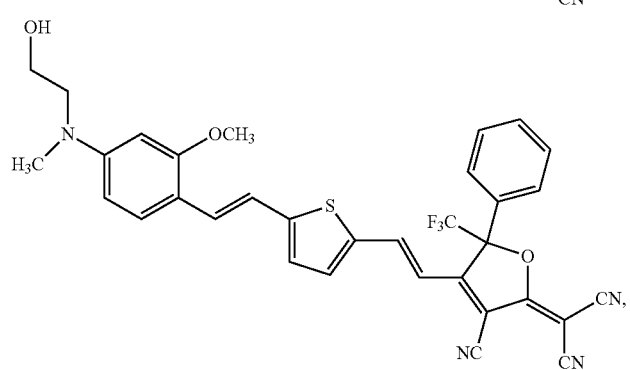
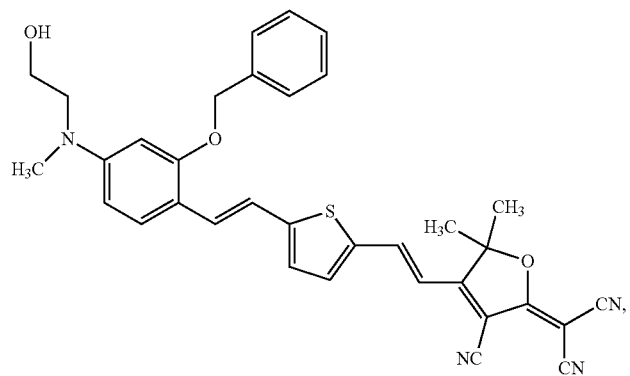
[Formula 42]
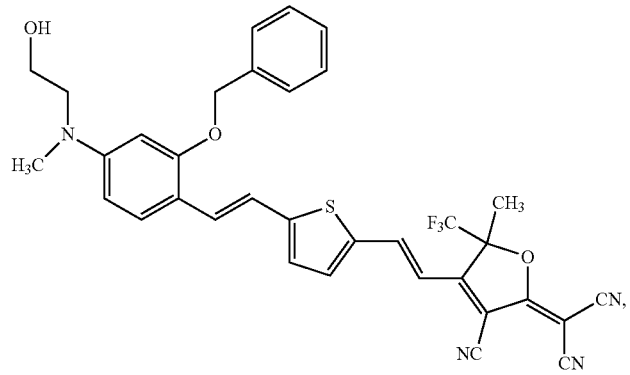

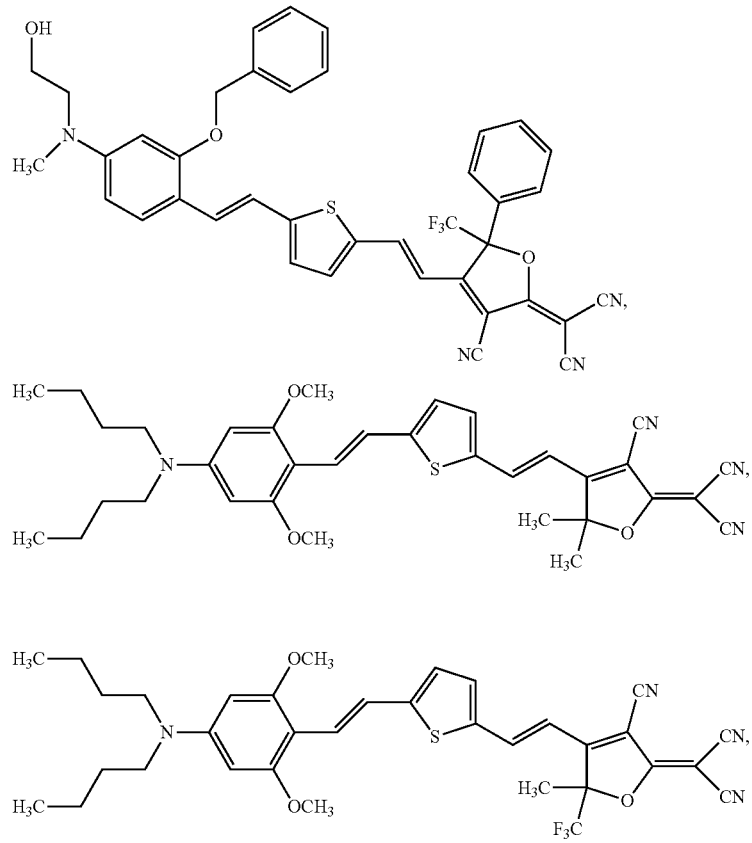
[Formula 43]
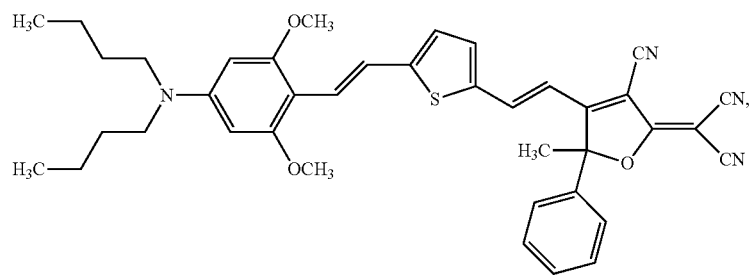
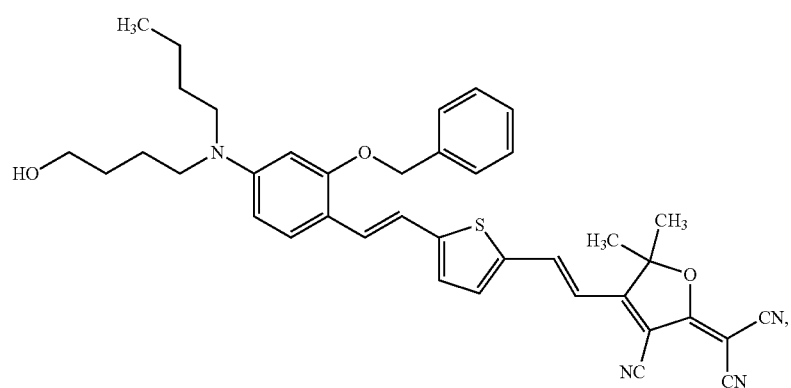

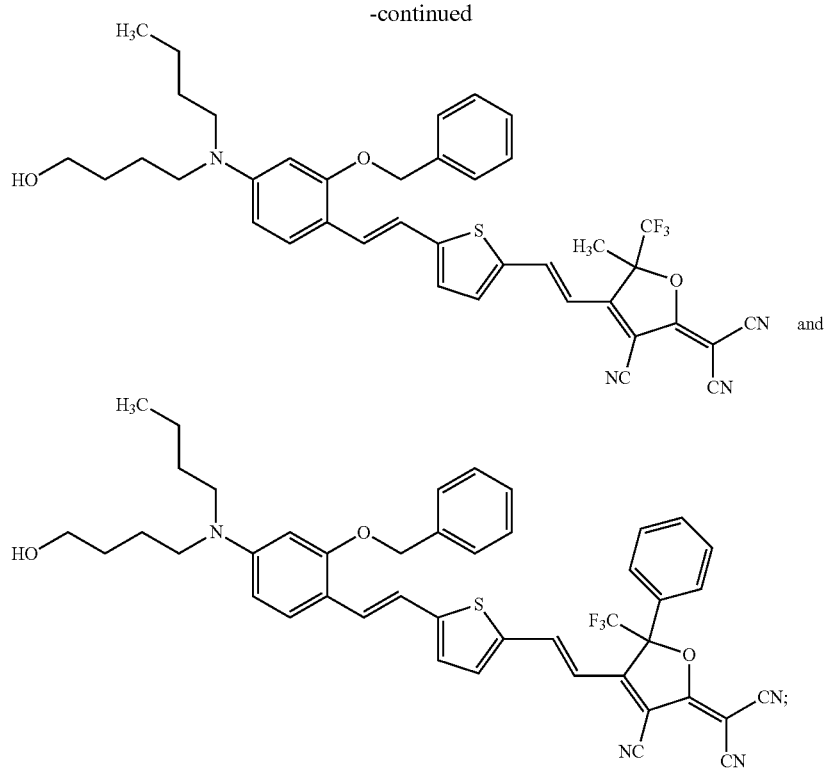
and
<34> the chromophore according to any of the above <1>, <2>, <4>, <5>, <9> to <13>, <16>, and <28> to <32>, wherein the chromophore is represented by the following formula:
[Formula 44]
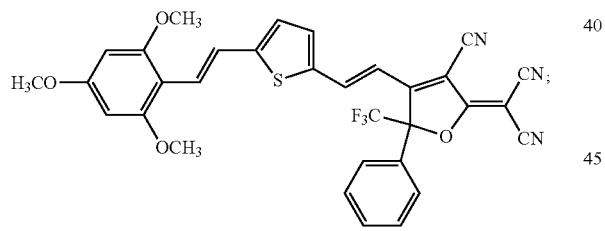
<35> the chromophore according to any of the above <1> to <7>, <11>, <12>, <17> to <19>, and <28> to <32>, wherein the chromophore is represented by the formula selected from the group consisting of:
[Formula 45]
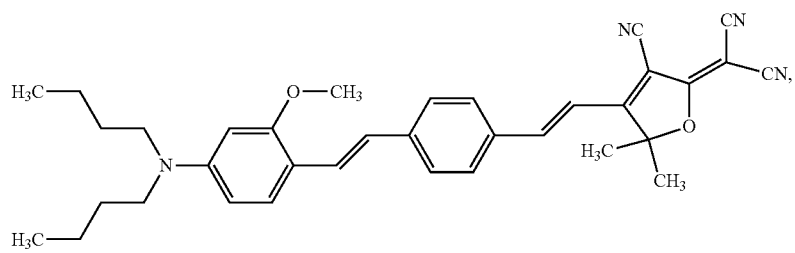

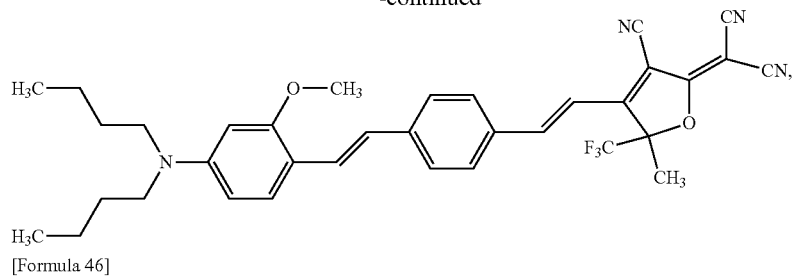
[Formula 46]
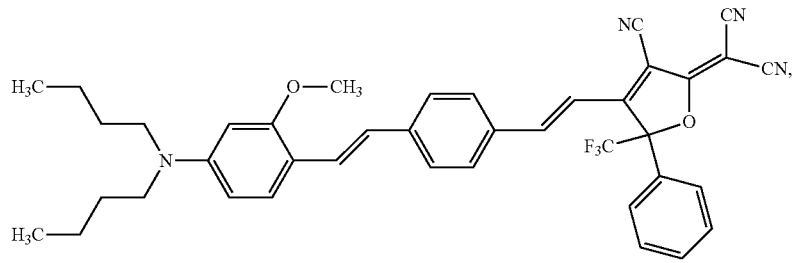
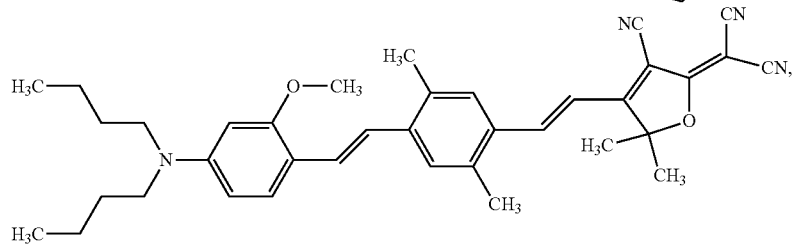
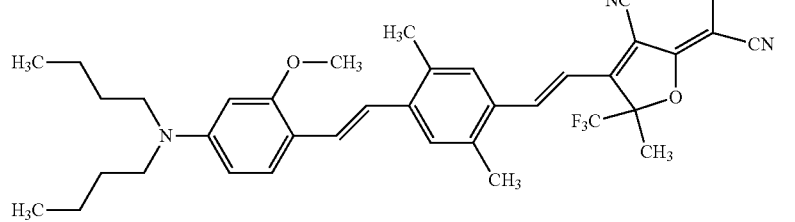 and
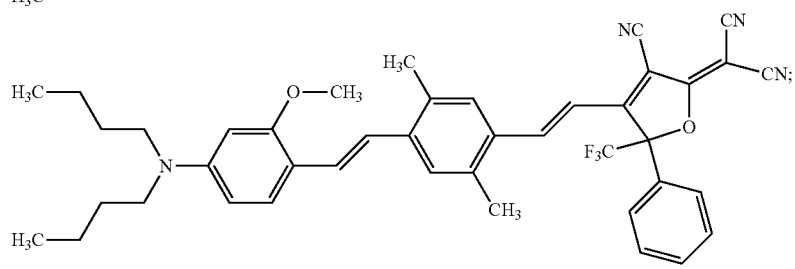
<36> the chromophore according to any of the above <1> to <7>, <11>, <12>, <20> to <22>, and <28> to <30>, wherein the chromophore is represented by the formula selected from the group consisting of:
[Formula 47]
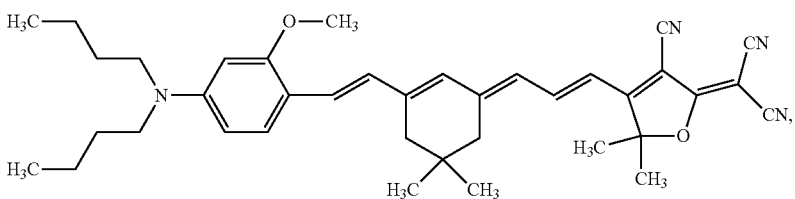

[Formula 48]
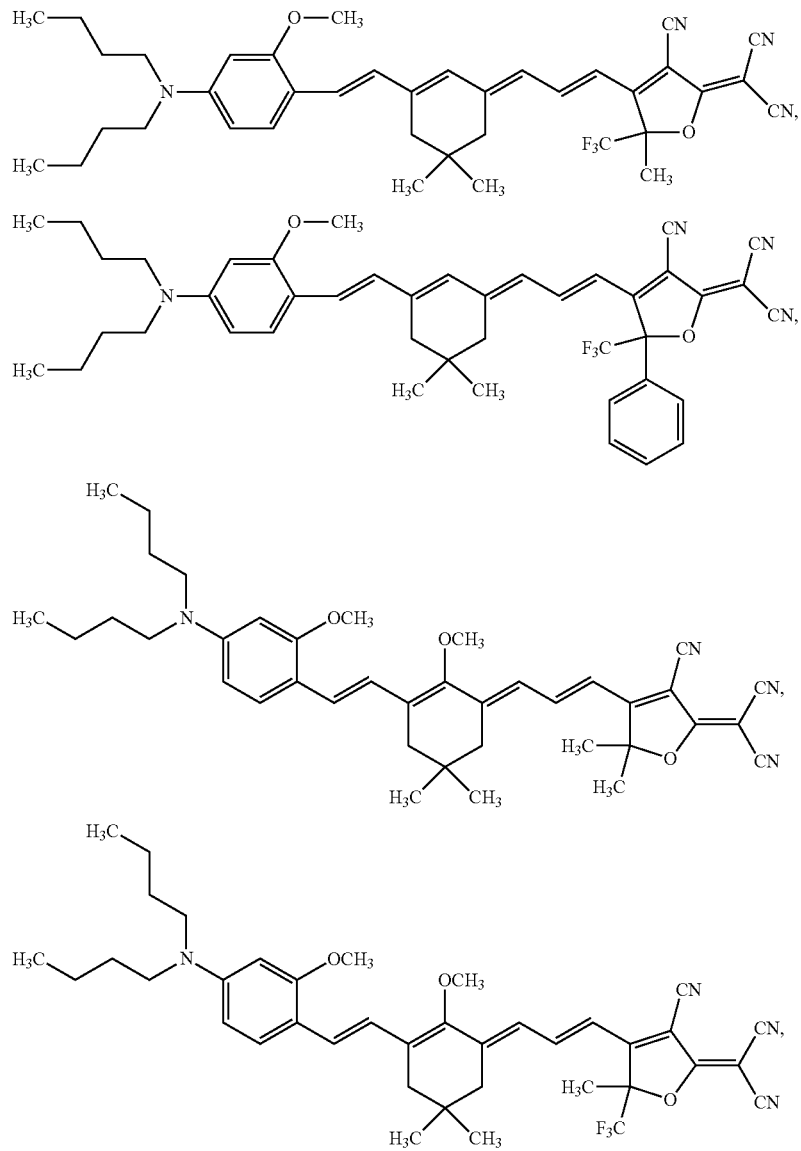
[Formula 49]
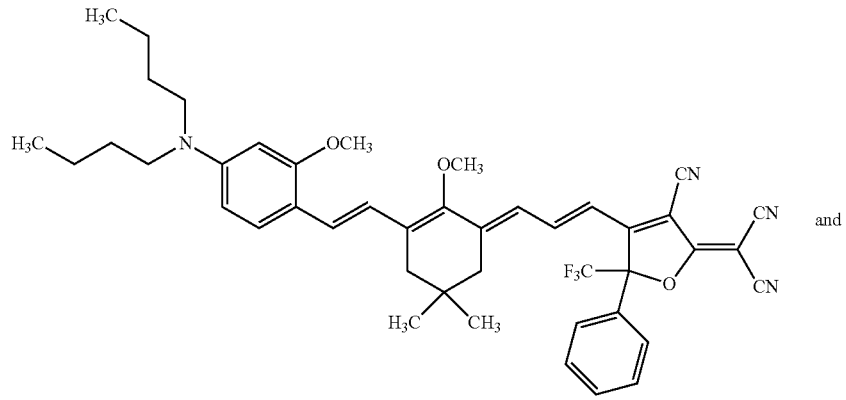
and

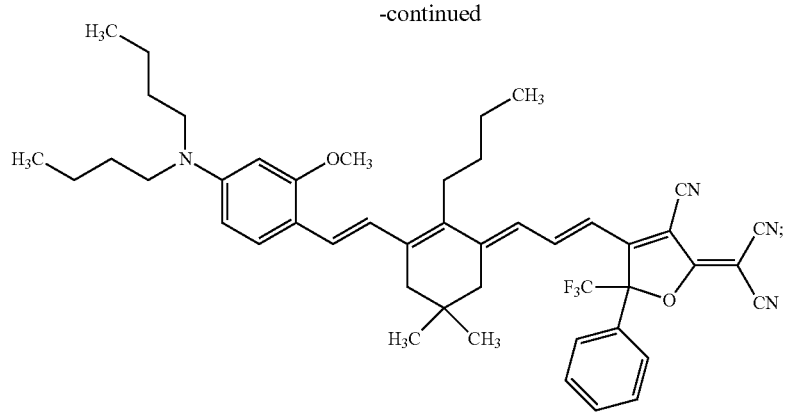
<37> the chromophore according to any of the above <1> to <7>, <11>, <12>, <23>, <24>, <28> to <30>, wherein the chromophore is represented by the formula selected from the group consisting of:
[Formula 50]
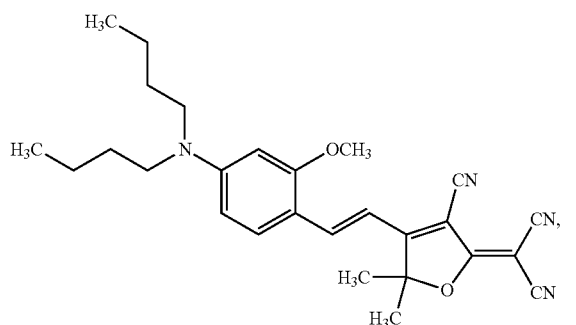
[Formula 51]
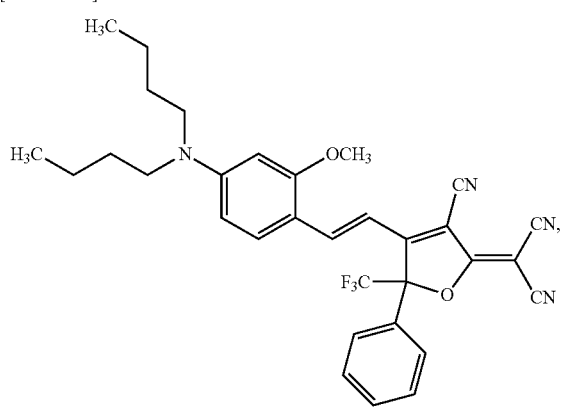
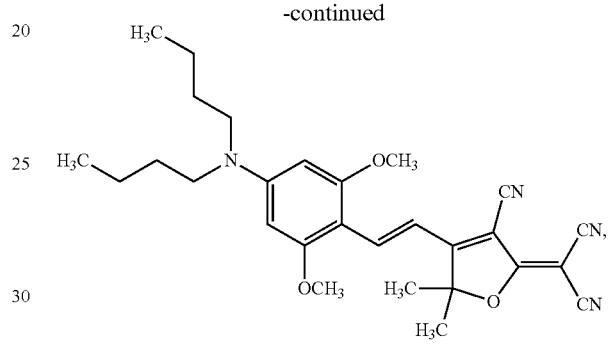

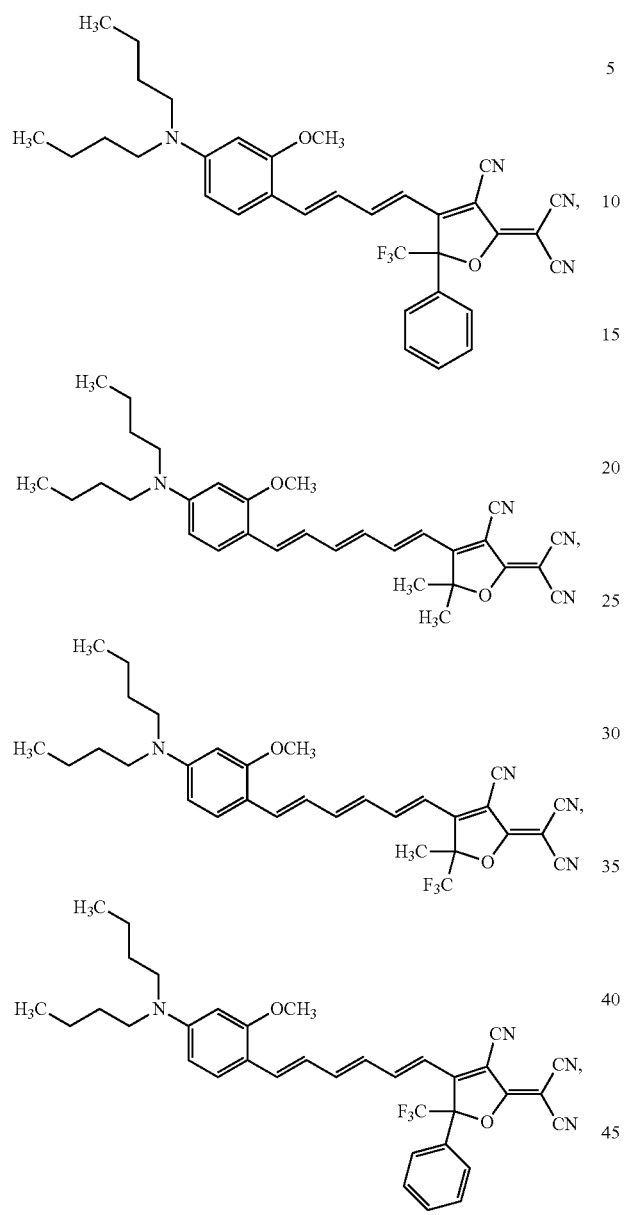
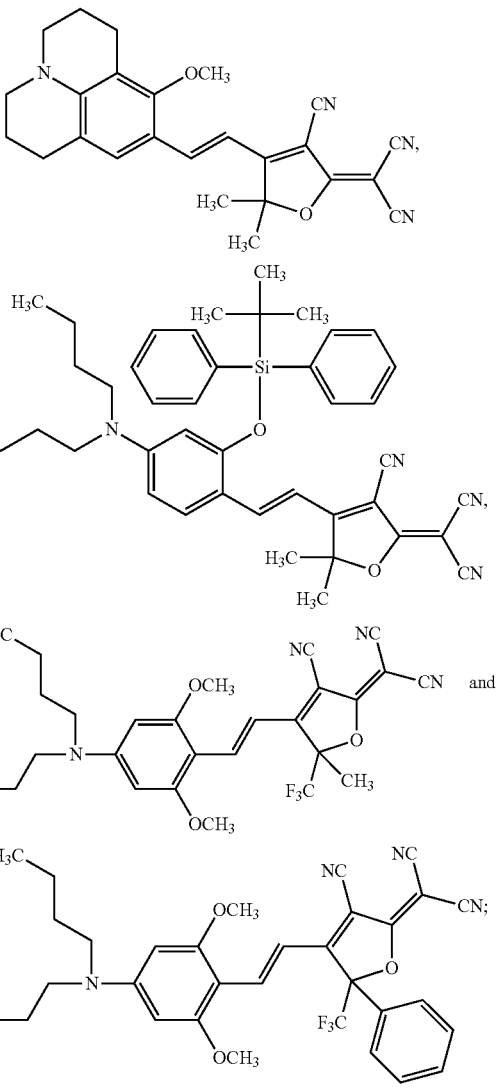
<38> the chromophore according to any of the above <1> to <7>, <11> to <15>, and <28> to <31>, wherein the chromophore is represented by the formula selected from the group consisting of:
[Formula 54]
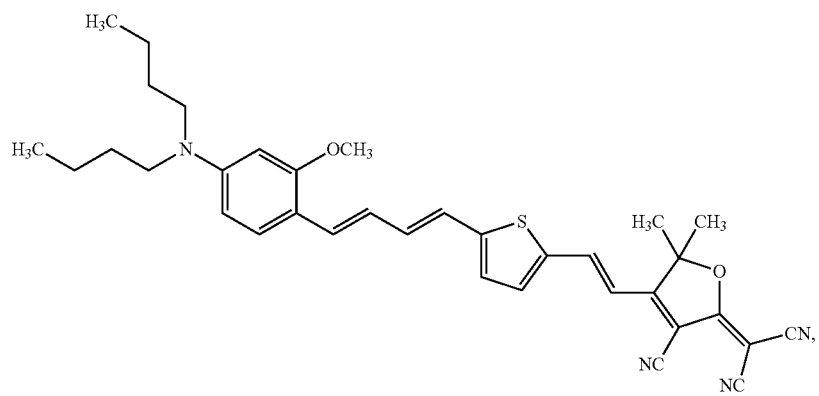

-continued
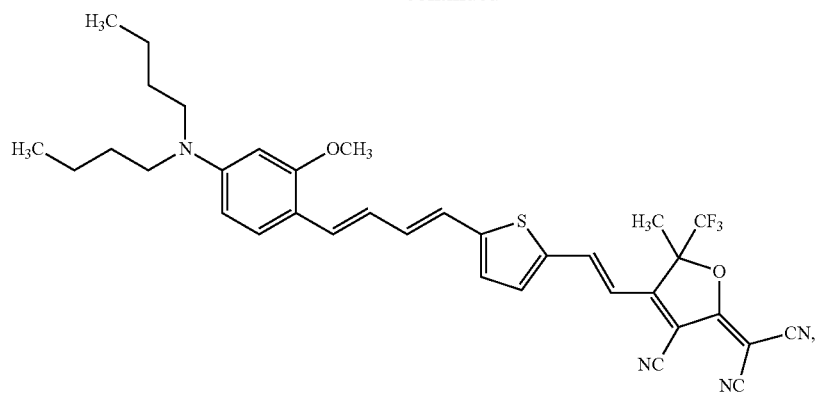
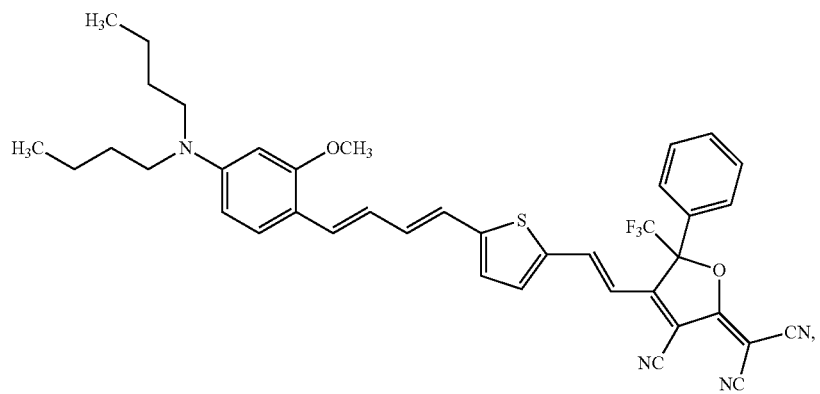
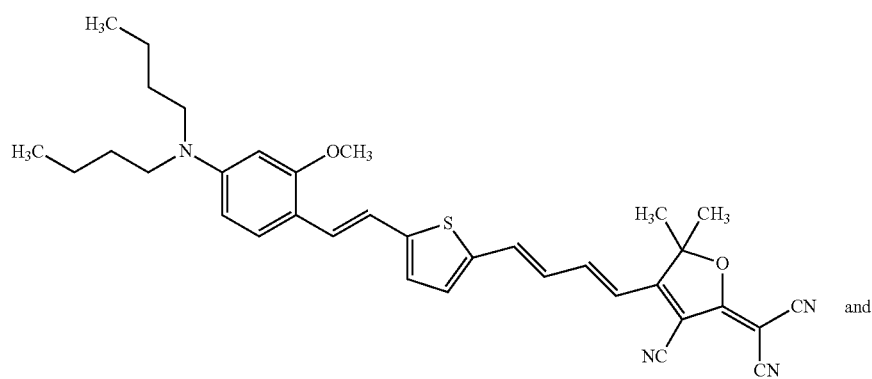
and
[Formula 55]
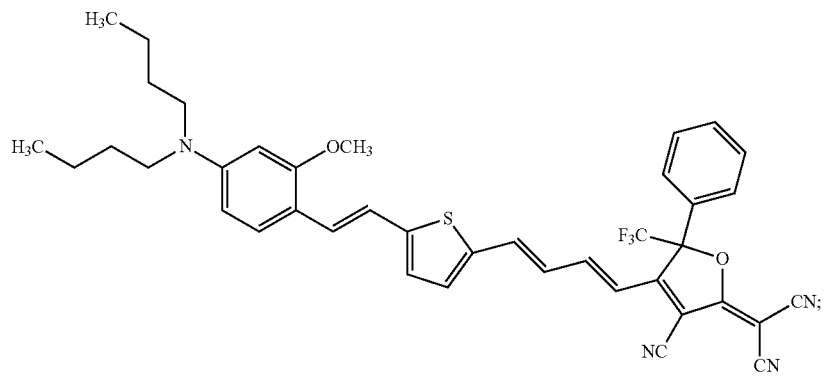

<39> the chromophore according to any of the above <1> to <7>, <11>, <12>, <25>, and <28> to <30>, wherein the chromophore is represented by the following formula:

[Formula 56]

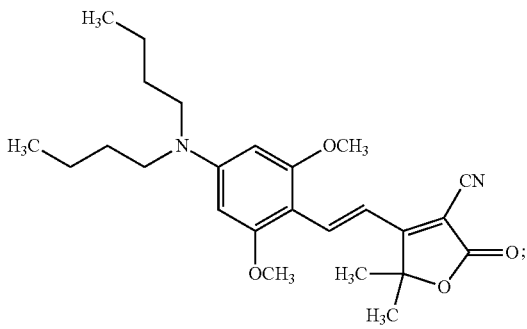

<40> the chromophore according to any of the above <1>, <2>, <4>, <5>, <9> to <12>, <26>, <28>, and <30>, wherein the chromophore is represented by the following formula:

[Formula 57]

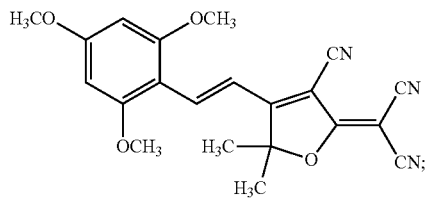

and
<41> the chromophore according to any of the above <1>, <2>, <4>, <5>, <9> to <12>, <27>, <28>, and <30>, wherein the chromophore is represented by the following formula:

[Formula 58]

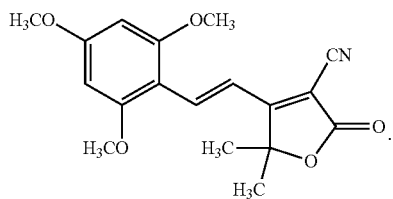

The present invention also relates to:
<42> a nonlinear optical material comprising the chromophore according to any of the above <1> to <41> and a host material in which the chromophore is dispersed; and
<43> the nonlinear optical material according to the above <42>, wherein the host material comprises a resin having a reactive functional group capable of forming a covalent bond with the chromophore, and at least part of the chromophore is attached to the resin.

The present invention further relates to:
<44> a nonlinear optical element having a film formed from the chromophore according to any of the above <1> to <41> or the nonlinear optical material according to the above <42> or <43>;

<45> a nonlinear optical element having an optical waveguide formed from the chromophore according to any of the above <1> to <41> or the nonlinear optical material according to the above <42> or <43>; and
<46> a nonlinear optical element comprising the chromophore according to any of the above <1> to <41>.

Advantageous Effects of Invention

By employing an aryl group substituted with a substituted oxy group in the donor structure D, the nonlinear optical property of the nonlinear optical compound of the present invention is improved without significant deterioration of the heat resistance. A material containing such a nonlinear optical compound exhibiting a larger nonlinear optical effect can give a nonlinear optical element that can change the intensity and phase of light in response to even a weaker external field applied thereto.

When such a nonlinear optical element is used in, for example, an optical modulator utilizing the electrooptic effect, the optical modulator can be driven by lower electric power, which makes possible energy saving and miniaturization. In addition, since the element has a larger nonlinear optical effect, which can change the intensity and phase of light in response to even a weaker electric field applied thereto, the element can be used for an electric field sensor that measures a leaked electric field of an electronic integrated circuit or for a sensor for terahertz electromagnetic waves. Further, the element in combination with an electronic circuit can be used for, for example, optical signal transmission between electronic circuits (See, for example, "Low (Sub-1-Volt) Halfwave Voltage Polymeric Electrooptic Modulators Achieved by Controlling Chromophore Shape." Y. Shi, et al., Science, vol. 288, 119 (2000)).

BRIEF DESCRIPTION OF DRAWING

The FIGURE is a schematic sectional view of an optical waveguide that is an embodiment of the nonlinear optical element of the present invention.

DESCRIPTION OF EMBODIMENTS

The definition of the terms used herein will be given below and the present invention will be explained in more detail.
Donor Structure D The "donor structure D" of the present invention is not particularly limited as long as it contains an aryl group substituted with a substituted oxy group.

The term "substituted oxy group" as used herein refers to a structure in which a hydroxy group (—OH) is substituted with a substituent or the hydrogen atom of a hydroxy group is replaced with a substituent.

The "aryl group" in the above "aryl group substituted with a substituted oxy group" includes a monocyclic aromatic hydrocarbon group (hereinafter referred to as a monocyclic aryl group) and a polycyclic aromatic hydrocarbon group (hereinafter referred to as a polycyclic aryl group).

The "monocyclic aryl group" is, for example, preferably a $C_{5-10}$ ring group, more preferably a $C_{5-7}$ ring group, further preferably a $C_{5-6}$ ring group, most preferably a $C_6$ ring group (namely, a phenyl group). For example, a $C_{5-10}$ ring means that the number of carbon atoms forming the ring is 5 to 10, and the same applies to the other ring groups mentioned above.

The "polycyclic aryl group" includes, for example, a two-ring fused aryl group and a three-ring fused aryl group. The two-ring fused aryl group is, for example, preferably a $C_{8-12}$ ring group and the like, more preferably a $C_{9-10}$ ring group and the like, most preferably a $C_{10}$ ring group (namely, a naphthyl group) and the like.

Examples of the "substituent" in the above "substituted oxy group" include (1) an alkyl group optionally having a substituent, (2) a haloalkyl group optionally having a substituent, (3) an aryl group optionally having a substituent, (4) a heteroaryl group optionally having a substituent, (5) an aralkyl group optionally having a substituent, (6) a silyl group optionally having a substituent, (7) an alkenyl group optionally having a substituent, (8) an alkynyl group optionally having a substituent, (9) an acyl group optionally having a substituent, and (10) an alkenylcarbonyl group optionally having a substituent.

The "alkyl group" in the above "(1) an alkyl group optionally having a substituent" includes a linear or branched $C_{1-20}$ alkyl group. The term "$C_{1-20}$ alkyl group" refers to an alkyl group in which the number of carbon atoms forming the group is 1 to 20, and the same applies to the other groups. Examples of the alkyl group include a methyl group, an ethyl group, an n-propyl group, an isopropyl group, an n-butyl group, an isobutyl group, a sec-butyl group, a tert-butyl group, a pentyl group, an isopentyl group, a hexyl group, an isohexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. Preferred examples of the alkyl group include a $C_{1-6}$ alkyl group. More preferred examples of the alkyl group include a methyl group, an ethyl group, an n-propyl group, an isopropyl group, an n-butyl group, an isobutyl group, a sec-butyl group, a tert-butyl group, a pentyl group, an isopentyl group, a hexyl group, and an isohexyl group.

The "haloalkyl group" in the above "(2) a haloalkyl group optionally having a substituent" includes a linear or branched $C_{1-20}$ alkyl group substituted with at least one halogen atom (for example, a fluorine atom, a chlorine atom, a bromine atom, an iodine atom, or the like) which may be the same as or different from each other. Preferred examples of the haloalkyl group include a halo $C_{1-6}$ alkyl group. More preferred examples of the haloalkyl group include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, a 2-bromoethyl group, a 1-bromopropyl group, a 2-bromopropyl group, a 3-bromopropyl group, and an iodomethyl group.

The "aryl group" in the above "(3) an aryl group optionally having a substituent" includes the same aryl group as the "aryl group" in the above substituted oxyaryl. Examples of the aryl group include a phenyl group and a naphthyl group.

The "heteroaryl group" in the above "(4) an heteroaryl group optionally having a substituent" includes (a) a 5- or 6-membered monocyclic aromatic heterocyclic group containing 1 or more, preferably 1 to 3, the same or different hetero atoms selected from the group consisting of an oxygen atom, a nitrogen atom, and a sulfur atom; (b) a fused-ring aromatic heterocyclic group obtainable by condensation of said monocyclic aromatic heterocyclic group with an aryl group (for example, an aryl group the same as the "aryl group" in the above substituted oxyaryl, or the like); and (c) a fused-ring aromatic heterocyclic group obtainable by condensation of the same or different monocyclic aromatic heterocyclic groups. Examples of the heteroaryl group include a pyrrolyl group, a furyl group, a thienyl group, an imidazolyl group, a pyrazolyl group, a triazolyl group, an isothiazole group, an oxazolyl group, a triazolyl group, a tetrazolyl group, an oxadiazolyl group, a thiadiazole group, a pyridyl group, a pyrazinyl group, a pyrimidinyl group, a pyridazinyl group, a triazinyl group, an indolyl group, a benzofuranyl group, a benzothienyl group, a benzimidazolyl group, a benzoxazolyl group, a benzisoxazolyl group, a benzothiadiazolyl group, a benzisothiadiazolyl group, an indazolyl group, a purinyl group, a quinolyl group, an isoquinolyl group, a phthalazinyl group, a naphthyridinyl group, a quinoxalinyl group, a quinazolyl group, a cinnolinyl group, a pteridinyl group, and a pyrido[3,2-b]pyridyl group.

The "aralkyl group" in the above "(5) an aralkyl group optionally having a substituent" includes an alkyl group substituted with at least one aryl group. Examples of the aryl group include the "aryl group" in the above substituted oxyaryl. Examples of the "alkyl group" include the "alkyl group" in the above "(1) an alkyl group optionally having a substituent". Examples of the aralkyl group include a benzyl group, a 1-phenylethyl group, a phenethyl group, a 1-naphthylmethyl group, a 2-naphthylmethyl group, a 1-naphthylethyl group, and a 2-naphthylethyl group.

The "alkenyl group" in the above "(7) an alkenyl group optionally having a substituent" includes a linear or branched $C_{2-20}$ alkenyl group. Preferred examples of the "alkenyl group" include a $C_{2-6}$ alkenyl group. More preferred examples of the alkenyl group include an ethenyl group, a 1-propenyl group, a 2-propenyl group, a 1-methylethenyl group, a 1-butenyl group, a 2-butenyl group, a 3-butenyl group, a 1-methyl-1-propenyl group, a 1-methyl-2-propenyl group, a 2-methyl-1-propenyl group, and a 2-methyl-2-propenyl group.

The "alkynyl group" in the above "(8) an alkynyl group optionally having a substituent" includes a linear or branched $C_{3-20}$ alkynyl group. Preferred examples of the alkynyl group include a $C_{3-6}$ alkynyl group. More preferred examples of the alkynyl group include a 2-propynyl group, a 1-methyl-2-propynyl group, a 1,1-dimethyl-2-propynyl group, a 2-butynyl group, a 3-butynyl group, a 1-pentynyl group, a 2-pentynyl group, a 3-pentynyl group, and a 4-pentynyl group.

The "acyl group" in the above "(9) an acyl group optionally having a substituent" includes a linear or branched $C_{1-20}$ acyl group. Preferred examples of the "acyl group" include a $C_{1-6}$ acyl group. More preferred examples of the "acyl group" include a formyl group, an acetyl group, a propionyl group, a butyryl group, an isobutyryl group, a valeryl group, an isovaleryl group, and a pivaloyl group.

The "alkenyl" in the above "(10) an alkenylcarbonyl group optionally having a substituent" include, for example, the "alkenyl group" in the above "(7) an alkenyl group optionally having a substituent".

The "substituent" in the above "(1) an alkyl group optionally having a substituent", "(2) a haloalkyl group optionally having a substituent", "(3) an aryl group optionally having a substituent", "(4) a heteroaryl group optionally having a substituent", "(5) an aralkyl group optionally having a substituent", "(6) a silyl group optionally having a substituent", "(7) an alkenyl group optionally having a substituent", "(8) an alkynyl group optionally having a substituent", "(9) an acyl group optionally having a substituent", and "(10) an alkenylcarbonyl group optionally having a substituent" is not particularly limited and examples of the substituent include an alkyl group, a haloalkyl group, an aryl group, an alkenyl group, an alkynyl group, an alkoxy group, a hydroxy group, an oxiranyl group, a mercapto group, an amino group, a carbamoyl group, a sulfamoyl group, a carboxy group, an alkoxycarbonyl group, a sulfo group, a sulfino group, a phosphono group, a nitro group, a cyano group, an amidino group, an imino group, a dihydroborono group, a halogen atom (a fluorine atom, a chlorine atom, a bromine atom, an iodine atom, or the like), a sulfinyl group, a sulfonyl group, an acyl group, an oxo group, and a thioxo group. The "substituent" may be one substituent or two or more substituents which may be the same as or different from each other.

The "alkyl group", the "haloalkyl group", the "aryl group", the "alkenyl group", the "alkynyl group", and the "acyl group" as the above "substituent" are, for example, the "alkyl group" in the above "(1) an alkyl group optionally having a substituent", the "haloalkyl group" in the above "(2) a haloalkyl group optionally having a substituent", the "aryl group" in the above "(3) an aryl group optionally having a substituent", the "alkenyl group" in the above "(7) an alkenyl group optionally having a substituent", the "alkynyl group" in the above "(8) an alkynyl group optionally having a substituent", and the "acyl group" in the above "(9) an acyl group optionally having a substituent", respectively.

Preferred examples of the "substituted oxy group" in the present invention include (a) an alkoxy group optionally having a substituent, (b) an aryloxy group optionally having a substituent, (c) an aralkyloxy group optionally having a substituent, (d) a silyloxy group optionally having a substituent, (e) an alkenyloxy group optionally having a substituent, (f) an alkenylcarbonyloxy group optionally having a substituent, (g) an alkynyloxy group optionally having a substituent, and (h) a hydroxy group.

The "alkoxy group" in the above "(a) an alkoxy group optionally having a substituent" includes, for example, a linear or branched $C_{1-20}$ alkoxy group. Preferred examples of the alkoxy group include a $C_{1-6}$ alkoxy group. More preferred examples of the alkoxy group include a methoxy group, an ethoxy group, a propoxy group, an isopropoxy group, a butoxy group, an isobutoxy group, a sec-butoxy group, and a tert-butoxy group.

The "aryloxy group" in the above "(b) an aryloxy group optionally having a substituent" includes, for example, a $C_{5-10}$ monocyclic aryloxy group and a $C_{8-12}$ bicyclic aryloxy group. Preferred examples of the aryloxy group include a phenoxy group and a naphthyloxy group, and more preferred examples thereof include a phenoxy group.

The "aralkyloxy group" in the above "(c) an aralkyloxy group optionally having a substituent" includes, for example, a group in which an oxy group is attached to the "aralkyl group" in the above "(5) an aralkyl group optionally having a substituent". Preferred examples of the aralkyloxy group include a benzyloxy group, a phenethyloxy group, 1-naphthylmethoxy group, and 2-naphthylmethoxy group. More preferred examples thereof include a benzyloxy group.

The above "(d) a silyloxy group optionally having a substituent" is preferably, for example, a tert-butyldiphenylsiloxy group and a tert-butyldimethylsiloxy group.

The "alkenyloxy group" in the above "(e) an alkenyloxy group optionally having a substituent" includes, for example, a linear or branched $C_{2-20}$ alkenyloxy group. Preferred examples of the alkenyloxy group include a $C_{2-6}$ alkenyloxy group. More preferred examples of the alkenyloxy group include an ethenyloxy group, a 1-propenyloxy group, a 2-propenyloxy group, a 1-methylethenyloxy group, a 1-butenyloxy group, a 2-butenyloxy group, a 3-butenyloxy group, a 1-methyl-1-propenyloxy group, a 1-methyl-2-propenyloxy group, a 2-methyl-1-propenyloxy group, and a 2-methyl-2-propenyloxy group.

The "alkenylcarbonyloxy group" in the above "(f) an alkenylcarbonyloxy group optionally having a substituent" includes, for example, a linear or branched $C_{2-20}$ alkenylcarbonyloxy group. Preferred examples of the alkenylcarbonyloxy group include a $C_{2-6}$ alkenylcarbonyloxy group. More preferred examples of the alkenylcarbonyloxy group include an ethenylcarbonyloxy group, a 1-propenylcarbonyloxy group, a 2-propenylcarbonyloxy group, a 1-methylethenylcarbonyloxy group, a 1-butenylcarbonyloxy group, a 2-butenylcarbonyloxy group, a 3-butenylcarbonyloxy group, a 1-methyl-1-propenylcarbonyloxy group, a 1-methyl-2-propenylcarbonyloxy group, a 2-methyl-1-propenylcarbonyloxy group, and a 2-methyl-2-propenylcarbonyloxy group.

The "alkynyloxy group" in the above "(g) an alkynyloxy group optionally having a substituent" includes, for example, a linear or branched $C_{2-20}$ alkynyloxy group. Preferred examples of the alkynyloxy group include a $C_{3-6}$ alkynyloxy group. More preferred examples of the alkynyloxy group include a 2-propynyloxy group, a 1-methyl-2-propynyloxy group, a 1,1-dimethyl-2-propynyloxy group, a 2-butynyloxy group, a 3-butynyloxy group, a 1-pentynyloxy group, a 2-pentynyloxy group, a 3-pentynyloxy group, and a 4-pentynyloxy group.

Examples of the "substituent" in the above (a) an alkoxy group optionally having a substituent, (b) an aryloxy group optionally having a substituent, (c) an aralkyloxy group optionally having a substituent, (d) a silyloxy group optionally having a substituent, (e) an alkenyloxy group optionally having a substituent, (f) an alkenylcarbonyloxy group optionally having a substituent, and (g) an alkynyloxy group optionally having a substituent include the "substituent" in the above "(1) an alkyl group optionally having a substituent", "(2) a haloalkyl group optionally having a substituent", "(3) an aryl group optionally having a substituent", "(4) a heteroaryl group optionally having a substituent", "(5) an aralkyl group optionally having a substituent", "(6) a silyl group optionally having a substituent", "(7) an alkenyl group optionally having a substituent", "(8) an alkynyl group optionally having a substituent", "(9) an acyl group optionally having a substituent", and "(10) an alkenylcarbonyl group optionally having a substituent".

Further preferred examples of the "substituted oxy group" of the present invention include a methoxy group, an oxiranylmethoxy group, an isopropoxy group, a hydroxybutoxy group, a 3-bromo-2-hydroxypropoxy group, a benzyloxy group, a methoxybenzyloxy group, a tert-butyldiphenylsiloxy group, a tert-butyldimethylsiloxy group, a 2-methyl-2-propoxy group, a 1-methylethenylcarbonyloxy group, and a hydroxy group.

In the donor structure D of the chromophore of the present invention, the substituted oxy group may be attached to any of the ortho-, meta-, and para-carbon atoms of the aryl group, and the same or different substituted oxy groups may be attached to the ortho-, meta-, or/and para-carbon atoms of the aryl group. For example, preferred embodiment is that at least one substituted oxy group is attached to an ortho-carbon atom of the aryl group, and more preferred embodiment is that the substituted oxy group is attached to an ortho-carbon atom of the aryl group or to two or more of the ortho- and para-carbon atoms of the aryl group.

In the chromophore of the present invention, the substituted oxy group in the donor structure D may form, together with the aryl carbon atom to which the substituted oxy group is attached and with a carbon atom which is adjacent to said carbon atom, a heterocyclic ring containing an oxygen atom as a hetero atom. The heterocyclic ring may have a substituent. The heterocyclic ring includes, for example, a 5- to 7-membered heterocyclic ring and may be an aliphatic ring or an aromatic ring.

Preferably, in the chromophore of the present invention, the aryl group in the donor structure D is further substituted with an amino group optionally having a substituent.

Examples of the "substituent" in the above "amino group optionally having a substituent" include (α) an alkyl group, (β) a haloalkyl group, (γ) a hydroxyalkyl group, (δ) an acyloxyalkyl group, (ε) a silyloxyalkyl group, (ζ) an aminoalkyl group, and (η) an aryl group. The mode of substitution in the amino group with the substituent may be mono-substitution or di-substitution, but preferred is di-substitution.

Examples of the "(α) alkyl group" as the "substituent" in the above "amino group optionally having a substituent" include the "alkyl group" in the above "(1) an alkyl group optionally having a substituent". Preferred examples of the (α) alkyl group include a $C_{1-6}$ alkyl group, and more preferred examples thereof include a methyl group, an ethyl group, a propyl group, an isopropyl group, a butyl group, an isobutyl group, a sec-butyl group, and a tert-butyl group.

Examples of the "(β) haloalkyl group" as the "substituent" in the above "amino group optionally having a substituent" include the "haloalkyl group" in the above "(2) a haloalkyl group optionally having a substituent".

Examples of the "(γ) hydroxyalkyl group" as the "substituent" in the above "amino group optionally having a substituent" include a linear or branched $C_{1-20}$ alkyl group substituted with at least one hydroxy group. Examples of the hydroxyalkyl group include a hydroxy $C_{1-6}$ alkyl group such as a hydroxymethyl group, a hydroxyethyl group, a hydroxypropyl group, and a hydroxybutyl group.

Examples of the "(δ) acyloxyalkyl group" as the "substituent" in the above "amino group optionally having a substituent" include a linear or branched $C_{1-20}$ alkyl group substituted with at least one acyloxy group which may be the same as or different from each other.

Examples of the "(ε) silyloxyalkyl group" as the "substituent" in the above "amino group optionally having a substituent" include a linear or branched $C_{1-20}$ alkyl group substituted with at least one silyloxy group.

Examples of the "(ζ) aminoalkyl group" as the "substituent" in the above "amino group optionally having a substituent" include a linear or branched $C_{1-20}$ alkyl group substituted with at least one amino group.

Examples of the "(η) aryl group" as the "substituent" in the above "amino group optionally having a substituent" include the "aryl group" in the above substituted oxyaryl, and preferred examples of the (η) aryl group include a phenyl group and a naphthyl group.

When the above amino group has a substituent, the substituent may form, together with the nitrogen atom to which the substituent is attached, a heterocyclic ring containing the nitrogen atom as a hetero atom. The heterocyclic ring may have a substituent. The heterocyclic ring includes, for example, a 5- to 7-membered heterocyclic ring and may be an aliphatic ring or an aromatic ring.

When the above amino group has a substituent, the amino group also may form, together with the aryl carbon atom to which the amino group is attached, a heterocyclic ring containing the nitrogen atom as a hetero atom. The heterocyclic ring may have a substituent. The heterocyclic ring includes, for example, a 5- to 7-membered heterocyclic ring and may be an aliphatic ring or an aromatic ring. When the amino group is di-substituted, each substituent may form a heterocyclic ring containing the nitrogen atom as a hetero atom.

Preferred donor structure D in the chromophore of the present invention will be illustrated below.

A preferred specific embodiment of the donor structure D is, for example, a structure represented by the formula D-1:

[Formula 59]

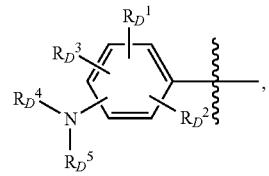

(D-1)

wherein at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a saturated heterocyclic ring optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent.

The phrase "at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group" as used herein means that (1) any one of $R_D^1$, $R_D^2$, and $R_D^3$ represents an alkoxy group, an aryloxy group, an aralkyloxy group, a silyloxy group, an alkenyloxy group, an alkenylcarbonyloxy group, an alkynyloxy group, or a hydroxy group; (2) two of $R_D^1$, $R_D^2$, and $R_D^3$ independently represent an alkoxy group, an aryloxy group, an aralkyloxy group, a silyloxy group, an alkenyloxy group, an alkenylcarbonyloxy group, an alkynyloxy group, or a hydroxy group; or (3) all of $R_D^1$, $R_D^2$, and $R_D^3$ independently represent an alkoxy group, an aryloxy group, an aralkyloxy group, a silyloxy group, an alkenyloxy group, an alkenylcarbonyloxy group, an alkynyloxy group, or a hydroxy group.

The phrase "the rest independently represent a hydrogen atom or an alkyl group" means that $R_D^1$, $R_D^2$, or/and $R_D^3$ not representing an alkoxy group, an aryloxy group, an aralkyloxy group, a silyloxy group, an alkenyloxy group, an alkenylcarbonyloxy group, an alkynyloxy group, or a hydroxy group independently represent a hydrogen atom or an alkyl group.

In the present invention, the "alkoxy group", "aryloxy group", "aralkyloxy group", "silyloxy group", "alkenyloxy group", "alkenylcarbonyloxy group", and "alkynyloxy group" that $R_D^1$, $R_D^2$ and $R_D^3$ represent are, for example, the "alkoxy group" in the above "(a) an alkoxy group optionally having a substituent", the "aryloxy group" in the above "(b) an aryloxy group optionally having a substituent", the "aralkyloxy group" in the above "(c) an aralkyloxy group optionally having a substituent", the "silyloxy group" in the above "(d) a silyloxy group optionally having a substituent", the "alkenyloxy group" in the above "(e) an alkenyloxy group optionally having a substituent", the "alkenylcarbonyloxy group" in the above "(f) an alkenylcarbonyloxy group optionally having a substituent", and the "alkynyloxy group" in the above "(g) an alkynyloxy group optionally having a substituent", respectively, as the above "substituted oxy group".

The "alkyl group" that $R_D^1$, $R_D^2$, and $R_D^3$ represent in the present invention includes, for example, the "alkyl group" in the above "(1) an alkyl group optionally having a substituent".

The phrase "$R_D^1$, $R_D^2$, and $R_D^3$ each may have the same or different substituents" as used herein means that $R_D^1$, $R_D^2$, and $R_D^3$ may be independently substituted with one or more substituents which may be the same as or different from each other. Examples of the substituent include the "substituent" in the above "(1) an alkyl group optionally having a substituent", "(2) a haloalkyl group optionally having a substituent", "(3) an aryl group optionally having a substituent", "(4) a heteroaryl group optionally having a substituent", "(5) an aralkyl group optionally having a substituent", "(6) a silyl group optionally having a substituent", "(7) an alkenyl group optionally having a substituent", "(8) an alkynyl group optionally having a substituent", "(9) an acyl group optionally having a substituent", and "(10) an alkenylcarbonyl group optionally having a substituent".

In the present invention, when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent. In this case, $R_D^1$ represents an alkoxy group optionally having a substituent, an aryloxy group optionally having a substituent, an aralkyloxy group optionally having a substituent, a silyloxy group optionally having a substituent, an alkenyloxy group optionally having a substituent, an alkenylcarbonyloxy group optionally having a substituent, an alkynyloxy group optionally having a substituent, or a hydroxy group. The ring that is formed by $R_D^2$ and $R_D^3$ together with the two adjacent carbon atoms and optionally has a substituent may be an aliphatic or aromatic carbocyclic ring, and may be an aliphatic or aromatic heterocyclic ring. For example, the donor structure D represented by the following formula:

[Formula 60]

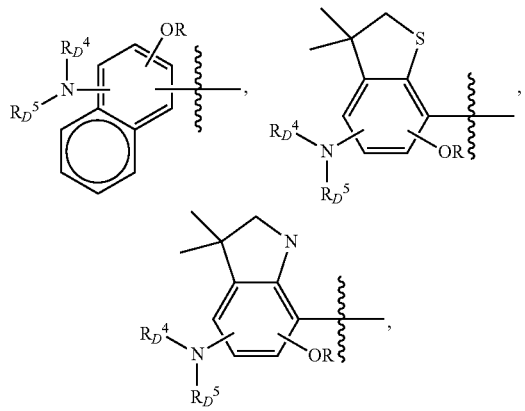

or the like
(wherein
R represents an alkyl group, an aryl group, an aralkyl group, a silyl group, an alkenyl group, an alkenylcarbonyl group, an alkynyl group, or a hydrogen atom, and R may have a substituent; and
$R_D^4$ and $R_D^5$ have the same meanings as defined for the above formula D-1)
is within the scope of the present invention.

In the present invention, when $R_D^2$ and $R_D^3$ are each attached to adjacent carbon atoms of the aryl of the donor structure D, $R_D^2$ and $R_D^3$ may form, together with the two adjacent carbon atoms, a heterocyclic ring containing an oxygen atom as a hetero atom. For example, the donor structure D represented by the following formula:

[Formula 61]

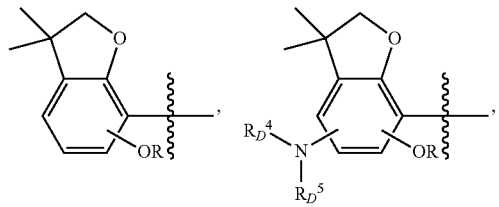

or the like
(wherein
R represents an alkyl group, an aryl group, an aralkyl group, a silyl group, an alkenyl group, an alkenylcarbonyl group, an alkynyl group, or a hydrogen atom, and R may have a substituent; and
$R_D^4$ and $R_D^5$ have the same meanings as defined for the above formula D-1)
is within the scope of the present invention.

The "alkyl group", "haloalkyl group", "hydroxyalkyl group", "acyloxyalkyl group", "silyloxyalkyl group", "aminoalkyl group", or "aryl group" that $R_D^4$ and $R_D^5$ represent are, for example, the (α) alkyl group, the (β) haloalkyl group, the (γ) hydroxyalkyl group, the (δ) acyloxyalkyl group, the (ε) silyloxyalkyl group, the (ζ) aminoalkyl group, and (η) the aryl group in the above "amino group optionally having a substituent", respectively.

In the present invention, $R_D^4$ and $R_D^5$ may form, together with the nitrogen atom to which they are attached, a heterocyclic ring optionally having a substituent. The heterocyclic ring may have a substituent. The heterocyclic ring includes, for example, a 5- to 7-membered heterocyclic ring and may be an aliphatic ring or an aromatic ring.

In the present invention, (a) $R_D^2$ and $-NR_D^4R_D^5$ and (b) $R_D^3$ and $-NR_D^4R_D^5$ may independently form, together with the carbon atoms to which they are attached, a heterocyclic ring containing the nitrogen atom as a hetero atom. The heterocyclic ring may have a substituent. The heterocyclic ring includes, for example, a 5- to 7-membered heterocyclic ring and may be an aliphatic ring or an aromatic ring. For example, the donor structure D represented by the following formula:

[Formula 62]

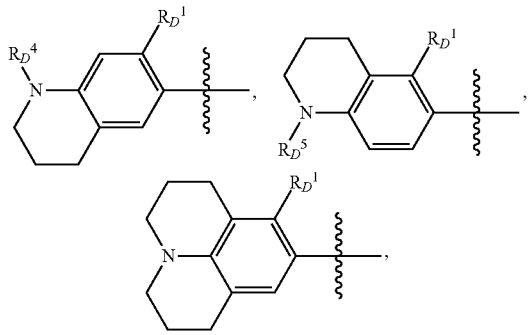

or the like
(wherein
$R_D^1$, $R_D^4$, and $R_D^5$ have the same meanings as defined for the above formula D-1)
is within the scope of the present invention.

A more preferred specific embodiment of the donor structure D is, for example, a structure represented by the formula D-1-1:

[Formula 63]

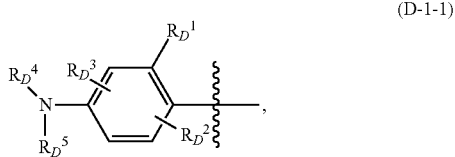

(D-1-1)

wherein
$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;
$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents
(when $R_D^2$ and $R_D^3$ are each attached to adjacent carbon atoms of the aryl of the donor structure D,
$R_D^2$ and $R_D^3$ may form, together with the two adjacent carbon atoms, a ring optionally having a substituent); and
$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a saturated heterocyclic ring optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent.

Another more preferred specific embodiment of the donor structure D is, for example, a structure represented by the formula D-1-2:

[Formula 64]

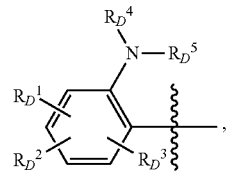

(D-1-2)

wherein
at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents
(when $R_D^2$ and $R_D^3$ are each attached to adjacent carbon atoms of the aryl of the donor structure D,
(1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or
(2) $R_D^2$ and $R_D^3$ may form, together with the two adjacent carbon atoms, a heterocyclic ring containing an oxygen atom as a hetero atom and optionally having a substituent); and $R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a saturated heterocyclic ring optionally having a substituent, or $R_D^4$ and $R_D^5$ form, together with the nitrogen atom to which they are attached, with the aryl carbon atom to which said nitrogen atom is attached, and with the aryl carbon atom which is adjacent to said carbon atom, a heterocyclic ring containing the nitrogen atom as a hetero atom and optionally having a substituent.

In the present invention, when "$R_D^4$ and $R_D^5$ form, together with the nitrogen atom to which they are attached, with the aryl carbon atom to which said nitrogen atom is attached, and with the aryl carbon atom which is adjacent to said carbon atom, a heterocyclic ring containing the nitrogen atom as a hetero atom and optionally having a substituent", the donor structure D may be, for example, a structure represented by the following formula:

[Formula 65]

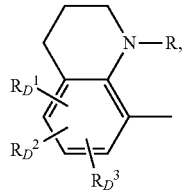

wherein $R_D^1$, $R_D^2$, and $R_D^3$ have the same meanings as defined for the above formula D-1-2; and R represents a substituent.

Another preferred specific embodiment of the donor structure D is, for example, a structure represented by the formula D-2:

[Formula 66]

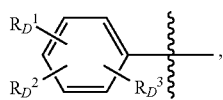
(D-2)

wherein at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent).

A more preferred specific embodiment of the donor structure D is, for example, a structure represented by the formula D-2-1:

[Formula 67]

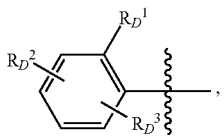
(D-2-1)

wherein $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent; and $R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent).

In the above preferred specific embodiments of the donor structure D, a further preferred embodiment is that, for example, at least one of $R_D^1$, $R_D^2$, and $R_D^3$ represents a $C_{1-6}$ alkoxy group (for example, a methoxy group, an ethoxy group, a propoxy group, an isopropoxy group, a butoxy group, or the like), a benzyloxy group, a tert-butyldiphenylsiloxy group, a tert-butyldimethylsiloxy group, or a $C_{2-6}$ alkenyloxy group (for example, a 2-methyl-2-propenyl group, or the like); the rest represent a hydrogen atom; and $R_D^1$, $R_D^2$, and $R_D^3$ each may have the same or different substituents (for example, a methoxy group, a hydroxy group, an oxiranyl group, a bromine atom, or the like).

In the above preferred specific embodiments of the donor structure D, another further preferred embodiment is that, for example, $R_D^4$ and $R_D^5$ each independently represent an alkyl group (for example, a $C_{1-6}$ alkyl group such as a methyl group, an ethyl group, a propyl group, a butyl group, or the like), a hydroxyalkyl group (for example, a hydroxy $C_{1-6}$ alkyl group such as a hydroxymethyl group, a hydroxyethyl group, a hydroxypropyl group, a hydroxybutyl group, or the like), or a silyloxyalkyl group, and $R_D^4$ and $R_D^5$ each may have the same or different substituents.

Acceptor Structure A

The acceptor structure A of the present invention is not particularly limited as long as it is an electron acceptor group that is free of —$SO_2$—.

Preferred specific embodiments of the acceptor structure A include, for example, structures represented by the following formulae:

[Formula 68]

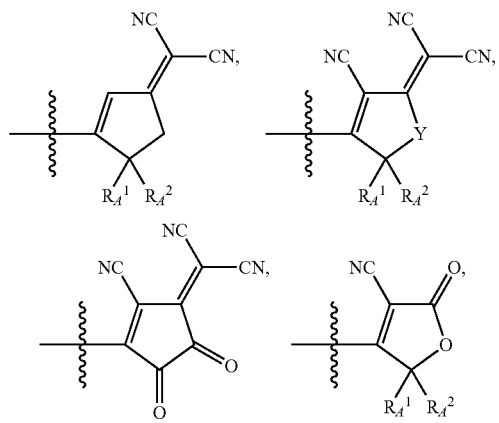

-continued

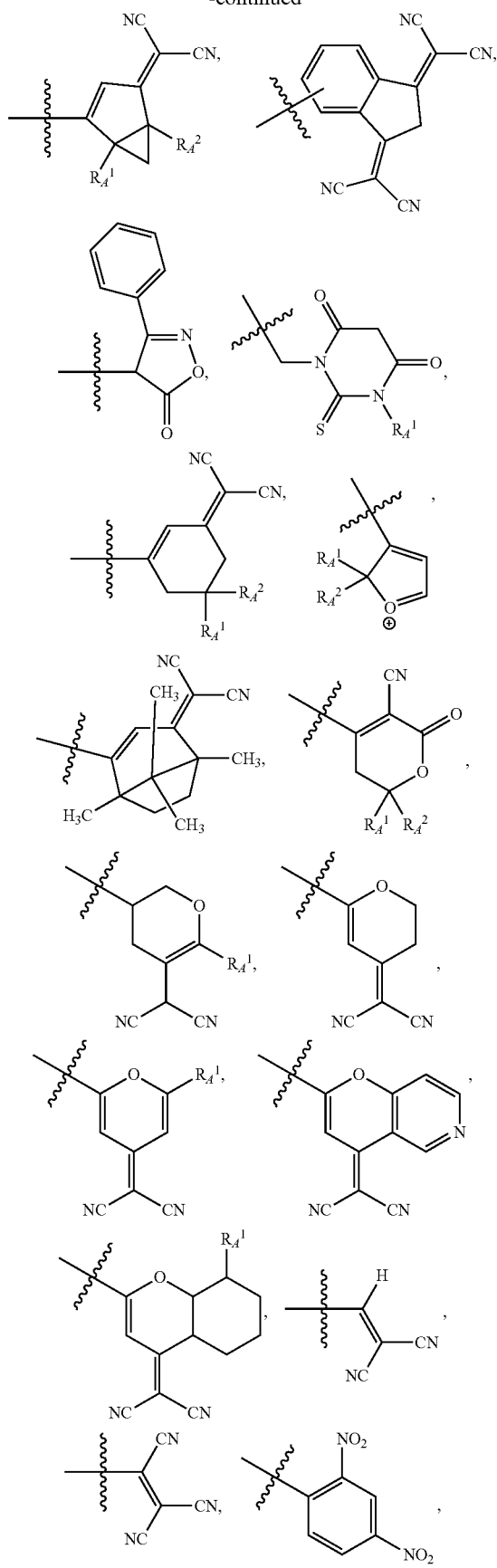

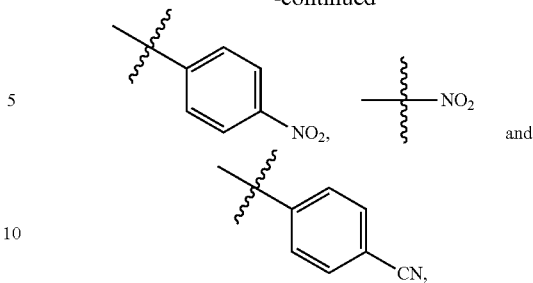

wherein

Y represents —CR$_A^1$R$_A^2$—, —O—, —S—, —SO—, —SiR$_A^1$R$_A^2$—, —NR— (wherein R represents a hydrogen atom or an alkyl group) or —C(═CH$_2$)—; and R$_A^1$ and R$_A^2$ independently represent a hydrogen atom, an alkyl group, an alkenyl group, a cycloalkyl group, a cycloalkenyl group, an alkoxy group, a haloalkyl group, or an aryl group, and R$_A^1$ and R$_A^2$ each may have the same or different substituents, or R$_A^1$ and R$_A^2$ form, together with the carbon atom to which they are attached, a structure that may have a substituent and is represented by the following formula:

[Formula 69]

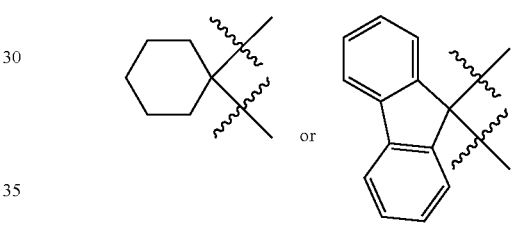

The "alkyl group" that R$_A^1$ and R$_A^2$ represent includes, for example, the "alkyl group" in the above "(1) an alkyl group optionally having a substituent". Preferred examples of the alkyl group include a methyl group and an isopropyl group.

The "alkenyl group" that R$_A^1$ and R$_A^2$ represent includes, for example, the "alkenyl group" in the above "(7) an alkenyl group optionally having a substituent".

The "cycloalkyl group" that R$_A^1$ and R$_A^2$ represent includes, for example, a C$_{3-15}$ monocyclic or polycyclic saturated aliphatic ring group. Examples of the cycloalkyl group include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group, and preferred examples thereof include a cyclohexyl group.

The "cycloalkenyl group" that R$_A^1$ and R$_A^2$ represent includes, for example, a C$_{3-15}$ monocyclic or polycyclic unsaturated aliphatic ring group. Examples of the cycloalkenyl group include a cyclopropenyl group, a cyclopentenyl group, a cyclohexenyl group, a cycloheptynyl group, a cyclooctenyl group, a cyclopentadienyl group, a cyclohexadienyl group, a cycloheptadienyl group, and a cyclooctadienyl group.

The "alkoxy group" that R$_A^1$ and R$_A^2$ represent includes, for example, the "alkoxy group" in the above "(a) an alkoxy group optionally having a substituent". Examples of the alkoxy group include a methoxy group, an ethoxy group, a propoxy group, an isopropoxy group, a butoxy group, an isobutoxy group, a sec-butoxy group, and a tert-butoxy group.

The "haloalkyl group" that $R_A^1$ and $R_A^2$ represent includes, for example, the "haloalkyl group" in the above "(2) a haloalkyl group optionally having a substituent". Examples of the haloalkyl group include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group, and more preferred examples thereof include a trifluoromethyl group.

The "aryl group" that $R_A^1$ and $R_A^2$ represent includes, for example, a phenyl group and a naphthyl group, and preferred examples thereof include a phenyl group.

Other preferred specific embodiments of the acceptor structure A include, for example, structures represented by the following formulae:

[Formula 70]

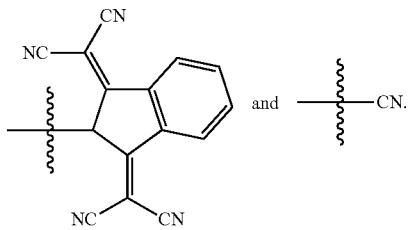

and

More preferred specific embodiments of the acceptor structure A include, for example,
a structure represented by the formula A-a:

[Formula 71]

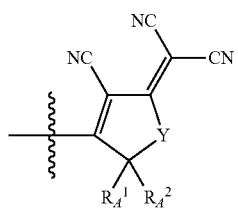

(A-a)

(wherein
Y represents —$CR_A^1R_A^2$—, —O—, —S—, —SO—, —$SiR_A^1R_A^2$—, —NR— (wherein R represents a hydrogen atom or an alkyl group), or —C(=$CH_2$)—; and
$R_A^1$ and $R_A^2$ independently represent a hydrogen atom, an alkyl group, an alkenyl group, a cycloalkyl group, a cycloalkenyl group, an alkoxy group, a haloalkyl group, or an aryl group, and $R_A^1$ and $R_A^2$ each may have the same or different substituents); and
a structure represented by the formula A-b:

[Formula 72]

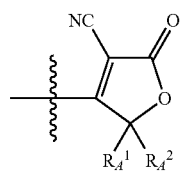

(A-b)

(wherein
$R_A^1$ and $R_A^2$ independently represent a hydrogen atom, an alkyl group, an alkenyl group, a cycloalkyl group, a cycloalkenyl group, an alkoxy group, a haloalkyl group, or an aryl group, and $R_A^1$ and $R_A^2$ each may have the same or different substituents).

Further preferred specific embodiments of the acceptor structure A include, for example,
a structure represented by the formula A-a-1:

[Formula 73]

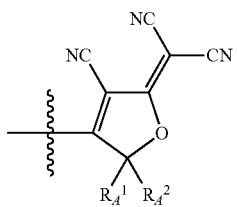

(A-a-1)

wherein
$R_A^1$ and $R_A^2$ independently represent a hydrogen atom, an alkyl group, a haloalkyl group, or an aryl group, and $R_A^1$ and $R_A^2$ each may have the same or different substituents.

In the above specific embodiments of the acceptor structure A of the chromophore of the present invention, $R_A^1$ and $R_A^2$ may form, together with the carbon atom to which they are attached, a structure that may have a substituent and is represented by the following formula:

[Formula 74]

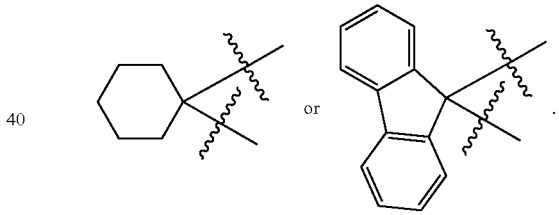

or

That is, the acceptor structure A of the chromophore of the present invention also includes, for example, a structure represented by the following formula:

[Formula 75]

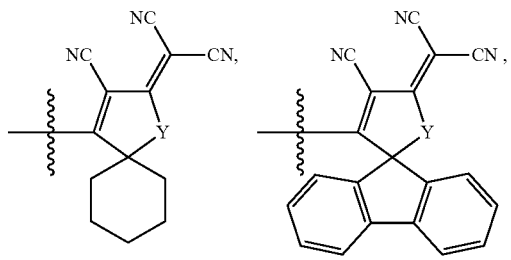

or the like,
wherein
Y represents —$CR_A^1R_A^2$—, —O—, —S—, —SO—, —$SiR_A^1R_A^2$—, —NR— (wherein R represents a hydrogen atom or an alkyl group), or —C(=$CH_2$)—.

π-Conjugated Bridge Structure B

The π-conjugated bridge structure B of the present invention is not particularly limited as long as it has a conjugated system having a conjugated multiple bond and π-electrons are delocalized from the donor structure D to the acceptor structure A through the electron orbitals of the bridge (cross-link).

The conjugated multiple bond in the π-conjugated bridge structure B may be either of a double bond or a triple bond, and preferred is a double bond. Examples of the π-conjugation include a carbon-carbon conjugation and a conjugation involving nitrogen. A preferred conjugation in the chromophore of the present invention is a carbon-carbon conjugation or the like.

Preferred embodiments of the π-conjugated bridge structure B include, for example, structures represented by the following formulae:

[Formula 76]

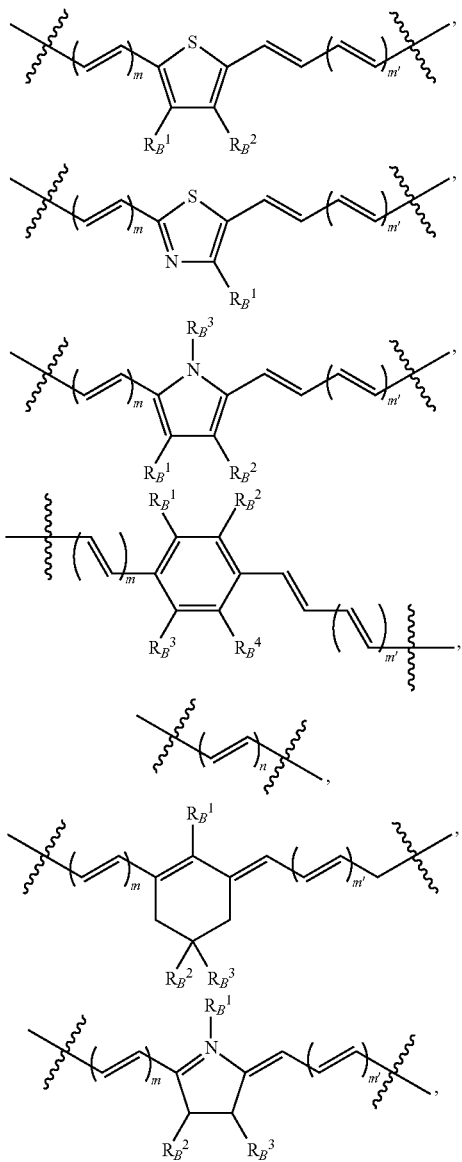

[Formula 77]

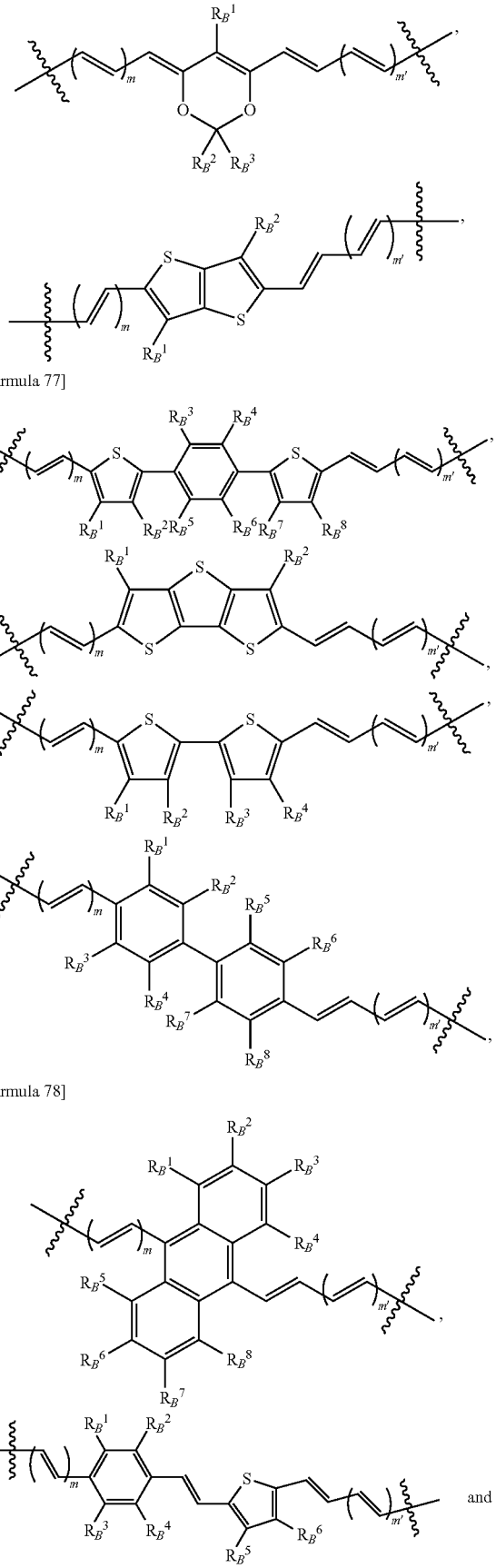

[Formula 78]

and

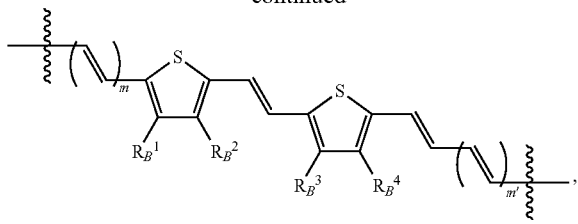

wherein $R_B^1$ to $R_B^8$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$ to $R_B^8$ each may have the same or different substituents;

n represents an integer of 1 to 5; and m and m' independently represent an integer of 0 to 3.

The "alkyl group" that $R_B^1$ to $R_B^8$ represent includes, for example, the "alkyl group" in the above "(1) an alkyl group optionally having a substituent". Preferred examples of the alkyl group include a methyl group, an ethyl group, a propyl group, an isopropyl group, an n-butyl group, an isobutyl group, a sec-butyl group, a tert-butyl group, a pentyl group, an isopentyl group, a hexyl group, an isohexyl group, and a heptyl group.

The "alkoxy group" that $R_B^1$ to $R_B^8$ represent includes, for example, the "alkoxy group" in the above "(a) an alkoxy group optionally having a substituent". Examples of the alkoxy group include a methoxy group, an ethoxy group, a propoxy group, an isopropoxy group, a butoxy group, an isobutoxy group, a sec-butoxy group, and a tert-butoxy group, and preferred examples thereof include a methoxy group.

The "aryl group" that $R_B^1$ to $R_B^8$ represent includes, for example, a phenyl group and a naphthyl group, and preferred examples of the aryl group include a phenyl group.

The "alkenyl group" that $R_B^1$ to $R_B^8$ represent includes, for example, a linear or branched $C_{2-20}$ alkenyl group. Examples of the alkenyl group include an ethenyl group, a propenyl group, a butenyl group, a pentenyl group, and a hexenyl group.

The "cycloalkyl group" that $R_B^1$ to $R_B^2$ represent includes, for example, a $C_{3-15}$ monocyclic or polycyclic saturated aliphatic ring group. Examples of the cycloalkyl group include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group, and preferred examples thereof include a cyclohexyl group.

The "cycloalkenyl group" that $R_B^1$ to $R_B^8$ represent includes, for example, a $C_{3-15}$ monocyclic or polycyclic unsaturated aliphatic ring group. Examples of the cycloalkenyl group include a cyclopropenyl group, a cyclopentenyl group, a cyclohexenyl group, a cycloheptynyl group, a cyclooctenyl group, a cyclopentadienyl group, a cyclohexadienyl group, a cycloheptadienyl group, and a cyclooctadienyl group.

The "haloalkyl group" that $R_B^1$ to $R_B^8$ represent includes, for example, the "haloalkyl group" in the above "(2) a haloalkyl group optionally having a substituent". Examples of the haloalkyl group include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group, and preferred examples thereof include a trifluoromethyl group.

The "aralkyl group" that $R_B^1$ to $R_B^8$ represent includes, for example, the "aralkyl group" in the above "(5) an aralkyl group optionally having a substituent". Examples of the aralkyl group include a benzyl group, a 1-phenylethyl group, a phenethyl group, a 1-naphthylmethyl group, a 2-naphthylmethyl group, a 1-naphthylethyl group, and a 2-naphthylethyl group, and preferred examples thereof include a benzyl group.

The "aryloxy group" that $R_B^1$ to $R_B^8$ represent includes, for example, the "aryloxy group" in the above "(b) an aryloxy group optionally having a substituent". Examples of the aryloxy group include a phenoxy group and a naphthyloxy group, and preferred examples thereof include a phenoxy group.

The "aralkyloxy group" that $R_B^1$ to $R_B^8$ represent includes, for example, the "aralkyloxy group" in the above "(c) an aralkyloxy group optionally having a substituent". Examples of the aralkyloxy group include a benzyloxy group, a phenethyloxy group, a 1-naphthylmethoxy group, a 2-naphthylmethoxy group, and preferred examples thereof include a benzyloxy group.

Other preferred embodiments of the π-conjugated bridge structure B include, for example, structures represented by the following formulae:

[Formula 79]

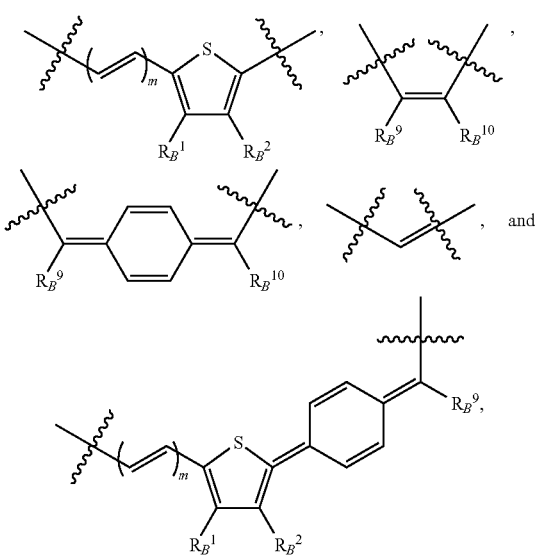

wherein $R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$ and $R_B^2$ each may have the same or different substituents;

$R_B^9$ and $R_B^{10}$ independently represent a hydrogen atom or a cyano group (—CN); and m represents an integer of 0 to 3.

More preferred specific embodiments of the π-conjugated bridge structure B include, for example, a structure represented by the formula B-I:

[Formula 80]

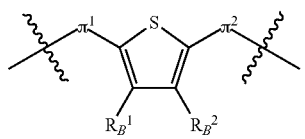

(B-I)

(wherein
$\pi^1$ and $\pi^2$ independently represent the same or different carbon-carbon conjugated π-bonds, and $\pi^1$ and $\pi^2$ each may have the same or different substituents; and
$R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$ and $R_B^2$ each may have the same or different substituents);
a structure represented by the formula B-II

[Formula 81]

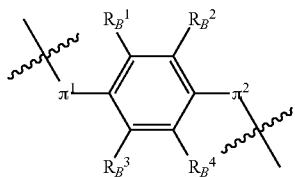

(B-II)

(wherein
$\pi^1$ and $\pi^2$ independently represent the same or different carbon-carbon conjugated π-bonds, and $\pi^1$ and $\pi^2$ each may have the same or different substituents; and
$R_B^1$, $R_B^2$, $R_B^3$, and $R_B^4$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$, $R_B^2$, $R_B^3$, and $R_B^4$ each may have the same or different substituents);
a structure represented by the formula B-III:

[Formula 82]

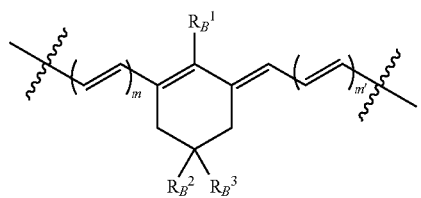

(B-III)

(wherein
m and m' independently represent an integer of 0 to 3; and
$R_B^1$, $R_B^2$, and $R_B^3$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$, $R_B^2$, and $R_B^3$ each may have the same or different substituents); and a structure represented by the formula B-IV:

[Formula 83]

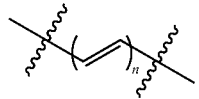

(B-IV)

(wherein
n represents an integer of 1 to 5).
Preferably, "the same or different carbon-carbon conjugated π-bonds" in the present invention are, for example, structures represented by the following formulae:

[Formula 84]

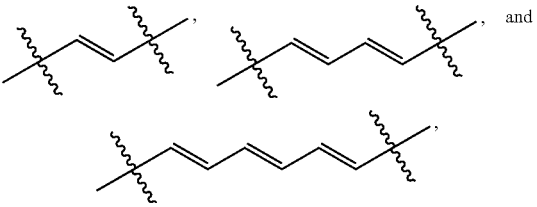

more preferably a structure represented by the following formula:

[Formula 85]

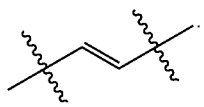

Preferred Specific Embodiments of Chromophore of the Present Invention

The chromophore of the present invention is represented by, for example, the formula D-B-A, wherein D represents the donor structure D, B represents the π-conjugated bridge structure B, and A represents the acceptor structure A.
Preferred specific embodiments of the chromophore of the present invention include, for example,
a compound represented by the formula I-1:

[Formula 86]

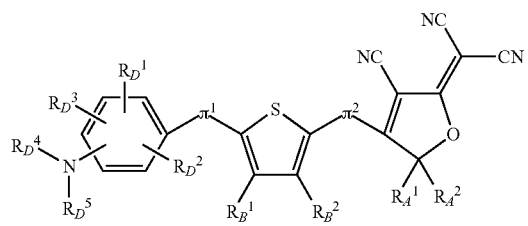

(I-1)

(wherein $\pi^1$ and $\pi^2$ independently represent the same or different carbon-carbon conjugated π-bonds, and $\pi^1$ and $\pi^2$ each may have the same or different substituents;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom and optionally having a substituent;

$R_B^1$ and $R_B^2$ independently represent a hydrogen atom, an alkyl group, an alkoxy group, an aryl group, an aralkyl group, an aryloxy group, or an aralkyloxy group, and $R_B^1$ and $R_B^2$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents);

a compound represented by the formula I-1-a:

[Formula 87]

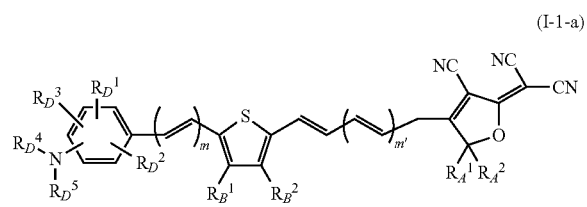

(I-1-a)

(wherein m and m' independently represents an integer of 0 to 3; and $R_D^1$ to $R_D^5$, $R_B^1$, $R_B^2$, $R_A^1$, and $R_A^2$ have the same meanings as defined for the above compound represented by the formula I-1);

a compound represented by the formula I-1-b:

[Formula 88]

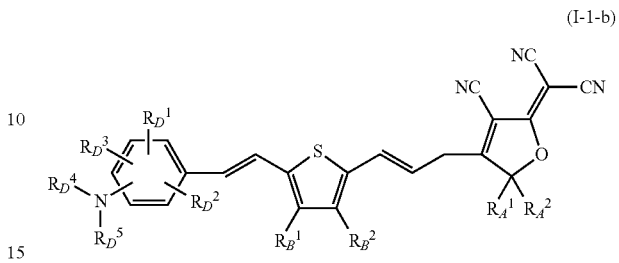

(I-1-b)

(wherein $R_D^1$ to $R_D^5$, $R_B^1$, $R_B^2$, $R_A^1$, and $R_A^2$ have the same meanings as defined for the above compound represented by the formula I-1); and a compound represented by the formula I-2:

[Formula 89]

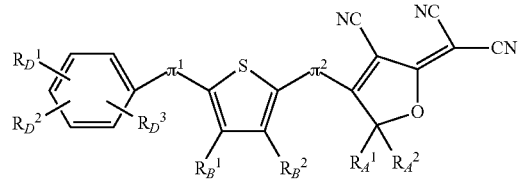

(I-2)

(wherein at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $\pi^1$, $\pi^2$, $R_B^1$, $R_B^2$, $R_A^1$, and $R_A^2$ have the same meanings as defined for the above compound represented by the formula I-1).

More preferred specific embodiments of the chromophore of the present invention include, for example, a compound represented by the formula I-1-1:

[Formula 90]

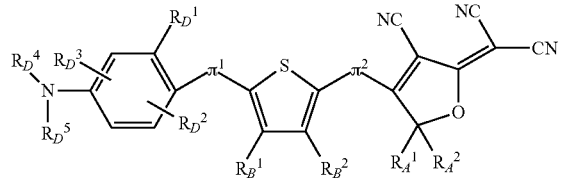

(I-1-1)

(wherein $\pi^1$ and $\pi^2$ independently represent the same or different carbon-carbon conjugated π-bonds, and $\pi^1$ and $\pi^2$ each may have the same or different substituents;

$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a saturated heterocyclic ring optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$ and $R_B^2$ independently represent a hydrogen atom, an alkyl group, an alkoxy group, an aryl group, an aralkyl group, an aryloxy group, or an aralkyloxy group, and $R_B^1$ and $R_B^2$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents);

a compound represented by the formula I-1-1-a:

[Formula 91]

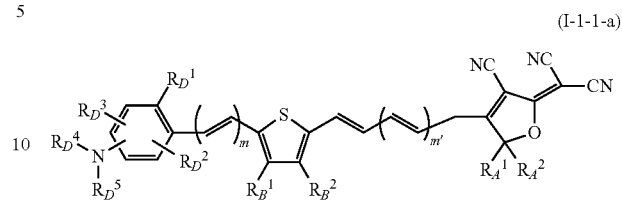

(I-1-1-a)

(wherein m and m' independently represents an integer of 0 to 3; and $R_D^1$ to $R_D^5$, $R_B^1$, $R_B^2$, $R_A^1$, and $R_A^2$ have the same meanings as defined for the above compound represented by the formula I-1-1); and a compound represented by the formula I-1-1-b:

[Formula 92]

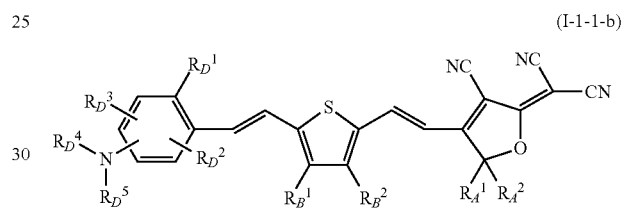

(I-1-1-b)

(wherein $R_D^1$ to $R_B^5$, $R_B^1$, $R_B^2$, $R_A^1$, and $R_A^2$ have the same meanings as defined for the above compound represented by the formula I-1-1).

Other preferred specific embodiments of the chromophore of the present invention include, for example, a compound represented by the formula II-1:

[Formula 93]

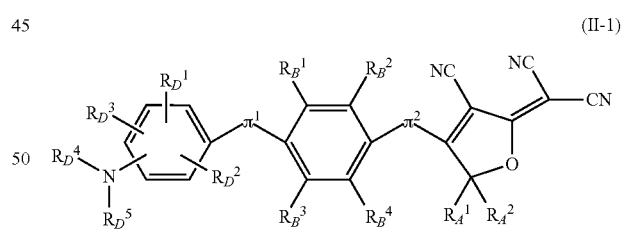

(II-1)

(wherein $\pi^1$ and $\pi^2$ independently represent the same or different carbon-carbon conjugated π-bonds, and $\pi^1$ and $\pi^2$ each may have the same or different substituents;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$, $R_B^2$, $R_B^3$, and $R_B^4$ independently represent a hydrogen atom, an alkyl group, an alkoxy group, an aryl group, an aralkyl group, an aryloxy group, or an aralkyloxy group, and $R_B^1$, $R_B^2$, $R_B^3$, and $R_B^4$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents);

a compound represented by the formula II-1-a:

[Formula 94]

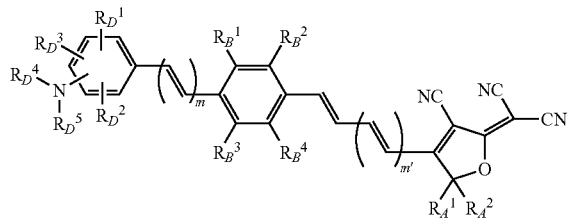

(II-1-a)

(wherein m and m' independently represent an integer of 0 to 3; and $R_D^1$ to $R_D^5$, $R_B^1$ to $R_B^4$, $R_A^1$, and $R_A^2$ have the same meanings as defined for the above compound represented by the formula II-1); and a compound represented by the formula II-1-b:

[Formula 95]

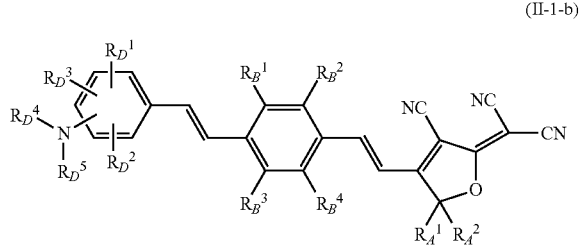

(II-1-b)

(wherein $R_D^1$ to $R_D^5$, $R_B^1$ to $R_B^4$, $R_A^1$, and $R_A^2$ have the same meanings as defined for the above compound represented by the formula II-1).

More preferred specific embodiments of the chromophore of the present invention include, for example, a compound represented by the formula II-1-1:

[Formula 96]

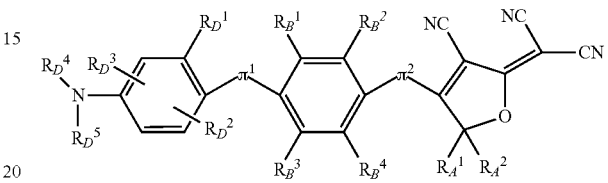

(II-1-1)

(wherein $\pi^1$ and $\pi^2$ independently represent the same or different carbon-carbon conjugated π-bonds, and $\pi^1$ and $\pi^2$ each may have the same or different substituents;

$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a saturated heterocyclic ring optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$, $R_B^2$, $R_B^3$, and $R_B^4$ independently represent a hydrogen atom, an alkyl group, an alkoxy group, an aryl group, an aralkyl group, an aryloxy group, or an aralkyloxy group, and $R_B^1$, $R_B^2$, $R_B^3$, and $R_B^4$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents);

a compound represented by the formula II-1-1-a:

[Formula 97]

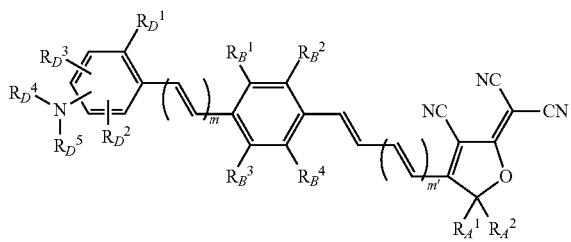

(II-1-1-a)

(wherein
m and m' independently represent an integer of 0 to 3; and $R_D^1$ to $R_D^5$, $R_B^1$ to $R_B^4$, $R_A^1$, and $R_A^2$ have the same meanings as defined for the above compound represented by the formula II-1-1); and
a compound represented by the formula II-1-1-b:

[Formula 98]

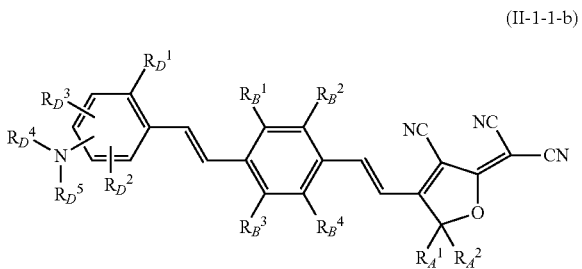

(II-1-1-b)

(wherein
$R_D^1$ to $R_D^5$, $R_B^1$ to $R_B^4$, $R_A^1$, and $R_A^2$ have the same meanings as defined for the above compound represented by the formula II-1-1).

Other preferred specific embodiments of the chromophore of the present invention include, for example,
a compound represented by the formula III-1:

[Formula 99]

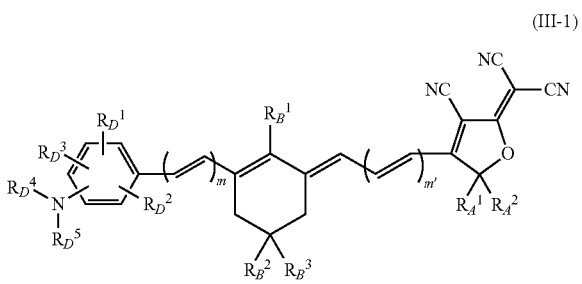

(III-1)

(wherein
m and m' independently represent an integer of 0 to 3;
at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$, $R_B^2$, and $R_B^3$ independently represent a hydrogen atom, an alkyl group, an alkoxy group, an aryl group, an aralkyl group, an aryloxy group, or an aralkyloxy group, and $R_B^1$, $R_B^2$, and $R_B^3$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents); and a compound represented by the formula III-1-a:

[Formula 100]

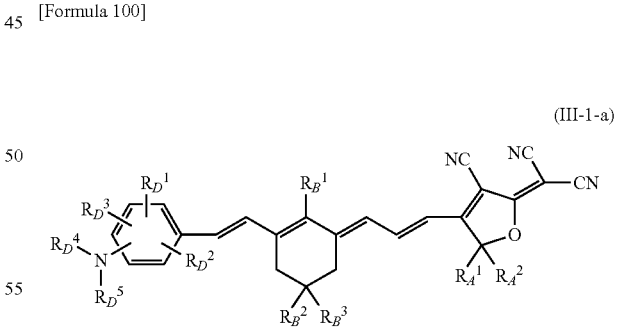

(III-1-a)

(wherein
$R_D^1$ to $R_D^5$, $R_B^1$ to $R_B^3$, $R_A^1$, and $R_A^2$ have the same meanings as defined for the above compound represented by the formula III-1).

More preferred specific embodiments of the chromophore of the present invention include, for example, a compound represented by the formula III-1-1:

[Formula 101]

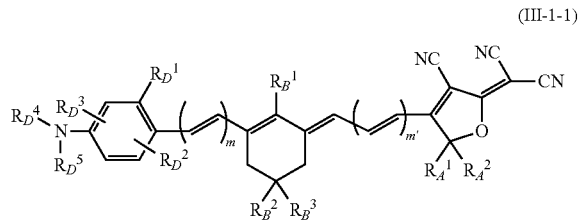

(III-1-1)

(wherein m and m' independently represent an integer of 0 to 3;

$R_D^1$ represents an alkoxy group, an aryloxy group, an aralkyloxy group, a silyloxy group, an alkenyloxy group, an alkenylcarbonyloxy group, or a hydroxy group, and $R_D^1$ may have the same or different substituents;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent;

$R_B^1$, $R_B^2$, $R_B^3$, and $R_B^4$ independently represent a hydrogen atom, an alkyl group, an alkoxy group, an aryl group, an aralkyl group, an aryloxy group, or an aralkyloxy group, and $R_B^1$, $R_B^2$, $R_B^3$, and $R_B^4$ each may have the same or different substituents; and $R_A^1$ and $R_A^2$ independently represent a hydrogen atom, an alkyl group, a haloalkyl group, or an aryl group, and $R_A^1$ and $R_A^2$ each may have the same or different substituents); and a compound represented by the formula III-1-1-a:

[Formula 102]

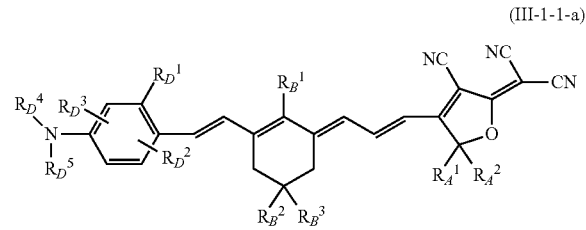

(III-1-1-a)

(wherein $R_D^1$ to $R_D^5$, $R_B^1$ to $R_B^3$, $R_A^1$, and $R_A^2$ have the same meanings as defined for the above compound represented by the formula III-1-1).

Other preferred specific embodiments of the chromophore of the present invention include, for example, a compound represented by the formula IV-1-a:

[Formula 103]

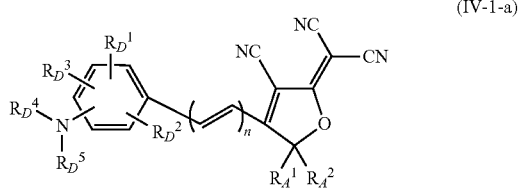

(IV-1-a)

(wherein n represents an integer of 1 to 5;

$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents (when $R_D^2$ and $R_D^3$ are each attached to adjacent carbon atoms of the aryl of the donor structure D, $R_D^2$ and $R_D^3$ may form, together with the two adjacent carbon atoms, a ring optionally having a substituent);

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, and $R_D^4$ and $R_D^5$ each may have the same or different substituents, or $R_D^4$ and $R_D^5$ form, together with the nitrogen atom to which they are attached, a heterocyclic ring containing the nitrogen atom as a hetero atom and optionally having a substituent; or (a) $R_D^2$ and $-NR_D^4R_D^5$ and (b) $R_D^3$ and $-NR_D^4R_D^5$ independently form, together with the carbon atoms to which they are attached, a heterocyclic ring containing the nitrogen atom as a hetero atom and optionally having a substituent; and $R_A^1$ and $R_A^2$ independently represent a hydrogen atom, an alkyl group, a haloalkyl group, or an aryl group, and $R_A^1$ and $R_A^2$ each may have the same or different substituents);

a compound represented by the formula IV-1-b:

[Formula 104]

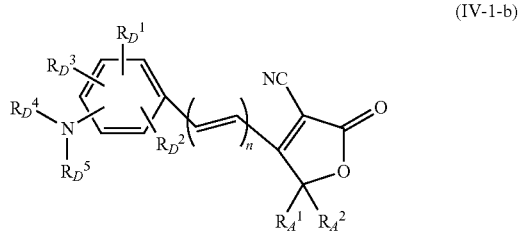

(IV-1-b)

(wherein n, $R_D^1$ to $R_D^5$, $R_A^1$, and $R_A^2$ have the same meanings as defined for the above compound represented by the formula IV-1-a);

a compound represented by the formula IV-2-a:

[Formula 105]

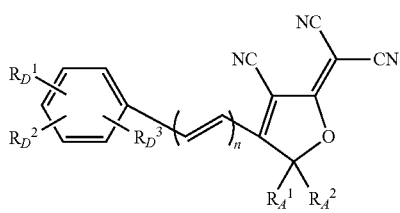

(IV-2-a)

(wherein n represents an integer of 1 to 5;

at least one of $R_D^1$, $R_D^2$, and $R_D^3$ independently represents an alkoxy group, an aryloxy group, an aralkyloxy group, a silyloxy group, an alkenyloxy group, an alkenylcarbonyloxy group, an alkynyloxy group, or a hydroxy group; the rest independently represent a hydrogen atom or an alkyl group; and $R_D^1$, $R_D^2$, and $R_D^3$ each may have the same or different substituents (when $R_D^2$ and $R_D^3$ are each attached to adjacent carbon atoms of the aryl of the donor structure D, (1) $R_D^2$ and $R_D^3$ may form, together with the two adjacent carbon atoms, a ring optionally having a substituent; and $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent, or (2) $R_D^2$ and $R_D^3$ may form, together with the two adjacent carbon atoms, a heterocyclic ring containing an oxygen atom as a hetero atom and optionally having a substituent); and $R_A^1$ and $R_A^2$ independently represent a hydrogen atom, an alkyl group, a haloalkyl group, or an aryl group, and $R_A^1$ and $R_A^2$ each may have the same or different substituents); and a compound represented by the formula IV-2-b:

[Formula 106]

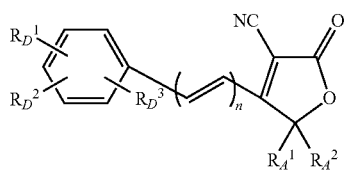

(IV-2-b)

(wherein n, $R_D^1$ to $R_D^3$, $R_A^1$, and $R_A^2$ have the same meanings as defined for the above compound represented by the formula IV-2-a).

Production Process for Chromophore of the Present Invention

The chromophore of the present invention can be produced by a method known per se. The chromophore of the present invention can be produced by various methods such as a method described in, for example, Ann., 580, 44 (1953); Angew. Chem., 92, 671 (1980); Chem. Ber., 95, 581 (1962); Macromolecules, 2001, 34, 253; Chem. Mater., 2007, 19, 1154; Org. Synth., VI, 901 (1980); Chem. Mater., 2002, 14, 2393; J. Mater. Sci., 39, 2335 (2004); "Preparative Organic Chemistry", John Wiley (1975), p. 217; J. Org. Chem., 42, 353 (1977); J. Org. Chem., 33, 3382 (1968); Synthesis, 1981, 165; or the like, an appropriately improved method thereof, a combination method thereof, and the methods described in Examples below.

The chromophore of the present invention can be produced by, for example, the production processes described below. However, the production process of the chromophore of the present invention is not limited to these reaction examples.

Production Process A

Among the chromophores of the present invention, the chromophore represented by the formula I-1-b:

[Formula 107]

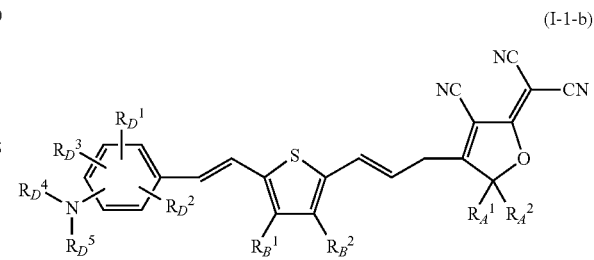

(I-1-b)

(wherein $R_D^1$ to $R_D^5$, $R_B^1$, $R_B^2$, $R_A^1$, and $R_A^2$ have the same meanings as defined for the above chromophore represented by the formula I-1-b)

can be produced by, for example, reacting a compound represented by the formula IV-I:

[Formula 108]

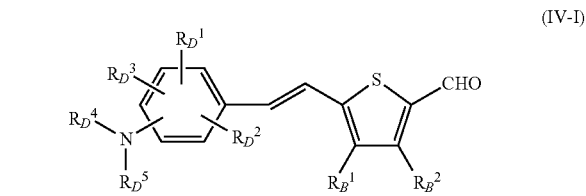

(IV-I)

(wherein $R_D^1$ to $R_D^5$, $R_B^1$, and $R_B^2$ have the same meanings as defined for the above chromophore represented by the formula I-1-b)

with a compound represented by the formula V:

[Formula 109]

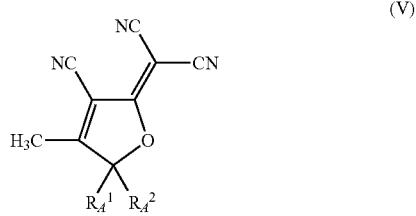

(V)

(wherein $R_A^1$ and $R_A^2$ have the same meanings as defined for the above chromophore represented by the formula I-1-b).

The reaction of the compound represented by the formula IV-I with the compound represented by the formula V is usually performed in a polar solvent. The polar solvent may be a protonic polar solvent, a non-protonic polar solvent, or a combined polar solvent thereof. Examples of the protonic polar solvent include water, methanol, ethanol, 1-propanol, 2-propanol, 1-butanol, acetic acid, formic acid, and a combined solvent thereof. Examples of the non-protonic polar solvent include tetrahydrofuran (THF), acetone, acetonitrile, N,N-dimethylformamide (DMF), dimethylsulfoxide (DMSO), methylene chloride, chloroform, dioxane, N-methylpyrrolidone, and a combined solvent thereof.

The reaction temperature is usually, for example, about 0 to 150° C., preferably, for example, about 20 to 80° C.

The reaction time depends on the reaction temperature, but usually, for example, about 1 hour to about 3 days.

The reaction atmosphere is usually air or the like.

After the reaction, usual treatment is carried out and the obtained crude product is purified as necessary according to a usual method, and thus the compound represented by the formula I-1-b can be obtained.

A raw material represented by the formula IV-I:

[Formula 110]

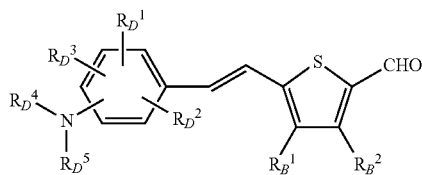

(IV-I)

(wherein $R_D^1$ to $R_D^5$, $R_B^1$, and $R_B^2$ have the same meanings as defined for the above chromophore represented by the formula I-1-b) for producing the compound represented by the formula I-1-b can be produced by, for example, the following methods.

The compound represented by the formula IV-I can be obtained by, for example, reacting a compound represented by the formula VI:

[Formula 111]

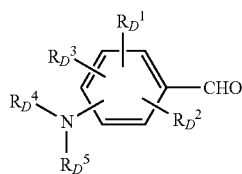

(VI)

(wherein $R_D^1$ to $R_D^5$ have the same meanings as defined for the above chromophore represented by the formula I-1-b) with a compound represented by the formula VII-I-1:

[Formula 112]

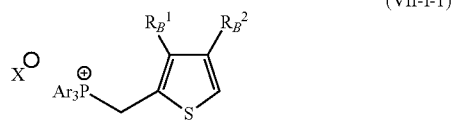

(VII-I-1)

(wherein $R_B^1$ and $R_B^2$ have the same meanings as defined for the above chromophore represented by the formula I-1-b;

Ar represents an aryl group; and

X represents a halogen atom)

or with a compound represented by the formula VII-I-2:

[Formula 113]

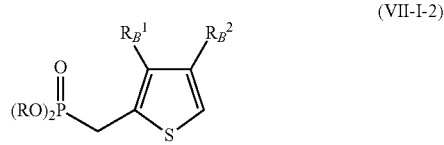

(VII-I-2)

(wherein $R_B^1$ and $R_B^2$ have the same meanings as defined for the above chromophore represented by the formula I-1-b; and R represents an alkyl group)

in the presence of a base to give a compound represented by the formula VIII-I-1:

[Formula 114]

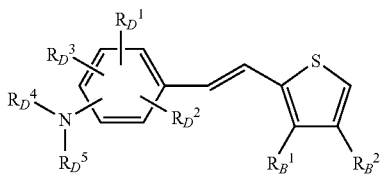

(VIII-I-1)

(wherein $R_B^1$ and $R_B^2$ have the same meanings as defined for the above chromophore represented by the formula I-1-b), reacting the obtained compound represented by the formula VIII-I-1 with an alkyllithium (for example, n-butyllithium) or the like in an organic solvent (for example, tetrahydrofuran), and reacting the resulting compound with N,N-dimethylformamide, N-formylpiperidine, or the like.

Alternatively, the compound represented by the formula IV-I can also be obtained by, for example, reacting a compound represented by the formula VI:

[Formula 115]

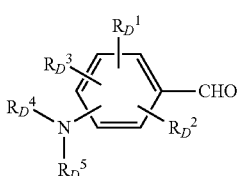

(VI)

(wherein
$R_D^1$ to $R_D^5$ have the same meanings as defined for the above chromophore represented by the formula I-1-b) with a compound represented by the formula VII-I-3:

[Formula 116]

(VII-I-3)

(wherein
$R_B^1$, $R_B^2$, and $R_B^3$ have the same meanings as defined for the above chromophore represented by the formula I-1-b;
Ar represents an aryl group;
X represents a halogen atom; and
Y represents a hydrogen atom or a protective group for a hydroxy group)
in the presence of a base to give a compound represented by the formula VIII-I-2:

[Formula 117]

(VIII-I-2)

(wherein
$R_D^1$ to $R_D^5$, $R_B^1$, and $R_B^2$ have the same meanings as defined for the above chromophore represented by the formula I-1-b; and
Y represents a hydrogen atom or a protective group for a hydroxy group), and
subjecting the obtained compound represented by the formula VIII-I-2 to oxidation (when Y represents a protective group for a hydroxy group, deprotection of the protective group is performed before the oxidation).

The aryl group in the above "an aryl group optionally having a substituent" that Ar represents includes, for example, a phenyl group.

The "halogen atom" that X represents includes, for example, a fluorine atom, a chlorine atom, a bromine atom, and an iodine atom.

The "protective group for a hydroxy group" that Y represents is not particularly limited as long as it has a function as a protective group, and examples thereof include an alkyl group (for example, a methyl group, an ethyl group, an isopropyl group, a tert-butyl group, and the like), an alkylsilyl group (for example, a trimethylsilyl group, a tert-butyldimethylsilyl group, and the like), an alkoxymethyl group (for example, a methoxymethyl group, a 2-methoxyethoxymethyl group, and the like), a tetrahydropyranyl group, a triethylsilylethoxymethyl group, an aralkyl group (for example, a benzyl group, a p-methoxybenzyl group, a 2,3-dimethoxybenzyl group, an o-nitrobenzyl group, a p-nitrobenzyl group, a trityl group, and the like), and an acyl group (for example, a formyl group, an acetyl group, and the like).

The deprotection method may be a method known per se. Deprotection can be carried out according to a method described in literature, for example, T. W. Greene, Protective Groups in Organic Synthesis, John Wiley & Sons, 1981, or a similar method thereto.

Production Process B

Among the chromophores of the present invention, the chromophore represented by the formula II-1-b:

[Formula 118]

(II-1-b)

(wherein
$R_D^1$ to $R_D^5$, $R_B^1$ to $R_B^4$, $R_A^1$, and $R_A^2$ have the same meanings as defined for the above chromophore represented by the formula II-1-b)
can be produced by, for example, reacting a compound represented by the formula IV-II:

[Formula 119]

(IV-II)

(wherein
$R_D^1$ to $R_D^5$ and $R_B^1$ to $R_B^4$ have the same meanings as defined for the above chromophore represented by the formula II-1-b) with a compound represented by the formula V:

[Formula 120]

(V)

(wherein
$R_A^1$ and $R_A^2$ have the same meanings as defined for the above chromophore represented by the formula II-1-b).

The reaction of the compound represented by the formula IV-II with the compound represented by the formula V can be usually performed under the same conditions as those in the reaction of the above compound represented by the formula IV-I with the compound represented by the formula V.

After the reaction, usual treatment is carried out and the obtained crude product is purified as necessary according to a usual method, and thus the compound represented by the formula II-1-b can be obtained.

A raw material represented by the formula IV-II:

[Formula 121]

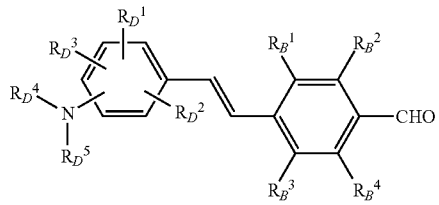

(IV-II)

(wherein $R_D^1$ to $R_D^5$ and $R_B^1$ to $R_B^4$ have the same meanings as defined for the above chromophore represented by the formula II-1-b) for producing the compound represented by the formula II-1-b can be produced by, for example, the following method.

The compound represented by the formula IV-II can be obtained by, for example, reacting a compound represented by the formula VI:

[Formula 122]

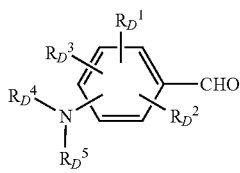

(VI)

(wherein $R_D^1$ to $R_D^5$ have the same meanings as defined for the above chromophore represented by the formula II-1-b) with a compound represented by the formula VII-II-1:

[Formula 123]

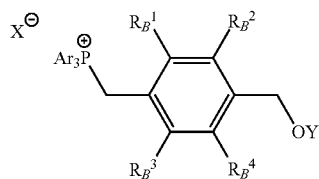

(VII-II-1)

(wherein $R_B^1$ to $R_B^4$ have the same meanings as defined for the above chromophore represented by the formula II-1-b;
Ar represents an aryl group;
X represents a halogen atom; and
Y represents a hydrogen atom or a protective group for a hydroxy group)

or with a compound represented by the formula VII-II-2:

[Formula 124]

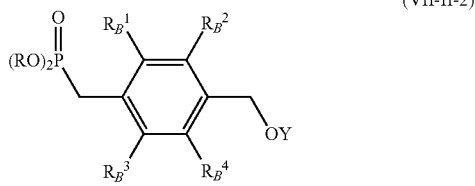

(VII-II-2)

(wherein $R_B^1$ to $R_B^4$ have the same meanings as defined for the above chromophore represented by the formula II-1-b; and
R represents an alkyl group)

in the presence of a base to give a compound represented by the formula VIII-II:

[Formula 125]

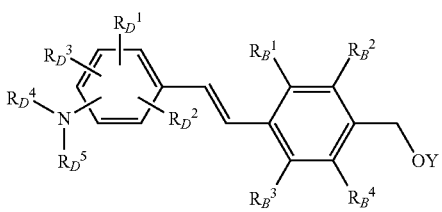

(VIII-II)

(wherein $R_D^1$ to $R_D^5$ and $R_B^1$ to $R_B^4$ have the same meanings as defined for the above chromophore represented by the formula II-1-b; and Y represents a hydrogen atom or a protective group for a hydroxy group), and subjecting the obtained compound represented by the formula VIII-II to oxidation (when Y represents a protective group for a hydroxy group, deprotection of the protective group is performed before the oxidation).

Production Process C

Besides Production Process B described above, the chromophore represented by the formula II-1-b:

[Formula 126]

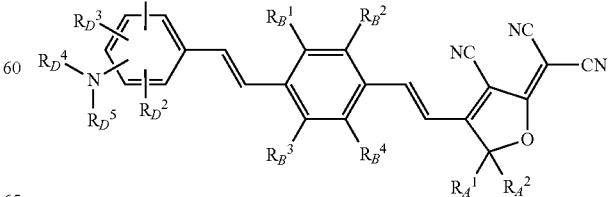

(II-1-b)

(wherein
$R_D^1$ to $R_D^5$, $R_B^1$ to $R_B^4$, $R_A^1$, and $R_A^2$ have the same meanings as defined for the above chromophore represented by the formula II-1-b)
also can be produced by, for example, the following method.

The chromophore represented by the formula II-1-b can be produced by, for example, reacting a compound represented by the formula IX-1:

[Formula 127]

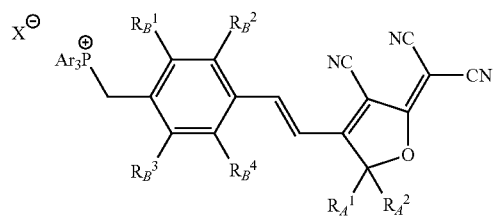

(IX-1)

(wherein
$R_B^1$ to $R_B^4$, $R_A^1$, and $R_A^2$ have the same meanings as defined for the above chromophore represented by the formula II-1-b;
Ar represents an aryl group; and
X represents a halogen atom)
or a compound represented by the formula IX-2:

[Formula 128]

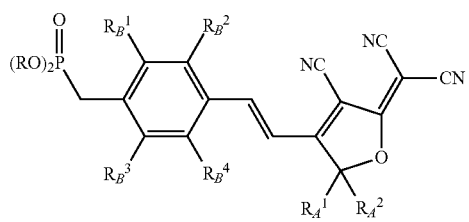

(IX-2)

(wherein
$R_B^1$ to $R_B^4$, $R_A^1$, and $R_A^2$ have the same meanings as defined for the above chromophore represented by the formula II-1-b; and
R represents an alkyl group)
with a compound represented by the formula VI:

[Formula 129]

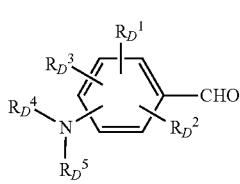

(VI)

(wherein
$R_D^1$ to $R_D^5$ have the same meanings as defined for the above chromophore represented by the formula II-1-b)
in the presence of a base.

The reaction of the compound represented by the formula IX-1 or the compound represented by the formula IX-2 with the compound represented by the formula VI is usually performed in a polar or non-polar solvent in the presence of a base such as an alkali metal alkoxide, an alkali metal hydride, n-butyllithium, and phenyllithium.

The reaction temperature is usually, for example, about −30 to 100° C., preferably, for example, about −10 to 50° C.

The reaction time is usually, for example, several minutes to about 5 hours and is determined as appropriate based on the reaction progress monitored by thin-layer chromatography or the like.

Preferably, the reaction atmosphere is usually, for example, an inert gas such as nitrogen and argon with exclusion of moisture.

After the reaction, usual treatment is carried out and the obtained crude product is purified as necessary according to a usual method, and thus the compound represented by the formula II-1-b can be obtained.

A raw material represented by the formula IX-1:

[Formula 130]

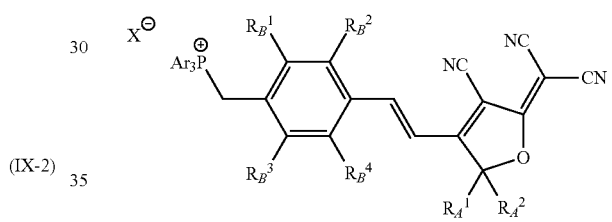

(IX-1)

(wherein
$R_B^1$ to $R_B^4$, $R_A^1$, and $R_A^2$ have the same meanings as defined for the above chromophore represented by the formula II-1-b;
Ar represents an aryl group; and
X represents a halogen atom)
for producing the compound represented by the formula II-1-b can be produced by, for example, the following method.

The compound represented by the formula IX-1 or the compound represented by the formula IX-2 can be obtained by, for example, reacting a compound represented by the formula V:

[Formula 131]

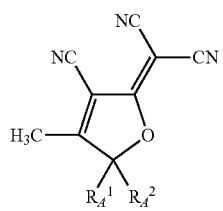

(V)

(wherein
$R_A^1$ and $R_A^2$ have the same meanings as defined for the above chromophore represented by the formula II-1-b) with a compound represented by the formula X:

[Formula 132]

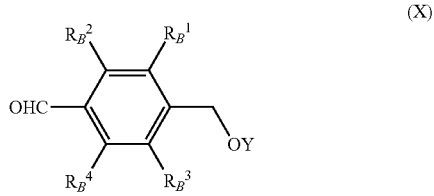

(X)

(wherein
$R_B^1$ to $R_B^4$ have the same meanings as defined for the above chromophore represented by the formula II-1-b; and
Y represents a hydrogen atom or a protective group for a hydroxy group)
to give a compound represented by the formula XI:

[Formula 133]

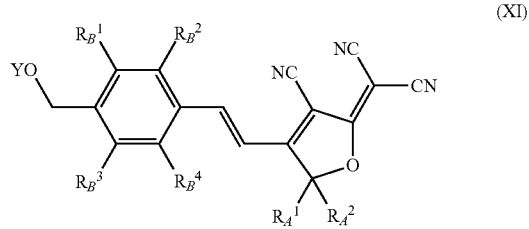

(XI)

(wherein
$R_B^1$ to $R_B^4$, $R_A^1$, and $R_A^2$ have the same meanings as defined for the above chromophore represented by the formula II-1-b; and
Y represents a hydrogen atom or a protective group for a hydroxy group),
subjecting the obtained compound represented by the formula XI to halogenation (when Y represents a protective group for a hydroxy group, deprotection of the protective group is performed before the halogenation) to give a compound represented by the formula XII:

[Formula 134]

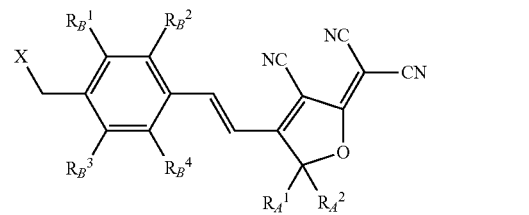

(XII)

(wherein
$R_B^1$ to $R_B^4$, $R_A^1$, and $R_A^2$ have the same meanings as defined for the above chromophore represented by the formula II-1-b; and
X represents a halogen atom), and
reacting the obtained compound represented by the formula XII with $PAr_3$ (wherein Ar represents an aryl group) or $P(OR)_3$ (wherein R represents an alkyl group).

Production Process D

Among the chromophores of the present invention, the chromophore represented by the formula III-1-a:

[Formula 135]

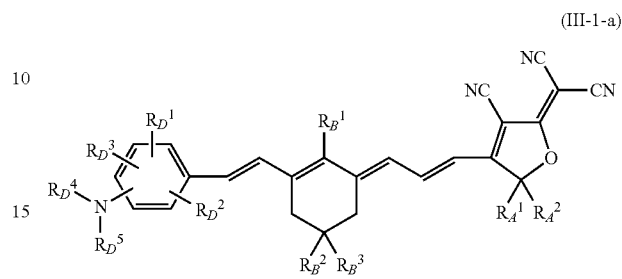

(III-1-a)

(wherein
$R_D^1$ to $R_D^5$, $R_B^1$ to $R_B^4$, $R_A^1$, and $R_A^2$ have the same meanings as defined for the above chromophore represented by the formula III-1-a)
can be produced by, for example, reacting a compound represented by the formula IV-III:

[Formula 136]

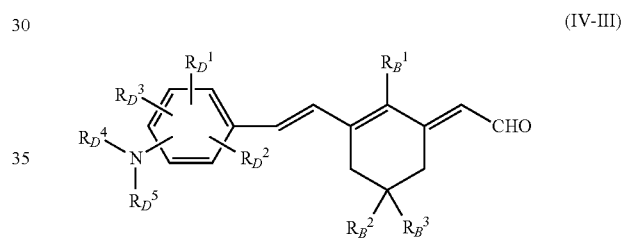

(IV-III)

(wherein
$R_D^1$ to $R_D^5$ and $R_B^1$ to $R_B^3$ have the same meanings as defined for the above chromophore represented by the formula III-1-a) with a compound represented by the formula V:

[Formula 137]

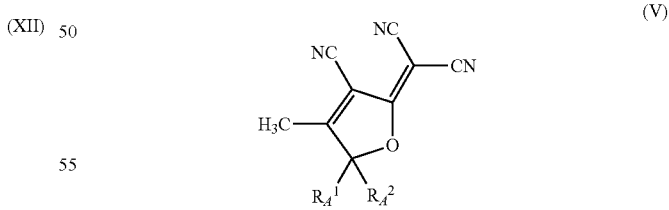

(V)

(wherein
$R_A^1$ and $R_A^2$ have the same meanings as defined for the above chromophore represented by the formula III-1-a).

The above reaction of the compound represented by the formula IV-III with the compound represented by the formula V is usually performed in a polar solvent.

The reaction temperature is usually, for example, about 0 to 150° C., preferably, for example, about 20 to 80° C.

The reaction time depends on the reaction temperature, but usually, for example, about 1 hour to about 3 days.

The reaction atmosphere is usually air or the like.

After the reaction, usual treatment is carried out and the obtained crude product is purified as necessary according to a usual method, and thus the compound represented by the formula III-1-a can be obtained.

A raw material represented by the formula IV-III:

[Formula 138]

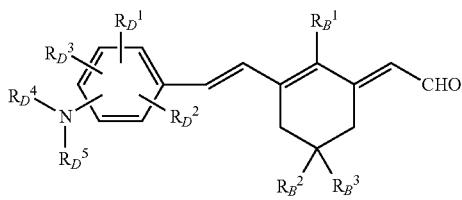

(IV-III)

(wherein $R_D^1$ to $R_D^5$ and $R_B^1$ to $R_B^3$ have the same meanings as defined for the above chromophore represented by the formula III-1-a) for producing the compound represented by the formula III-1-a can be produced by, for example, the following method.

The compound represented by the formula IV-III can be produced by, for example, reacting a compound represented by the formula VI:

[Formula 139]

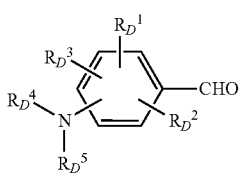

(VI)

(wherein $R_D^1$ to $R_D^5$ have the same meanings as defined for the above chromophore represented by the formula III-1-a) with a compound represented by the formula XIII:

[Formula 140]

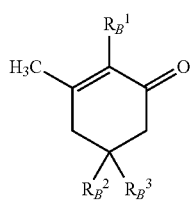

(XIII)

(wherein $R_B^1$ to $R_B^3$ have the same meanings as defined for the above chromophore represented by the formula III-1-a) to give a compound represented by the formula XIV:

[Formula 141]

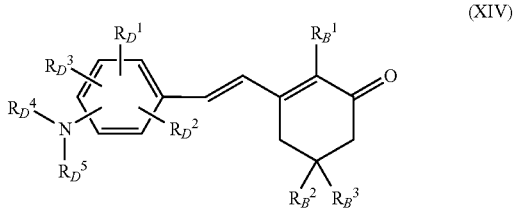

(XIV)

(wherein $R_D^1$ to $R_D^5$ and $R_B^1$ to $R_B^3$ have the same meanings as defined for the above chromophore represented by the formula III-1-a), reacting the obtained compound represented by the formula XIV with an alkylidene imine such as $C_6H_{11}N\!\!=\!\!CHCH_2Li$, and treating the resulting compound with water.

The production process of the chromophore of the present invention has been described above. In the step of constructing an alkene, a cis or trans isomer can be stereoselectively obtained by selecting an appropriate reaction, but usually the alkene is mostly obtained as a mixture of cis and trans isomers. In cases where a desired stereoisomer is required, this purpose can be achieved by using a method known per se, such as chromatography, fractional crystallization, distillation, and isomerization.

Nonlinear Optical Material and Nonlinear Optical Element of the Present Invention The nonlinear optical material and nonlinear optical element of the present invention can be produced according to a known method (for example, methods described in Oh et al., IEEE Journal on Selected Topics in Quantum Electronics, Vol. 7, No. 5, pp. 826-835, September/October 2001; Dalton et al., Journal of Materials Chemistry, 1999, 9, pp. 1905-1920; Kaino, Denshi Joho Tsushin Gakkai Ronbunshi (IEICE TRANSACTIONS on Electronics), C Vol. J84-C, No. 9, pp. 744-755, September, 2001; Ma et al., Advanced Materials, 2002, 14, No. 19, 2002, pp. 1339-1365; and the like).

The nonlinear optical material of the present invention comprises the chromophore of the present invention and a host material in which the chromophore is dispersed. Preferably, the chromophore of the present invention at a high concentration is uniformly dispersed in the host material so that the nonlinear optical material of the present invention can achieve excellent nonlinearity. For this purpose, the host material preferably has high compatibility with the chromophore of the present invention.

Examples of the host material include resins such as polymethacrylate (e.g., polymethylmethacrylate (PMMA)), polyimide, polycarbonate, polystyrene, polysulfone, polyethersulfone, a silicone resin, and an epoxy resin. These resins are preferred in that the resins are excellent in compatibility with the chromophore of the present invention and that, when the chromophore is used for a nonlinear optical element, the resins are excellent in transparency and formability.

Dispersion of the chromophore of the present invention in the host material can be achieved by, for example, dissolving an appropriate mixing ratio of the chromophore and the host material in an organic solvent, spin-coating a substrate with the mixture, and heating the substrate, and thus a thin film of the nonlinear optical material can be obtained.

The host material in the nonlinear optical material of the present invention preferably comprises a resin having a reactive functional group capable of forming a covalent bond with the chromophore of the present invention. Further, at least part of the chromophore of the present invention is preferably attached to the resin having a reactive functional group. Such a nonlinear optical material in which the chromophore can be dispersed in the host material in a high density can achieve higher nonlinearity.

Examples of the above reactive functional group include a haloalkyl group, a halogenated acyl group, an alkoxycarbonyl group, an aryloxycarbonyl group, a hydroxy group, an amino group, an isocyanate group, an epoxy group, and a carboxy group. Such a reactive functional group can react with a hydroxy group, an amino group, an alkoxycarbonyl group, or the like contained in the chromophore of the present invention, thereby forming a covalent bond.

The nonlinear optical element of the present invention can be produced using the nonlinear optical material of the present invention. Since the nonlinear optical material of the present invention is excellent in nonlinearity and heat resistance, use of this material can give the nonlinear optical element an excellent optical performance and an excellent durability for prolonged use.

The FIGURE shows a schematic sectional view of an optical waveguide constituting an arm of a Mach-Zehnder modulator, a specific embodiment of the nonlinear optical element of the present invention, but the present invention is not limited thereto.

In the optical waveguide 10 shown in the FIGURE, the following are stacked in the following order: a substrate 1, a lower electrode 2, a first clad layer 3, a core layer 4, a second clad layer 6, and an upper electrode 8. In the optical waveguide 10, the core layer 4 is formed with the above nonlinear optical material that has been subjected to electric field poling, and the optical waveguide core 9 formed by reactive ion etching or the like serves as a Mach-Zehnder interferometer. When an electric field is applied from the lower electrode 2 and the upper electrode 8, the refractive index of the core layer 4 positioned between these electrodes varies, thereby changing the phase difference between both arms of the Mach-Zehnder interferometer to modulate the intensity of a transmission light.

The first clad layer 3 and the second clad layer 6 are not particularly limited as long as their refractive indexes are lower than that of the core layer 4, and preferred examples thereof include ultraviolet curable or thermosetting resins, such as acrylic resins, epoxy resins, and silicone resins; organic or inorganic composite sol-gel curable materials such as polyimides and glass; silicon oxide; and the like. The lower electrode 2 is, for example, a metal or a conductive film such as a conductive oxide film and a conductive organic polymer, and is used as an electrode during poling or during operation as an element. The upper electrode 8 is an electrode for providing an input electric signal.

Although an example in which the optical waveguide 10 forms a Mach-Zehnder modulator is illustrated herein, embodiments of the nonlinear optical element of the present invention are not limited to Mach-Zehnder devices and may be other types of devices (for example, directional couplers or the like).

The applications of the nonlinear optical element of the present invention are not limited to optical modulators as long as the applications involve the use of a film, optical waveguide, or the like made of the chromophore or nonlinear optical material of the present invention. The nonlinear optical element of the present invention can be used for, besides optical modulators (e.g., for ultra high-speed transmission, optical interconnection, optical signal processing, or the like), for example, optical switches; optical memories; wavelength converters; electric field sensors for microwaves, millimeter waves, terahertz waves, or the like; biopotential sensors for muscle potentials, brain waves, or the like; spatial light modulators; optical scanners; or the like, and further can be combined with electronic circuits and used for optical signal transmission or the like between electronic circuits.

EXAMPLES

The present invention will be illustrated below with reference to Examples, but the present invention is not limited thereto.

In the following Examples, the melting points were measured with a micro melting point apparatus (Yanagimoto Seisakusho) and the values were not corrected. The nuclear magnetic resonance spectra ($^1$H-NMR and $^{13}$C-NMR) were measured with JNM-ECP600 (JEOL Ltd.) using, as solvent, $CDCl_3$, THF-$d_8$, or DMSO-$d_6$, and chemical shifts δ from tetramethylsilane as the internal standard were reported in ppm. The symbols used herein mean the following: s: singlet, d: doublet, dd: double doublet, t: triplet, m: multiplet, b: broad, J: coupling constant.

Example 1

2-[4-2-[5-[2-(4-dibutylamino-2-methoxypheny)vinyl]thiophene-2-yl]vinyl]-3-cyano-5,5-dimethyl-2 (5H)-furanylidene] propanedinitrile

[Formula 142]

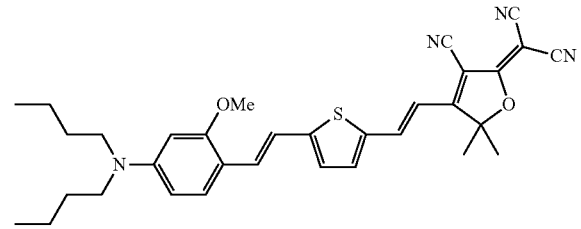

(1-1) 4-dibutylamino-2-methoxybenzaldehyde

[Formula 143]

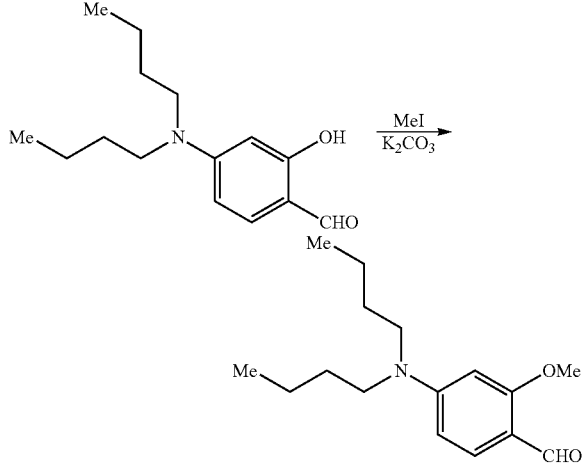

In 20 ml of 1-methyl-2-pyrrolidone were dissolved 2.49 g (9.9 mmol) of 4-dibutylamino-2-hydroxybenzaldehyde and 3.5 g (24.6 mmol) of methyl iodide. To this mixture was added 4.1 g (29.7 mmol) of anhydrous potassium carbonate and the mixture was stirred with heating at 50° C. for 2 hours. After the reaction mixture was added to water, extraction with ethyl acetate, washing with a saturated saline solution, drying over anhydrous sodium sulfate, and concentration were performed. The residue was purified by silica gel column chromatography to give 2.58 g of a colorless oily matter (yield: 98.1%).

$^1$H-NMR (600 MHz, CDCl$_3$) δ: 0.98 (6H, t, J=7.1 Hz), 1.35-1.41 (4H, m), 1.59-1.63 (4H, m), 3.34 (4H, t, J=7.7 Hz), 3.88 (3H, s), 6.02 (1H, s), 6.26 (1H, d, J=8.8 Hz), 7.69 (1H, d, J=8.8 Hz), 10.12 (1H, s)

(1-2) Dibutyl[3-methoxy-4-[2-(thiophene-2-yl)vinyl]phenyl] amine

[Formula 144]

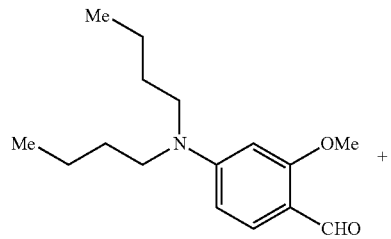

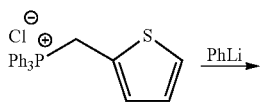

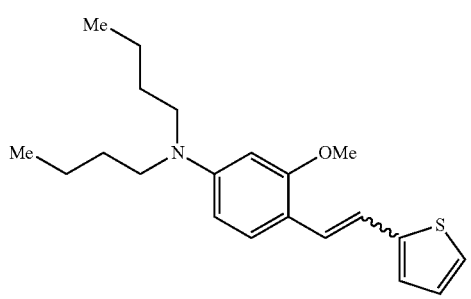

In a stream of argon, to 20 ml of tetrahydrofuran was added 2.4 g of phenyllithium (19% solution in dibutylether) (5.43 mmol), and 1.95 g (4.94 mmol) of 2-thenyl triphenylphosphonium chloride was added thereto under ice cooling. Next, 1.3 g (4.94 mmol) of 4-dibutylamino-2-methoxybenzaldehyde was dissolved in tetrahydrofuran and added dropwise. The mixture was stirred under ice cooling for 1.5 hours. After the reaction mixture was poured into water, extraction with ethyl acetate, washing with a saturated saline solution, drying over anhydrous sodium sulfate, and concentration were performed. The residue was purified by silica gel column chromatography to give 1.51 g of an orange oily matter (yield: 89.2%).

(1-3) 5-[2-(4-dibutylamino-2-methoxyphenyl)vinyl]thiophene-2-carboaldehyde

[Formula 145]

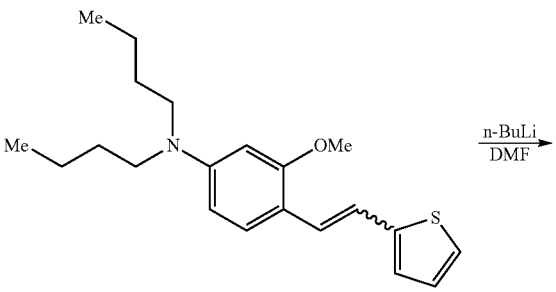

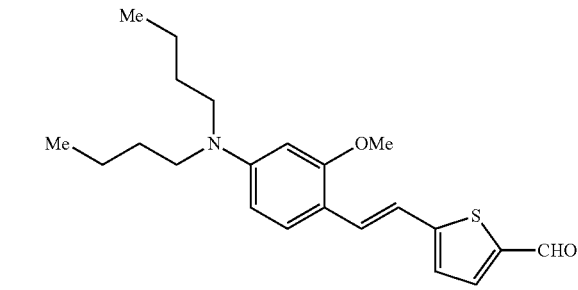

In a stream of argon, in 25 ml of tetrahydrofuran was dissolved 1.5 g (4.37 mmol) of dibutyl[3-methoxy-4-[2-(thiophene-2-yl)vinyl]phenyl]amine, and 4.1 ml of n-butyllithium (1.6 mol solution in hexane) (6.56 mmol) was added dropwise thereto under cooling at −70 to −73° C. After the mixture was stirred for 1 hour, 0.43 ml (5.54 mmol) of N,N-dimethylformamide was added dropwise. After the reaction mixture was stirred for 1 hour, the bath was removed and the temperature was allowed to rise. To this mixture, 10 ml of water was added dropwise. After the reaction mixture was poured into water, extraction with ethyl acetate, washing with a saturated saline solution, drying over anhydrous sodium sulfate, and concentration were performed. The residual liquid was dissolved in 200 ml of ether and 70 mg of iodine pieces were added thereto. After stirred at room temperature, the mixture was washed with a 5% sodium bisulfite solution and then with a saturated saline solution. After drying over anhydrous sodium sulfate and concentration were performed, the residue was purified by silica gel column chromatography to give 1.27 g of a reddish orange crystal (yield: 79.2%).

$^1$H-NMR (600 MHz, CDCl$_3$) δ: 0.97 (6H, t, J=7.7 Hz), 1.34-1.40 (4H, m), 1.57-1.63 (4H, m), 3.31 (4H, t, J=7.7 Hz), 3.88 (3H, s), 6.12 (1H, d, J=2.2 Hz), 6.25 (1H, dd, J=2.2 Hz, 8.8 Hz), 7.02 (1H, d, J=3.8 Hz), 7.06 (1H, d, J=15.9 Hz), 7.35 (1H, d, J=8.8 Hz), 7.41 (1H, d, J=15.9 Hz), 7.61 (1H, d, J=3.8 Hz), 9.79 (1H, s)

$^{13}$C-NMR (150 MHz, CDCl$_3$) δ: 14.0, 20.3, 29.5, 50.9, 55.2, 94.4, 104.6, 112.4, 116.0, 124.3, 128.7, 129.2, 137.7, 139.6, 150.1, 155.8, 159.1, 182.2

(1-4) 2-[4-[2-[5-[2-(4-dibutylamino-2-methoxyphenyl)vinyl] thiophene-2-yl]vinyl]-3-cyano-5,5-dimethyl-2(5H)-furanylidene]propanedinitrile

[Formula 146]

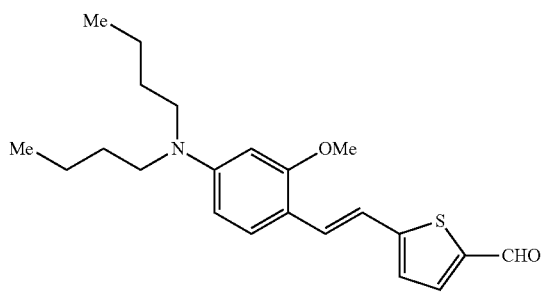

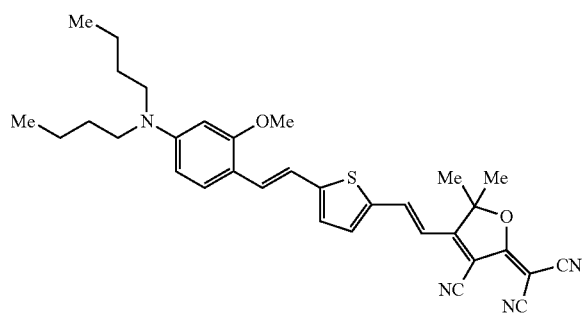

In 10 ml of ethanol and 3 ml of tetrahydrofuran were dissolved 300 mg (0.81 mmol) of 5-[2-(4-dibutylamino-2-methoxyphenyl)vinyl]thiophene-2-carboaldehyde and 177 mg (0.89 mmol) of 2-(3-cyano-4,5,5-trimethyl-2(5H)-furanylidene)propanedinitrile. To this mixture was added 63 mg of ammonium acetate, and the mixture was stirred at room temperature for 24 hours and further at 50° C. for 2.5 hours. The solvent was evaporated off and the residue was washed with ethanol to give 335 mg of a brown powdered crystal (yield: 75.1%; mp: 191-192° C.)

$^1$H-NMR (600 MHz, CDCl$_3$) δ: 0.98 (6H, t, J=7.7 Hz), 1.35-1.41 (4H, m), 1.59-1.64 (4H, m), 1.74 (6H, s), 3.33 (4H, t, J=7.7 Hz), 3.91 (3H, s), 6.11 (1H, d, J=2.2 Hz), 6.28 (1H, dd, J=2.2 Hz, 8.8 Hz), 6.53 (1H, d, J=15.4 Hz), 6.99 (1H, d, J=4.4 Hz), 7.08 (1H, d, J=15.9 Hz), 7.34 (1H, d, J=4.4 Hz), 7.37 (1H, d, J=8.8 Hz), 7.44 (1H, d, J=15.9 Hz), 7.75 (1H, d, J=15.4 Hz)

$^{13}$C-NMR (150 MHz, CDCl$_3$) δ: 14.0, 20.3, 26.6, 29.6, 50.9, 55.2, 55.3, 94.2, 96.7, 104.9, 111.1, 111.3, 111.7, 112.4, 115.7, 126.5, 129.0, 130.8, 137.0, 138.1, 139.4, 150.7, 156.6, 159.6, 172.8, 175.9

Example 2

2-[4-[2-[5-[2-(4-dibutylamino-2-methoxyphenyl)vinyl] thiophene-2-yl]vinyl]-3-cyano-5-methyl-5-trifluoromethyl-2(5H)-furanylidene]propanedinitrile

[Formula 147]

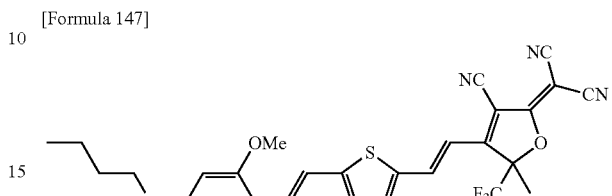

[Formula 148]

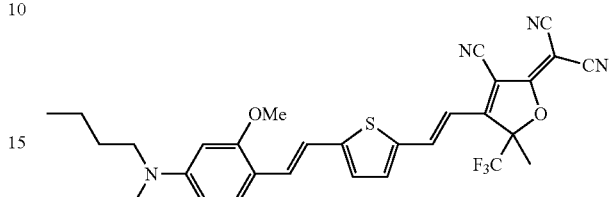

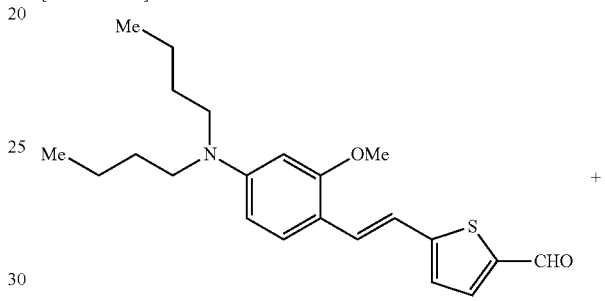

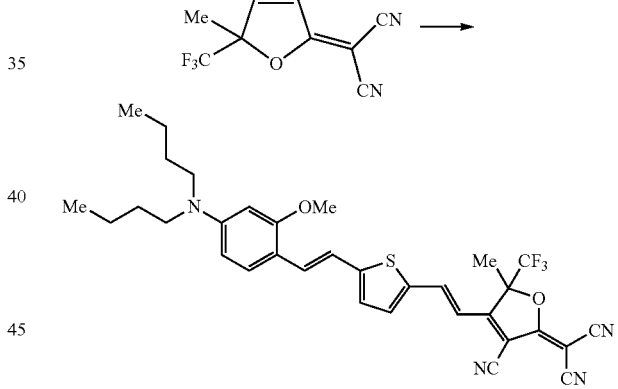

In 4 ml of ethanol and 1.5 ml of tetrahydrofuran were dissolved 100 mg (0.27 mmol) of 5-[2-(4-dibutylamino-2-methoxyphenyl)vinyl]thiophene-2-carboaldehyde and 75 mg (0.3 mmol) of 2-(3-cyano-4,5-dimethyl-5-trifluoromethyl-2(5H)-furanylidene)propanedinitrile. After the mixture was stirred at 50° C. for 2 hours, the solvent was evaporated off. The residue was washed with ethanol to give 120 mg of a brown powdered crystal (yield: 73.5%; mp: 191-193° C.)

$^1$H-NMR (600 MHz, DMSO-d$_6$) δ: 0.93 (6H, t, J=7.7 Hz), 1.31-1.37 (4H, m), 1.52-1.57 (4H, m), 2.09 (3H, s), 3.38 (4H, t, J=7.7 Hz), 3.88 (3H, s), 6.17 (1H, d, J=2.2 Hz), 6.35 (1H, dd, J=2.2 Hz, 8.8 Hz), 6.65 (1H, d, J=14.8 Hz), 7.30 (1H, d, J=3.8 Hz), 7.34 (1H, d, J=15.9 Hz), 7.47 (1H, d, J=15.9 Hz), 7.50 (1H, d, J=8.8 Hz), 7.87 (1H, d, J=3.8 Hz), 8.22 (1H, d, J=14.8 Hz)

$^{13}$C-NMR (150 MHz, DMSO-d$_6$) δ: 13.7, 17.9, 19.5, 29.1, 49.9, 54.3, 55.2, 94.0, 94.7, 105.1, 110.2, 111.25, 111.34, 111.8, 112.0, 115.7, 120.8, 128.3, 129.7, 131.6, 137.5, 141.1, 141.6, 150.9, 158.7, 159.5, 161.9, 176.1

Example 3

2-[4-[2-[5-[2-(4-dibutylamino-2-methoxyphenyl)vinyl]thiophene-2-yl]vinyl]-3-cyano-5-phenyl-5-trifluoromethyl-2(5H)-furanylidene]propanedinitrile

[Formula 149]

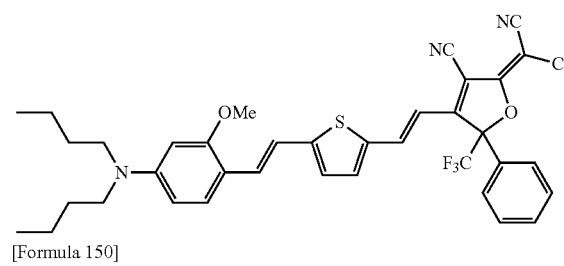

[Formula 150]

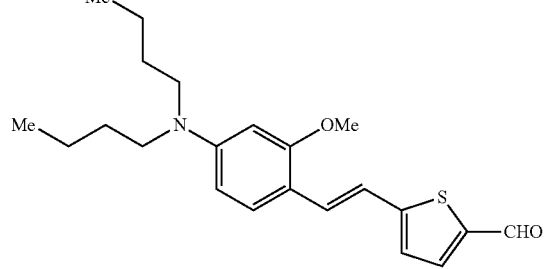

+

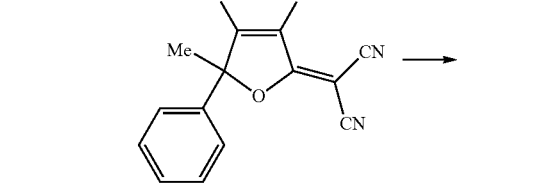

→

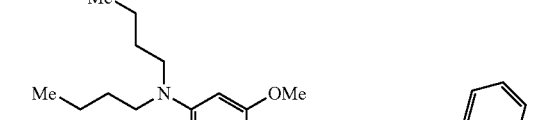

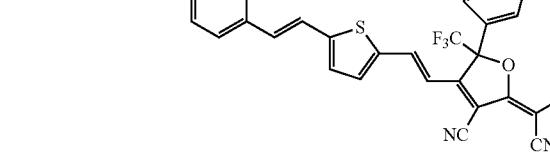

In 8 ml of ethanol and 2.5 ml of tetrahydrofuran were dissolved 226 mg (0.61 mmol) of 5-[2-(4-dibutylamino-2-methoxyphenyl)vinyl]thiophene-2-carboaldehyde and 210 mg (0.62 mmol) of 2-(3-cyano-4-methyl-5-phenyl-5-trifluoromethyl-2(5H)-furanylidene)propanedinitrile. The mixture was stirred with heating at 70° C. for 4 hours. The solvent was evaporated off and the residue was washed with ethanol. The residue was purified by silica gel column chromatography and washed with ethanol to give 378 mg of a dark brown powdered crystal (yield: 92.9%; mp: 203-204° C.)

$^1$H-NMR (600 MHz, CDCl$_3$) δ: 0.98 (6H, t, J=7.7 Hz), 1.35-1.41 (4H, m), 1.59-1.64 (4H, m), 3.34 (4H, t, J=7.7 Hz), 3.90 (3H, s), 6.09 (1H, d, J=2.2 Hz), 6.27 (1H, dd, J=2.2 Hz, 8.8 Hz), 6.56 (1H, d, J=15.4 Hz), 6.99 (1H, d, J=4.4 Hz), 7.09 (1H, d, J=15.4 Hz), 7.29 (1H, d, J=4.4 Hz), 7.37 (1H, d, J=8.8 Hz), 7.49 (1H, d, J=15.9 Hz), 7.51-7.56 (5H, m), 7.76 (1H, d, J=15.9 Hz)

$^{13}$C-NMR (150 MHz, CDCl$_3$) δ: 14.0, 20.3, 29.6, 51.0, 55.2, 57.4, 94.0, 105.2, 110.9, 111.1, 111.3, 111.4, 112.5, 115.7, 126.9, 127.3, 129.6, 129.7, 129.9, 131.4, 132.6, 137.7, 140.2, 141.6, 151.2, 159.7, 160.1, 161.7, 175.5

Example 4

2-[4-[2-[5-[2-(2-benzyloxy-4-dibutylaminophenyl)vinyl]thiophene-2-yl]vinyl]-3-cyano-5,5-dimethyl-2(5H)-furanylidene]propanedinitrile

[Formula 151]

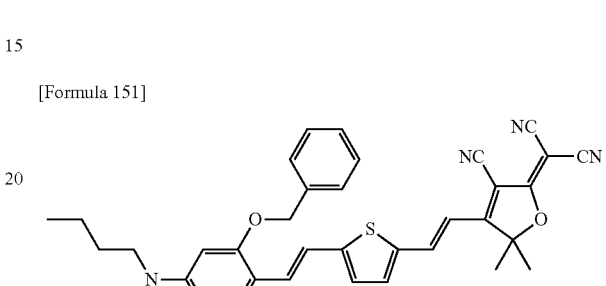

(4-1) 2-benzyloxy-4-dibutylaminobenzaldehyde

[Formula 152]

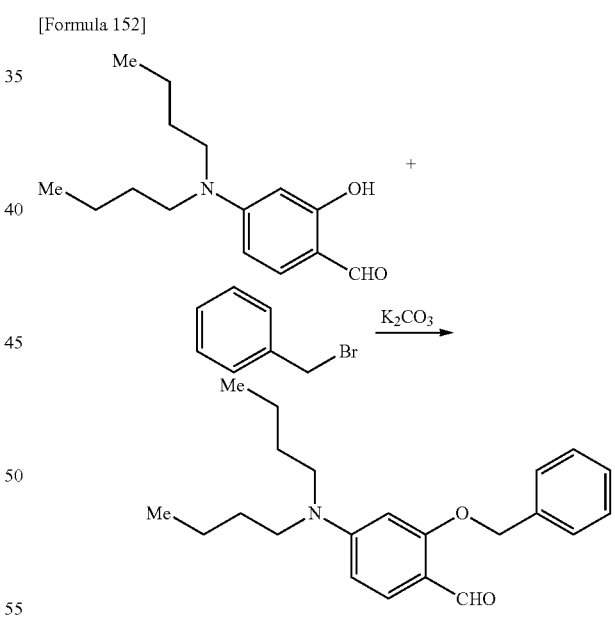

In 20 ml of 1-methyl-2-pyrrolidone were dissolved 1.86 g (7.46 mmol) of 4-dibutylamino-2-hydroxybenzaldehyde and 1.66 g (9.71 mmol) of benzyl bromide. To this mixture was added 2.06 g (14.9 mmol) of anhydrous potassium carbonate and the mixture was stirred with heating at 50° C. for 2 hours. After the reaction mixture was added to water, extraction with ethyl acetate, washing with a saturated saline solution, drying over anhydrous sodium sulfate, and concentration were performed. The residue was purified by silica gel column chromatography to give 2.31 g of a pale yellow crystal (yield: 91.3%).

¹H-NMR (600 MHz, CDCl₃) δ: 0.94 (6H, t, J=7.1 Hz), 1.29-1.34 (4H, m), 1.49-1.54 (4H, m), 3.27 (4H, t, J=7.1 Hz), 5.18 (2H, s), 6.02 (1H, s), 6.26 (1H, d, J=8.8 Hz), 7.31 (1H, m), 7.37-7.40 (2H, m), 7.40-7.44 (2H, m), 7.72 (1H, d, J=8.8 Hz), 10.24 (1H, s)

(4-2) [3-benzyloxy-4-[2-(thiophene-2-yl)vinyl]phenyl] dibutylamine

[Formula 153]

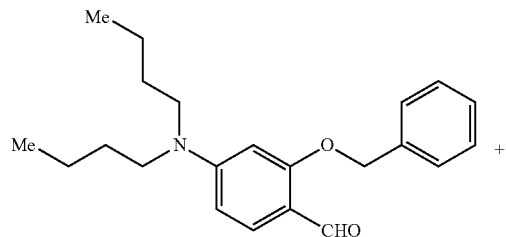

+

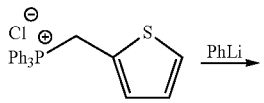

→ PhLi

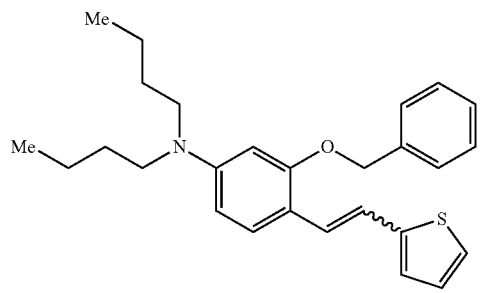

In a stream of argon, to 25 ml of tetrahydrofuran was added 3.3 g of phenyllithium (19% solution in dibutylether) (7.46 mmol), and 2.68 g (6.79 mmol) of 2-thenyl triphenylphosphonium chloride was added thereto under ice cooling. Next, 2.3 g (6.78 mmol) of 2-benzyloxy-4-dibutylaminobenzaldehyde was dissolved in tetrahydrofuran and added dropwise. The mixture was stirred under ice cooling for 2 hours. After the reaction mixture was poured into water, extraction with ethyl acetate, washing with a saturated saline solution, drying over anhydrous sodium sulfate, and concentration were performed. To the residue, 40 ml of ethyl acetate/hexane (4/1) was added and the precipitate was filtered off. The filtrate was concentrated and then purified by silica gel column chromatography to give 2.64 g of a yellow oily matter (yield: 92.9%).

(4-3) 5-[2-(2-benzyloxy-4-dibutylaminophenyl)vinyl] thiophene-2-carboaldehyde

[Formula 154]

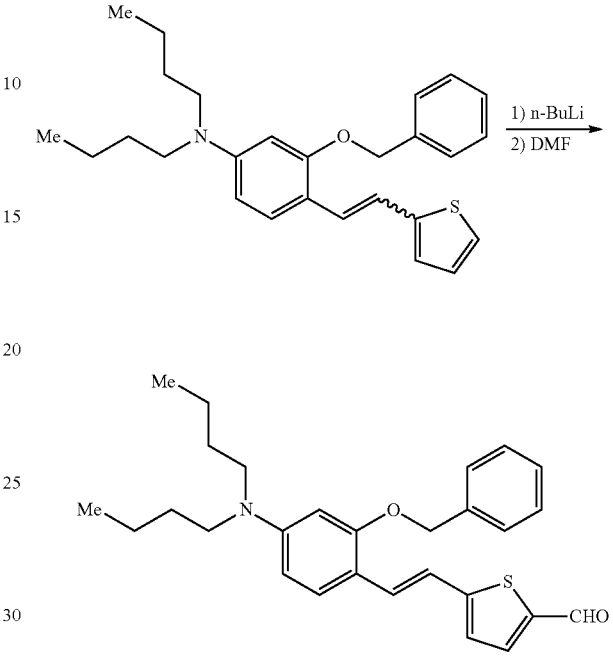

In a stream of argon, in 35 ml of tetrahydrofuran was dissolved 2.6 g (6.2 mmol) of [3-benzyloxy-4-[2-(thiophene-2-yl)vinyl]phenyl]dibutylamine, and 5.8 ml of n-butyllithium (1.6 mol solution in hexane) (9.28 mmol) was added dropwise thereto under cooling at −71 to −74° C. The mixture was stirred for 1 hour. Next, 0.59 g (8.07 mmol) of N,N-dimethylformamide was added dropwise. The reaction mixture was stirred for 1 hour and the temperature was allowed to rise. To this mixture, 10 ml of water was added dropwise. After the reaction mixture was poured into water, extraction with ethyl acetate, washing with a saturated saline solution, drying over anhydrous sodium sulfate, and concentration were performed. The residual liquid was dissolved in 300 ml of ether and 130 mg of iodine pieces were added thereto. After stirred at room temperature, the mixture was washed with a 5% sodium bisulfite solution and then with a saturated saline solution. After drying over anhydrous magnesium sulfate and concentration, the residue was crystallized from ethyl acetate/hexane (1/6) and the precipitate was separated by filtration to give 1.76 g of a reddish orange crystal. Further, the mother liquor was purified by silica gel column chromatography and the residue was crystallized in the same manner as described above to further give 0.12 g of the crystal (In total: 1.88 g; yield: 67.8%).

¹H-NMR (600 MHz, CDCl₃) δ: 0.94 (6H, t, J=7.7 Hz), 1.28-1.34 (4H, m), 1.48-1.53 (4H, m), 3.23 (4H, t, J=7.7 Hz), 5.16 (2H, s), 6.12 (1H, d, J=2.2 Hz), 6.26 (1H, dd, J=2.2 Hz, 8.8 Hz), 6.98 (1H, d, J=3.8 Hz), 7.11 (1H, d, J=15.9 Hz), 7.32-7.48 (7H, m), 7.60 (1H, d, J=3.8 Hz), 9.79 (1H, s)

¹³C-NMR (150 MHz, CDCl₃) δ: 14.1, 20.4, 29.6, 51.0, 70.5, 96.5, 105.0, 112.8, 116.0, 116.3, 127.1, 128.0, 128.8, 129.0, 129.4, 137.3, 137.8, 139.8, 150.0, 155.8, 158.4, 182.3

(4-4) 2-[4-[2-[5-[2-(2-benzyloxy-4-dibutylamino-phenyl) vinyl]thiophene-2-yl]vinyl]-3-cyano-5,5-dimethyl-2(5H)-furanylidene]propanedinitrile

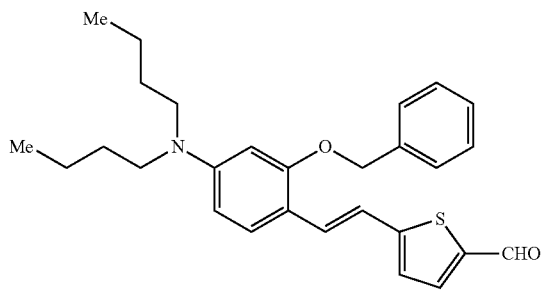

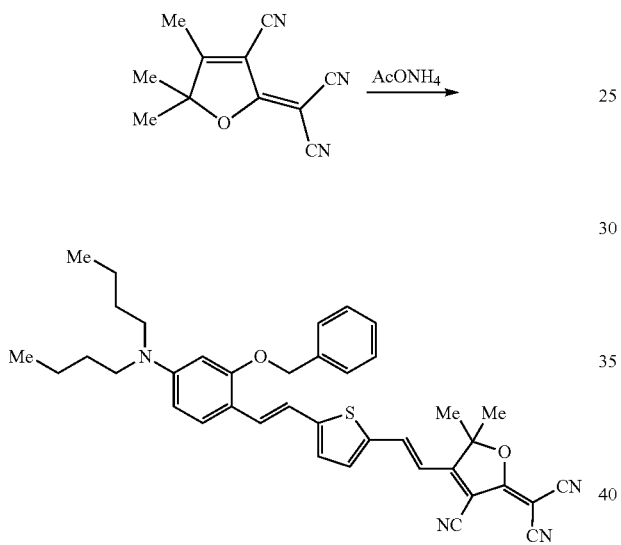

In 10 ml of ethanol and 5 ml of tetrahydrofuran were dissolved 300 mg (0.67 mmol) of 5-[2-(2-benzyloxy-4-dibutylaminophenyl)vinyl]thiophene-2-carboaldehyde and 147 mg (0.74 mmol) of 2-(3-cyano-4,5,5-trimethyl-2(5H)-furanylidene)propanedinitrile. To this mixture was added 52 mg of ammonium acetate, and the mixture was stirred at room temperature for 18 hours and further stirred with heating at 50° C. for 7 hours. The solvent was evaporated off and the residue was washed with ethanol to give 246 mg of a dark brown crystal (yield: 58.4%; mp: 218-219° C.)

$^1$H-NMR (600 MHz, DMSO-d$_6$) δ: 0.89 (6H, t, J=7.7 Hz), 1.25-1.311 (4H, m), 1.40-1.45 (4H, m), 1.78 (6H, s), 3.27 (4H, t, J=7.7 Hz), 5.27 (2H, s), 6.18 (1H, d, J=2.2 Hz), 6.29 (1H, dd, J=2.2 Hz, 8.8 Hz), 6.63 (1H, d, J=15.4 Hz), 7.15 (1H, d, J=3.8 Hz), 7.30 (1H, d, J=15.9 Hz), 7.32-7.35 (1H, m), 7.41-7.48 (5H, m), 7.43 (1H, d, J=15.9H), 7.73 (1H, d, J=3.8 Hz), 8.09 (1H, d, J=15.4 Hz)

$^{13}$C-NMR (150 MHz, DMSO-d$_6$) δ: 13.7, 19.5, 25.5, 29.0, 49.9, 52.3, 69.3, 95.5, 96.0, 98.3, 104.9, 111.25, 111.33, 111.9, 112.3, 113.0, 115.9, 126.9, 127.2, 127.6, 128.4, 129.1, 137.0, 137.3, 139.1, 140.2, 150.0, 154.7, 157.9, 174.3, 176.8

Example 5

2-[4-[2-[5-[2-(2-benzyloxy-4-dibutylaminophenyl) vinyl] thiophene-2-yl]vinyl]-3-cyano-5-methyl-5-trifluoromethyl-2(5H)-furanylidene]propanedinitrile

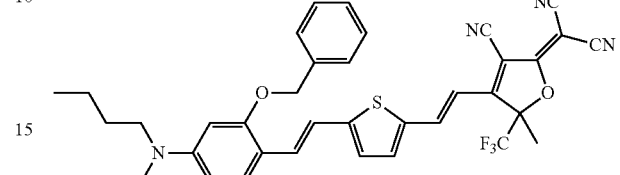

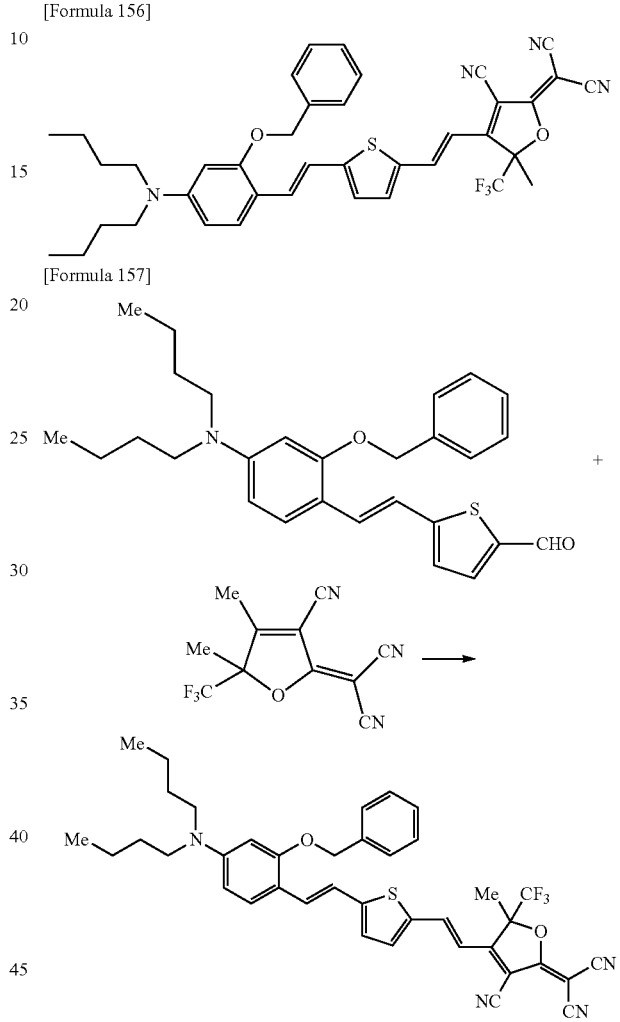

In 10 ml of ethanol and 2 ml of tetrahydrofuran were dissolved 730 mg (1.63 mmol) of 5-[2-(2-benzyloxy-4-dibutylaminophenyl)vinyl]thiophene-2-carboaldehyde and 380 mg (1.5 mmol) of 2-(3-cyano-4,5-dimethyl-5-trifluoromethyl-2(5H)-furanylidene)propanedinitrile. The mixture was stirred at room temperature for 19 hours and further stirred with heating at 50° C. for 6 hours. The solvent was evaporated off and the residue was washed with ethanol to give 860 mg of a dark reddish brown crystal (yield: 94.0%; mp: 184-185° C.)

$^1$H-NMR (600 MHz, CDCl$_6$) δ: 0.94 (6H, t, J=7.7 Hz), 1.28-1.35 (4H, m), 1.49-1.54 (4H, m), 1.90 (3H, s), 3.26 (4H, t, J=7.7 Hz), 5.21 (2H, s), 6.09 (1H, d, J=2.2 Hz), 6.28 (1H, dd, J=2.2 Hz, 8.8 Hz), 6.43 (1H, d, J=15.4 Hz), 7.00 (1H, d, J=3.8 Hz), 7.17 (1H, d, J=15.9 Hz), 7.34-7.46 (6H, m), 7.38 (1H, d, J=8.8 Hz), 7.56 (1H, d, J=15.9 Hz), 8.15 (1H, d, J=15.4 Hz)

$^{13}$C-NMR (150 MHz, CDCl$_3$) δ: 14.0, 19.3, 20.3, 29.5, 51.0, 70.4, 96.1, 105.4, 109.9, 110.8, 111.4, 112.8, 116.0, 122.4, 126.9, 127.4, 128.1, 128.8, 129.9, 132.7, 136.9, 137.7, 140.2, 141.1, 151.0159.2, 159.4, 161.7, 174.9, 175.5

Example 6

2-[4-[2-[5-[2-(2-benzyloxy-4-dibutylaminophenyl)vinyl] thiophene-2-yl]vinyl]-3-cyano-5-phenyl-5-trifluoromethyl-2(5H)-furanylidene]propanedinitrile

[Formula 158]

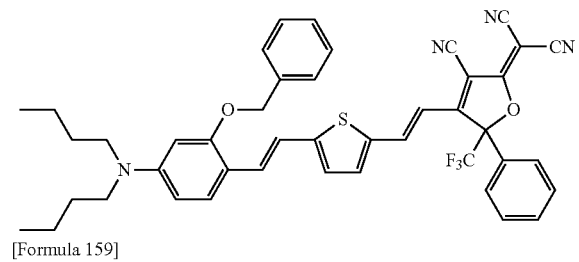

[Formula 159]

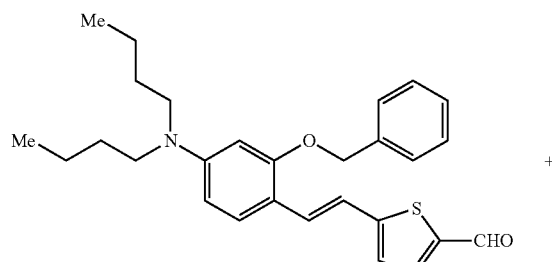

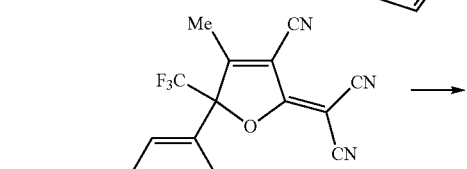

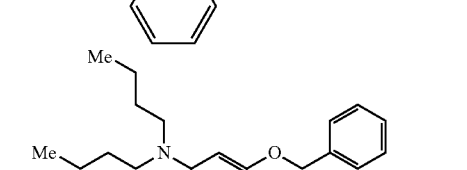

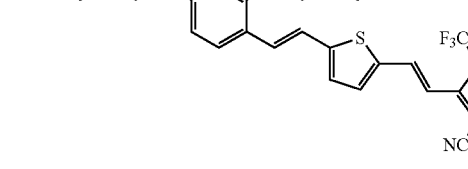

In 15 ml of ethanol and 5 ml of tetrahydrofuran were dissolved 730 mg (1.63 mmol) of 5-[2-(2-benzyloxy-4-dibutylaminophenyl)vinyl]thiophene-2-carboaldehyde and 573 mg (1.82 mmol) of 2-(3-cyano-4-methyl-5-phenyl-5-trifluoromethyl-2(5H)-furanylidene)propanedinitrile. The mixture was stirred at room temperature for 21 hours and further stirred with heating at 50° C. for 3 hours. The solvent was evaporated off and the residue was washed with ethanol to give 1.15 g of a dark reddish brown crystal (yield: 94.7%; mp: 196-197° C.)

$^1$H-NMR (600 MHz, CDCl$_6$) δ: 0.94 (6H, t, J=7.7 Hz), 1.28-1.34 (4H, m), 1.48-1.53 (4H, m), 3.25 (4H, t, J=7.7 Hz), 5.20 (2H, s), 6.08 (1H, d, J=2.2 Hz), 6.27 (1H, dd, J=2.2 Hz, 8.8 Hz), 6.55 (1H, d, J=15.4 Hz), 6.93 (1H, d, J=3.8 Hz), 7.13 (1H, d, J=15.9 Hz), 7.28 (1H, d, J=3.8 Hz), 7.33-7.45 (6H, m), 7.50-7.56 (6H, m), 7.79 (1H, d, J=15.4 Hz)

$^{13}$C-NMR (150 MHz, CDCl$_3$) δ: 13.9, 20.3, 29.5, 51.0, 57.5, 70.4, 96.1, 105.4, 110.9, 111.1, 111.2, 111.3, 112.8, 116.0, 126.8, 126.9, 127.3, 128.1, 128.7, 129.7, 129.9, 131.4, 132.7, 136.9, 137.8, 140.1, 141.6, 151.0, 159.2, 159.6, 161.7, 175.5

Example 7

2-[4-[2-[4-[2-(4-dibutylamino-2-methoxyphenyl)vinyl]phenyl] vinyl]-3-cyano-5,5-dimethyl-2(5H)-furanylidene] propanedinitrile

[Formula 160]

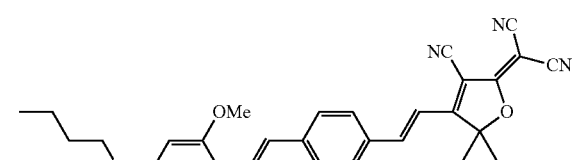

(7-1) Dibutyl[4-[2-[4-(tert-butyldiphenylsiloxymethyl) phenyl]vinyl]-3-methoxyphenyl]amine

[Formula 161]

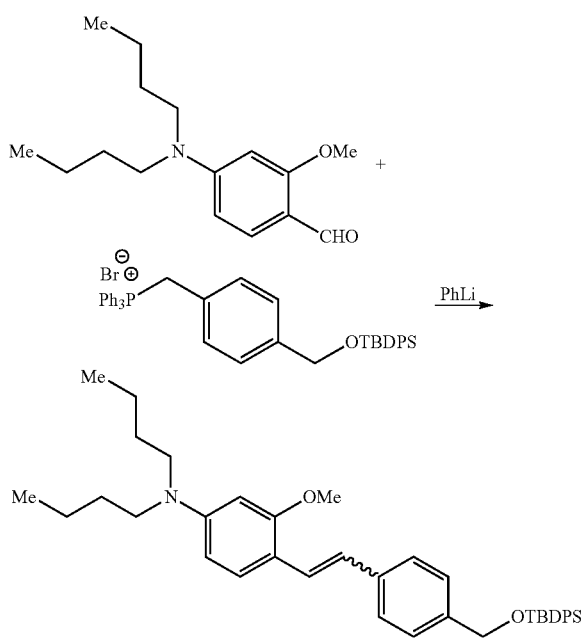

In a stream of argon, to 35 ml of tetrahydrofuran was added 3.33 g of phenyllithium (19% solution in dibutylether) (7.53 mmol), and 4.8 g (6.84 mmol) of 4-(tert-butyldiphenylsiloxymethyl)benzyltriphenylphosphonium bromide was added thereto under ice cooling. Next, 1.8 g (6.838 mmol) of 4-dibutylamino-2-methoxybenzaldehyde was dissolved in tetrahydrofuran and added dropwise. The mixture was stirred for 1.5 hours. After the reaction mixture was poured into water, extraction with ethyl acetate, washing with a saturated saline solution, drying over anhydrous sodium sulfate, and concentration were performed. Ethyl acetate/hexane (5/1) was added to the residue and the precipitate was filtered off. The filtrate was reconcentrated and the residue was purified by silica gel column chromatography to give 3.92 g of a yellow liquid (yield: 94.7%).

(7-2) [4-[2-(4-dibutylamino-2-methoxyphenyl)vinyl]phenyl] methanol

[Formula 162]

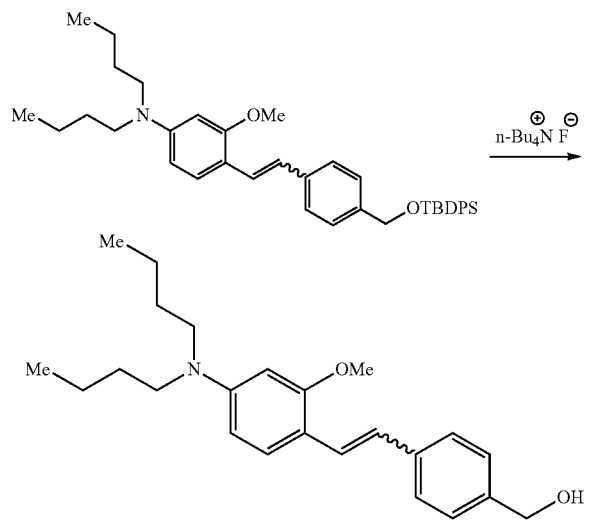

In 50 ml of tetrahydrofuran was dissolved 3.9 g (6.44 mmol) of dibutyl[4-[2-[4-(tert-butyldiphenylsiloxymethyl)phenyl] vinyl]-3-methoxyphenyl]amine, and 20 ml of tetrabutylammonium fluoride (1 mol solution in tetrahydrofuran) was added dropwise thereto with stirring at room temperature. The mixture was stirred for 2.5 hours. After the reaction mixture was poured into water, extraction with ethyl acetate, washing with a saturated saline solution, drying over anhydrous sodium sulfate, and concentration were performed. The residue was purified by silica gel column chromatography to give 2.28 g of a yellow liquid (yield: 96.4%).

(7-3) 4-[2-(4-dibutylamino-2-methoxyphenyl)vinyl]benzaldehyde

[Formula 163]

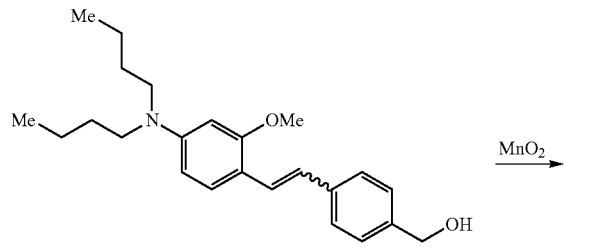

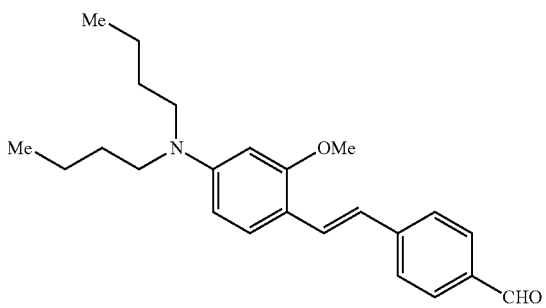

In 60 ml of dichloromethane was dissolved 2.28 g (6.2 mmol) of [4-[2-(4-dibutylamino-2-methoxyphenyl)vinyl]phenyl] methanol, and 10.8 g of active manganese dioxide was added thereto. The mixture was stirred at room temperature for 18 hours. After the reaction mixture was filtrated and concentrated, the residue was dissolved in 170 ml of ether, 80 mg of iodine pieces were added thereto, and the mixture was stirred. The reaction mixture was washed with a 5% sodium bisulfite solution and then with a saturated saline solution, and dried over anhydrous magnesium sulfate. After ether was evaporated off, the residue was purified by silica gel column chromatography to give 1.54 g of an orange oily matter (yield: 67.9%).

$^1$H-NMR (600 MHz, CDCl$_3$) δ: 0.97 (6H, t, J=7.7 Hz), 1.35-1.41 (4H, m), 1.58-1.63 (4H, m), 3.31 (4H, t, J=7.7 Hz), 3.88 (3H, s), 6.15 (1H, d, J=2.2 Hz), 6.28 (1H, dd, J=2.2 Hz, 8.8 Hz), 6.95 (1H, d, J=15.9 Hz), 7.45 (1H, d, J=8.8 Hz), 7.56 (1H, d, J=15.9 Hz), 7.60 (2H, d, J=8.2 Hz), 7.80 (2H, d, J=8.2 Hz), 9.94 (1H, s)

$^{13}$C-NMR (150 MHz, CDCl$_3$) δ: 14.0, 20.4, 29.6, 50.9, 55.3, 94.6, 104.6, 113.2, 122.3, 126.1, 127.6, 128.0, 130.2, 134.1, 145.6, 149.9, 158.8, 191.7

(7-4) 2-[4-[2-[4-[2-(4-dibutylamino-2-methoxyphenyl)vinyl] phenyl]vinyl]-3-cyano-5, 5-dimethyl-2(5H)-furanylidene] propanedinitrile

[Formula 164]

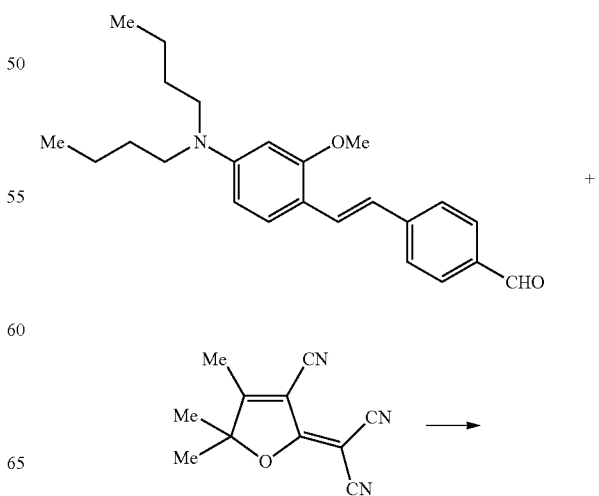

-continued

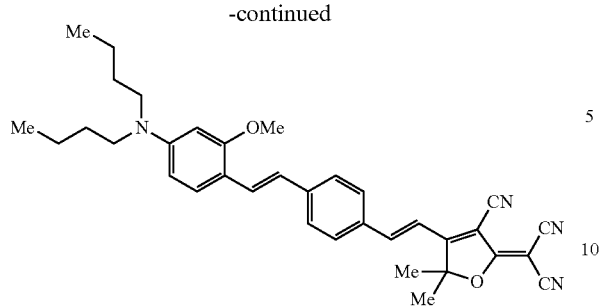

In 15 ml of ethanol and 5 ml of tetrahydrofuran were dissolved 500 mg (1.37 mmol) of 4-[2-(4-dibutylamino-2-methoxyphenyl)vinyl]benzaldehyde and 300 mg (1.51 mmol) of 2-(3-cyano-4,5,5-trimethyl-2(5H)-furanylidene)propanedinitrile. To this mixture was added 106 mg of ammonium acetate, and the mixture was stirred at room temperature for 23 hours. The solvent was evaporated off in a reduced pressure. The residue was washed with ethanol and then purified by silica gel column chromatography. The crystal was washed with ethanol to give 693 mg of a black powder (yield: 92.6%; mp: 258-260° C.)

$^1$H-NMR (600 MHz, CDCl$_3$) δ: 0.98 (6H, t, J=7.7 Hz), 1.35-1.41 (4H, m), 1.59-1.64 (4H, m), 1.80 (6H, s), 3.33 (4H, t, J=7.7 Hz), 3.90 (3H, s), 6.14 (1H, d, J=2.2 Hz), 6.29 (1H, dd, J=2.2 Hz, 8.8 Hz), 6.94 (1H, d, J=16.5 Hz), 6.98 (1H, d, J=15.9 Hz), 7.45 (1H, d, J=8.8 Hz), 7.54 (2H, d, J=8.8 Hz), 7.56 (2H, d, J=8.8 Hz), 7.58 (1H, d, J=15.9 Hz), 7.59 (1H, d, J=16.5 Hz)

$^{13}$C-NMR (150 MHz, CDCl$_3$) δ: 14.0, 20.4, 26.6, 29.6, 50.9, 55.3, 57.0, 94.4, 97.3, 98.4, 104.8, 110.6, 111.2, 111.9, 113.0, 122.0, 126.7, 128.0, 128.2, 129.8, 131.3, 144.7, 147.3, 150.1, 159.0, 173.8, 175.5

Example 8

2-[4-[2-[4-[2-(4-dibutylamino-2-methoxyphenyl)vinyl]phenyl] vinyl]-3-cyano-5-methyl-5-trifluoromethyl-2(5H)-furanylidene]propanedinitrile

[Formula 165]

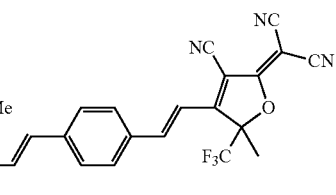

[Formula 166]

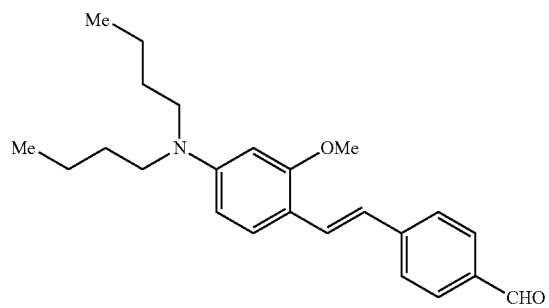

+

-continued

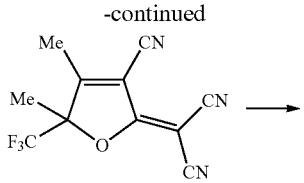

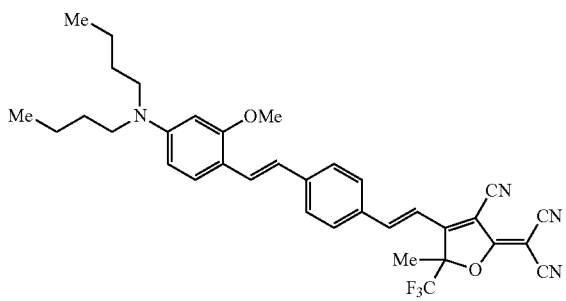

In 15 ml of ethanol and 5 ml of tetrahydrofuran were dissolved 500 mg (1.37 mmol) of 4-[2-(4-dibutylamino-2-methoxyphenyl)vinyl]benzaldehyde and 380 mg (1.50 mmol) of 2-(3-cyano-4,5-dimethyl-5-trifluoromethyl-2(5H)-furanylidene)propanedinitrile. The mixture was stirred at 50° C. for 9 hours. The solvent was evaporated off and the residue was washed with ethanol. The residue was purified by silica gel column chromatography and washed with ethanol to give 320 mg of a black powder (yield: 38.9%; mp: 175-177° C.)

$^1$H-NMR (600 MHz, CDCl$_3$) δ: 0.98 (6H, t, J=7.7 Hz), 1.35-1.42 (4H, m), 1.59-1.64 (4H, m), 1.97 (3H, s), 3.33 (4H, t, J=7.7 Hz), 3.90 (3H, s), 6.14 (1H, d, J=2.2 Hz), 6.29 (1H, dd, J=2.2 Hz, 8.8 Hz), 6.91 (1H, d, J=15.9 Hz), 6.96 (1H, d, J=16.5 Hz), 7.46 (1H, d, J=8.8 Hz), 7.55 (2H, d, J=8.8 Hz), 7.58 (2H, d, J=8.8 Hz), 7.63 (1H, d, J=16.5 Hz), 8.00 (1H, d, J=15.9 Hz)

$^{13}$C-NMR (150 MHz, CDCl$_3$) δ: 14.0, 19.2, 20.3, 29.6, 50.9, 55.3, 59.8, 94.3, 99.3, 104.8, 110.0, 110.4, 110.6, 111.9, 113.0, 121.9, 126.8, 128.4, 128.9, 130.5, 131.4, 145.8, 149.6, 150.3, 159.2, 163.3, 174.8, 186.4

Example 9

2-[4-[2-[4-[2-(4-dibutylamino-2-methoxyphenyl)vinyl]phenyl] vinyl]-3-cyano-5-phenyl-5-trifluoromethyl-2(5H)-furanylidene]propanedinitrile

[Formula 167]

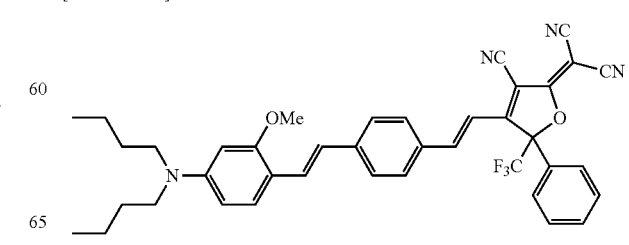

-continued

[Formula 168]

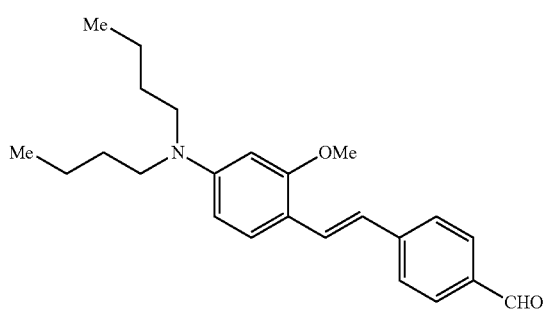

+

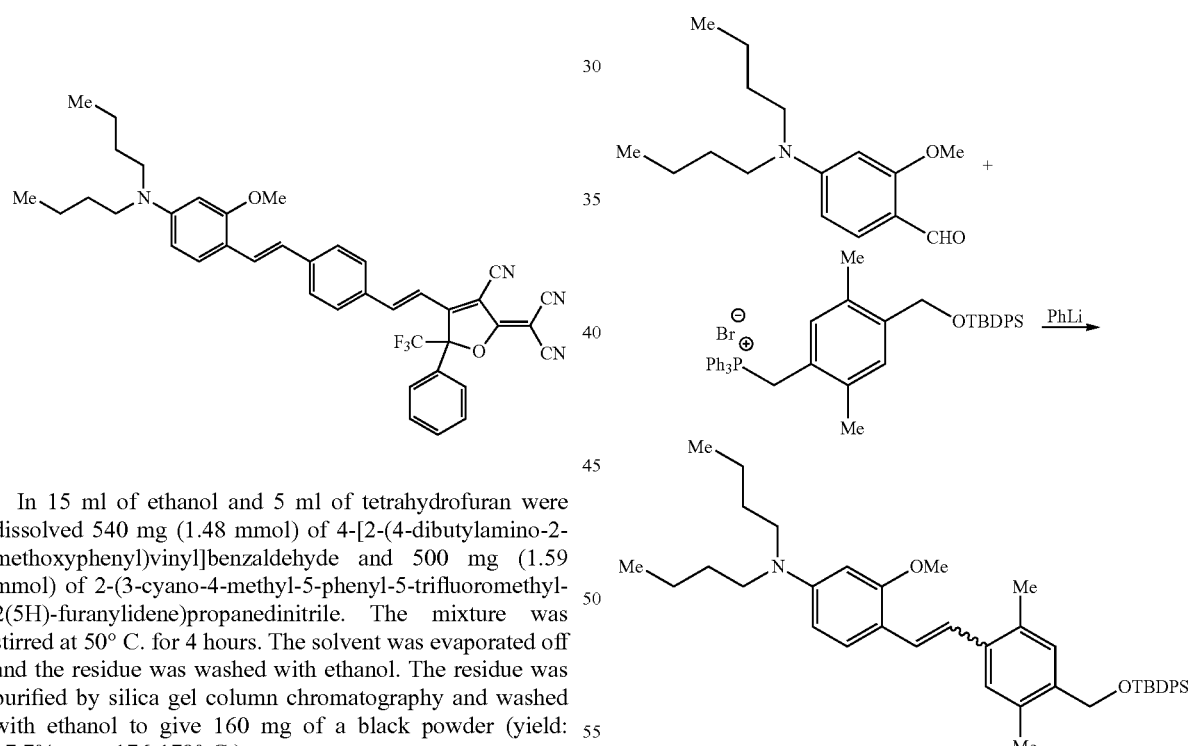

In 15 ml of ethanol and 5 ml of tetrahydrofuran were dissolved 540 mg (1.48 mmol) of 4-[2-(4-dibutylamino-2-methoxyphenyl)vinyl]benzaldehyde and 500 mg (1.59 mmol) of 2-(3-cyano-4-methyl-5-phenyl-5-trifluoromethyl-2(5H)-furanylidene)propanedinitrile. The mixture was stirred at 50° C. for 4 hours. The solvent was evaporated off and the residue was washed with ethanol. The residue was purified by silica gel column chromatography and washed with ethanol to give 160 mg of a black powder (yield: 17.7%; mp: 176-178° C.)

$^1$H-NMR (600 MHz, CDCl$_3$) δ: 0.97 (6H, t, J=7.7 Hz), 1.35-1.41 (4H, m), 1.58-1.63 (4H, m), 3.32 (4H, t, J=7.7 Hz), 3.89 (3H, s), 6.12 (1H, d, J=2.2 Hz), 6.27 (1H, dd, J=2.2 Hz, 8.8 Hz), 6.92 (1H, d, J=15.9 Hz), 7.00 (1H, d, J=15.9 Hz), 7.43-7.59 (10H, m), 7.59 (1H, d, J=15.9 Hz), 7.66 (1H, d, J=15.9 Hz)

$^{13}$C-NMR (150 MHz, CDCl$_3$) δ: 14.0, 20.3, 29.6, 50.9, 55.3, 60.0, 94.3, 99.9, 104.8, 110.1, 110.3, 110.6, 112.9, 113.1, 121.9, 126.7, 126.9, 128.4, 128.9, 129.3, 129.9, 130.5, 131.4, 131.7, 145.8, 150.3, 150.4, 159.2, 163.5, 175.0

Example 10

2-[4-[2-[4-[2-(4-dibutylamino-2-methoxyphenyl)vinyl]-2,5-dimethylphenyl]vinyl]-3-cyano-5,5-dimethyl-2(5H)-furanylidene]propanedinitrile

[Formula 169]

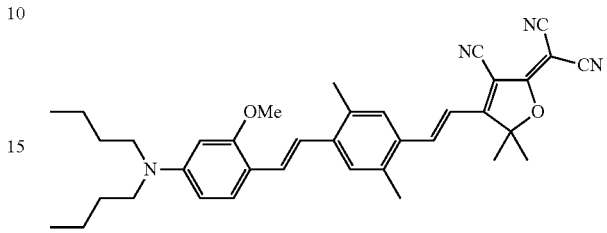

(10-1) Dibutyl[4-[2-[4-(tert-butyldiphenylsiloxymethyl)-2,5-dimethylphenyl]vinyl]-3-methoxyphenyl]amine

[Formula 170]

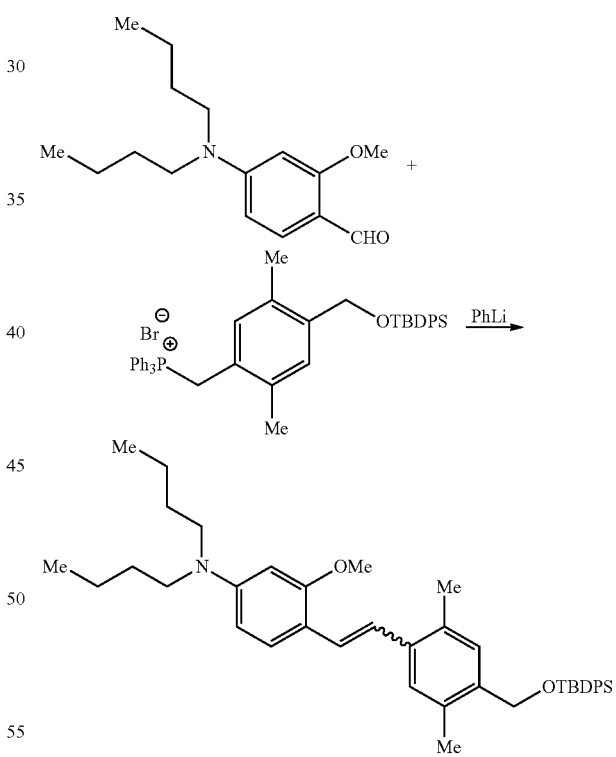

In a stream of argon, to 20 ml of tetrahydrofuran was added 2.54 g of phenyllithium (19% solution in dibutylether) (5.74 mmol), and 3.57 g (4.89 mmol) of 4-(tert-butyldiphenylsiloxymethyl)-2,5-dimethylbenzyltriphenylphosphonium bromide was added thereto under ice cooling. Next, 1.26 g (4.78 mmol) of 4-dibutylamino-2-methoxybenzaldehyde was dissolved in tetrahydrofuran and added dropwise. The mixture was stirred for 1.5 hours. After the reaction mixture was poured into water, extraction with ethyl acetate, washing with a saturated saline solution, drying over anhydrous sodium sulfate, and concentration were performed. The residue was purified by silica gel column chromatography to give 2.7 g of an orange liquid (yield: 89.1%).

(10-2) [4-[2-(4-dibutylamino-2-methoxyphenyl)vinyl]-2,5-dimethylphenyl]methanol

[Formula 171]

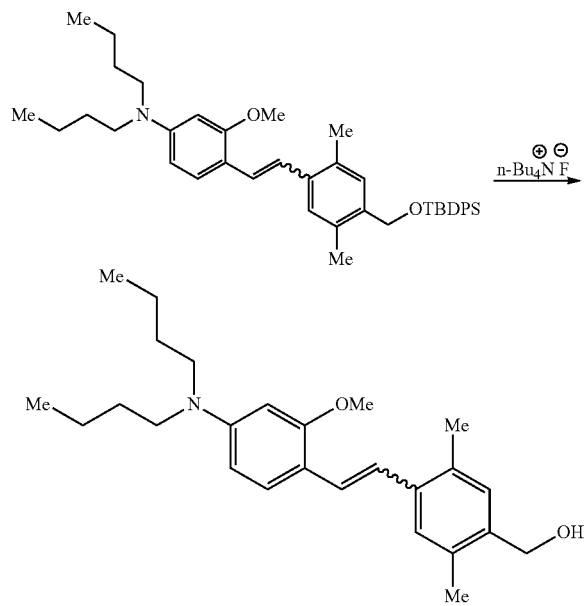

In 30 ml of tetrahydrofuran was dissolved 2.7 g (4.26 mmol) of dibutyl[4-[2-[4-(tert-butyldiphenylsiloxymethyl)-2,5-dimethylphenyl]vinyl]-3-methoxyphenyl]amine, and 13.0 ml of tetrabutylammonium fluoride (1 mol solution in tetrahydrofuran) was added dropwise thereto with stirring at room temperature. The mixture was stirred for 3 hours. After the reaction mixture was poured into water, extraction with ethyl acetate, washing with a saturated saline solution, drying over anhydrous sodium sulfate, and concentration were performed. The residue was purified by silica gel column chromatography to give 1.57 g of a yellow liquid (yield: 93.5%).

(10-3) 4-[2-(4-dibutylamino-2-methoxyphenyl)vinyl]-2,5-dimethylbenzaldehyde

[Formula 172]

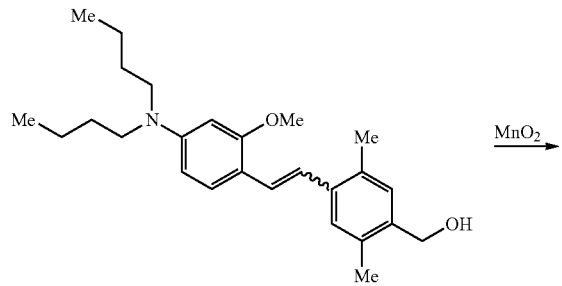

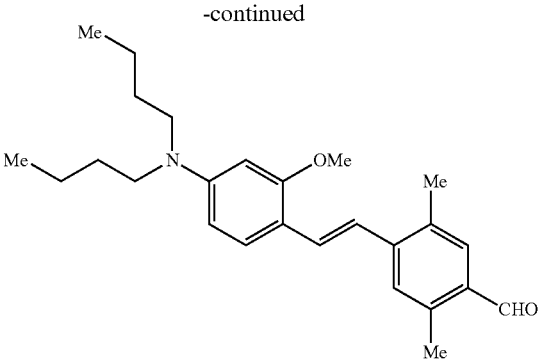

In 50 ml of dichloromethane was dissolved 1.5 g (3.79 mmol) of [4-[2-(4-dibutylamino-2-methoxyphenyl)vinyl]-2,5-dimethylphenyl]methanol, and 6.6 g of active manganese dioxide was added thereto. The mixture was stirred at room temperature for 21 hours. After the reaction mixture was filtrated and concentrated, the residue was dissolved in 50 ml of ether. 60 mg of iodine pieces were added thereto, and the reaction mixture was stirred. The reaction mixture was washed with a 5% sodium bisulfite solution and then with a saturated saline solution, and dried over anhydrous magnesium sulfate. After ether was evaporated off, the residue was purified by silica gel column chromatography to give 1.09 g of a reddish orange crystal (yield: 72.4%).

$^1$H-NMR (600 MHz, CDCl$_3$) δ: 0.97 (6H, t, J=7.7 Hz), 1.35-1.41 (4H, m), 1.58-1.63 (4H, m), 2.41 (3H, s), 2.65 (3H, s), 3.32 (4H, t, J=7.7 Hz), 3.89 (3H, s), 6.16 (1H, d, J=2.2 Hz), 6.29 (1H, dd, J=2.2 Hz, 8.8 Hz), 7.10 (1H, d, J=15.9 Hz), 7.44 (1H, d, J=15.9 Hz), 7.46 (1H, d, J=8.8 Hz), 7.49 (1H, s), 7.56 (1H, s), 10.17 (1H, s)

$^{13}$C-NMR (150 MHz, CDCl$_3$) δ: 14.0, 19.3, 19.4, 20.4, 29.5, 50.9, 55.3, 94.7, 104.6, 113.7, 120.1, 127.5, 128.0, 131.8, 132.8, 134.0, 134.8, 138.1, 143.4, 149.7, 158.7, 192.2

(10-4) 2-[4-[2-[4-[2-(4-dibutylamino-2-methoxyphenyl)vinyl]-2,5-dimethylphenyl]vinyl]-3-cyano-5,5-dimethyl-2(5H)-furanylidene]propanedinitrile

[Formula 173]

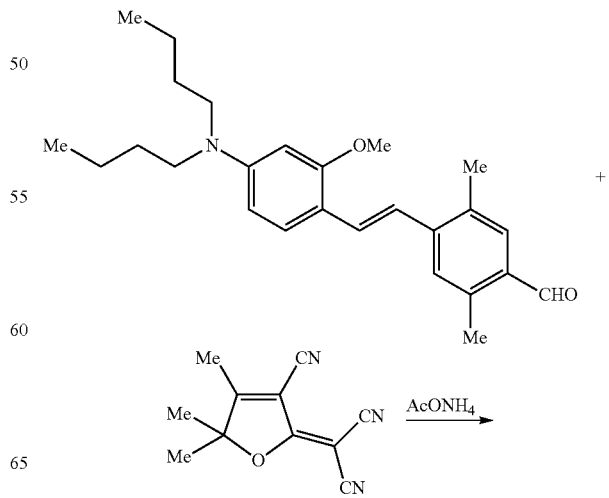

-continued

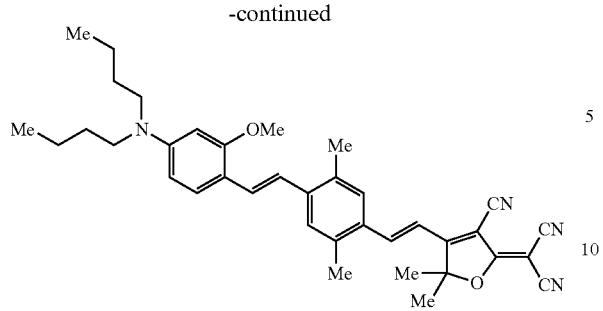

In 6 ml of ethanol and 2 ml of tetrahydrofuran were dissolved 250 mg (0.64 mmol) of 4-[2-(4-dibutylamino-2-methoxyphenyl) vinyl]-2,5-dimethylbenzaldehyde and 140 mg (0.70 mmol) of 2-(3-cyano-4,5,5-trimethyl-2(5H)-furanylidene) propanedinitrile. To this mixture was added 49 mg of ammonium acetate, and the mixture was stirred at 70° C. for 4 hours. The solvent was evaporated off, and the residue was purified by silica gel column chromatography and washed with ethanol to give 205 mg of a black powder (yield: 56.2%; mp: 242-244° C.).

$^1$H-NMR (600 MHz, CDCl$_3$) δ: 0.98 (6H, t, J=7.7 Hz), 1.36-1.42 (4H, m), 1.59-1.64 (4H, m), 1.79 (6H, s), 2.42 (3H, s), 2.47 (3H, s), 3.33 (4H, t, J=7.7 Hz), 3.90 (3H, s), 6.15 (1H, s), 6.30 (1H, d, J=8.8 Hz), 6.89 (1H, d, J=15.9 Hz), 7.10 (1H, d, J=15.9 Hz), 7.47 (1H, d, J=8.8 Hz), 7.49 (1H, d, J=15.9 Hz), 7.50 (1H, s), 7.53 (1H, s), 8.03 (1H, d, J=15.9 Hz)

$^{13}$C-NMR (150 MHz, CDCl$_3$) δ: 14.0, 19.4, 19.6, 20.4, 26.6, 29.6, 50.9, 55.3, 56.6, 94.5, 97.3, 104.7, 111.0, 111.3, 112.1, 112.9, 113.5, 119.6, 126.8, 128.2, 128.25, 128.28, 130.0, 133.8, 137.7, 143.4, 144.8, 150.1, 159.0, 174.2, 175.8

Example 11

2-[4-[2-[4-[2-(4-dibutylamino-2-methoxyphenyl)vinyl]-2,5-dimethylphenyl]vinyl]-3-cyano-5-methyl-5-trifluoromethyl-2(5H)-furanylidene]propanedinitrile

[Formula 174]

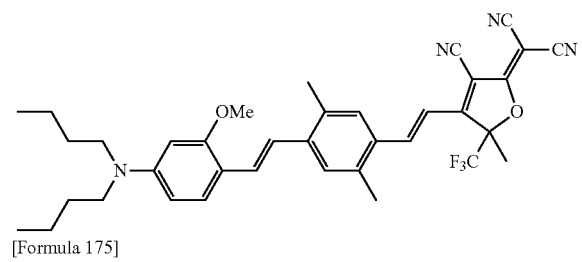

[Formula 175]

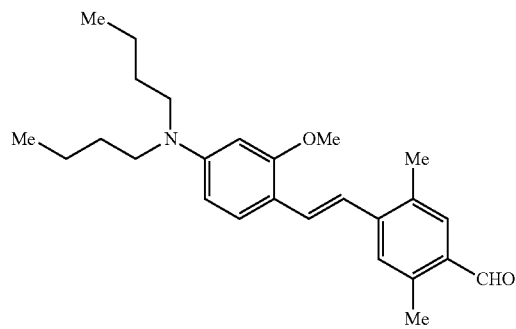

+

-continued

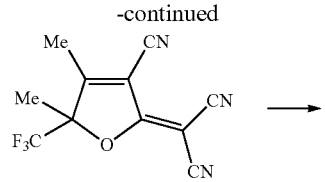

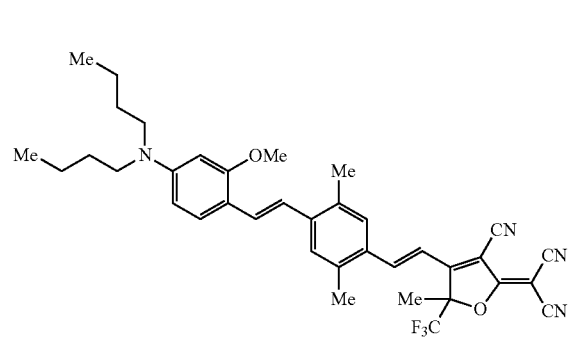

In 9 ml of ethanol and 3 ml of tetrahydrofuran were dissolved 440 mg (1.12 mmol) of 4-[2-(4-dibutylamino-2-methoxyphenyl) vinyl]-2,5-dimethylbenzaldehyde and 310 mg (1.22 mmol) of 2-(3-cyano-4,5-dimethyl-5-trifluoromethyl-2(5H)-furanylidene)propanedinitrile. After the mixture was stirred at 70° C. for 6 hours, the solvent was evaporated off. The residue was purified by silica gel column chromatography and washed with ethanol to give 522 mg of a black powder (yield: 74.3%; mp: 205-207° C.)

$^1$H-NMR (600 MHz, CDCl$_3$) δ: 0.98 (6H, t, J=7.7 Hz), 1.36-1.42 (4H, m), 1.60-1.65 (4H, m), 1.96 (3H, s), 2.42 (3H, s), 2.48 (3H, s), 3.33 (4H, t, J=7.7 Hz), 3.90 (3H, s), 6.15 (1H, d, J=2.2 Hz), 6.30 (1H, dd, J=2.2 Hz, 8.8 Hz), 6.84 (1H, d, J=15.9 Hz), 7.11 (1H, d, J=15.9 Hz), 7.48 (1H, d, J=8.8 Hz), 7.50 (1H, s), 7.55 (1H, s), 7.55 (1H, d, J=15.9 Hz), 8.43 (1H, d, J=15.9 Hz)

$^{13}$C-NMR (150 MHz, CDCl$_3$) δ: 14.0, 19.2, 19.4, 19.7, 20.3, 29.6, 50.9, 55.3, 59.3, 94.4, 98.1, 104.8, 110.2, 110.8, 110.9, 111.5, 119.3, 126.8, 128.4, 128.6, 129.2, 130.1, 134.0, 139.3, 144.7, 147.0, 150.3, 159.2, 163.7, 175.0

Example 12

2-[4-[2-[4-[2-(4-dibutylamino-2-methoxyphenyl)vinyl]-2,5-dimethylphenyl]vinyl]-3-cyano-5-phenyl-5-trifluoromethyl-2(5H)-furanylidene]propanedinitrile

[Formula 176]

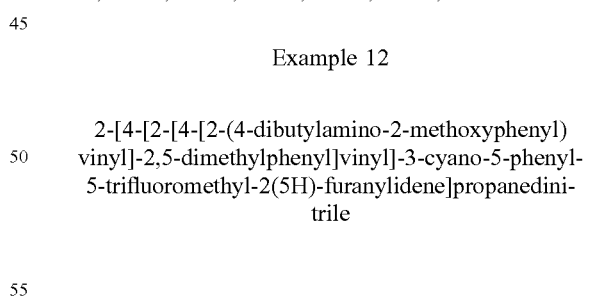

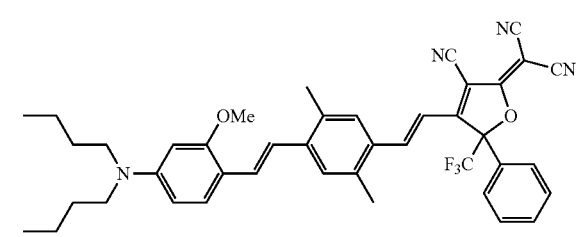

-continued

[Formula 177]

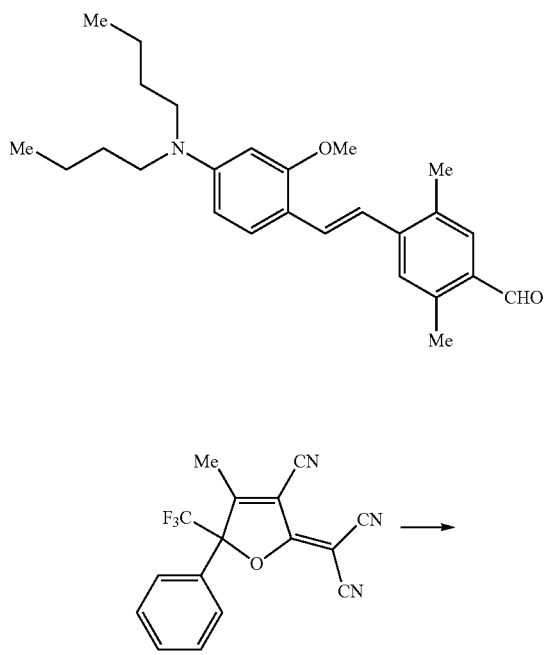

In 9 ml of ethanol and 3 ml of tetrahydrofuran were dissolved 400 mg (1.02 mmol) of 4-[2-(4-dibutylamino-2-methoxyphenyl) vinyl]-2,5-dimethylbenzaldehyde and 360 mg (1.14 mmol) of 2-(3-cyano-4-methyl-5-phenyl-5-trifluoromethyl-2(5H)-furanylidene)propanedinitrile. The mixture was stirred at 70° C. for 2 hours. The solvent was evaporated off and the residue was washed with ethanol. The residue was purified by silica gel column chromatography to give 441 mg of a black powder (yield: 62.8%; mp: 177-179° C.).

$^1$H-NMR (600 MHz, CDCl$_3$) δ: 0.97 (6H, t, J=7.7 Hz), 1.35-1.41 (4H, m), 1.58-1.63 (4H, m), 2.14 (3H, s), 2.38 (3H, s), 3.32 (4H, t, J=7.7 Hz), 3.88 (3H, s), 6.13 (1H, d, J=2.2 Hz), 6.29 (1H, dd, J=2.2 Hz, J=8.8 Hz), 7.00 (1H, d, J=15.4 Hz), 7.08 (1H, d, J=15.9 Hz), 7.45-7.59 (9H, m), 7.86 (1H, d, J=15.4 Hz)

$^{13}$C-NMR (150 MHz, CDCl$_3$) δ: 14.0, 19.1, 19.6, 20.3, 29.5, 50.9, 55.3, 59.6, 94.3, 99.5, 104.8, 110.3, 110.4, 110.7, 112.7, 113.5, 119.4, 126.7, 126.9, 128.4, 128.6, 129.1, 129.6, 129.9, 130.1, 131.7, 134.0, 139.1, 144.7, 148.1, 150.2, 159.1, 164.2, 175.1

Example 13

2-[4-[2-[5-[2-[4-dibutylamino-2-(tert-butyldiphenylsiloxy) phenyl)vinyl]thiophene-2-yl]vinyl]-3-cyano-5,5-dimethyl-2(5H)-furanylidene]propanedinitrile

[Formula 178]

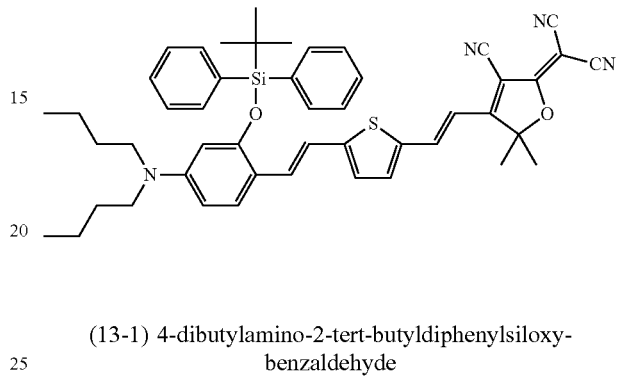

(13-1) 4-dibutylamino-2-tert-butyldiphenylsiloxybenzaldehyde

[Formula 179]

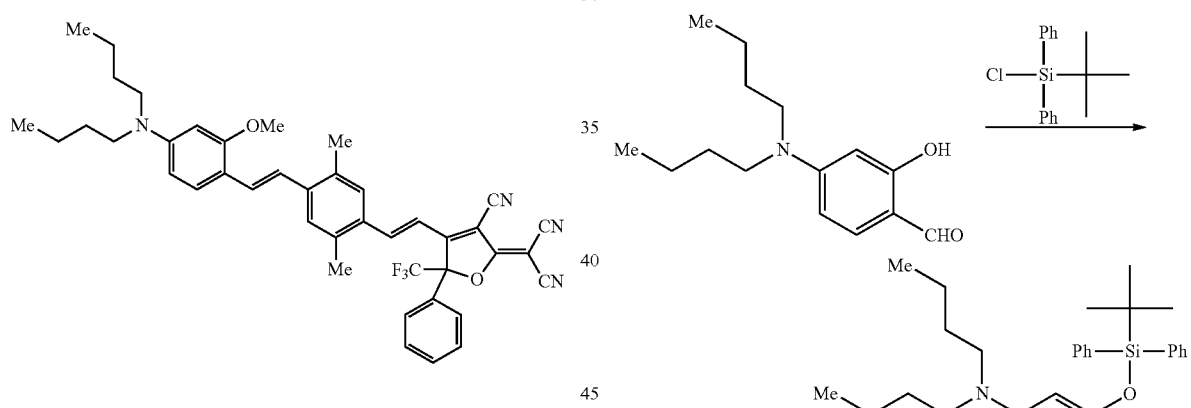

In 40 ml of N,N-dimethylformamide were dissolved 5.39 g (21.6 mmol) of 4-dibutylamino-2-hydroxybenzaldehyde and 4.08 g (60.0 mmol) of imidazole. Next, 6.13 g (22.3 mmol) of tert-butylchlorodiphenylsilane was added dropwise thereto with stirring at room temperature. The mixture was stirred for 3.5 hours. After the reaction mixture was poured into water, extraction with ethyl acetate, washing with a saturated saline solution, drying over anhydrous sodium sulfate, and concentration were performed. The residue was purified by silica gel column chromatography to give 10.3 g of a colorless oily matter (yield: 97.7%).

$^1$H-NMR (600 MHz, CDCl$_3$) δ: 0.74 (6H, t, J=7.1 Hz), 0.97-1.03 (4H, m), 1.10 (9H, s), 1.13-1.18 (4H, m), 2.84 (4H, t, J=7.1 Hz), 5.56 (1H, d, J=2.2 Hz), 6.18 (1H, dd, J=2.2 Hz, 9.3 Hz), 7.37-7.40 (4H, m), 7.41-7.45 (2H, m), 7.69-7.76 (5H, m), 10.48 (1H, s)

(13-2) Dibutyl[3-(tert-butyldiphenylsiloxy)-4-[2-(thiophene-2-yl)vinyl]phenyl]amine

[Formula 180]

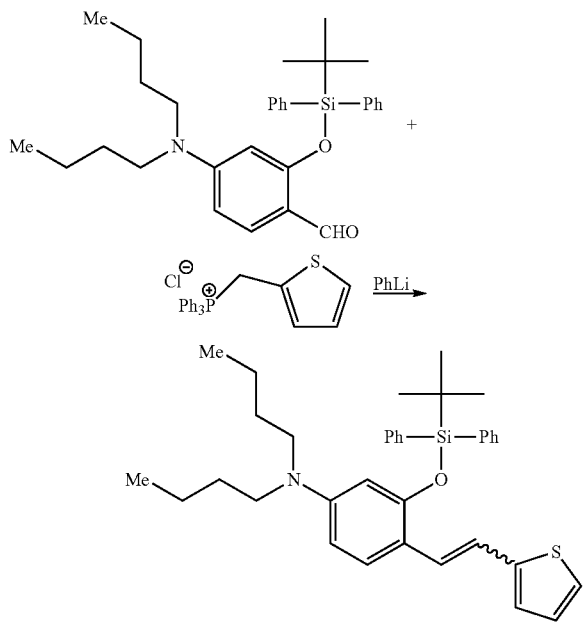

In a stream of argon, to 30 ml of tetrahydrofuran was added 3.17 g of phenyllithium (19% solution in dibutylether) (7.16 mmol), and 2.57 g (6.5 mmol) of 2-thenyl triphenylphosphonium chloride was added thereto under ice cooling. Next, 3.17 g (6.5 mmol) of 4-dibutylamino-2-tert-butyldiphenylsiloxybenzaldehyde was dissolved in tetrahydrofuran and added dropwise. The mixture was stirred for 3 hours. After the reaction mixture was poured into water, extraction with ethyl acetate, washing with a saturated saline solution, drying over anhydrous sodium sulfate, and concentration were performed. The residue was purified by silica gel column chromatography to give 2.32 g of a yellowish brown oily matter (yield: 62.9%).

(13-3) 5-[2-[4-dibutylamino-2-(tert-butyldiphenylsiloxy)phenyl]vinyl]thiophene-2-carboaldehyde

[Formula 181]

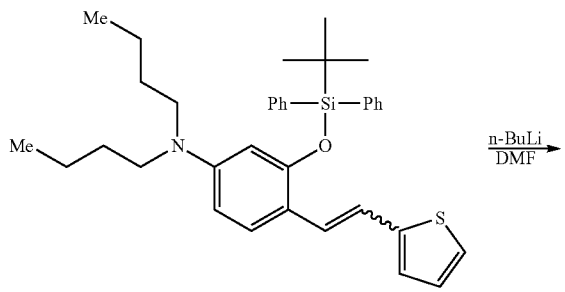

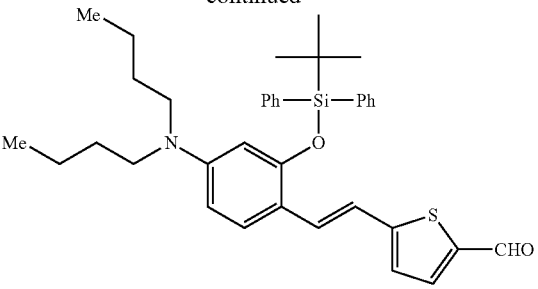

In a stream of argon, in 25 ml of tetrahydrofuran was dissolved 2.32 g (4.09 mmol) of dibutyl[3-(tert-butyldiphenylsiloxy)-4-[2-(thiophene-2-yl)vinyl]phenyl] amine, and 3.8 ml of n-butyllithium (1.6 mol solution in hexane) (6.08 mmol) was added dropwise thereto under cooling at −70 to −73° C. After the mixture was stirred for 1 hour, 0.4 ml (5.77 mmol) of N,N-dimethylformamide was added dropwise. The reaction mixture was stirred for 1 hour and the temperature was allowed to rise. To this mixture, 10 ml of water was added dropwise. After the reaction mixture was poured into water, extraction with ethyl acetate, washing with a saturated saline solution, drying over anhydrous sodium sulfate, and concentration were performed. The residual liquid was dissolved in 200 ml of ether and 100 mg of iodine pieces were added thereto. After stirred at room temperature, the mixture was washed with a 5% sodium bisulfite solution and then with a saturated saline solution. Drying over anhydrous sodium sulfate and concentration were performed. The residue was purified by silica gel column chromatography to give 1.99 g of a dark red oily matter (yield: 81.9%).

$^1$H-NMR (600 MHz, CDCl$_3$) δ: 0.74 (6H, t, J=7.1 Hz), 0.97-1.03 (4H, m), 1.06-1.21 (4H, m), 1.17 (9H,$), 2.82 (4H, t, J=7.1 Hz), 5.70 (1H, s), 6.18 (1H, d, J=8.8 Hz), 7.02 (1H, d, J=3.8 Hz), 7.06 (1H, d, J=15.9 Hz), 7.37-7.43 (7H, m), 7.63 (1H, d, J=3.8 Hz), 7.75-7.78 (5H, m), 9.81 (1H, s)

$^{13}$C-NMR (150 MHz, CDCl$_3$) δ: 13.8, 19.6, 20.0, 26.6, 26.6, 29.2, 50.7, 102.8, 105.5, 113.8, 115.1, 124.4, 127.1, 127.8, 129.0, 129.9, 132.7, 135.4, 137.9, 139.6, 149.4, 155.1, 155.8, 182.2

(13-4) 2-[4-[2-[5-[2-[4-dibutylamino-2-(tert-butyldiphenylsiloxy)phenyl]vinyl]thiophene-2-yl]vinyl]-3-cyano-5,5-dimethyl-2(5H)-furanylidene]propanedinitrile

[Formula 182]

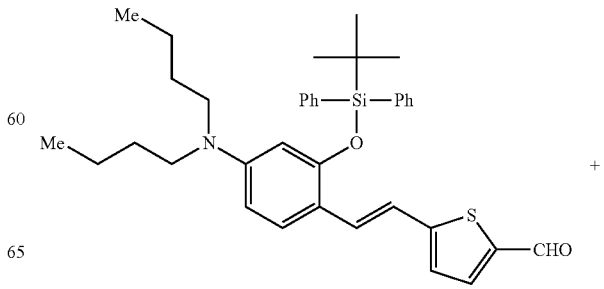

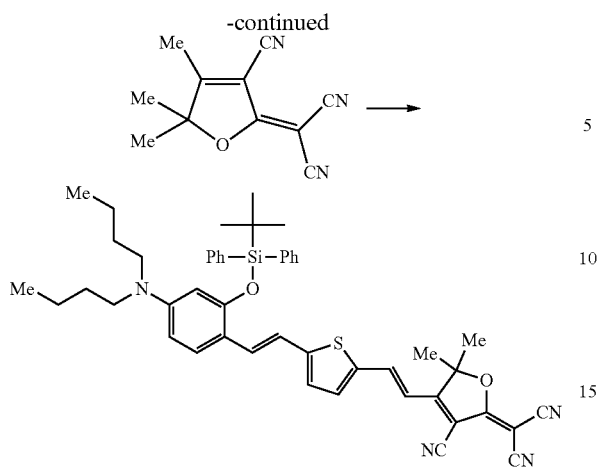

In 12 ml of ethanol and 4 ml of tetrahydrofuran were dissolved 500 mg (0.84 mmol) of 5-[2-[4-dibutylamino-2-(tert-butyldiphenylsiloxy)phenyl]vinyl]thiophene-2-carboaldehyde and 185 mg (0.93 mmol) of 2-(3-cyano-4,5,5-trimethyl-2(5H)-furanylidene)propanedinitrile. To this mixture was added 65 mg of ammonium acetate, and the mixture was stirred at room temperature for 47 hours. The solvent was evaporated off and the residue was washed with ethanol. The residue was purified by silica gel column chromatography and washed with ethanol to give 369 mg of a dark greenish brown crystal (yield: 56.6%; mp: 218-219° C.)

$^1$H-NMR (600 MHz, CDCl$_3$) δ: 0.75 (6H, t, J=7.1 Hz), 0.98-1.04 (4H, m), 1.14-1.21 (4H, m), 1.19 (9H, s), 1.74 (6H, s), 2.84 (4H, t, J=7.7 Hz), 5.71 (1H, d, J=2.2 Hz), 6.21 (1H, dd, J=2.2 Hz, 8.8 Hz), 6.52 (1H, d, J=15.4 Hz), 7.01 (1H, d, J=3.8 Hz), 7.09 (1H, d, J=15.9 Hz), 7.38-7.45 (8H, m), 7.75-7.79 (5H, m), 7.82 (1H, d, J=15.9 Hz)

$^{13}$C-NMR (150 MHz, CDCl$_3$) δ: 13.8, 19.7, 20.0, 26.6, 26.7, 29.3, 50.7, 55.5, 95.2, 96.7, 102.7, 105.9, 111.1, 111.2, 111.7, 112.5, 113.9, 114.8, 126.3, 127.7, 127.9, 130.1, 130.9, 132.5, 135.4, 136.9, 138.0, 139.3, 150.0, 155.7, 156.5, 172.7, 176.0

Example 14

2-[4-[2-[5-[2-[4-dibutylamino-2-(tert-butyldiphenylsiloxy) phenyl)vinyl]thiophene-2-yl]vinyl]-3-cyano-5-methyl-5-trifluoromethyl-2(5H)-furanylidene]propanedinitrile

[Formula 183]

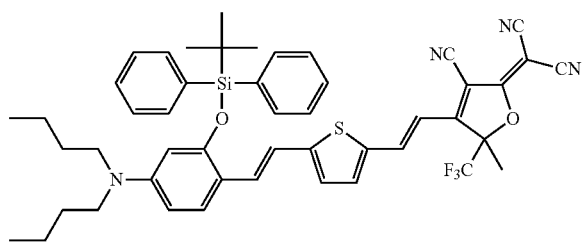

[Formula 184]

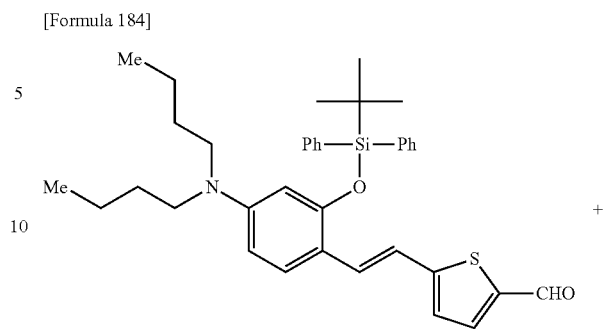

+

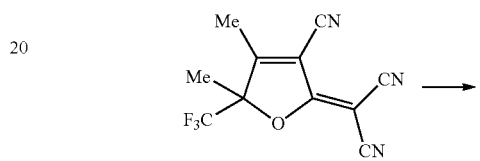

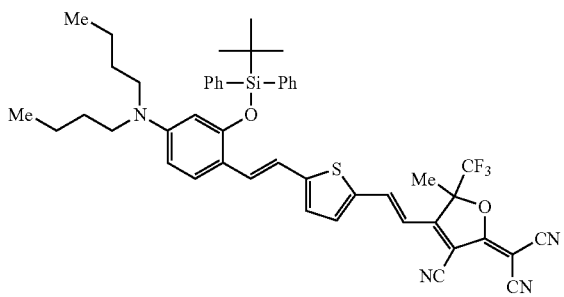

In 12 ml of ethanol and 4 ml of tetrahydrofuran were dissolved 500 mg (0.84 mmol) of 5-[2-[4-dibutylamino-2-(tert-butyldiphenylsiloxy)phenyl]vinyl]thiophene-2-carboaldehyde and 234 mg (0.92 mmol) of 2-(3-cyano-4,5-dimethyl-5-trifluoromethyl-2 (5H)-furanylidene)propanedinitrile. The mixture was stirred with heating at 60° C. for 4.5 hours. The solvent was evaporated off and the residue was washed with ethanol. The residue was purified by silica gel column chromatography and washed with ethanol to give 576 mg of a dark reddish brown crystal (yield: 82.6%; mp: 186-187° C.)

$^1$H-NMR (600 MHz, CDCl$_3$) δ: 0.76 (6H, t, J=7.1 Hz), 0.98-1.04 (4H, m), 1.08-1.21 (4H, m), 1.19 (9H), 1.89 (3H, s), 2.86 (4H, t, J=7.1 Hz), 5.70 (1H, d, J=2.2 Hz), 6.22 (1H, dd, J=2.2 Hz, 8.8 Hz), 6.42 (1H, d, J=15.4 Hz), 7.05 (1H, d, J=4.4 Hz), 7.10 (1H, d, J=15.4 Hz), 7.38-7.46 (7H, m), 7.48 (1H, d, J=4.4 Hz), 7.74-7.76 (4H, m), 7.93 (1H, d, J=15.4 Hz), 8.18 (1H, d, J=15.4 Hz)

$^{13}$C-NMR (150 MHz, CDCl$_3$) δ: 13.8, 19.3, 19.7, 20.0, 26.7, 29.3, 50.8, 57.3, 93.3, 102.6, 106.2, 109.8, 110.8, 111.4, 114.0, 114.7, 121.2, 127.2, 128.0, 130.1, 132.3, 132.4, 132.6, 135.4, 137.6, 140.3, 141.0, 150.6, 156.2, 159.5, 161.5, 175.5

Example 15

2-[4-[2-[5-[2-[4-dibutylamino-2-(tert-butyldiphenyl-siloxy) phenyl)vinyl]thiophene-2-yl]vinyl]-3-cyano-5-phenyl-5-trifluoromethyl-2(5H)-furanylidene]propanedinitrile

[Formula 185]

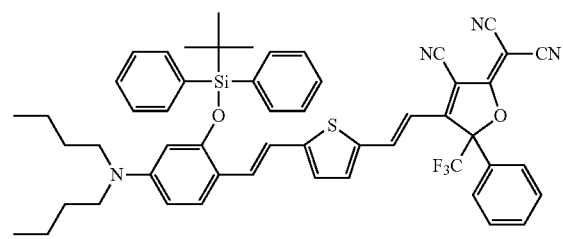

[Formula 186]

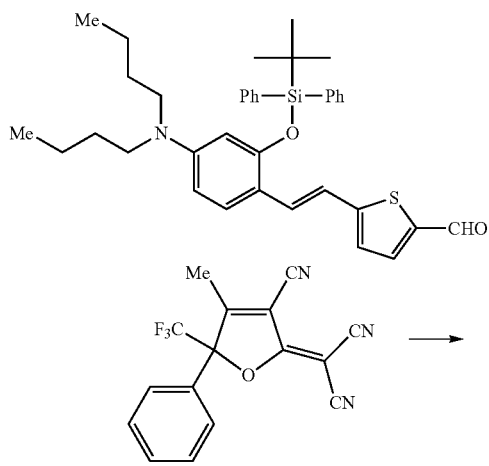

In 12 ml of ethanol and 4 ml of tetrahydrofuran were dissolved 500 mg (0.84 mmol) of 5-[2-[4-dibutylamino-2-(tert-butyldiphenylsiloxy)phenyl]vinyl]thiophene-2-carboaldehyde and 290 mg (0.92 mmol) of 2-(3-cyano-4-methyl-5-phenyl-5-trifluoromethyl-2(5H)-furanylidene)propanedinitrile. The mixture was stirred with heating at 60° C. for 3 hours. The solvent was evaporated off and the residue was washed with ethanol. The residue was purified by silica gel column chromatography and washed with ethanol to give 604 mg of a dark reddish brown crystal (yield: 80.6%; mp: 188-200° C.)

$^1$H-NMR (600 MHz, CDCl$_3$) δ: 0.75 (6H, t, J=7.1 Hz), 0.98-1.04 (4H, m), 1.10-1.21 (4H, m), 1.17 (9H, s), 2.85 (4H, t, J=7.7 Hz), 5.69 (1H, d, J=2.2 Hz), 6.21 (1H, dd, J=2.2 Hz, 8.8 Hz), 6.52 (1H, d, J=15.9 Hz), 6.98 (1H, d, J=4.4 Hz), 7.06 (1H, d, J=15.9 Hz), 7.33 (1H, d, J=4.4 Hz), 7.37-7.45 (7H, m), 7.50-7.55 (5H, m), 7.73-7.75 (4H, m), 7.88-7.90 (1H, m), 7.90 (1H, d, J=15.9 Hz)

$^{13}$C-NMR (150 MHz, CDCl$_3$) δ: 13.8, 19.7, 20.0, 26.6, 29.3, 50.8, 57.5, 95.9, 102.6, 106.2, 110.9, 111.1, 111.3, 114.0, 114.6, 121.2, 123.1, 126.7, 127.2, 127.86, 127.95, 129.7, 129.9, 130.4, 131.4, 132.3, 132.6, 135.4, 137.7, 140.3, 141.4, 150.6, 156.2, 159.6, 161.4, 175.6

Example 16

2-[3-cyano-4-[2-[5-[2-(8-methoxy-2,3,6,7-tetrahydro-1H,5H-benzo[ij]quinolizine-9-yl)vinyl]thiophene-2-yl]vinyl]-5,5-dimethyl-2(5H)-furanylidene]propanedinitrile

[Formula 187]

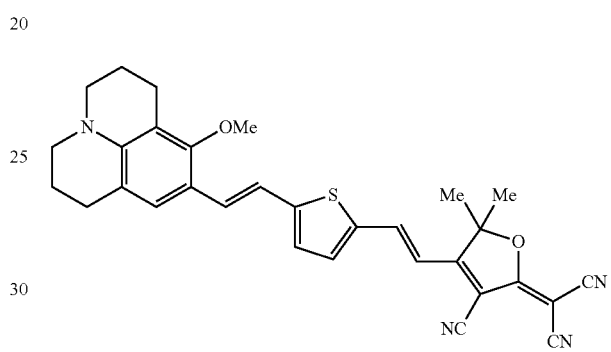

(16-1) 8-methoxy-2,3,6,7-tetrahydro-1H, 5H-benzo[ij] quinolizine-9-carboaldehyde

[Formula 188]

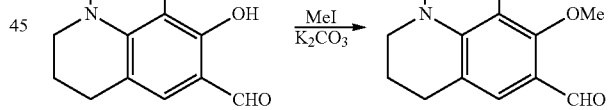

In 20 ml of 1-methyl-2-pyrrolidone was dissolved 2.5 g (11.5 mmol) of 8-hydroxy-2,3,6,7-tetrahydro-1H,5H-benzo[ij] quinolizine-9-carboaldehyde, and 4.1 g (28.9 mmol) of methyl iodide and 4.8 g (34.7 mmol) of anhydrous potassium carbonate were added thereto. The mixture was stirred at 50° C. for 4 hours. After the reaction mixture was added to water, extraction with ethyl acetate, drying over anhydrous sodium sulfate, and concentration were performed. The residue was purified by silica gel column chromatography to give 2.63 g of a yellow crystal (yield: 99.0%).

$^1$H-NMR (600 MHz, CDCl$_3$) δ: 1.91-1.96 (4H, m), 2.71 (2H, t, J=6.6 Hz), 2.75 (2H, t, J=6.6 Hz), 3.26-3.28 (4H, m), 3.81 (3H, s), 7.33 (1H, s), 10.00 (1H, s)

$^{13}$C-NMR (150 MHz, CDCl$_3$) δ: 20.8, 21.4, 27.3, 49.8, 50.1, 62.8, 112.3, 116.8, 117.2, 127.0, 149.0, 160.7, 187.6

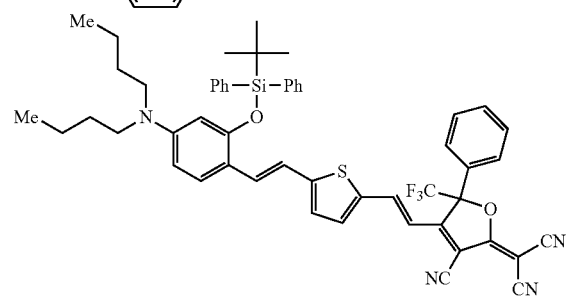

(16-2) 8-methoxy-9-[2-(thiophene-2-yl)vinyl]-2,3,6,7-tetrahydro-1H,5H-benzo[ij]quinolizine

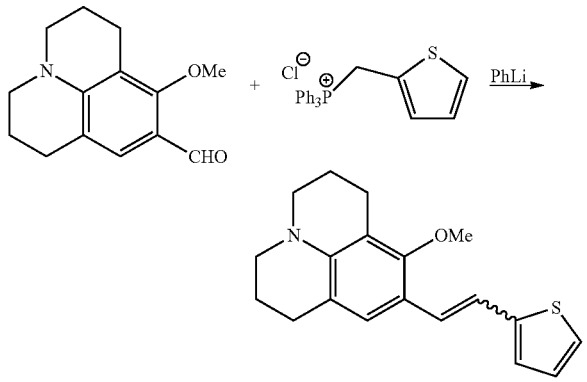

[Formula 189]

In a stream of argon, to 30 ml of tetrahydrofuran was added 3.2 g of phenyllithium (19% solution in dibutylether) (7.23 mmol), and 2.6 g (6.58 mmol) of 2-thenyl triphenylphosphonium chloride was added thereto under ice cooling. Next, 1.5 g (6.49 mmol) of 8-methoxy-2,3,6,7-tetrahydro-1H,5H-benzo[ij] quinolizine-9-carboaldehyde was dissolved in tetrahydrofuran and added dropwise. The mixture was stirred for 1.5 hours. After the reaction mixture was poured into water, extraction with ethyl acetate, washing with a saturated saline solution, drying over anhydrous sodium sulfate, and concentration were performed. The residue was purified by silica gel column chromatography to give 1.29 g of an orange oily matter (yield: 63.9%).

(16-3) 5-[2-(8-methoxy-2,3,6,7-tetrahydro-1H,5H-benzo[ij] quinolizine-9-yl)vinyl]thiophene-2-carboaldehyde

[Formula 190]

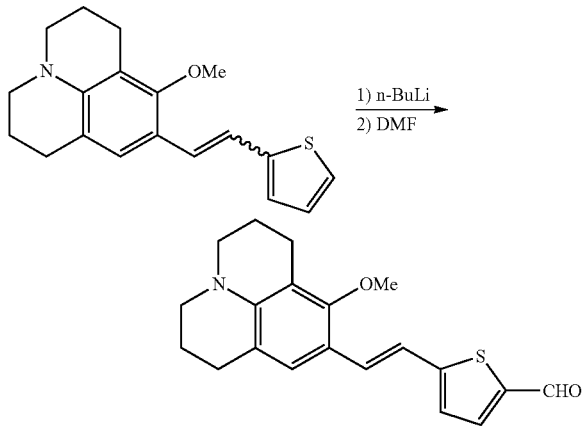

In a stream of argon, in 25 ml of tetrahydrofuran was dissolved 1.29 g (4.14 mmol) of 8-methoxy-9-[2-(thiophene-2-yl)vinyl]-2,3,6,7-tetrahydro-1H,5H-benzo[ij] quinolizine, and 3.9 ml of n-butyllithium (1.6 mol solution in hexane) (6.24 mmol) was added dropwise thereto under cooling at −70° C. After the mixture was stirred for 1 hour, 0.43 g (5.88 mmol) of N,N-dimethylformamide was added dropwise thereto. The reaction mixture was stirred for 1 hour and the temperature was allowed to rise. To this mixture, 10 ml of water was added dropwise. After the reaction mixture was added to water, extraction with ethyl acetate, washing with a saturated saline solution, drying over anhydrous sodium sulfate, and concentration were performed. The residual liquid was dissolved in 300 ml of ether and 50 mg of iodine pieces were added thereto. After stirred at room temperature, the mixture was washed with a 5% sodium bisulfite solution and then with a saturated saline solution. Drying over anhydrous sodium sulfate and concentration were performed. The residue was purified by silica gel column chromatography to give 496 mg of a dark reddish brown oily matter (yield: 35.5%).

$^1$H-NMR (600 MHz, CDCl$_3$) δ: 1.93-1.98 (4H, m), 2.73 (2H, t, J=6.6 Hz), 2.77 (2H, t, J=6.6 Hz), 3.18-3.12 (4H, m), 3.72 (3H, s), 7.02 (1H, d, J=15.9 Hz), 7.04 (1H, d, J=3.8 Hz), 7.06 (1H, s), 7.34 (1H, d, J=15.9 Hz), 7.62 (1H, d, J=3.8 Hz), 9.80 (1H, s)

$^{13}$C-NMR (150 MHz, CDCl$_3$) δ: 21.3, 21.4, 21.9, 27.5, 49.6, 49.9, 61.1, 116.1, 124.6, 128.8, 137.6, 139.9, 155.3, 155.5, 182.3

(16-4) 2-[3-cyano-4-[2-[5-[2-(8-methoxy-2,3,6,7-tetrahydro-1H,5H-benzo[ij]quinolizine-9-yl)vinyl]thiophene-2-yl]vinyl]-5,5-dimethyl-2(5H)-furanylidene]propanedinitrile

[Formula 191]

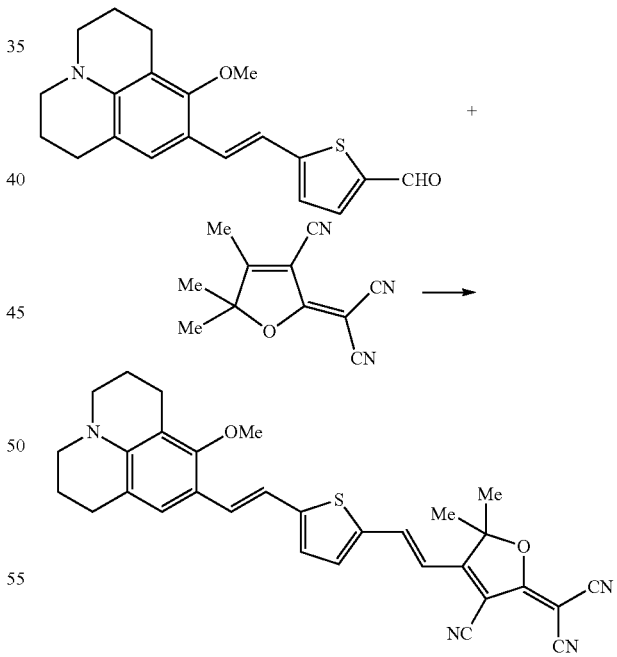

In 5 ml of ethanol and 1.5 ml of tetrahydrofuran were dissolved 158 mg (0.47 mmol) of 5-[2-(8-methoxy-2,3,6,7-tetrahydro-1H,5H-benzo[ij]quinolizine-9-yl)vinyl]thiophene-2-carboaldehyde and 102 mg (0.51 mmol) of 2-(3-cyano-4,5,5-trimethyl-2(5H)-furanylidene)propanedinitrile. To this mixture was added 36 mg of ammonium acetate, and the mixture was stirred at room temperature for 42 hours. The crystal was filtrated and washed with ethanol. The residue was purified by silica gel column chromatography and washed with ethanol to give 150 mg of a black powdered crystal (yield: 62.0%; mp: 201-204° C.)

$^1$H-NMR (600 MHz, CDCl$_3$) δ: 1.75 (6H, s), 1.93-1.99 (4H, m), 2.74 (2H, t, J=6.6 Hz), 2.77 (2H, t, J=6.6 Hz), 3.22-3.25 (4H, m), 3.76 (3H, s), 6.53 (1H, d, J=15.4 Hz), 7.01 (1H, d, J=3.8 Hz), 7.03 (1H, d, J=15.9 Hz), 7.08 (1H, s), 7.35 (1H, d, J=15.9 Hz), 7.36 (1H, d, J=3.8 Hz), 7.77 (1H, d, J=15.9 Hz)

$^{13}$C-NMR (150 MHz, CDCl$_3$) δ: 21.2, 21.3, 21.8, 26.6, 27.6, 49.7, 50.0, 55.6, 61.3, 95.3, 96.8, 111.2, 111.6, 112.4, 113.9, 115.7, 115.8, 117.9, 124.8, 126.7, 130.4, 137.1, 138.0, 139.4, 145.3, 155.9, 156.0, 172.8, 175.9

Example 17

2-[3-cyano-4-[2-[5-[2-(8-methoxy-2,3,6,7-tetrahydro-1H,5H-benzo[ij]quinolizine-9-yl)vinyl]thiophene-2-yl]vinyl]-5-methyl-5-trifluoromethyl-2(5H)-furanylidene] propanedinitrile

[Formula 192]

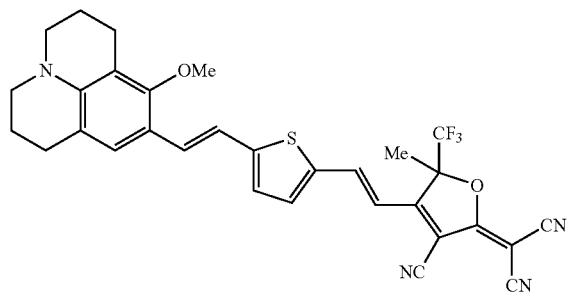

[Formula 193]

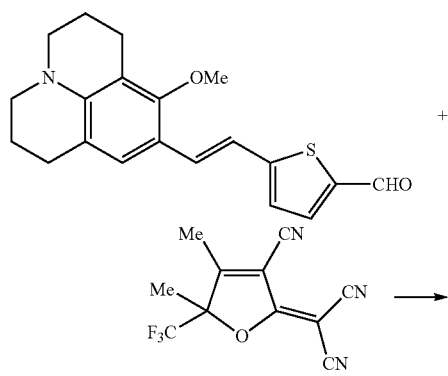

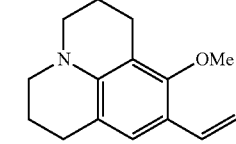

In 5 ml of ethanol and 1.5 ml of tetrahydrofuran were dissolved 135 mg (0.40 mmol) of 5-[2-(8-methoxy-2,3,6,7-tetrahydro-1H,5H-benzo[ij]quinolizine-9-yl)vinyl]thiophene-2-carboaldehyde and 110 mg (0.43 mmol) of 2-(3-cyano-4,5-dimethyl-5-trifluoromethyl-2(5H)-furanylidene) propanedinitrile. The mixture was stirred with heating at 60° C. for 3.5 hours. The solvent was evaporated off and the residue was washed with ethanol. The residue was purified by silica gel column chromatography and washed with methanol to give 178 mg of a dark brown crystal (yield: 78.1%; mp: 159-161° C.)

$^1$H-NMR (600 MHz, CDCl$_3$) δ: 1.91 (3H, s), 1.94-1.99 (4H, m), 2.74 (2H, t, J=6.0H), 2.77 (2H, t, J=6.6 Hz), 3.25-3.28 (4H, m), 3.76 (3H, s), 6.43 (1H, d, J=15.4 Hz), 7.05 (1H, d, J=4.4 Hz), 7.06 (1H, d, J=15.9 Hz), 7.10 (1H, s), 7.42 (1H, d, J=15.9 Hz), 7.45 (1H, d, J=4.4 Hz), 8.15 (1H, d, J=15.4 Hz)

$^{13}$C-NMR (150 MHz, CDCl$_3$) δ: 19.4, 21.1, 21.4, 21.8, 27.7, 49.8, 50.1, 57.5, 61.5, 93.5, 93.7, 94.9, 110.1, 110.9, 111.4, 114.0, 115.7, 118.2, 122.5, 125.4, 127.6, 132.1, 137.9, 140.3, 141.1, 146.0, 156.5, 158.9, 161.8, 175.5

Example 18

2-[3-cyano-4-[2-[5-[2-(8-methoxy-2, 3, 6, 7-tetrahydro-1H, 5H-benzo[ij]quinolizine-9-yl)vinyl]thiophene-2-yl]vinyl]-5-phenyl-5-trifluoromethyl-2(5H)-furanylidene] propanedinitrile

[Formula 194]

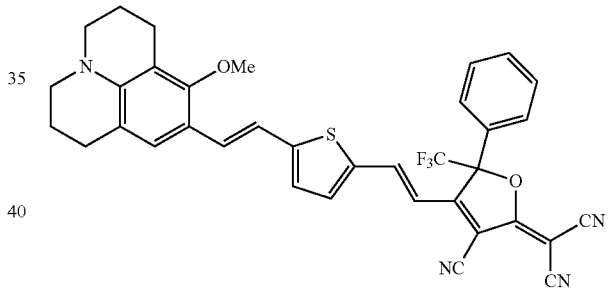

[Formula 195]

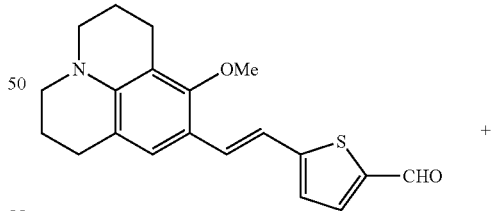

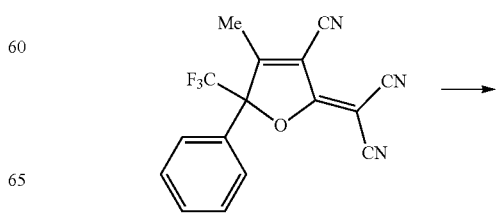

-continued

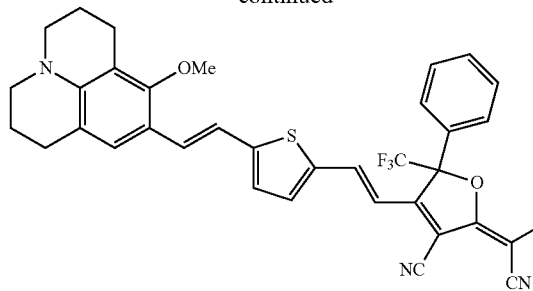

In 5 ml of ethanol and 1.5 ml of tetrahydrofuran were dissolved 120 mg (0.35 mmol) of 5-[2-(8-methoxy-2,3,6,7-tetrahydro-1H,5H-benzo[ij]quinolizine-9-yl)vinyl]thiophene-2-carboaldehyde and 123 mg (0.39 mmol) of 2-(3-cyano-4-methyl-5-phenyl-5-trifluoromethyl-2(5H)-furanylidene)propanedinitrile. The mixture was stirred with heating at 60° C. for 3 hours. The solvent was evaporated off and the residue was washed with ethanol. The residue was purified by silica gel column chromatography and washed with ethanol to give 100 mg of a dark brown crystal (yield: 44.4%; mp: 156-160° C.)

$^1$H-NMR (600 MHz, CDCl$_3$) δ: 1.93-1.98 (4H, m), 2.72 (2H, t, J=6.0 Hz), 2.77 (2H, t, J=6.6 Hz), 3.24-3.27 (4H, m), 3.75 (3H, s), 6.57 (1H, d, J=14.9 Hz), 6.99 (1H, d, J=3.8 Hz), 7.03 (1H, d, J=15.9 Hz), 7.07 (1H, s), 7.29 (1H, d, J=3.8 Hz), 7.39 (1H, d, J=15.9 Hz), 7.51-7.57 (5H, m), 7.77 (1H, d, J=14.9 Hz)

$^{13}$C-NMR (150 MHz, CDCl$_3$) δ: 21.1, 21.3, 21.7, 27.6, 49.7, 50.0, 57.7, 61.5, 95.8, 104.3, 110.8, 111.3, 113.9, 115.7, 118.1, 125.3, 126.8, 127.4, 129.76, 129.83, 131.5, 132.0, 137.8, 134.0, 141.6, 145.9, 156.4, 158.8, 161.8, 175.5

Example 19

The 2-substituted oxybenzaldehyde compounds 19-1 to 19-4 shown in Table 1 were synthesized in the same manner as in Examples 1-1, 4-1, 13-1, and 16-1.

TABLE 1

| Example No. | Structural Formula | $^1$H-NMR (600 MHz, CDCl$_3$) δ ppm<br>$^{13}$C-NMR (150 MHz, CDCl$_3$) δ ppm |
|---|---|---|
| 19-1 | | 0.97 (6H, t, J = 7.7 Hz), 1.34-1.40 (4H, m), 1.39 (6H, d, J = 6.0 Hz), 1.57-1.63 (4H, m), 3.32 (4H, t, J = 7.7 Hz), 4.56-4.60 (1H, m), 6.02 (1H, s), 6.25 (1H, dd, J = 2.2 Hz, 8.8 Hz), 7.70 (1H, d, J = 8.8 Hz), 10.15 (1H, s)<br>13.9, 20.3, 22.1, 29.4, 51.0, 70.8, 95.2, 99.9, 104.7, 130.0, 154.0, 162.7, 187.5 |
| 19-2 | | 0.27 (6H, s), 0.97 (6H, t, J = 7.7 Hz), 1.02 (9H, s), 1.33-1.40 (4H, m), 1.56-1.62 (4H, m), 3.29 (4H, t, J = 7.7 Hz), 5.94 (1H, s), 6.30 (1H, dd, J = 2.2 Hz, 8.8 Hz), 7.68 (1H, d, J = 8.8 Hz), 10.13 (1H, s)<br>−4.23, 13.9, 18.4, 20.3, 25.7, 29.4, 51.1, 100.9, 105.8, 129.9, 161.0 187.5 |
| 19-3 | | 1.21 (6H, t, J = 7.1 Hz), 1.40 (6H, d, J = 6.0 Hz), 3.41 (4H, q, J = 7.1 Hz), 4.60-4.64 (1H, m), 6.06 (1H, d, J = 7.7 Hz), 6.29 (1H, d, J = 7.7 Hz), 7.72 (1H, d, J = 8.8 Hz), 10.16 (1H, s)<br>12.6, 22.1, 45.0, 71.0, 104.7, 130.2, 162.8, 187.6 |
| 19-4 | | 0.97 (6H, t, J = 7.7 Hz), 1.34-1.40 (4H, m), 1.57-1.62 (4H, m), 1.85 (3H, s), 3.31 (4H, t, J = 7.7 Hz), 4.52 (2H, s), 5.02 (1H, s), 5.11 (1H, s), 6.01 (1H, d, J = 2.2 Hz), 6.25 (1H, dd, J = 2.2 Hz, 8.8 Hz), 7.71 (1H, d, J = 8.8 Hz), 10.20 (1H, s)<br>13.9, 19.3, 20.3, 29.4, 51.0, 71.8, 93.9, 104.6, 112.8, 130.2, 140.8, 154.1, 163.3, 187.0 |

Example 20

The dibutyl[3-substituted oxy-4-[2-(thiophene-2-yl)vinyl]phenyl]amine compounds 20-1 to 20-4 shown in Table 2 were synthesized in the same manner as in Examples 1-2, 4-2, 13-2, and 16-2.

TABLE 2

| Example No. | Structural Formula |
|---|---|
| 20-1 | (structure) |
| 20-2 | (structure) |
| 20-3 | (structure) |
| 20-4 | (structure) |

Example 21

The 5-[2-[2,4-disubstituted phenyl]vinyl]thiophene-2-carboaldehyde compounds 21-1 to 21-4 shown in Table 3 were synthesized in the same manner as in Examples 1-3, 4-3, 13-3, and 16-3.

TABLE 3

| Example No. | Structural Formula | $^1$H-NMR (600 MHz, CDCl$_3$) δ ppm / $^{13}$C-NMR (150 MHz, CDCl$_3$) δ ppm |
|---|---|---|
| 21-1 | (structure) | 0.97 (6H, t, J = 7.7 Hz), 1.34-1.40 (4H, m), 1.41 (6H, d, J = 6.0 Hz), 1.56-1.62 (4H, m), 3.29 (4H, t, J = 7.7 Hz), 4.50-4.55 (1H, m), 6.13 (1H, d, J = 2.2 Hz), 6.26 (1H, dd, J = 2.2 Hz, 8.8 Hz), 7.01 (1H, d, J = 3.8 Hz), 7.06 (1H, d, J = 15.9 Hz), 7.37 (1H, d, J = 8.8 Hz), 7.44 (1H, d, J = 15.9 Hz), 7.61 (1H, d, J = 3.8 Hz), 9.79 (1H, s) 14.0, 20.3, 22.3, 29.6, 50.9, 71.1, 97.5, 105.0, 113.6, 115.7, 124.4, 128.5, 129.6, 137.8, 139.6, 150.0, 156.0, 157.5, 182.3 |

TABLE 3-continued

| Example No. | Structural Formula | $^1$H-NMR (600 MHz, CDCl$_3$) δ ppm<br>$^{13}$C-NMR (150 MHz, CDCl$_3$) δ ppm |
|---|---|---|
| 21-2 | | 0.25 (6H, s), 0.96 (6H, t, J = 7.7 Hz),<br>1.07 (9H, s,), 1.33-1.39 (4H, m),<br>1.56-1.60 (4H, m),<br>3.26 (4H, t, J = 7.7 Hz),<br>6.05 (1H, d, J = 2.2 Hz),<br>6.29 (1H, dd, J = 2.2 Hz, 8.8 Hz),<br>6.96 (1H, d, J = 15.9 Hz),<br>6.99 (1H, d, J = 3.8 Hz),<br>7.40 (1H, d, J = 8.8 Hz),<br>7.47 (1H, d, J = 15.9 Hz),<br>7.61 (1H, d, J = 3.8 Hz), 9.79 (1H, s)<br>−4.1, 14.0, 18.4, 20.4, 25.9, 29.6, 51.0,<br>102.4, 106.0, 114.6, 115.1,<br>124.4, 127.3, 129.1, 137.9, 139.6,<br>149.8, 155.3, 155.7, 182.3 |
| 21-3 | | 1.19 (6H, t, J = 7.1 Hz),<br>1.40 (6H, d, J = 6.0 Hz),<br>3.38 (4H, q, J = 7.1 Hz),<br>4.52-4.58 (1H, m),<br>6.16 (1H, d, J = 2.2 Hz),<br>6.30 (1H, dd, J = 2.2 Hz, 8.8 Hz),<br>7.01 (1H, d, J = 3.8 Hz),<br>7.06 (1H, d, J = 15.9 Hz),<br>7.39 (1H, d, J = 8.8 Hz),<br>7.45 (1H, d, J = 15.9 Hz),<br>7.61 (1H, d, J = 3.8 Hz),<br>9.79 (1H, s)<br>12.8, 22.3, 44.6, 71.2, 97.6,<br>105.0, 113.9, 115.7, 124.4, 128.5, 129.5,<br>137.7, 139.6, 149.5, 155.9, 157.6, 182.3 |
| 21-4 | | 0.97 (6H, t, J = 7.7 Hz),<br>1.33-1.39 (4H, m),<br>1.56-1.61 (4H, m),<br>1.88 (3H, s), 3.28 (4H, t, J = 7.7 Hz),<br>4.50 (2H, s), 5.04 (1H, s),<br>5.13 (1H, s), 6.12 (1H, d, J = 2.2 Hz),<br>6.26 (1H, dd, J = 2.2 Hz, 8.8 Hz),<br>7.01 (1H, d, J = 4.4 Hz),<br>7.07 (1H, d, J = 16.5 Hz),<br>7.37 (1H, d, J = 8.8 Hz),<br>7.47 (1H, d, J = 15.9 Hz),<br>7.61 (1H, d, J = 4.4 Hz),<br>9.79 (1H, s)<br>14.0, 19.5, 20.4, 29.6, 50.9,<br>72.2, 95.9, 104.8, 112.6, 112.7,<br>115.9, 124.4, 128.4, 129.1, 137.7, 139.6,<br>141.2, 150.0, 155.8, 158.3, 182.3 |

Example 22

5-[2-(4-dibutylamino-2-hydroxyphenyl)vinyl]thiophene-2-carboaldehyde

[Formula 196]

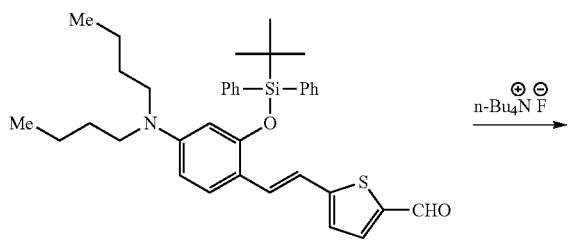

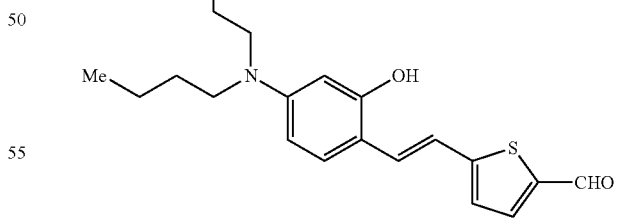

-continued

In 10 ml of tetrahydrofuran was dissolved 488 mg (0.82 mmol) of 5-[2-[4-dibutylamino-2-(tert-butyldiphenylsiloxy)phenyl] vinyl]thiophene-2-carboaldehyde, and 2.5 ml of tetrabutylammonium fluoride (1 mol solution in tetrahydrofuran) was added dropwise thereto with stirring at room temperature. The mixture was stirred for 35 minutes. After the reaction mixture was poured into water, extraction with ethyl acetate, washing with a saturated saline solution,

147 drying over anhydrous sodium sulfate, and concentration were performed. The residue was purified by silica gel column chromatography to give 274 mg of a blackish brown crystal (yield: 93.6%).

$^1$H-NMR (600 MHz, CDCl$_3$) δ: 0.96 (6H, t, J=7.7 Hz), 1.33-1.39 (4H, m), 1.53-1.58 (4H, m), 3.26 (4H, t, J=7.7 Hz), 5.07 (1H, s), 6.01 (1H, s), 6.26 (1H, d, J=8.8 Hz), 7.04 (1H, d, J=3.8 Hz), 7.08 (1H, d, J=15.9 Hz), 7.32 (1H, d, J=8.8 Hz), 7.35 (1H, d, J=16.5 Hz), 7.62 (1H, d, J=3.8 Hz), 9.80 (1H, s)

Example 23

5-[2-(4-dibutylamino-2-hydroxyphenyl)vinyl]thiophene-2-carboaldehyde

[Formula 197]

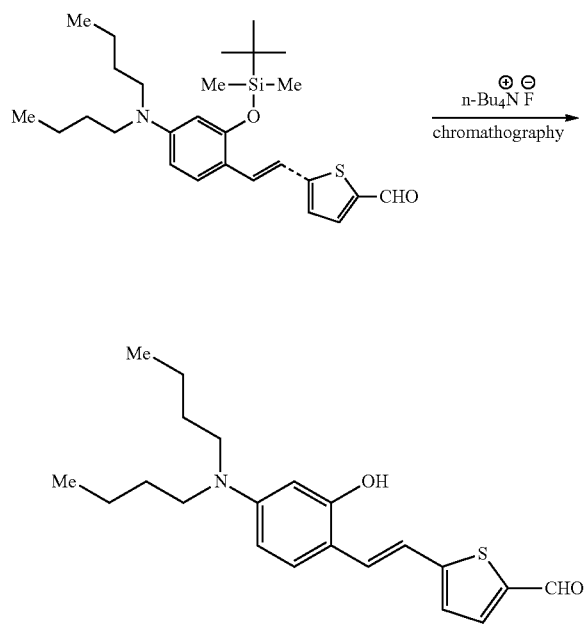

In 75 ml of tetrahydrofuran was dissolved 4.02 g (8.52 mmol) of 5-[2-[4-dibutylamino-2-(tert-butyldimethylsiloxy)phenyl] vinyl]thiophene-2-carboaldehyde, and 25.5 ml of tetrabutylammonium fluoride (1 mol solution in tetrahydrofuran) was added dropwise thereto with stirring at room temperature. The mixture was stirred for 1.5 hours. After the reaction mixture was poured into water, extraction with ethyl acetate, washing with a saturated saline solution, drying over anhydrous sodium sulfate, and concentration were performed. The residue was purified by silica gel column chromatography to give 2.74 g of a blackish brown crystal (yield: 89.9%).

148

Example 24

5-[2-[4-dibutylamino-2-(oxiranylmethoxy)phenyl] vinyl] thiophene-2-carboaldehyde

[Formula 198]

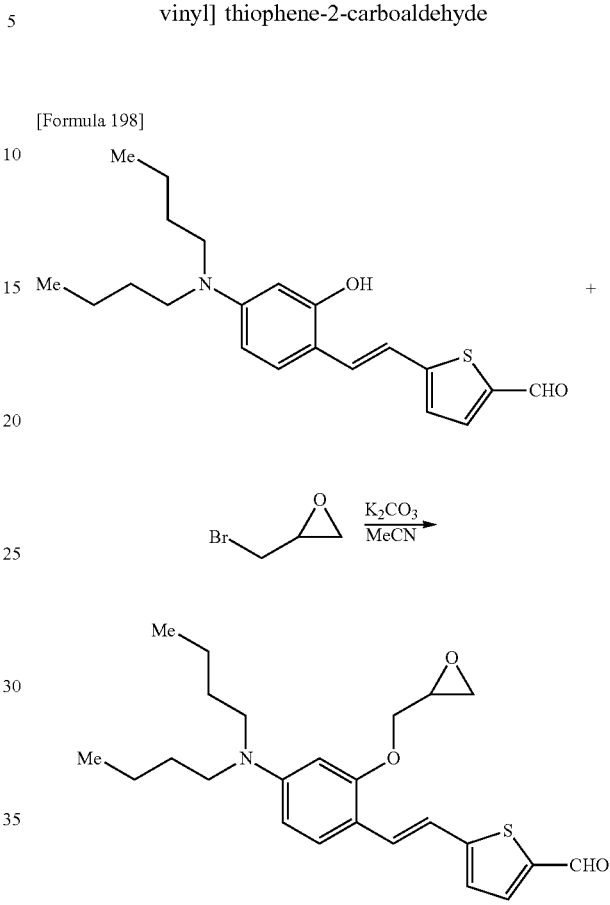

In 10 ml of acetonitrile were dissolved 390 mg (1.09 mmol) of 5-[2-(4-dibutylamino-2-hydroxyphenyl)vinyl] thiophene-2-carboaldehyde and 0.22 g (1.61 mmol) of epibromohydrin. To this mixture were added 0.3 g (2.17 mmol) of anhydrous potassium carbonate and 40 mg of tetrabutylammonium iodide, and the mixture was stirred with heating at 60° C. for 4 hours. After the reaction mixture was poured into water, extraction with ethyl acetate, washing with a saturated saline solution, drying over anhydrous sodium sulfate, and concentration were performed. The residue was purified by silica gel column chromatography. The oily matter was dissolved in 50 ml of ether and 10 mg of iodine was added thereto. The mixture was stirred for 1 hour. The mixture was washed with a 5% sodium bisulfite solution and then with a saturated saline solution. Drying over anhydrous magnesium sulfate and concentration were performed. The residual liquid was purified by silica gel column chromatography to give 264 mg of a dark reddish brown oily matter (yield: 58.5%).

$^1$H-NMR (600 MHz, CDCl$_3$) δ: 0.97 (6H, t, J=7.7 Hz), 1.34-1.39 (4H, m), 1.56-1.61 (4H, m), 2.81 (1H, dd, J=2.5 Hz, 4.6 Hz), 2.96 (1H, t, J=4.6 Hz), 3.30 (4H, t, J=7.7 Hz), 3.40-3.43 (1H, m), 4.05 (1H, dd, J=5.5 Hz, 11.0 Hz), 4.26 (2H, dd, J=3.3 Hz, 11.5 Hz), 6.16 (1H, d, J=2.2 Hz), 6.28 (1H, dd, J=2.2 Hz, 8.8 Hz), 7.04 (1H, d, J=3.8 Hz), 7.07 (1H, d, J=15.9 Hz), 7.37 (1H, d, J=8.8 Hz), 7.43 (1H, d, J=15.9 Hz), 7.62 (1H, d, J=3.8 Hz), 9.80 (1H, s)

Example 25

5-[2-[2-(3-bromo-2-hydroxypropoxy)-4-dibutylaminophenyl] vinyl]thiophene-2-carboaldehyde

[Formula 199]

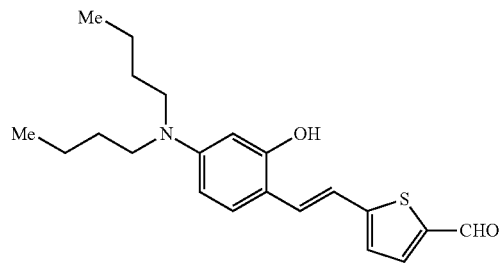

+

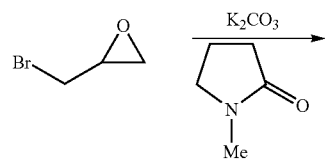

$\xrightarrow{K_2CO_3}$

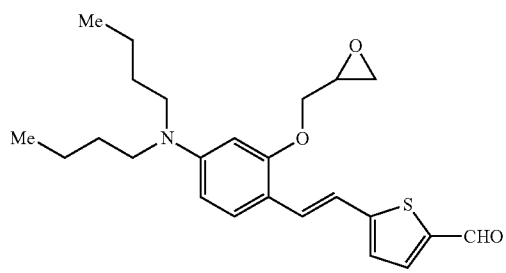

+

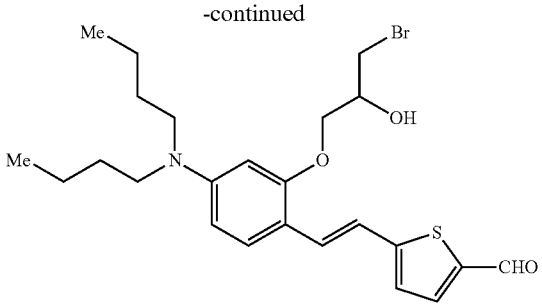

In 15 ml of 1-methyl-2-pyrrolidone were dissolved 0.76 g (2.13 mmol) of 5-[2-(4-dibutylamino-2-hydroxyphenyl)vinyl] thiophene-2-carboaldehyde and 0.8 g (5.84 mmol) of epibromohydrin. To this mixture was added 0.59 g (4.27 mmol) of anhydrous potassium carbonate and the mixture was stirred with heating at 60° C. for 4 hours. After the reaction mixture was poured into water, extraction with ethyl acetate, washing with a saturated saline solution, drying over anhydrous sodium sulfate, and concentration were performed. The residual liquid was purified by silica gel column chromatography. From the earlier fraction, 0.31 g of 5-[2-[4-dibutylamino-2-(oxiranylmethoxy)phenyl]vinyl]thiophene-2-carboaldehyde was obtained. From the later fraction, 0.45 g of 5-[2-[2-(3-bromo-2-hydroxypropoxy)-4-dibutylaminophenyl]vinyl] thiophene-2-carboaldehyde was obtained.

$^1$H-NMR (600 MHz, CDCl$_3$) δ: 0.97 (6H, t, J=7.7 Hz), 1.34-1.40 (4H, m), 1.56-1.60 (4H, m), 3.30 (4H, t, J=7.7 Hz), 4.19 (1H, dd, J=3.3 Hz, 10.5 Hz), 4.30 (1H, dd, J=3.8 Hz, 10.4 Hz), 4.61-4.63 (1H, m), 4.69 (1H, t, J=8.5 Hz), 5.09-5.12 (1H, m), 6.08 (1H, d, J=2.2 Hz), 6.32 (1H, dd, J=2.2 Hz, 8.8 Hz), 7.00 (1H, d, J=15.9 Hz), 7.13 (1H, d, J=3.8 Hz), 7.31 (1H, d, J=15.9 Hz), 7.37 (1H, d, J=8.8 Hz), 7.63 (1H, d, J=3.8 Hz), 9.80 (1H, s)

Example 26

The 5-[2-[2,4-disubstituted phenyl]vinyl]thiophene-2-carboaldehyde compounds 26-1 to 26-3 shown in Table 4 were synthesized in the same manner as in Examples 24 and 25.

TABLE 4

| Example No. | Structural Formula | $^1$H-NMR (600 MHz, CDCl$_3$) δ ppm<br>$^{13}$C-NMR (150 MHz, CDCl$_3$) δ ppm |
|---|---|---|
| 26-1 | (structure shown) | 0.95 (6H, t, J = 7.7 Hz),<br>1.30-1.36 (4H, m),<br>1.50-1.55 (4H, m),<br>3.25 (4H, t, J = 7.7 Hz),<br>3.83 (3H, s), 5.08 (2H, s),<br>6.15 (1H, d, J = 2.2 Hz),<br>6.25 (1H, dd, J = 2.2 Hz, 8.8 Hz),<br>6.94 (2H, d, J = 8.8 Hz),<br>6.97 (1H, d, J = 3.8 Hz),<br>7.09 (1H, d, J = 15.9 Hz),<br>7.35 (1H, d, J = 8.8 Hz),<br>7.37 (2H, d, J = 8.8 Hz),<br>7.43 (1H, d, J = 15.9 Hz),<br>7.59 (1H, d, J = 3.8 Hz), 9.78 (1H, s)<br>14.1, 20.4, 29.6, 51.0, 55.4, 70.4, 96.6,<br>105.0, 112.9, 114.2, 116.3, 124.5, 128.8,<br>129.0, 129.3, 129.4, 137.8, 139.7, 150.0,<br>155.9, 158.5, 159.5, 182.3 |

TABLE 4-continued

| Example No. | Structural Formula | ¹H-NMR (600 MHz, CDCl₃) δ ppm<br>¹³C-NMR (150 MHz, CDCl₃) δ ppm |
|---|---|---|
| 26-2 | (structure: N,N-dibutylamino phenyl with methacrylate ester O-C(=O)-C(CH₂)=Me group, vinyl-thiophene-CHO) | 0.96 (6H, t, J = 7.1 Hz),<br>1.33-1.39 (4H, m),<br>1.56-1.60 (4H, m),<br>2.13 (3H, s), 3.28 (4H, t, J = 7.7 Hz),<br>5.85 (1H, m),<br>6.31 (1H, d, J = 2.2 Hz), 6.44 (1H, s),<br>6.53 (1H, dd, J = 2.2 Hz, 8.8 Hz),<br>6.97 (1H, d, J = 15.9 Hz),<br>7.00 (1H, d, J = 3.8 Hz),<br>7.087 (1H, d, J = 15.9 Hz),<br>7.49 (1H, d, J = 8.8 Hz),<br>7.61 (1H, d, J = 3.8 Hz), 9.80 (1H, s)<br>14.0, 18.6, 20.3, 29.4, 50.8, 105.1,<br>109.9, 115.0, 117.1, 125.3,<br>126.9, 127.4, 127.6,<br>135.8, 137.6, 140.3, 149.6,<br>150.5, 154.4, 156.7, 182.4 |
| 26-3 | (structure: N,N-dibutylamino phenyl with O-(CH₂)₄-OH substituent, vinyl-thiophene-CHO) | 0.97 (6H, t, J = 7.7 Hz),<br>1.34-1.40 (4H, m),<br>1.57-1.62 (4H, m),<br>1.81-1.85 (2H, m),<br>1.97-2.10 (2H, m),<br>3.30 (4H, t, J = 7.7 Hz),<br>3.78 (2H, t, J = 6.6 Hz),<br>4.05 (2H, t, J = 6.0 Hz),<br>6.11 (1H, d, J = 2.2 Hz),<br>6.26 (1H, dd, J = 2.2 Hz, 8.8 Hz),<br>7.01 (1H, d, J = 3.8 Hz),<br>7.08 (1H, d, J = 15.9 Hz),<br>7.36 (1H, d, J = 8.8 Hz),<br>7.43 (1H, d, J = 15.9 Hz),<br>7.61 (1H, d, J = 3.8 Hz),<br>9.79 (1H, s)<br>14.0, 20.3, 25.9, 29.55, 29.61, 50.9, 62.6,<br>68.0, 95.5, 104.8, 112.5, 115.9,<br>124.4, 128.6, 129.2, 137.8,<br>139.6, 150.1, 155.8, 158.5, 182.3 |

Example 27

The secondary nonlinear optical compounds 27-1 to 27-29 shown in Table 5 were synthesized in the same manner as in Examples 1-4, 2, and 3.

TABLE 5

| Example No. | Structural Formula<br>Melting Point | ¹H-NMR (600 MHz, CDCl₃) δ ppm<br>¹³C-NMR (150 MHz, CDCl₃) δ ppm |
|---|---|---|
| 27-1 | (structure: N,N-dibutylamino phenyl with O-CH(Me)₂ (isopropyl) group, vinyl-thiophene-vinyl-furan with Me, Me, CN, CN, NC substituents)<br>mp 222-223° C. | 0.98 (6H, t, J = 7.7 Hz),<br>1.35-1.41 (4H, m),<br>1.44 (6H, d, J = 6.0 Hz),<br>1.58-1.63 (4H, m),<br>1.75 (6H, s),<br>3.31 (4H, t, J = 7.7 Hz),<br>4.55-4.56 (1H, m),<br>6.11 (1H, s),<br>6.27 (1H, d, J = 8.8 Hz),<br>6.52 (1H, d, J = 15.9 Hz),<br>7.00 (1H, d, J = 4.4 Hz),<br>7.12 (1H, d, J = 15.9 H),<br>7.36 (1H, d, J = 3.8 Hz),<br>7.37 (1H, d, J = 8.8 Hz),<br>7.42 (1H, d, J = 15.9 Hz),<br>7.77 (1H, d, J = 15.9 Hz)<br>14.0, 20.3, 22.3, 26.6, 29.6,<br>50.9, 55.4, 70.8, 96.75, 96.82,<br>105.1, 110.9, 111.3, 111.7, 112.5,<br>113.5, 115.7, 126.5, 129.3, 131.3,<br>136.9, 138.2, 139.5, 150.5, 156.7,<br>158.1, 172.9, 176.0 |

TABLE 5-continued

| Example No. | Structural Formula Melting Point | ¹H-NMR (600 MHz, CDCl₃) δ ppm ¹³C-NMR (150 MHz, CDCl₃) δ ppm |
|---|---|---|
| 27-2 | 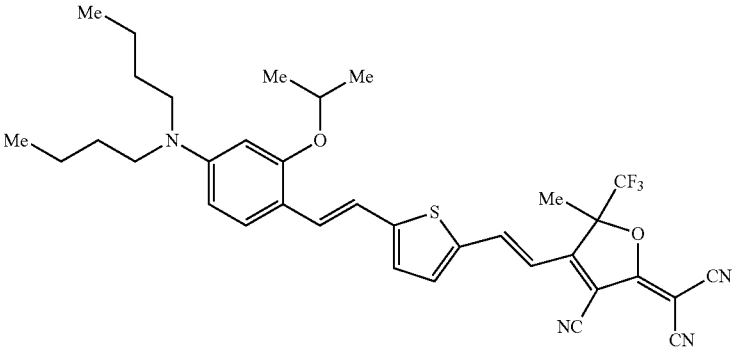 [SMILES: CCCCN(CCCC)c1ccc(/C=C/c2ccc(/C=C/C3=C(C#N)C(=C(C#N)C#N)OC3(C)C(F)(F)F)s2)c(OC(C)C)c1]<br>mp 197-198° C. | 0.98 (6H, t, J = 7.7 Hz),<br>1.35-1.41 (4H, m),<br>1.45 (6H, d, J = 6.0 Hz),<br>1.59-1.64 (4H, m),<br>1.91 (3H, s),<br>3.33 (4H, t, J = 7.7 Hz),<br>4.57-4.61 (1H, m),<br>6.10 (1H, s),<br>6.28 (1H, d, J = 8.8 Hz),<br>6.43 (1H, d, J = 15.9 Hz),<br>7.05 (1H, d, J = 4.4 Hz),<br>7.16 (1H, d, J = 15.9 Hz),<br>7.37 (1H, d, J = 8.8 Hz),<br>7.46 (1H, d, J = 4.4 Hz),<br>7.50 (1H, d, J = 15.9 Hz),<br>8.15 (1H, d, J = 15.9 Hz)<br>14.0, 19.4, 20.3, 22.3, 29.6, 51.0,<br>57.2, 70.9, 96.5, 105.3,<br>109.7, 110.9, 111.5, 113.5,<br>115.7, 121.2, 127.3, 129.9,<br>133.2, 137.6, 140.4, 141.1,<br>151.1, 158.5, 159.8, 161.6,<br>164.3, 175.5 |
| 27-3 | 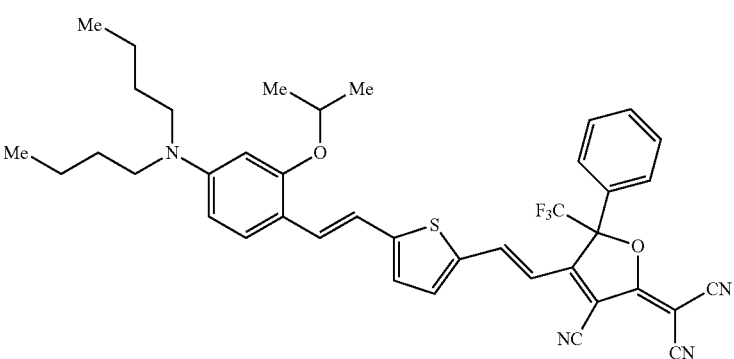 [SMILES: CCCCN(CCCC)c1ccc(/C=C/c2ccc(/C=C/C3=C(C#N)C(=C(C#N)C#N)OC3(c3ccccc3)C(F)(F)F)s2)c(OC(C)C)c1]<br>mp 184-186° C. | 0.97 (6H, t, J = 7.7 Hz),<br>1.35-1.41 (4H, m),<br>1.44 (6H, d, J = 6.0 Hz),<br>1.56-1.63 (4H, m),<br>3.32 (4H, t, J = 7.7 Hz),<br>4.56 (1H, m),<br>6.09 (1H, d, J = 2.2 Hz),<br>6.27 (1H, dd, J = 2.2 Hz, 8.8 Hz),<br>6.57 (1H, d, J = 14.8 Hz),<br>6.99 (1H, d, J = 4.4 Hz),<br>7.12 (1H, d, J = 15.9 Hz),<br>7.29 (1H, d, J = 4.4 Hz),<br>7.35 (1H, d, J = 8.8 Hz),<br>7.46 (1H, d, J = 15.9 Hz),<br>7.51-7.57 (5H, m),<br>7.75 (1H, d, J = 14.8 Hz)<br>14.0, 20.3, 22.2, 29.6, 51.0,<br>57.4, 70.8, 95.3, 96.5, 105.3,<br>110.9, 111.0, 111.3, 111.4,<br>113.5, 115.7, 126.9, 127.2,<br>129.7, 130.0, 131.4, 133.2,<br>137.7, 140.2, 151.0, 158.6,<br>159.9, 161.7, 175.5 |
| 27-4 | 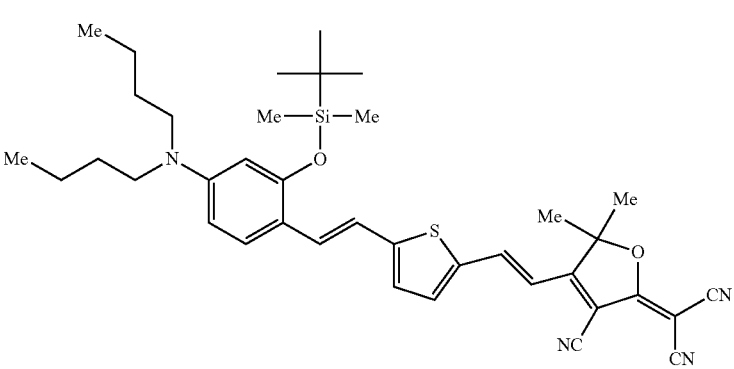 [SMILES: CCCCN(CCCC)c1ccc(/C=C/c2ccc(/C=C/C3=C(C#N)C(=C(C#N)C#N)OC3(C)C)s2)c(O[Si](C)(C)C(C)(C)C)c1]<br>mp 242-243° C. | 0.27 (6H, s),<br>0.97 (6H, t, J = 7.1 Hz),<br>1.09 (9H, s), 1.34-1.40 (4H, m),<br>1.56-1.62 (4H, m),<br>1.74 (6H, s),<br>3.28 (4H, t, J = 7.1 Hz),<br>6.05 (1H, d, J = 2.2 Hz),<br>6.31 (1H, dd, J = 2.2 Hz, 8.8 Hz),<br>6.51 (1H, d, J = 15.4 Hz),<br>6.98 (1H, d, J = 3.8 Hz),<br>6.99 (1H, d, J = 15.9 Hz),<br>7.36 (1H, d, J = 3.8 Hz),<br>7.40 (1H, d, J = 8.8 Hz),<br>7.50 (1H, d, J = 15.9 Hz),<br>7.76 (1H, d, J = 15.4 Hz)<br>−4.1, 14.0, 18.5, 20.3, 26.6, 29.6,<br>51.0, 55.5, 95.3, 96.8, 102.1,<br>106.2, 111.2, 111.6, 112.4,<br>114.7, 114.9, 126.2, 127.8,<br>130.9, 136.9, 137.8, 139.3,<br>150.4, 155.9, 156.3, 172.7, 175.9 |

TABLE 5-continued

| Example No. | Structural Formula Melting Point | $^1$H-NMR (600 MHz, CDCl$_3$) δ ppm<br>$^{13}$C-NMR (150 MHz, CDCl$_3$) δ ppm |
|---|---|---|
| 27-5 | mp 199-201° C. | 0.28 (6H, s),<br>0.97 (6H, t, J = 7.1 Hz),<br>1.09 (9H, s), 1.34-1.40 (4H, m),<br>1.57-1.62 (4H, m), 1.90 (3H, s),<br>3.29 (4H, t, J = 7.1 Hz),<br>6.04 (1H, d, J = 2.2 Hz),<br>6.32 (1H, dd, J = 2.2 Hz, 8.8 Hz),<br>6.42 (1H, d, J = 15.4 Hz),<br>7.01 (1H, d, J = 15.9 Hz),<br>7.02 (1H, d, J = 3.8 Hz),<br>7.42 (1H, d, J = 8.8 Hz),<br>7.45 (1H, d, J = 3.8 Hz),<br>7.59 (1H, d, J = 15.9 Hz),<br>8.15 (1H, d, J = 15.4 Hz)<br>−4.1, 14.0, 18.5, 19.3, 20.3, 25.8,<br>29.6, 51.1, 57.4, 93.3, 93.6, 94.8,<br>102.0, 106.5, 109.9, 110.8, 111.3,<br>111.4, 114.7, 123.1, 127.1,<br>128.2, 132.6, 137.6, 140.1, 141.0,<br>150.9, 156.4, 159.2, 161.6, 175.4 |
| 27-6 | mp 215-216° C. | 0.27 (6H, s),<br>0.97 (6H, t, J = 7.7 Hz),<br>1.08 (9H, s), 1.34-1.40 (4H, m),<br>1.56-1.62 (4H, m),<br>3.28 (4H, t, J = 7.7 Hz),<br>6.03 (1H, d, J = 2.2 Hz),<br>6.31 (1H, dd, J = 2.2 Hz, 8.8 Hz),<br>6.53 (1H, d, J = 15.4 Hz),<br>6.96 (1H, d, J = 3.8 Hz),<br>6.97 (1H, d, J = 15.9 Hz),<br>7.31 (1H, d, J = 3.8 Hz),<br>7.40 (1H, d, J = 8.8 Hz),<br>7.50-7.56 (6H, m),<br>7.84 (1H, d, J = 15.4 Hz)<br>−4.1, 14.0, 18.4, 20.3, 25.7, 25.8,<br>29.6, 51.1, 57.6, 95.3,<br>96.1, 101.9, 106.5, 110.8,<br>111.2, 111.3, 114.66, 114.73,<br>123.1, 126.7, 127.1, 128.1, 129.7,<br>129.9, 131.4, 132.6,<br>137.7, 140.1, 141.4, 150.9,<br>156.4, 159.3, 161.6, 175.6 |
| 27-7 | mp 246-248° C. | 1.21 (6H, t, J = 7.1 Hz),<br>1.44 (6H, d, J = 6.0 Hz),<br>1.74 (6H, s),<br>3.40 (4H, q, J = 7.1 Hz),<br>4.58-4.64 (1H, m),<br>6.15 (1H, d, J = 2.2 Hz),<br>6.31 (1H, dd, J = 2.2 Hz, 8.8 Hz),<br>6.52 (1H, d, J = 15.4 Hz),<br>7.00 (1H, d, J = 3.8 Hz),<br>7.12 (1H, d, J = 15.4 Hz),<br>7.36 (1H, d, J = 3.8 Hz),<br>7.38 (1H, d, J = 8.8 Hz),<br>7.43 (1H, d, J = 15.9 Hz),<br>7.76 (1H, d, J = 15.4 Hz)<br>12.8, 22.3, 26.6, 44.7, 55.4, 70.9,<br>95.0, 96.77, 96.84, 105.1, 110.9,<br>111.3, 111.7, 112.5, 113.7,<br>115.8, 126.5, 129.3, 131.3,<br>136.9, 138.1, 139.5, 150.1,<br>156.6, 158.1, 172.9, 176.0 |

TABLE 5-continued

| Example No. | Structural Formula Melting Point | ¹H-NMR (600 MHz, CDCl₃) δ ppm ¹³C-NMR (150 MHz, CDCl₃) δ ppm |
|---|---|---|
| 27-8 | mp 205-208° C. | 1.22 (6H, t, J = 7.1 Hz), 1.45 (6H, d, J = 6.0 Hz), 1.91 (3H, s), 3.42 (4H, q, J = 7.1 Hz), 4.59-4.66 (1H, m), 6.14 (1H, d, J = 2.2 Hz), 6.32 (1H, dd, J = 2.2 Hz, 8.8 Hz), 6.43 (1H, d, J = 15.4 Hz), 7.05 (1H, d, J = 3.8 Hz), 7.16 (1H, d, J = 15.4 Hz), 7.39 (1H, d, J = 8.8 Hz), 7.45 (1H, d, J = 3.8 Hz), 7.50 (1H, d, J = 15.4 Hz), 8.14 (1H, d, J = 15.4 Hz) 12.8, 19.3, 22.3, 44.8, 57.2, 70.9, 93.3, 93.5, 94.5, 96.5, 105.3, 109.7, 110.9, 111.4, 113.7, 115.8, 122.1, 127.3, 130.0, 133.1, 137.6, 140.3, 141.1, 150.7, 158.6, 159.7, 161.7, 175.5 |
| 27-9 | mp 118-123° C. | 1.22 (6H, t, J = 7.1 Hz), 1.44 (6H, d, J = 6.0 Hz), 3.41 (4H, q, J = 7.1 Hz), 4.58-4.64 (1H, m), 6.13 (1H, d, J = 2.2 Hz), 6.30 (1H, dd, J = 2.2 Hz, 8.8 Hz), 6.57 (1H, d, J = 15.4 Hz), 6.99 (1H, d, J = 3.8 Hz), 7.13 (1H, d, J = 15.4 Hz), 7.29 (1H, d, J = 3.8 Hz), 7.36 (1H, d, J = 8.8 Hz), 7.47 (1H, d, J = 15.4 Hz), 7.51-7.57 (5H, m), 7.76 (1H, d, J = 15.4 Hz) 12.8, 22.3, 44.8, 57.4, 70.9, 95.3, 96.5, 105.3, 110.9, 111.0, 111.3, 111.4, 113.7, 115.8, 122.2, 126.9, 127.2, 129.7, 129.9, 130.0, 131.5, 133.2, 137.7, 140.2, 141.7, 150.6, 158.7, 159.8, 161.7, 175.5 |
| 27-10 | mp 207-208° C. | 0.97 (6H, t, J = 7.7 Hz), 1.34-1.43 (4H, m), 1.56-1.62 (4H, m), 1.74 (6H, s), 1.88 (3H, s), 3.30 (4H, t, J = 7.7 Hz), 4.56 (2H, s), 5.06 (1H, s), 5.13 (1H, s), 6.12 (1H, d, J = 2.2 Hz), 6.27 (1H, dd, J = 2.2 Hz, 8.8 Hz), 6.52 (1H, d, J = 15.9 Hz), 7.00 (1H, d, J = 4.4 Hz), 7.11 (1H, d, J = 15.9 Hz), 7.36 (1H, d, J = 4.4 Hz), 7.37 (1H, d, J = 8.8 Hz), 7.47 (1H, d, J = 15.9 Hz), 7.77 (1H, d, J = 15.9 Hz) 14.0, 19.4, 20.3, 26.6, 29.6, 51.0, 55.4, 72.1, 95.1, 95.7, 96.8, 105.1, 111.0, 111.2, 111.7, 112.5, 112.66, 112.74, 115.8, 126.5, 129.1, 130.9, 136.9, 138.1, 139.4, 141.1, 150.5, 156.5, 158.8, 172.8, 176.0 |

TABLE 5-continued

| Example No. | Structural Formula Melting Point | $^1$H-NMR (600 MHz, CDCl$_3$) δ ppm $^{13}$C-NMR (150 MHz, CDCl$_3$) δ ppm |
|---|---|---|
| 27-11 | mp 191-193° C. | 0.98 (6H, t, J = 7.7 Hz), 1.34-1.40 (4H, m), 1.57-1.62 (4H, m), 1.88 (3H, s), 1.91 (3H, s), 3.31 (4H, t, J = 7.7 Hz), 4.56 (2H, s), 5.06 (1H, s), 5.13 (1H, s), 6.11 (1H, d, J = 2.2 Hz), 6.29 (1H, dd, J = 2.2 Hz, 8.8 Hz), 6.43 (1H, d, J = 14.8 Hz), 7.05 (1H, d, J = 4.4 Hz), 7.15 (1H, d, J = 15.9 Hz), 7.38 (1H, d, J = 8.8 Hz), 7.45 (1H, d, J = 4.4 Hz), 7.55 (1H, d, J = 15.9 Hz), 8.14 (1H, d, J = 14.8 Hz) 14.0, 19.3, 19.4, 20.3, 29.6, 51.1, 57.2, 72.2, 93.3, 93.5, 94.6, 95.6, 105.4, 109.8, 110.9, 111.4, 112.7, 112.8, 115.8, 121.2, 127.3, 129.7, 132.6, 137.7, 140.3, 141.0, 141.1, 151.0, 159.2, 159.5, 161.7, 175.5 |
| 27-12 | mp 199-202° C. | 0.97 (6H, t, J = 7.7 Hz), 1.33-1.40 (4H, m), 1.56-1.61 (4H, m), 1.87 (3H, s), 3.30 (4H, t, J = 7.7 Hz), 4.55 (2H, s), 5.06 (1H, s), 5.12 (1H, s), 6.10 (1H, d, J = 2.2 Hz), 6.27 (1H, dd, J = 2.2 Hz, 8.8 Hz), 6.56 (1H, d, J = 15.4 Hz), 6.99 (1H, d, J = 4.4 Hz), 7.11 (1H, d, J = 15.9 Hz), 7.29 (1H, d, J = 4.4 Hz), 7.36 (1H, d, J = 8.8 Hz), 7.51-7.56 (6H, m), 7.77 (1H, d, J = 15.4 Hz) 14.0, 19.4, 20.3, 29.6, 51.0, 57.4, 72.1 95.3, 95.6, 105.3, 110.9, 111.1, 111.2, 111.4, 112.7, 112.8, 115.8, 121.2, 126.9, 127.2, 129.68, 129.73, 129.9, 131.4, 132.7, 137.7, 140.2, 140.9, 141.6, 151.0, 159.2, 159.6, 161.7, 175.5 |
| 27-13 | mp 210-211° C. | 0.97 (6H, t, J = 7.7 Hz), 1.34-1.40 (4H, m), 1.56-1.60 (4H, m), 1.73 (6H, s), 3.28 (4H, t, J = 7.7 Hz), 5.29 (1H, s), 6.01 (1H, s), 6.28 (1H, d, J = 8.8 Hz), 6.50 (1H, d, J = 15.9 Hz), 7.00 (1H, d, J = 3.8 Hz), 7.10 (1H, d, J = 15.9 Hz), 7.33 (1H, d, J = 8.8 Hz), 7.35 (1H, d, J = 3.8 Hz), 7.38 (1H, d, J = 15.9 Hz), 7.77 (1H, d, J = 15.9 Hz) 14.0, 20.3, 26.6, 29.5, 50.9, 55.3, 95.1, 96.9, 98.2, 105.8, 111.0, 111.1, 111.3, 111.7, 112.5, 116.0, 126.6, 129.3, 130.5, 137.1, 138.1, 139.5, 150.5, 155.8, 156.3, 172.9, 176.0 |

TABLE 5-continued

| Example No. | Structural Formula Melting Point | ¹H-NMR (600 MHz, CDCl₃) δ ppm<br>¹³C-NMR (150 MHz, CDCl₃) δ ppm |
|---|---|---|
| 27-14 | | 0.97 (6H, t, J = 7.7 Hz),<br>1.34-1.40 (4H, m),<br>1.57-1.62 (4H, m), 1.90 (3H, s),<br>3.30 (4H, t, J = 7.7 Hz),<br>5.36 (1H, s), 6.00 (1H, s),<br>6.29 (1H, d, J = 8.8 Hz),<br>6.43 (1H, d, J = 15.4 Hz),<br>7.06 (1H, d, J = 3.8 Hz),<br>7.14 (1H, d, J = 15.9 Hz),<br>7.35 (1H, d, J = 8.8 Hz),<br>7.45 (1H, d, J = 3.8 Hz),<br>7.46 (1H, d, J = 15.9 Hz),<br>8.15 (1H, d, J = 15.4 Hz)<br>14.0, 19.3, 20.7, 29.5, 50.9,<br>57.0, 94.8, 98.1, 106.1,<br>109.9, 110.8, 111.0, 111.4,<br>116.0, 127.4, 129.8, 132.2, 137.8,<br>140.3, 141.2, 150.9, 156.3, 159.3,<br>161.7, 175.5 |
| 27-15 | mp 198-200° C. | 0.96 (6H, t, J = 7.7 Hz),<br>1.33-1.43 (4H, m),<br>1.56-1.61 (4H, m),<br>3.29 (4H, t, J = 7.7 Hz),<br>5.30 (1H, s), 5.99 (1H, s),<br>6.28 (1H, d, J = 8.8 Hz),<br>6.54 (1H, d, J = 15.4 Hz),<br>7.00 (1H, d, J = 4.4 Hz),<br>7.11 (1H, d, J = 15.9 Hz),<br>7.30 (1H, d, J = 3.8 Hz),<br>7.32 (1H, d, J = 8.8 Hz),<br>7.43 (1H, d, J = 15.9 Hz),<br>7.50-7.53 (5H, m),<br>7.80 (1H, d, J = 15.4 Hz)<br>14.0, 20.3, 29.6, 50.9, 57.4,<br>95.3, 98.1, 106.1, 110.9, 111.1,<br>111.27, 111.33, 116.0, 126.8, 127.4,<br>129.7, 129.8, 131.5, 132.3,<br>137.8, 140.2, 141.6, 150.9, 156.3,<br>159.4, 161.7, 175.6 |
| 27-16 | mp 162-165° C. | 0.95 (6H, t, J = 7.7 Hz),<br>1.30-1.36 (4H, m),<br>1.50-1.56 (4H, m),<br>1.74 (6H, s), 3.26 (4H, t, J = 7.7 Hz),<br>3.83 (3H, s,), 5.13 (2H, s),<br>6.13 (1H, d, J = 2.2 H),<br>6.27 (1H, dd, J = 2.2 Hz, 8.8 Hz),<br>6.50 (1H, d, J = 15.4 Hz),<br>6.94 (1H, d, J = 3.8 Hz),<br>6.94 (2H, d, J = 8.8 Hz),<br>7.13 (1H, d, J = 15.9 Hz),<br>7.33 (1H, d, J = 3.8 Hz),<br>7.36 (1H, d, J = 8.8 Hz),<br>7.38 (2H, d, J = 8.8 Hz),<br>7.44 (1H, d, J = 15.9 Hz),<br>7.76 (1H, d, J = 15.9 Hz)<br>14.0, 20.3, 26.6, 29.6, 51.0,<br>55.4, 70.2, 95.0, 96.3,<br>96.8, 105.2, 111.0, 111.3,<br>111.7, 112.5, 112.8, 114.1, 116.1,<br>126.5, 128.7, 129.1, 129.5, 131.1,<br>137.0, 138.1, 139.4, 150.5,<br>156.6, 158.9, 159.5, 172.8, 176.0 |

TABLE 5-continued

| Example No. | Structural Formula Melting Point | $^1$H-NMR (600 MHz, CDCl$_3$) δ ppm $^{13}$C-NMR (150 MHz, CDCl$_3$) δ ppm |
|---|---|---|
| 27-17 | 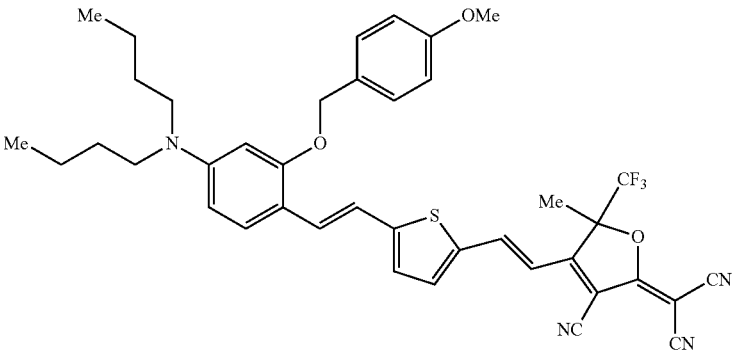 [SMILES: CCCCN(CCCC)c1ccc(/C=C/c2ccc(/C=C/C3=C(C#N)C(=C(C#N)C#N)OC3(C)C(F)(F)F)s2)c(OCc2ccc(OC)cc2)c1]<br>mp 175-178° C. | 0.95 (6H, t, J = 7.7 Hz), 1.30-1.37 (4H, m), 1.51-1.56 (4H, m), 1.89 (3H, s), 3.28 (4H, t, J = 7.7 Hz), 3.83 (3H, s), 5.13 (2H, s), 6.12 (1H, d, J = 2.2 Hz), 6.28 (1H, dd, J = 2.2 Hz, 8.8 Hz), 6.41 (1H, d, J = 14.8 Hz), 6.94 (2H, d, J = 8.8 Hz), 6.98 (1H, d, J = 3.8 Hz), 7.16 (1H, d, J = 15.9 Hz), 7.37 (1H, d, J = 8.8 Hz), 7.38 (2H, d, J = 8.8 Hz), 7.43 (1H, d, J = 3.8 Hz), 7.52 (1H, d, J = 15.9 Hz), 8.14 (1H, d, J = 15.4 Hz) 13.9, 20.3, 29.6, 51.0, 55.3, 57.4, 70.2, 96.1, 105.4, 110.9, 111.1, 111.3, 111.4, 112.9, 114.1, 116.1, 121.2, 126.8, 127.3, 128.6, 128.8, 129.7, 129.9, 130.1, 131.4, 132.9, 137.7, 140.1, 141.6, 151.0, 159.5, 159.7, 161.6, 168.3, 175.5 |
| 27-18 | 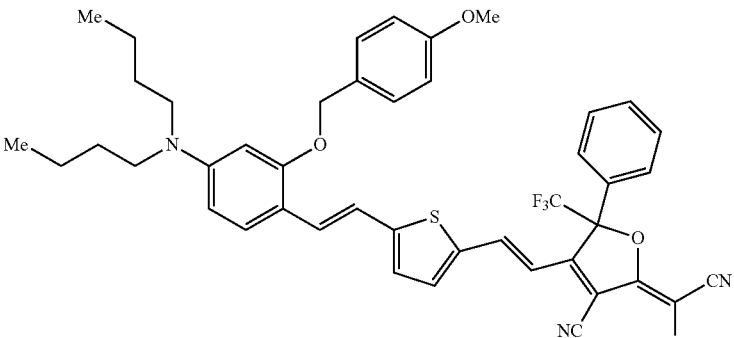<br>mp 182-183° C. | 0.95 (6H, t, J = 7.7 Hz), 1.30-1.36 (4H, m), 1.50-1.55 (4H, m), 3.27 (4H, t, J = 7.7 Hz), 3.82 (3H, s), 5.11 (2H, s), 6.11 (1H, d, J = 2.2 Hz), 6.26 (1H, dd, J = 2.2 Hz, 8.8 Hz), 6.54 (1H, d, J = 14.8 Hz), 6.92 (1H, d, J = 3.8 Hz), 6.93 (2H, d, J = 8.8 Hz), 7.13 (1H, d, J = 15.4 Hz), 7.28 (1H, d, J = 3.8 Hz), 7.34 (1H, d, J = 8.8 Hz), 7.38 (2H, d, J = 8.8 Hz), 7.47-7.56 (6H, m), 7.79 (1H, d, J = 14.3 Hz) 14.0, 19.3, 20.3, 29.6, 51.0, 55.3, 57.2, 70.3, 93.3, 93.5, 94.5, 96.1, 105.4, 109.8, 110.9, 111.4, 112.9, 114.1, 116.0, 123.1, 127.4, 128.7, 128.9, 130.1, 132.9, 137.7, 140.3, 141.1, 151.0, 159.3, 159.5, 159.6, 161.6, 175.5 |
| 27-19 | 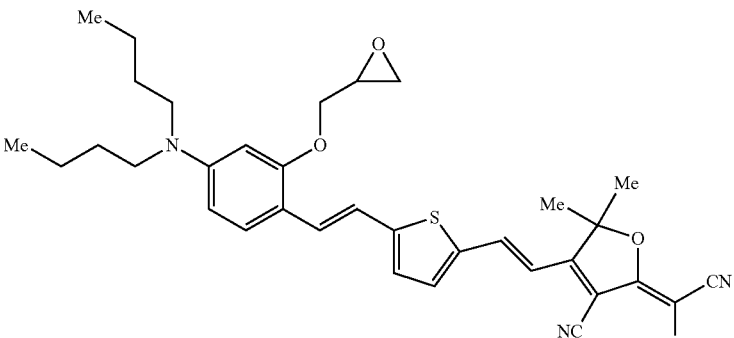<br>mp 151-154° C. | 0.97 (6H, t, J = 7.1 Hz), 1.35-1.41 (4H, m), 1.58-1.63 (4H, m), 1.74 (6H, s), 2.81 (1H, dd, J = 2.6 Hz, 4.9 Hz), 2.98 (1H, t, J = 4.4 Hz), 3.32 (4H, t, J = 7.1 Hz), 3.44-3.46 (1H, m), 4.00 (1H, dd, J = 6.0 Hz, 11.5 Hz), 4.38 (1H, dd, J = 2.7 Hz, 11.5 Hz), 6.17 (1H, d, J = 2.2 Hz), 6.30 (1H, dd, J = 2.2 Hz, 8.8 Hz), 6.52 (1H, d, J = 15.9 Hz), 7.01 (1H, d, J = 3.8 Hz), 7.11 (1H, d, J = 15.9 Hz), 7.36 (1H, d, J = 3.8 Hz), 7.38 (1H, d, J = 8.8 Hz), 7.44 (1H, d, J = 15.9 Hz), 7.78 (1H, d, J = 15.4 Hz) 14.0, 20.3, 26.6, 29.5, 44.7, 50.4, 50.9, 55.5, 69.5, 95.1, 95.8, 96.8, 105.6, 111.1, 111.3, 111.7, 112.5, 112.7, 116.0, 126.6, 129.1, 130.5, 137.1, 138.1, 139.5, 150.6, 156.2, 158.5, 172.9, 176.0 |

TABLE 5-continued

| Example No. | Structural Formula Melting Point | $^1$H-NMR (600 MHz, CDCl$_3$) δ ppm $^{13}$C-NMR (150 MHz, CDCl$_3$) δ ppm |
|---|---|---|
| 27-20 | 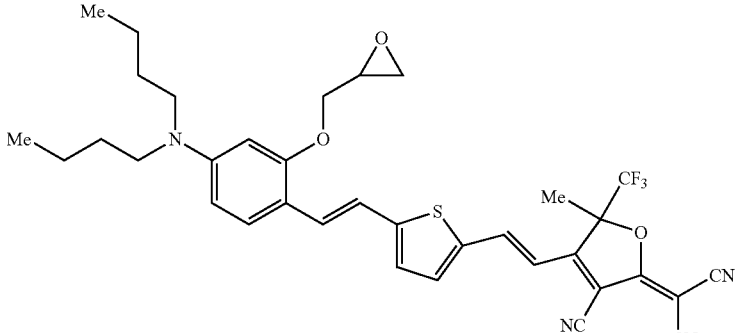<br>mp 127-130° C. | 0.98 (12H, t, J = 7.7 Hz),<br>1.35-1.41 (8H, m),<br>1.58-1.63 (8H, m), 1.91 (6H, s),<br>2.79-2.82 (2H, m),<br>2.98 (2H, t, J = 4.4 Hz),<br>3.33 (8H, t, J = 7.7 Hz),<br>3.44-3.46 (2H, m),<br>3.97-4.02 (2H, m),<br>4.41 (2H, dd, J = 2.7 Hz, 11.4 Hz), 6.17 (2H, s),<br>6.31 (2H, d, J = 8.8 Hz),<br>6.42 (1H, d, J = 15.9 Hz),<br>6.43 (1H, d, J = 15.9 Hz),<br>7.01 (2H, d, J = 3.8 Hz),<br>7.14 (2H, d, J = 15.9 Hz),<br>7.38 (1H, d, J = 8.8 Hz),<br>7.39 (1H, d, J = 8.8 Hz),<br>7.45 (2H, d, J = 3.8 Hz),<br>7.50 (1H, d, J = 15.9 Hz),<br>7.51 (1H, d, J = 15.9 Hz),<br>8.14 (1H, d, J = 15.4 Hz)<br>8.15 (1H, d, J = 15.4 Hz)<br>14.0, 19.3, 20.3, 29.6, 44.6, 50.4, 51.0, 57.4, 69.5, 93.4, 95.6, 105.8, 109.9, 110.8, 111.4, 112.7, 116.0, 121.2, 123.1, 127.4, 129.59, 129.63, 132.2, 137.8, 140.2, 141.1, 151.1, 158.9, 159.2, 161.7, 175.4 |
| 27-21 | 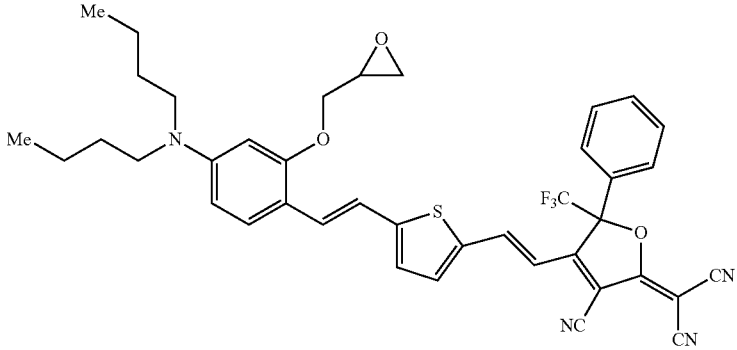 [SMILES: CCCCN(CCCC)c1ccc(/C=C/c2ccc(/C=C/C3=C(C#N)C(=C(C#N)C#N)OC3(c3ccccc3)C(F)(F)F)s2)c(OCC2CO2)c1]<br>mp 176-179° C. | 0.97 (6H, t, J = 7.1 Hz),<br>1.35-1.41 (4H, m),<br>1.56-1.63 (4H, m), 2.79-2.80 (1H, m),<br>2.97-2.98 (1H, m),<br>3.33 (4H, t, J = 7.1 Hz), 3.43 (1H, bs),<br>3.98-4.02 (1H, m),<br>4.39 (1H, dd, J = 3.3 Hz, 11.5 Hz),<br>6.17 (1H, s), 6.30 (1H, d, J = 8.8 Hz),<br>6.58 (1H, d, J = 15.4 Hz),<br>7.01 (1H, d, J = 3.8 Hz),<br>7.11 (1H, d, J = 15.9 Hz),<br>7.29 (1H, d, J = 3.8 Hz),<br>7.36 (1H, d, J = 8.8 Hz),<br>7.48 (1H, d, J = 15.4 Hz),<br>7.51-7.57 (5H, m),<br>7.77 (1H, d, J = 14.8 Hz)<br>14.0, 20.3, 29.6, 44.7, 50.3, 51.0, 57.6, 69.5, 95.7, 105.8, 110.9, 111.2, 111.3, 112.8, 116.0, 123.1, 126.9, 127.4, 129.7, 129.8, 129.9, 131.5, 132.3, 137.8, 140.1, 141.7, 151.1, 159.0, 159.3, 161.8, 175.5 |
| 27-22 | 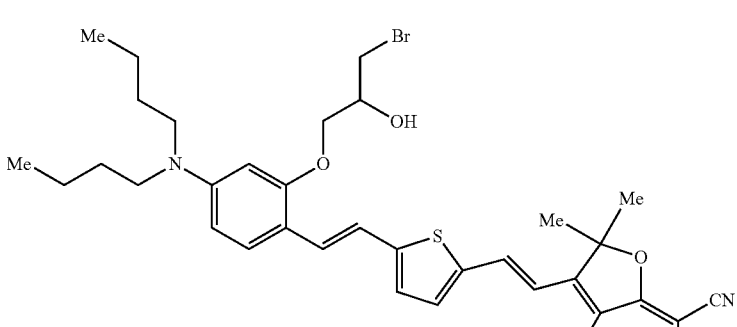<br>mp 239-241° C. | 0.98 (6H, t, J = 7.1 Hz),<br>1.35-1.41 (4H, m), 1.58-1.63 (4H, m),<br>1.72 (6H, s), 3.33 (4H, t, J = 7.1 Hz),<br>4.20 (1H, dd, J = 2.7 Hz, 10.4 Hz),<br>4.38 (1H, dd, J = 2.7 Hz, 10.4 Hz),<br>4.67-4.71 (2H, m), 5.13-5.16 (1H, m),<br>6.08 (1H, d, J = 2.2 Hz),<br>6.34 (1H, dd, J = 2.2 Hz, 8.8 Hz),<br>6.53 (1H, d, J = 15.4 Hz),<br>7.00 (1H, d, J = 15.9 Hz),<br>7.05 (1H, d, J = 3.8 Hz),<br>7.32 (1H, d, J = 3.8 Hz),<br>7.38 (1H, d, J = 8.8 Hz),<br>7.38 (1H, d, J = 15.9 Hz),<br>7.85 (1H, d, J = 15.9 Hz)<br>14.0, 20.3, 26.3, 29.5, 50.9, 55.3, 65.9, 67.3, 74.3, 94.6, 95.4, 97.2, 106.3, 111.5, 111.8, 112.5, 112.6, 116.2, 126.8, 128.9, 129.3, 137.6, 138.0, 139.7, 150.4, 154.7, 155.7, 157.5, 173.1, 176.1 |

TABLE 5-continued

| Example No. | Structural Formula Melting Point | $^1$H-NMR (600 MHz, CDCl$_3$) δ ppm<br>$^{13}$C-NMR (150 MHz, CDCl$_3$) δ ppm |
|---|---|---|
| 27-23 | 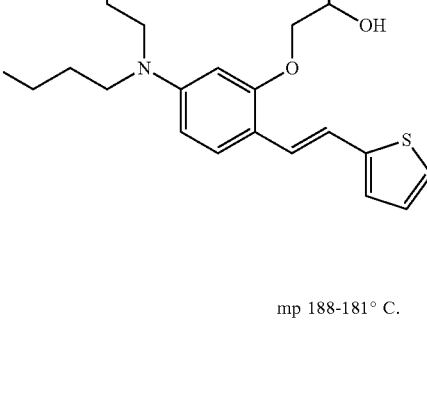<br>mp 188-181° C. | 0.98 (12H, t, J = 7.7 Hz),<br>1.36-1.42 (8H, m), 1.59-1.64 (8H, m),<br>1.91 (6H, s), 3.34 (8H, t, J = 7.7 Hz),<br>4.18-4.21 (2H, m), 4.37-4.40 (2H, m),<br>4.69 (4H, t, J = 4.7 Hz),<br>5.13-5.14 (2H, m),<br>6.07 (1H, d, J = 2.2 Hz),<br>6.08 (1H, d, J = 2.2 Hz),<br>6.35 (2H, d, J = 8.8 Hz),<br>6.46 (1H, d, J = 15.4 Hz),<br>6.47 (1H, d, J = 15.4 Hz),<br>7.02 (1H, d, J = 15.9 Hz),<br>7.04 (1H, d, J = 15.9 Hz),<br>7.11 (1H, d, J = 3.8 Hz),<br>7.13 (1H, d, J = 3.8 Hz),<br>7.38 (2H, d, J = 8.8 Hz),<br>7.39 (1H, d, J = 3.8 Hz),<br>7.40 (1H, d, J = 3.8 Hz),<br>7.44 (1H, d, J = 15.9 Hz),<br>7.47 (1H, d, J = 15.9 Hz),<br>8.12 (1H, d, J = 15.9 Hz),<br>8.17 (1H, d, J = 15.9 Hz)<br>14.0, 19.0, 19.1, 20.3, 29.5,<br>51.0, 57.2, 65.9, 67.2, 67.5,<br>74.2, 95.1, 95.3, 106.37, 106.42,<br>110.1, 110.9, 111.4, 112.46, 112.57,<br>115.9, 116.1, 121.2, 127.6, 129.2, 129.5,<br>130.9, 131.0, 138.2, 138.3, 140.2,<br>141.2, 150.9, 154.6, 154.6, 157.8,<br>157.9, 158.7, 158.8, 161.8, 175.5, 175.6 |
| 27-24 | 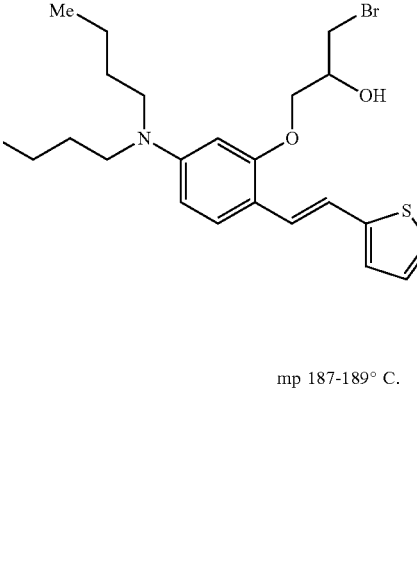<br>mp 187-189° C. | 0.98 (12H, t, J = 7.7 Hz),<br>1.35-1.41 (8H, m), 1.58-1.63 (8H, m),<br>3.33 (8H, t, J = 7.7 Hz),<br>4.17-4.20 (2H, m),<br>4.36-4.39 (2H, m),<br>4.67-4.70 (4H, m), 5.12-5.15 (2H, m),<br>6.05 (1H, d, J = 2.2 Hz),<br>6.06 (1H, d, J = 2.2 Hz),<br>6.32 (1H, d , 8.8 Hz), 6.33 (1H, d, 8.8 Hz),<br>6.60 (1H, d, J = 15.4 Hz),<br>6.63 (1H, d, J = 15.4 Hz),<br>6.99 (1H, d, J = 15.9 Hz),<br>7.00 (1H, d, J = 15.9 Hz),<br>7.09 (1H, d, J = 3.8 Hz),<br>7.10 (1H, d, J = 3.8 Hz),<br>7.27 (2H, d, J = 3.8 Hz),<br>7.30 (1H, d, J = 8.8 Hz),<br>7.31 (1H, d, J = 8.8 Hz),<br>7.39 (1H, d, J = 15.9 Hz),<br>7.42 (1H, d, J = 15.9 Hz),<br>7.52-7.57 (10H, m), 7.82 (1H, d, J = 15.9 Hz),<br>7.85 (1H, d, J = 15.9 Hz)<br>14.0, 20.3, 29.5, 51.0, 57.5,<br>66.0, 67.38, 67.43, 74.1,<br>95.0, 95.2, 106.3, 110.9, 111.3,<br>111.4, 112.6, 116.2, 116.3, 121.1,<br>123.0, 126.65, 126.73, 127.6, 129.6, 129.72,<br>129.75, 131.2, 131.4, 138.21, 138.24,<br>141.7, 150.8, 154.5, 158.0, 158.86,<br>158.93, 161.8, 175.56, 175.59 |

TABLE 5-continued

| Example No. | Structural Formula Melting Point | $^1$H-NMR (600 MHz, CDCl$_3$) δ ppm $^{13}$C-NMR (150 MHz, CDCl$_3$) δ ppm |
|---|---|---|
| 27-25 | 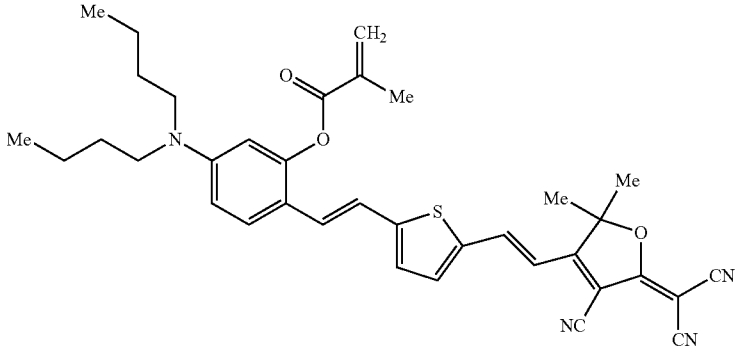 [SMILES: C=C(C)C(=O)Oc1cc(N(CCCC)CCCC)ccc1/C=C/c1ccc(/C=C/C2=C(C#N)C(=C(C#N)C#N)OC2(C)C)s1]<br>mp 247-250° C. | 0.97 (6H, t, J = 7.7 Hz),<br>1.33-1.40 (4H, m),<br>1.56-1.61 (4H, m), 1.75 (6H, s),<br>2.14 (3H, s), 3.30 (4H, t, J = 7.7 Hz),<br>5.89 (1H, m), 6.31 (1H, d, J = 2.2 Hz),<br>6.47 (1H, S),<br>6.54 (1H, dd, J = 2.2 Hz, 8.8 Hz),<br>6.57 (1H, d, J = 15.4 Hz),<br>6.99 (1H, d, J = 15.9 Hz),<br>7.00 (1H, d, J = 3.8 Hz),<br>7.07 (1H, d, J = 15.9 Hz),<br>7.35 (1H, d, J = 3.8 Hz),<br>7.49 (1H, d, J = 8.8 Hz),<br>7.72 (1H, d, J = 15.9 Hz)<br>14.0, 18.5, 20.3, 26.6, 29.4, 50.9,<br>56.1, 96.3, 96.9, 105.2, 110.0, 111.0,<br>111.4, 111.8, 112.2, 115.1, 117.0, 127.0,<br>127.7, 128.0, 128.2, 135.8,<br>137.4, 137.5, 139.3, 145.0,<br>150.8, 154.4, 165.7, 172.9, 175.7 |
| 27-26 | 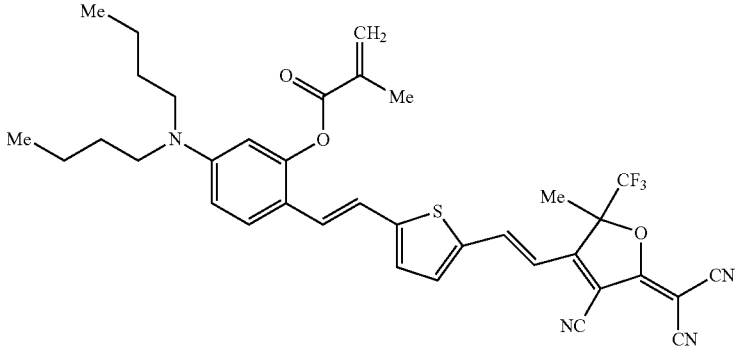 [SMILES: C=C(C)C(=O)Oc1cc(N(CCCC)CCCC)ccc1/C=C/c1ccc(/C=C/C2=C(C#N)C(=C(C#N)C#N)OC2(C)C(F)(F)F)s1]<br>mp 213-215° C. | 0.97 (6H, t, J = 7.7 Hz),<br>1.34-1.40 (4H, m),<br>1.56-1.62 (4H, m), 1.92 (3H, s),<br>2.14 (3H, s), 3.31 (4H, t, J = 7.7 Hz),<br>5.89 (1H, m), 6.32 (1H, d, J = 2.7 Hz),<br>6.47 (1H, s), 6.49 (1H, d, J = 15.4 Hz),<br>6.54 (1H, dd, J = 2.2 Hz, 8.8 Hz),<br>7.01 (1H, d, J = 15.4 Hz),<br>7.04 (1H, d, J = 3.8 Hz),<br>7.14 (1H, d, J = 15.9 Hz),<br>7.45 (1H, d, J = 3.8 Hz),<br>7.50 (1H, d, J = 8.8 Hz),<br>8.10 (1H, d, J = 15.4 Hz)<br>14.0, 18.6, 19.3, 20.3, 29.4,<br>50.9, 58.4, 93.6, 93.8, 96.5, 105.2,<br>110.2, 110.4, 110.7, 110.9,<br>111.0, 115.0 116.8, 123.0, 127.6,<br>127.8, 128.2, 129.5, 135.8, 138.0,<br>139.3, 141.2, 150.3, 151.1,<br>156.9, 162.1, 165.6, 175.1 |
| 27-27 | 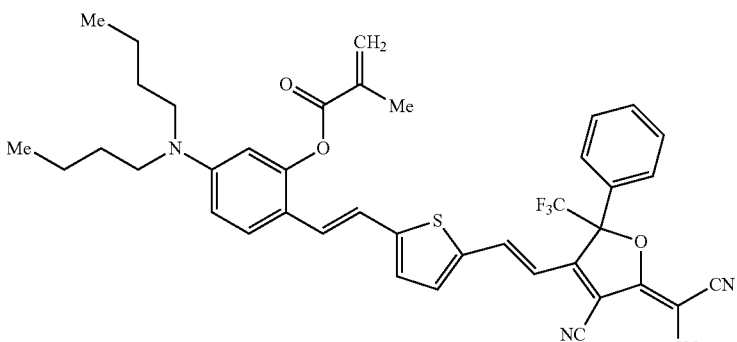<br>mp 174-176° C. | 0.96 (6H, t, J = 7.7 Hz),<br>1.33-1.39 (4H, m), 1.55-1.61 (4H, m),<br>2.13 (3H, s), 3.30 (4H, t, J = 7.7 Hz),<br>5.88 (1H, m), 6.31 (1H, d, J = 2.2 Hz),<br>6.46 (1H, s),<br>6.53 (1H, dd, J = 2.2 Hz, 8.8 Hz),<br>6.62 (1H, d, J = 15.4 Hz),<br>6.97 (1H, d, J = 4.4 Hz),<br>6.97 (1H, d, J = 15.9 Hz),<br>7.11 (1H, d, J = 15.9 Hz),<br>7.27 (1H, d, J = 4.4 Hz),<br>7.48 (1H, d, J = 8.8 Hz),<br>7.49-7.58 (5H, m),<br>7.70 (1H, d, J = 15.9 Hz)<br>13.9, 18.5, 20.3, 29.4, 50.9,<br>58.7, 97.3, 105.2, 110.0, 110.5,<br>110.7, 111.0, 111.9, 115.0, 116.8,<br>126.9, 127.5, 127.8, 128.2, 129.6,<br>129.8, 131.6, 135.8, 138.1, 139.2,<br>141.8, 150.3, 151.1, 156.9,<br>162.1, 165.6, 175.2 |

TABLE 5-continued

| Example No. | Structural Formula Melting Point | ¹H-NMR (600 MHz, CDCl₃) δ ppm ¹³C-NMR (150 MHz, CDCl₃) δ ppm |
|---|---|---|
| 27-28 | 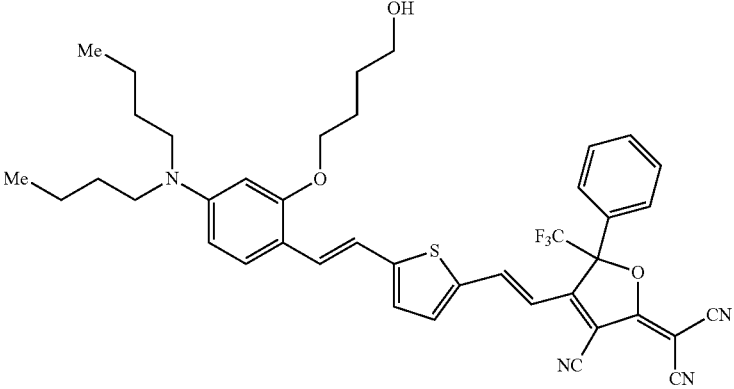 [SMILES: CCCCN(CCCC)c1ccc(/C=C/c2ccc(/C=C/C3=C(C#N)C(=C(C#N)C#N)OC3(c3ccccc3)C(F)(F)F)s2)c(OCCCCO)c1]<br>mp 187° C. | 0.98 (6H, t, J = 7.7 Hz),<br>1.35-1.41 (4H, m),<br>1.57-1.63 (4H, m),<br>1.82-1.86 (2H, m),<br>1.98-2.03 (2H, m),<br>3.33 (4H, t, J = 7.7 Hz),<br>3.79 (2H, t, J = 6.6 Hz),<br>4.08 (2H, t, J = 6.0 Hz),<br>6.09 (1H, d, J = 2.2 Hz),<br>6.27 (1H, dd, J = 2.2 Hz, 8.8 Hz),<br>6.60 (1H, d, J = 14.9 Hz),<br>6.97 (1H, d, J = 4.4 Hz),<br>7.11 (1H, d, J = 15.9 Hz),<br>7.27 (1H, d, J = 4.4 Hz),<br>7.35 (1H, d, J = 8.8 Hz),<br>7.49-7.57 (6H, m),<br>7.67 (1H, d, J = 14.9 Hz)<br>14.0, 20.3, 25.8, 29.5, 29.6,<br>50.9, 57.4, 62.5, 68.1, 95.0, 95.5,<br>105.3, 110.9, 111.2, 111.4,<br>112.7, 115.6, 121.2, 123.1, 126.9,<br>127.3, 129.7, 129.9, 131.5, 132.8,<br>137.7, 140.3, 141.6, 151.2,<br>159.5, 159.8, 161.7, 175.4 |

Example 28

2-[4-[2-(4-dibutylamino-2-methoxyphenyl)vinyl]-3-cyano-5,5-dimethyl-2(5H)-furanylidene]propanedinitrile

[Formula 200]

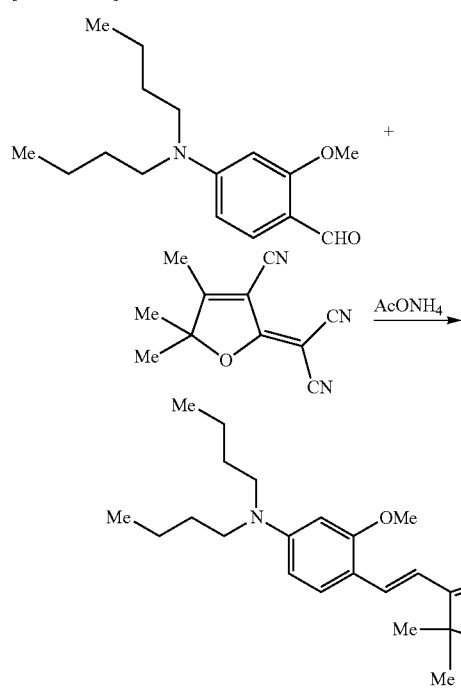

In 5 ml of ethanol were dissolved 170 mg (0.65 mmol) of 4-dibutylamino-2-methoxybenzaldehyde and 141 mg (0.71 mmol) of 2-(3-cyano-4,5,5-trimethyl-2(5H)-furanylidene) propanedinitrile. To this mixture was added 50 mg of ammonium acetate, and the mixture was stirred at 50° C. for 4 hours. Ethanol was evaporated off and the residue was purified by silica gel column chromatography to give 273 mg of a dark brown crystal (yield: 95.1%; mp: 222-226° C.)

¹H-NMR (600 MHz, CDCl₃) δ: 0.99 (6H, t, J=7.7 Hz), 1.37-1.43 (4H, m), 1.62-1.67 (4H, m), 1.74 (6H, s), 3.41 (4H, t, J=7.7 Hz), 3.91 (3H, s), 6.05 (1H, s), 6.35 (1H, dd, J=2.2 Hz, 8.8 Hz), 6.82 (1H, d, J=15.9 Hz), 7.53 (1H, d, J=8.8 Hz), 7.95 (1H, d, J=15.9 Hz)

¹³C-NMR (150 MHz, CDCl₃) δ: 13.9, 20.3, 27.1, 29.6, 51.2, 53.1, 55.5, 93.3, 96.4, 106.5, 108.1, 111.8, 112.2, 112.4, 113.3, 131.4, 143.4, 154.2, 162.4, 175.0, 176.6

Example 29

2-[4-[2-(4-dibutylamino-2-methoxyphenyl)vinyl]-3-cyano-5-methyl-5-trifluoromethyl-2(5H)-furanylidene] propanedinitrile

[Formula 201]

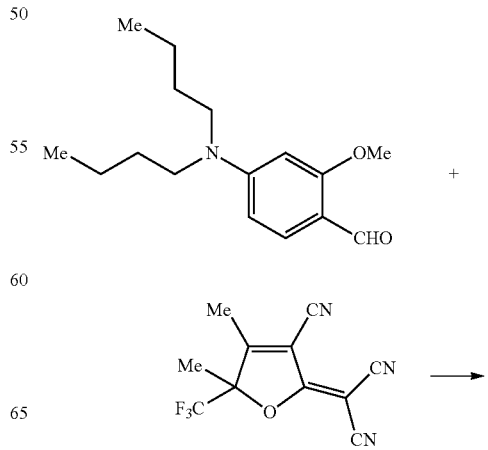

-continued

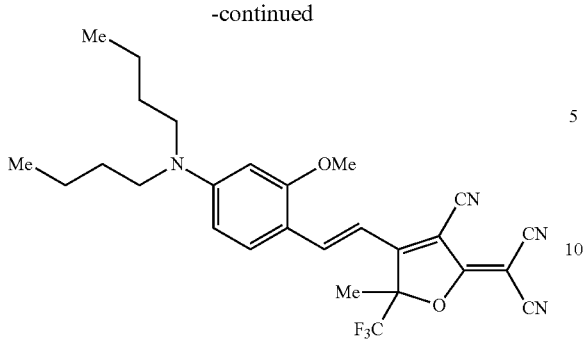

In 5 ml of ethanol were dissolved 149 mg (0.57 mmol) of 4-dibutylamino-2-methoxybenzaldehyde and 158 mg (0.62 mmol) of 2-(3-cyano-4,5-dimethyl-5-trifluoromethyl-2(5H)-furanylidene)propanedinitrile. After the mixture was stirred at 50° C. for 2 hours, ethanol was evaporated off. The residue was purified by silica gel column chromatography to give 262 mg of a dark brown crystal (yield: 92.9%; mp: 211-213° C.).

$^1$H-NMR (600 MHz, CDCl$_3$) δ: 1.00 (6H, t, J=7.7 Hz), 1.38-1.44 (4H, m), 1.63-1.69 (4H, m), 1.89 (3H, s), 3.44 (4H, t, J=7.7 Hz), 3.93 (3H, s), 6.03 (1H, d, J=2.2 Hz), 6.39 (1H, dd, J=2.2 Hz, 8.8 Hz), 6.76 (1H, b), 7.51 (1H, d, J=8.8 Hz), 8.43 (1H, b)

$^{13}$C-NMR (150 MHz, CDCl$_3$) δ: 13.9, 19.7, 20.2, 29.6, 51.5, 54.6, 55.6, 93.2, 93.4, 107.4, 111.6, 112.2, 112.3, 113.7, 121.4, 123.3, 145.7, 146.0, 155.3, 155.4, 163.5, 163.6, 176.3

Example 30

2-[4-[2-(4-dibutylamino-2-methoxyphenyl) vinyl]-3-cyano-5-phenyl-5-trifluoromethyl-2(5H)-furanylidene] propanedinitrile

[Formula 202]

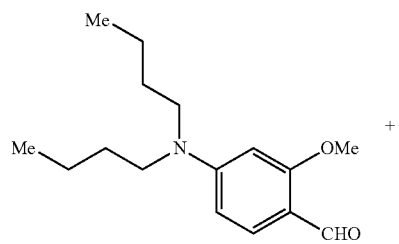

+

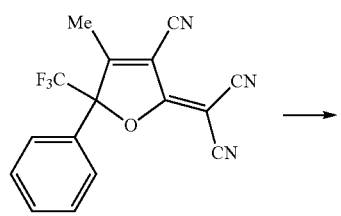

→

-continued

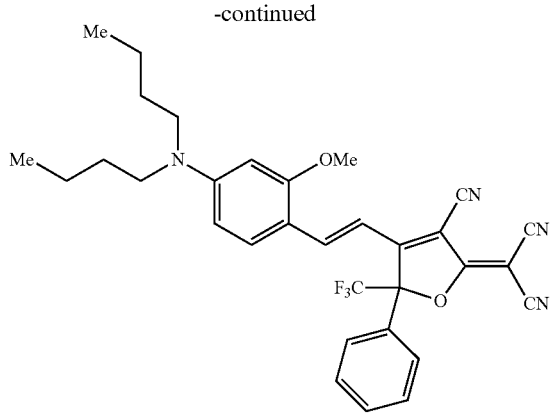

In 5 ml of ethanol were dissolved 150 mg (0.57 mmol) of 4-dibutylamino-2-methoxybenzaldehyde and 197 mg (0.63 mmol) of 2-(3-cyano-4-methyl-5-phenyl-5-trifluoromethyl-2(5H)-furanylidene)propanedinitrile. After the mixture was stirred at 50° C. for 2 hours, ethanol was evaporated off. The residue was purified by silica gel column chromatography to give 272 mg of a dark brown crystal (yield: 85.2%; mp: 191-194° C.)

$^1$H-NMR (600 MHz, CDCl$_3$) δ: 0.98 (6H, t, J=7.7 Hz), 1.35-1.41 (4H, m), 1.60-1.65 (4H, m), 3.40 (4H, t, J=7.7 Hz), 3.83 (3H, s), 5.96 (1H, s), 6.32 (1H, dd, J=2.2 Hz, 8.8 Hz), 6.87 (1H, b), 7.37 (1H, b), 7.46-7.52 (5H, m), 8.12 (1H, b)

$^{13}$C-NMR (150 MHz, CDCl$_3$) δ: 13.8, 20.2, 29.6, 51.5, 54.9, 55.5, 93.2, 95.7, 107.2, 111.6, 112.0, 112.1, 113.8, 121.3, 123.2, 126.8, 129.4, 130.8, 131.0, 146.8, 155.3, 163.5, 163.6, 176.5

Example 31

5,5-dimethyl-2-oxo-4-[2-(2,4,6-trimethoxyphenyl) vinyl]-2,5-dihydrofuran-3-carbonitrile

[Formula 203]

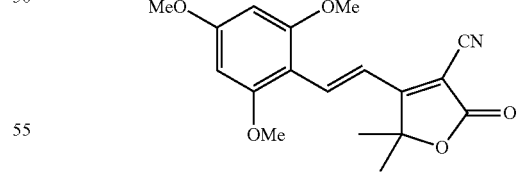

The compound was synthesized in the same procedure as in Example 30 mp: 186° C.

$^1$H-NMR (600 MHz, CDCl$_3$) δ: 1.67 (6H, s), 3.91 (3H, s), 3.92 (6H, s), 6.12 (2H, s), 7.36 (1H, d, J=18 Hz), 8.12 (1H, d, J=18 Hz)

$^{13}$C-NMR (150 MHz, CDCl$_3$) δ: 26.4, 55.5, 56.0, 86.7, 90.7, 94.8, 106.0, 112.8, 114.7, 137.9, 162.0, 164.7, 167.2, 179.4

Example 32

2-{3-cyano-4-[2-(2,4,6-trimethoxyphenyl)vinyl]-5,5-dimethyl-2(5H)-furanylidene}propanedinitrile

[Formula 204]

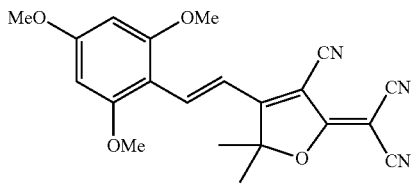

The compound was synthesized in the same procedure as in Example 30 mp: 250° C.

$^1$H-NMR (600 MHz, CDCl$_3$) δ: 1.77 (6H, s), 3.93 (3H, s), 3.94 (6H, s), 6.12 (2H, s), 7.34 (1H, d, J=18 Hz), 8.09 (1H, d, J=18 Hz)

Example 33

4-[2-(4-dibutylamino-2,6-dimethoxyphenyl)vinyl]-5,5-dimethyl-2-oxo-2,5-dihydrofuran-3-carbonitrile

[Formula 205]

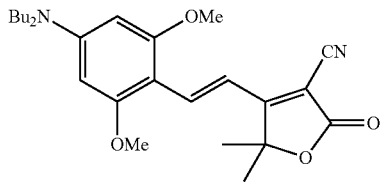

The compound was synthesized in the same procedure as in Example 30 (mp: 119-120° C.)

$^1$H-NMR (600 MHz, CDCl$_3$) δ: 1.00 (6H, t, J=7 Hz), 1.40 (4H, m), 1.64 (6H, s), 1.67 (4H, m), 3.38 (4H, t, J=8 Hz), 3.90 (6H, s), 5.78 (2H, s), 7.18 (1H, d, J=16 Hz), 8.17 (1H, d, J=16 Hz)

$^{13}$C-NMR (150 MHz, CDCl$_3$) δ: 13.9, 20.2, 26.7, 29.5, 50.9, 55.6, 86.4, 87.6, 90.8, 102.4, 111.0, 113.8, 138.7, 152.9, 162.6, 168.3, 179.6

Example 34

2-{4-[2-(4-dibutylamino-2,6-dimethoxyphenyl)vinyl]-3-cyano-5,5-dimethyl-2(5H)-furanylidene}propanedinitrile

[Formula 206]

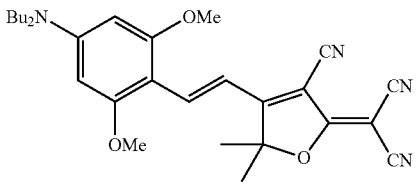

The compound was synthesized in the same procedure as in Example 30 mp: 216° C.

$^1$H-NMR (600 MHz, CDCl$_3$) δ: 1.00 (6H, t, J=7 Hz), 1.41 (4H, m), 1.68 (4H, m), 1.73 (6H, s), 3.42 (4H, t, J=8 Hz), 3.92 (6H, s), 5.78 (2H, s), 7.26 (1H, d, J=16 Hz), 8.14 (1H, d, J=16 Hz)

$^{13}$C-NMR (150 MHz, CDCl$_3$) δ: 13.8, 20.2, 27.2, 29.6, 51.2, 55.7, 87.9, 96.1, 103.9, 110.2, 112.0, 112.9, 113.8, 140.8, 154.7, 163.6, 177.0, 177.1

Example 35

2-[4-[4-(4-dibutylamino-2-methoxyphenyl)-1,3-butadienyl]-3-cyano-5,5-dimethyl-2(5H)-furanylidene]propanedinitrile (35-1)
3-(4-dibutylamino-2-methoxyphenyl)acrylonitrile

[Formula 207]

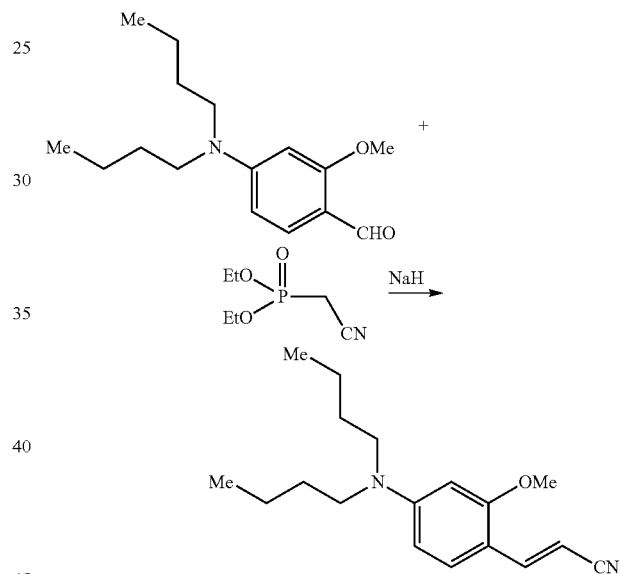

To 0.52 g (21.7 mmol) of sodium hydride, 20 ml of tetrahydrofuran was added. To this mixture, 3.87 g (21.4 mmol) of diethyl cyanomethylphosphonate was added dropwise under ice cooling, and the mixture was stirred for 25 minutes. Next, 2.8 g (10.6 mmol) of 4-dibutylamino-2-methoxybenzaldehyde in tetrahydrofuran was added dropwise, and the mixture was stirred for 1 hour. To the mixture water was added and the mixture was subjected to extraction with ethyl acetate. The extract was washed with a saturated saline solution, dried over anhydrous sodium sulfate, and concentrated. The residue was purified by silica gel column chromatography to give 3.04 g of an orange oily matter (yield: 100%).

$^1$H-NMR (600 MHz, CDCl$_3$) δ: 0.97 (6H, t, J=7.1 Hz), 1.34-1.40 (4H, m), 1.56-1.60 (4H, m), 3.31 (4H, t, J=7.1 Hz), 3.85 (3H, s), 5.74 (1H, d, J=16.5 Hz), 6.06 (1H, s), 6.21 (1H, d, J=8.8 Hz), 7.18 (1H, d, J=8.8 Hz), 7.46 (1H, d, J=16.5 Hz)

$^{13}$C-NMR (150 MHz, CDCl$_3$) δ: 13.9, 20.3, 29.4, 50.9, 55.1, 89.8, 93.8, 104.3, 110.5, 120.9, 130.6, 146.4, 151.5, 160.2

177

(35-2) 3-(4-dibutylamino-2-methoxyphenyl)propenal

[Formula 208]

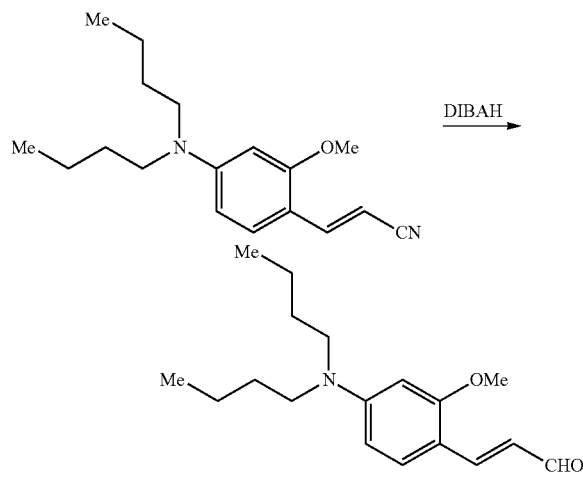

In 40 ml of toluene was dissolved 3.0 g (10.5 mmol) of 3-(4-dibutylamino-2-methoxyphenyl)acrylonitrile. To this mixture, 10.4 ml of diisobutylaluminium hydride (1.5 mol solution in toluene) (15.6 mmol) was added dropwise under cooling at −68 to −72° C. under argon atmosphere. The reaction mixture was stirred for 2 hours and the temperature was allowed to rise. To the mixture, 50 ml of a 5% ammonium chloride solution was added dropwise. The mixture was stirred for 30 minutes and filtrated. The phases were separated and the organic layer was washed with a saturated saline solution. The organic layer was dried over anhydrous sodium sulfate and concentrated. The residual liquid was purified by silica gel column chromatography to give 2.51 g of an orange crystal (yield: 82.8%).

$^1$H-NMR (600 MHz, CDCl$_3$) δ: 0.98 (6H, t, J=7.7 Hz), 1.35-1.41 (4H, m), 1.58-1.63 (4H, m), 3.33 (4H, t, J=7.1 Hz), 3.87 (3H, s), 6.08 (1H, s), 6.26 (1H, dd, J=2.2 Hz, 8.8 Hz), 6.61 (1H, dd, J=8.2 Hz, 15.4 Hz), 7.39 (1H, d, J=8.8 Hz), 7.70 (1H, d, J=15.4 Hz), 9.55 (1H, d, J=8.2 Hz)

$^{13}$C-NMR (150 MHz, CDCl$_3$) δ: 13.9, 20.3, 29.4, 50.9, 55.1, 93.7, 104.8, 110.9, 123.6, 130.8, 149.4, 152.3, 160.5

(35-3) 2-[4-[4-(4-dibutylamino-2-methoxyphenyl)-1,3-butadienyl]-3-cyano-5,5-dimethyl-2(5H)-furanylidene] propanedinitrile

[Formula 209]

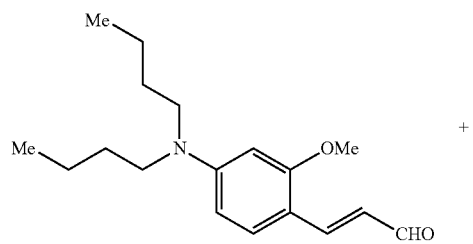

178

-continued

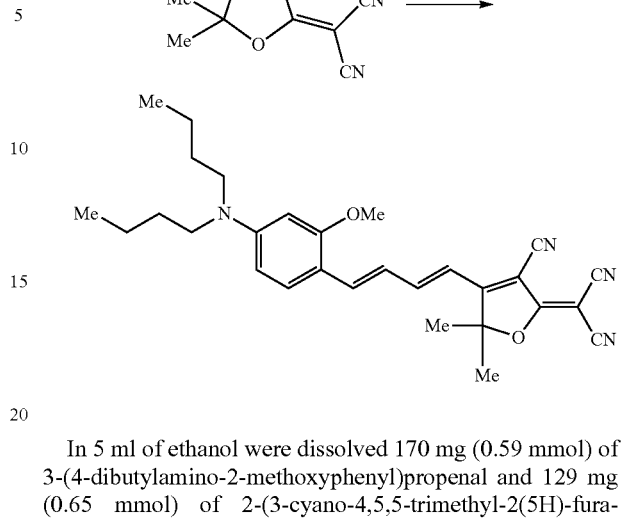

In 5 ml of ethanol were dissolved 170 mg (0.59 mmol) of 3-(4-dibutylamino-2-methoxyphenyl)propenal and 129 mg (0.65 mmol) of 2-(3-cyano-4,5,5-trimethyl-2(5H)-furanylidene) propanedinitrile. To this mixture was added 46 mg of ammonium acetate, and the mixture was stirred with heating at 50° C. for 2 hours. The solvent was evaporated off and the residue was purified by silica gel column chromatography to give 206 mg of a dark greenish brown crystal (yield: 74.5%; mp: 181-184° C.)

$^1$H-NMR (600 MHz, CDCl$_3$) δ: 0.99 (6H, t, J=7.7 Hz), 1.37-1.42 (4H, m), 1.61-1.66 (4H, m), 1.69 (6H, s), 3.37 (4H, t, J=7.7 Hz), 3.91 (3H, s), 6.06 (1H, b), 6.30 (1H, d, J=14.8 Hz), 6.32 (1H, b), 6.94 (1H, dd, J=14.9 Hz, 11.5 Hz), 7.40 (1H, d, J=8.8 Hz), 7.46 (1H, d, J=14.8 Hz), 7.63 (1H, dd, J=13.7 Hz, 13.2 Hz)

$^{13}$C-NMR (150 MHz, CDCl$_3$) δ: 13.9, 20.3, 26.7, 29.6, 51.2, 54.0, 55.3, 96.4, 105.9, 111.9, 112.2, 113.0, 113.3, 122.9, 131.4, 145.3, 151.7, 161.4, 173.4, 176.5

Example 36

2-[4-[4-(4-dibutylamino-2-methoxyphenyl)-1,3-butadienyl]-3-cyano-5-methyl-5-trifluoromethyl-2(5H)-furanylidene] propanedinitrile

[Formula 210]

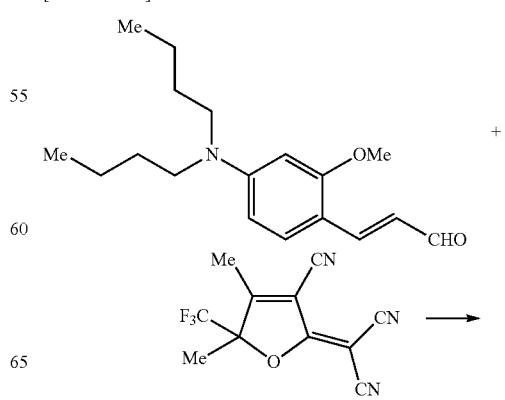

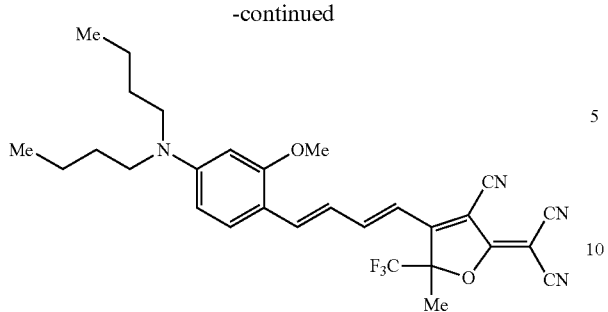

In 5 ml of ethanol were dissolved 145 mg (0.50 mmol) of 3-(4-dibutylamino-2-methoxyphenyl)propenal and 140 mg (0.55 mmol) of 2-(3-cyano-4,5-dimethyl-5-trifluoromethyl-2(5H)-furanylidene)propanedinitrile. After the mixture was stirred with heating at 50° C. for 2 hours, the solvent was evaporated off. The residue was purified by silica gel column chromatography to give 242 mg of a dark greenish brown crystal (yield: 92.1%; mp: 169-170° C.)

$^{1}$H-NMR (600 MHz, CDCl$_3$) δ: 1.00 (6H, t, J=7.7 Hz), 1.37-1.44 (4H, m), 1.62-1.68 (4H, m), 1.83 (3H, s), 3.41 (4H, t, J=7.7 Hz), 3.92 (3H, s), 6.04 (1H, s), 6.18 (1H, d, J=14.8H), 6.34 (1H, dd, J=13.7 Hz, 13.2 Hz), 6.35 (1H, dd, J=2.2 Hz, 8.8 Hz), 7.44 (1H, d, J=8.8 Hz), 7.63 (1H, d, J=14.8 Hz), 8.09 (1H, b)

$^{13}$C-NMR (150 MHz, CDCl$_3$) δ: 13.9, 19.4, 20.3, 29.6, 51.3, 54.5, 55.3, 92.7, 93.4, 106.7, 111.7, 112.0, 112.3, 112.5, 114.3, 121.4, 123.3, 123.7, 132.5, 148.7, 154.0, 154.2, 161.2, 162.6, 176.2

Example 37

2-[4-[4-(4-dibutylamino-2-methoxyphenyl)-1,3-butadienyl]-3-cyano-5-phenyl-5-trifluoromethyl-2(5H)-furanylidene] propanedinitrile

[Formula 211]

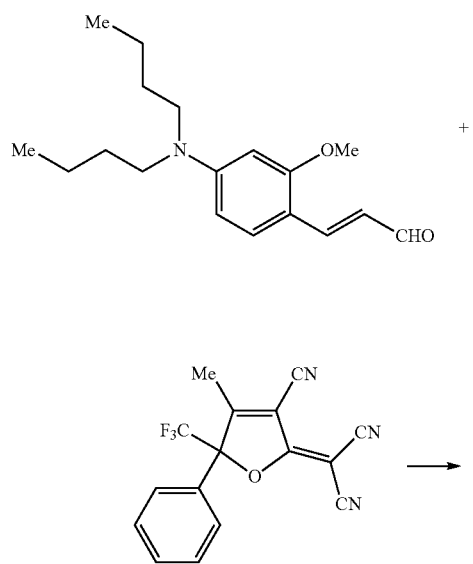

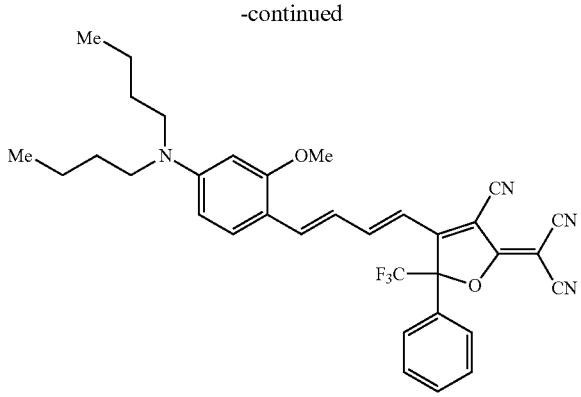

In 5 ml of ethanol were dissolved 130 mg (0.45 mmol) of 3-(4-dibutylamino-2-methoxyphenyl)propenal and 156 mg (0.50 mmol) of 2-(3-cyano-4-methyl-5-phenyl-5-trifluoromethyl-2(5H)-furanylidene)propanedinitrile. After the mixture was stirred with heating at 50° C. for 2 hours, the solvent was evaporated off. The residue was purified by silica gel column chromatography to give 229 mg of a dark greenish brown crystal (yield: 86.9%; mp: 190-192° C.)

$^{1}$H-NMR (600 MHz, CDCl$_3$) δ: 0.99 (6H, t, J=7.7 Hz), 1.36-1.43 (4H, m), 1.60-1.66 (4H, m), 3.40 (4H, t, J=7.7 Hz), 3.89 (3H, s), 6.01 (1H, s), 6.26 (1H, d, J=13.7 Hz), 6.31 (1H, dd, J=2.2 Hz, 8.8 Hz), 6.92 (1H, dd, J=14.3 Hz, 13.2 Hz), 7.38 (1H, d, J=8.8 Hz), 7.48-7.52 (6H, m), 7.90 (1H, b)

$^{13}$C-NMR (150 MHz, CDCl$_3$) δ: 13.9, 20.3, 29.6, 51.3, 55.0, 55.3, 93.4, 106.7, 111.7, 112.2, 112.4, 113.4, 114.4, 123.9, 126.8, 129.5, 130.6, 131.0, 148.7, 154.17, 154.24, 161.1, 162.6, 176.3

Example 38

2-[4-[6-(4-dibutylamino-2-methoxyphenyl)-1,3,5-hexatrienyl]-3-cyano-5,5-dimethyl-2(5H)-furanylidene]propanedinitrile (38-1) 5-(4-dibutylamino-2-methoxyphenyl)-2,4-pentadienenitrile

[Formula 212]

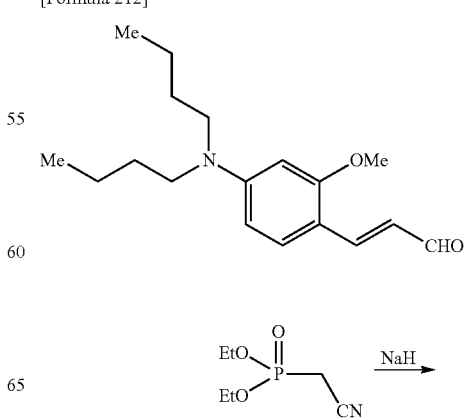

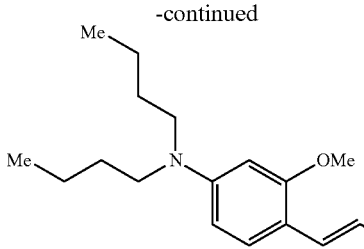

To 200 mg (8.3 mmol) of sodium hydride, 14 ml of tetrahydrofuran was added. To this mixture, 1.47 g (8.3 mmol) of diethyl cyanomethylphosphonate was added dropwise under ice cooling, and the mixture was stirred for 20 minutes. Next, 1.02 g (3.52 mmol) of 3-(4-dibutylamino-2-methoxyphenyl)propenal in tetrahydrofuran was added dropwise. After stirred for 30 minutes, the reaction mixture was poured into 100 ml of water and subjected to extraction with ethyl acetate. The extract was washed with a saturated saline solution, dried over anhydrous sodium sulfate, and concentrated. The residue was purified by silica gel column chromatography to give 1.0 g of an orange oily matter (yield: 91.2%).

$^{1}$H-NMR (600 MHz, CDCl$_{3}$) δ: 0.97 (6H, t, J=7.7 Hz), 1.35-1.40 (4H, m), 1.55-1.60 (4H, m), 3.31 (4H, t, J=7.7 Hz), 3.85 (3H, s), 4.97 and 5.20 (1H, d, J=15.4 Hz), 6.04 (1H, s), 6.22-6.26 (1H, m), 6.71 and 6.73 (1H, dd, J=0.7 Hz, 15.4 Hz), 7.07-7.18 (2H, m), 7.29 and 7.42 (1H, d, J=8.8 Hz)

$^{13}$C-NMR (150 MHz, CDCl$_{3}$) δ: 14.0, 20.3, 29.5, 50.8, 55.2, 92.8, 94.1, 104.6, 104.7, 111.9, 119.8, 128.0, 129.2, 129.3, 137.4, 137.6, 150.7, 152.6, 159.6

(38-2) 5-(4-dibutylamino-2-methoxyphenyl)-2,4-pentadienal

[Formula 213]

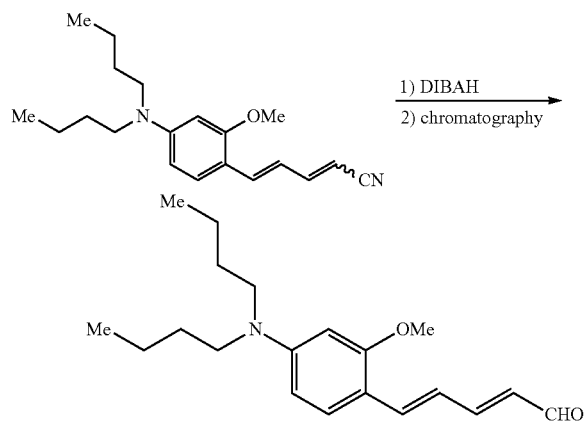

In 25 ml of toluene was dissolved 1.0 g (3.2 mmol) of 5-(4-dibutylamino-2-methoxyphenyl)-2,4-pentadienenitrile. To this mixture, 3.2 ml of diisobutylaluminium hydride (1.5 mol solution in toluene) (4.8 mmol) was added dropwise under cooling at −73 to −76° C. under argon atmosphere. The reaction mixture was stirred for 1 hour and the temperature was allowed to rise. To the mixture, 30 ml of a 5% ammonium chloride solution was added dropwise. The mixture was stirred for 30 minutes and filtrated. The phases were separated. The organic layer was washed with a saturated saline solution, dried over anhydrous sodium sulfate and concentrated. The residual liquid was purified by silica gel column chromatography to give 383 mg of a deep red crystal (yield: 37.9%).

$^{1}$H-NMR (600 MHz, CDCl$_{3}$) δ: 0.97 (6H, t, J=7.1 Hz), 1.34-1.40 (4H, m), 1.58-1.63 (4H, m), 3.32 (4H, t, J=7.1 Hz), 3.86 (3H, s), 6.09 (1H, s), 6.14 (1H, dd, J=15.4 Hz, 8.2 Hz), 6.25 (1H, d, J=8.8 Hz), 6.87 (1H, dd, J=15.4 Hz, 11.5 Hz), 7.26 (1H, d, J=15.4 Hz), 7.28 (1H, d, J=15.4 Hz), 7.37 (1H, d, J=8.8 Hz), 9.53 (1H, d, J=8.2 Hz)

$^{13}$C-NMR (150 Hz, CDCl$_{3}$) δ: 13.9, 20.3, 29.5, 50.9, 55.2, 94.1, 104.7, 121.4, 128.0, 129.4, 139.1, 150.9, 155.4, 159.7

(38-3) 2-[4-[6-(4-dibutylamino-2-methoxyphenyl)-1,3,5-hexatrienyl]-3-cyano-5,5-dimethyl-2(5H)-furanylidene] propanedinitrile

[Formula 214]

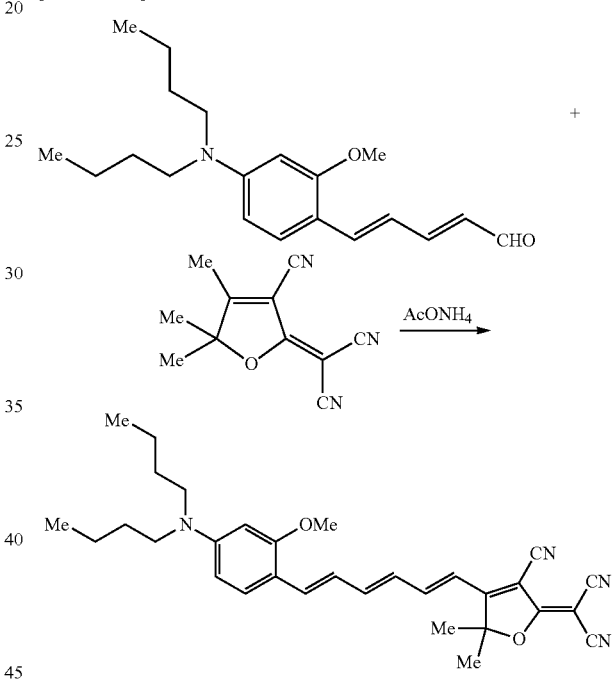

In 3 ml of ethanol and 1 ml of tetrahydrofuran were dissolved 146 mg (0.46 mmol) of 5-(4-dibutylamino-2-methoxyphenyl)-2,4-pentadienal and 101 mg (0.51 mmol) of 2-(3-cyano-4,5,5-trimethyl-2(5H)-furanylidene)propanedinitrile. To this mixture was added 36 mg of ammonium acetate, and the mixture was stirred at room temperature for 19 hours. The precipitate was separated by filtration, washed with ethanol, and purified by silica gel column chromatography to give 140 mg of a dark greenish brown crystal (yield: 60.9%; mp: 156-160° C.)

$^{1}$H-NMR (600 MHz, CDCl$_{3}$) δ: 0.98 (6H, t, J=7.7 Hz), 1.35-1.41 (4H, m), 1.60-1.63 (4H, m), 1.68 (6H, s), 3.35 (4H, t, J=7.7 Hz), 3.88 (3H, s), 6.07 (1H, s), 6.26 (1H, d, J=8.8 Hz), 6.27 (1H, d, J=15.4 Hz), 6.45 (1H, dd, J=13.2 Hz, 12.1 Hz), 6.90 (1H, dd, J=14.8 Hz, 11.5 Hz), 7.08 (1H, dd, J=14.3 Hz, 11.5 Hz), 7.27 (1H, d, J=15.4 Hz), 7.31 (1H, d, J=8.8 Hz), 7.52 (1H, dd, J=14.8 Hz, 11.5 Hz)

$^{13}$C-NMR (150 MHz, CDCl$_{3}$) δ: 13.9, 20.3, 26.6, 29.6, 51.0, 55.3, 93.9, 96.6, 105.3, 111.6, 112.0, 112.8, 113.3, 114.4, 123.3, 127.8, 130.1, 140.5, 149.4, 151.9, 160.4, 173.0, 176.2

Example 39

2-[4-[6-(4-dibutylamino-2-methoxyphenyl)-1,3,5-hexatrienyl]-3-cyano-5-methyl-5-trifluoromethyl-2(5H)-furanylidene] propanedinitrile

Example 40

2-[4-[6-(4-dibutylamino-2-methoxyphenyl)-1,3,5-hexatrienyl]-3-cyano-5-phenyl-5-trifluoromethyl-2(5H)-furanylidene] propanedinitrile

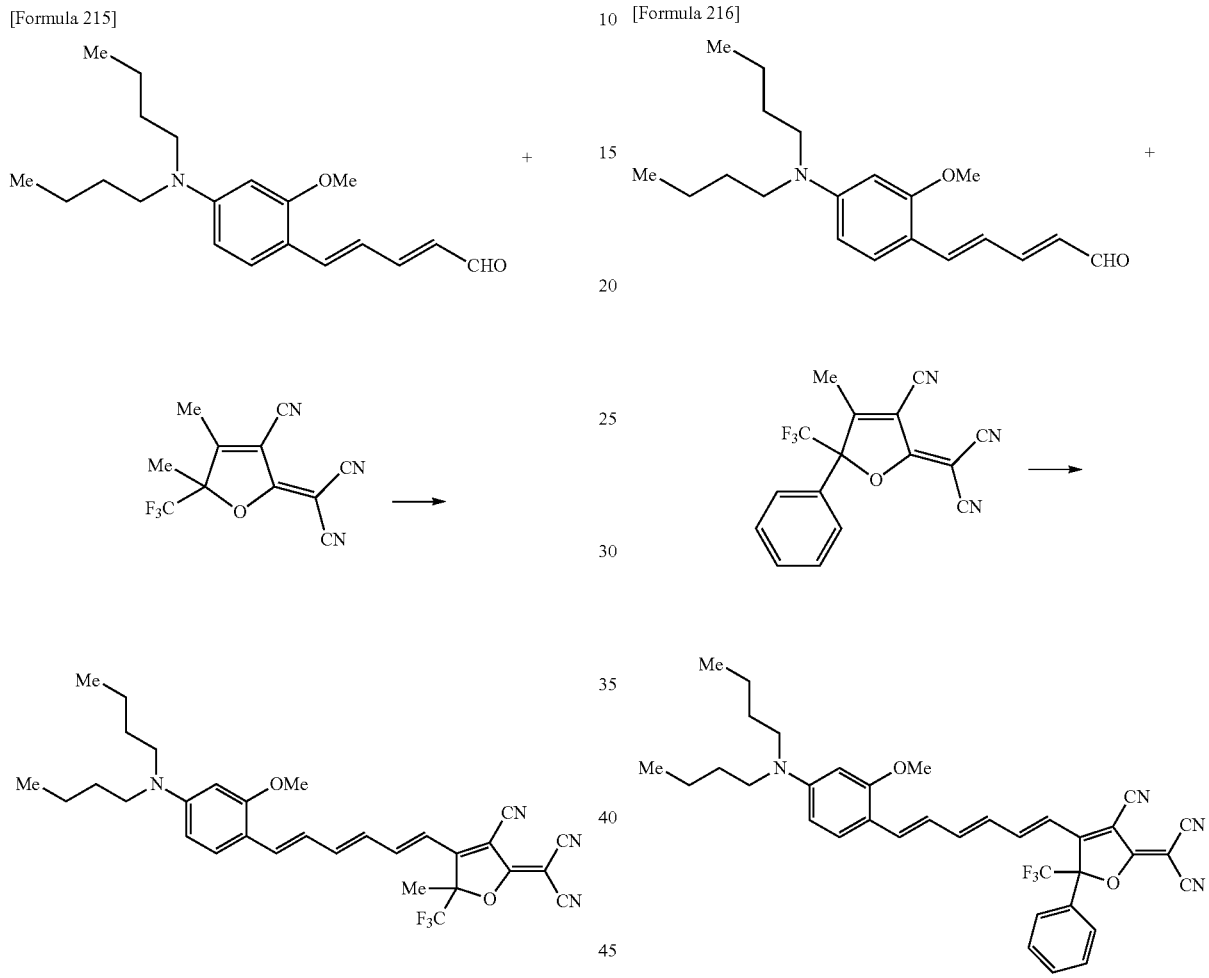

[Formula 215]

[Formula 216]

To 5 ml of ethanol were added 130 mg (0.41 mmol) of 5-(4-dibutylamino-2-methoxyphenyl)-2,4-pentadienal and 115 mg (0.45 mmol) of 2-(3-cyano-4,5-dimethyl-5-trifluoromethyl-2(5H)-furanylidene)propanedinitrile, and the mixture was stirred with heating at 50° C. for 2 hours. The precipitate was separated by filtration and purified by silica gel column chromatography to give 187 mg of a greenish brown crystal (yield: 82.5%; mp: 168-172° C.)

$^1$H-NMR (600 MHz, CDCl$_3$) δ: 0.99 (6H, t, J=7.7 Hz), 1.36-1.42 (4H, m), 1.61-1.66 (4H, m), 1.82 (3H, s), 3.38 (4H, t, J=7.7 Hz), 3.90 (3H, s), 6.05 (1H, s), 6.15 (1H, d, J=14.3 Hz), 6.32 (1H, d, J=8.8 Hz), 6.49 (1H, dd, J=13.2 Hz, 12.6 Hz), 6.97 (1H, dd, J=14.7 Hz, 11.5 Hz), 7.23 (1H, d, J=13.2 Hz), 7.42 (1H, d, J=8.8 Hz), 7.43 (1H, d, J=13.7 Hz), 7.97 (1H, bt)

$^{13}$C-NMR (150 MHz, CDCl$_3$) δ: 13.9, 19.3, 20.3, 29.6, 51.16, 51.21, 55.3, 93.1, 93.6, 106.1, 111.5, 112.1, 113.0, 114.1, 121.3. 123.2, 123.8, 128.6, 131.1, 144.2, 151.5, 155.4, 160.9, 161.4, 175.9

To 5 ml of ethanol were added 100 mg (0.32 mmol) of 5-(4-dibutylamino-2-methoxyphenyl)-2,4-pentadienal and 110 mg (0.35 mmol) of 2-(3-cyano-4-methyl-5-phenyl-5-trifluoromethyl-2(5H)-furanylidene)propanedinitrile, and the mixture was stirred with heating at 50° C. for 2.5 hours. The precipitate was separated by filtration and purified by silica gel column chromatography to give 173 mg of a yellowish brown crystal (yield: 89.1%; mp: 208-210° C.)

$^1$H-NMR (600 MHz, CDCl$_3$) δ: 0.98 (6H, t, J=7.1 Hz), 1.35-1.41 (4H, m), 1.60-1.63 (4H, m), 3.37 (4H, t, J=7.7 Hz), 3.87 (3H, s), 6.03 (1H, s), 6.25 (1H, d, J=14.3 Hz), 6.30 (1H, d, 8.8 Hz), 6.42 (1H, dd, J=13.2 Hz, 12.1 Hz), 6.91 (1H, dd, J=14.8 Hz, 12.1 Hz), 7.10 (1H, dd, J=12.6 Hz, 12.3 Hz), 7.36 (1H, d, J=13.7 Hz), 7.39 (1H, d, J=8.8 Hz), 7.48-7.53 (5H, m), 7.71 (1H, b)

$^{13}$C-NMR (150 MHz, CDCl$_3$) δ: 13.9, 20.3, 29.6, 51.2, 55.3, 93.6, 106.1, 111.5, 112.0, 112.1, 114.4, 121.3, 123.2, 123.7, 126.6, 126.8, 128.7, 129.5, 130.4, 131.1, 144.2, 151.9, 152.8, 154.2, 155.3, 160.8, 161.4, 176.0

Example 41

2-[4-[2-[5-[4-(4-dibutylamino-2-methoxyphenyl)-1,3-butadienyl]thiophene-2-yl]vinyl]-3-cyano-5,5-dimethyl-2(5H)-furanylidene]propanedinitrile

(41-1) Dibutyl[3-methoxy-4-[4-(thiophene-2-yl)-1,3-butadienyl]phenyl]amine

[Formula 217]

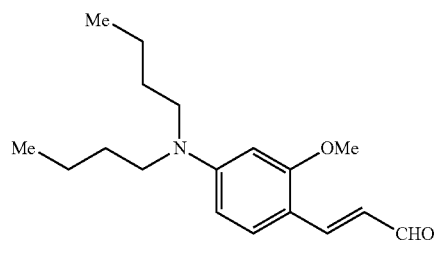

+

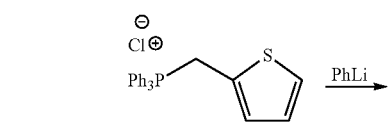

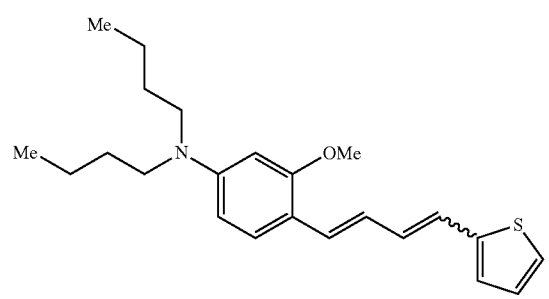

In a stream of argon, to 15 ml of tetrahydrofuran was added 1.68 g of phenyllithium (19% solution in dibutylether) (3.8 mmol), and 1.37 g (3.5 mmol) of 2-thenyl triphenylphosphonium chloride was added thereto under ice cooling. Next, 1.0 g (3.5 mmol) of 3-(4-dibutylamino-2-methoxyphenyl)propenal was dissolved in tetrahydrofuran and added dropwise. The mixture was stirred under ice cooling for 2 hours. After the reaction mixture was poured into water, extraction with ethyl acetate, washing with a saturated saline solution, drying over anhydrous sodium sulfate, and concentration were performed. The residue was purified by silica gel column chromatography to give 0.92 g of an orange oily matter (yield: 72.0%).

(41-2) 5-[4-(4-dibutylamino-2-methoxyphenyl)-1,3-butadienyl]thiophene-2-carboaldehyde

[Formula 218]

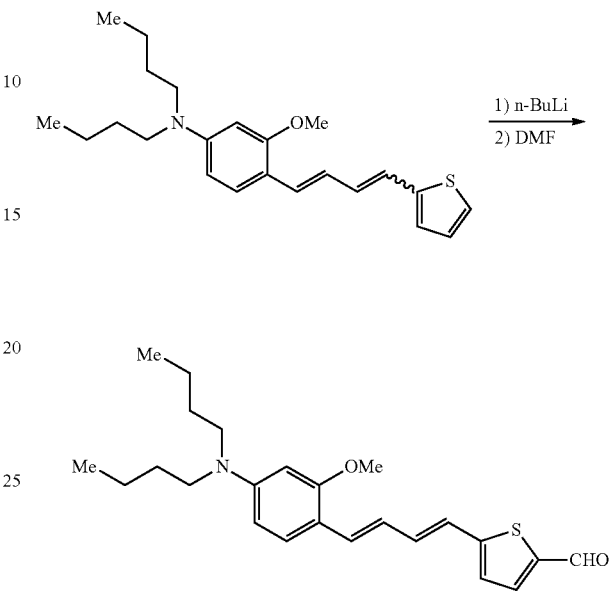

In a stream of argon, in 13 ml of tetrahydrofuran was dissolved 0.83 g (2.25 mmol) of dibutyl[3-methoxy-4-[4-(thiophene-2-yl)-1,3-butadienyl]phenyl]amine, and 2.1 ml of n-butyllithium (1.6 mol solution in hexane) (3.36 mmol) was added dropwise thereto under cooling at −68 to −70° C. After the mixture was stirred for 30 minutes, 0.21 ml (2.87 mmol) of N,N-dimethylformamide was added dropwise thereto. The reaction mixture was stirred for 1.5 hours and the temperature was allowed to rise. To this mixture, 5 ml of water was added dropwise. After the reaction mixture was poured into 50 ml of water, extraction with ethyl acetate, washing with a saturated saline solution, drying over anhydrous sodium sulfate, and concentration were performed. The residual liquid was purified by silica gel column chromatography to give a dark reddish brown oily matter. After this oily matter was dissolved in 100 ml of ether, 600 mg of iodine was added thereto and the mixture was stirred. The mixture was washed with a 5% sodium bisulfite solution and then with a saturated saline solution. Drying over anhydrous sodium sulfate and concentration were performed. The residue was purified by silica gel column chromatography to give 715 mg of a dark reddish brown liquid (yield: 80.1%).

$^1$H-NMR (600 MHz, CDCl$_3$) δ: 0.97 (6H, t, J=7.7 Hz), 1.34-1.40 (4H, m), 1.57-1.62 (4H, m), 3.30 (4H, t, J=7.7 Hz), 3.86 (3H, s), 6.11 (1H, d, J=2.2 Hz), 6.25 (1H, dd, J=2.2 Hz, 8.8 Hz), 6.62 (1H, d, J=15.4 Hz), 6.78 (1H, dd, J=15.4 Hz, 11.0 Hz), 6.99 (1H, d, J=3.8 Hz), 7.01 (1H, dd, J=15.4 Hz, 12.7 Hz), 7.02 (1H, d, J=15.4 Hz), 7.34 (1H, d, J=8.8 Hz), 7.60 (1H, d, J=3.8 Hz), 9.80 (1H, s)

$^{13}$C-NMR (150 MHz, CDCl$_3$) δ: 14.0, 20.3, 29.6, 50.9, 55.3, 94.5, 104.6, 113.4, 120.7, 123.4, 124.9, 128.2, 132.2, 136.1, 137.6, 140.3, 149.7, 154.2, 158.8, 182.3

(41-3) 2-[4-[2-[5-[4-(4-dibutylamino-2-methoxyphenyl)-1,3-butadienyl]thiophene-2-yl]vinyl]-3-cyano-5,5-dimethyl-2(5H)-furanylidene]propanedinitrile

[Formula 219]

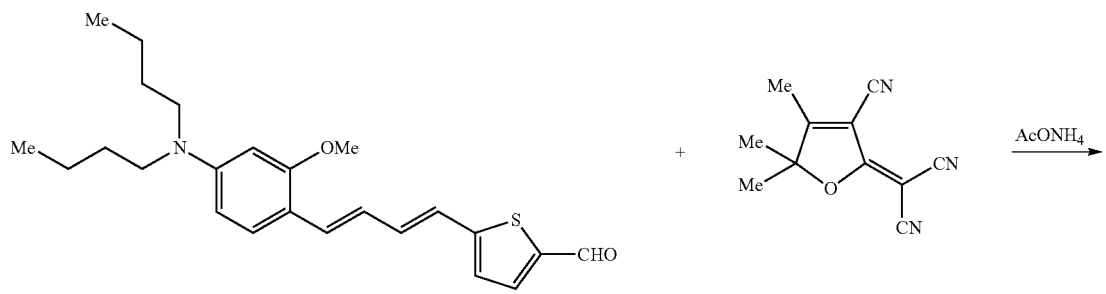

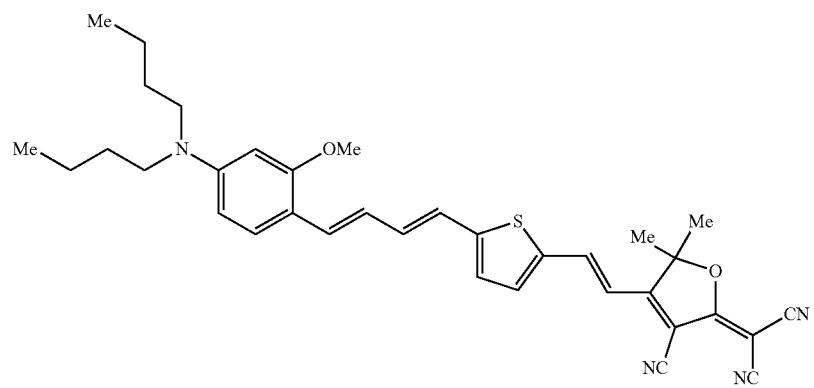

In 7 ml of ethanol and 2 ml of tetrahydrofuran were dissolved 248 mg (0.62 mmol) of 5-[4-(4-dibutylamino-2-methoxyphenyl)-1,3-butadienyl]thiophene-2-carboaldehyde and 137 mg (0.61 mmol) of 2-(3-cyano-4,5,5-trimethyl-2(5H)-furanylidene) propanedinitrile. To this mixture was added 50 mg of ammonium acetate, and the mixture was stirred with heating at 50° C. for 4 hours. The product was separated by filtration, washed with ethanol, and purified by silica gel column chromatography to give 241 mg of a dark brown crystal (yield: 66.8%; mp: 185-187° C.)

$^1$H-NMR (600 MHz, CDCl$_3$) δ: 0.97 (6H, t, J=7.7 Hz), 1.34-1.41 (4H, m), 1.58-1.63 (4H, m), 1.74 (6H, s), 3.32 (4H, t, J=7.7 Hz), 3.87 (3H, s), 6.11 (1H, d, J=2.2 Hz), 6.26 (1H, dd, J=2.2 Hz, 8.8 Hz), 6.51 (1H, d, J=15.9 Hz), 6.62 (1H, d, J=15.4 Hz), 6.81 (1H, dd, J=14.8 Hz, 11.0 Hz), 6.96 (1H, d, J=3.8 Hz), 7.02 (1H, dd, J=14.8 Hz, 11.0H), 7.07 (1H, d, J=14.8 Hz), 7.34 (1H, d, J=3.8 Hz), 7.35 (1H, d, J=8.8 Hz), 7.76 (1H, d, J=15.4 Hz)

$^{13}$C-NMR (150 MHz, CDCl$_3$) δ: 13.9, 20.3, 26.5, 29.6, 50.9, 55.2, 55.7, 94.3, 95.6, 96.9, 104.8, 111.2, 111.5, 112.4, 113.3, 120.4, 123.3, 126.9, 128.6, 133.9, 137.6, 137.7, 137.8, 139.2, 150.2, 154.5, 159.1, 172.7, 175.8

Example 42

2-[4-[2-[5-[4-(4-dibutylamino-2-methoxyphenyl)-1,3-butadienyl]thiophene-2-yl]vinyl]-3-cyano-5-methyl-5-trifluoromethyl-2(5H)-furanylidene]propanedinitrile

[Formula 220]

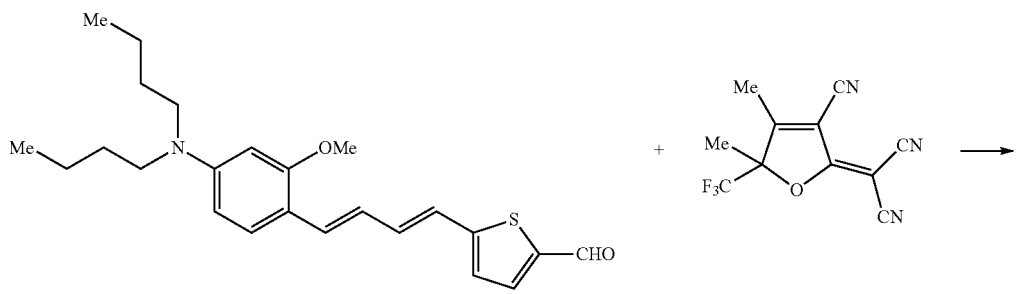

-continued

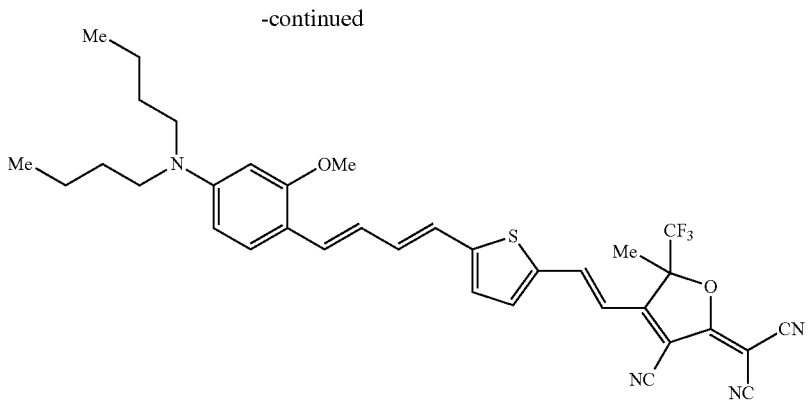

In 8 ml of ethanol were dissolved 230 mg (0.58 mmol) of 5-[4-(4-dibutylamino-2-methoxyphenyl)-1,3-butadienyl]thiophene-2-carboaldehyde and 160 mg (0.63 mmol) of 2-(3-cyano-4, 5-dimethyl-5-trifluoromethyl-2(5H)-furanylidene) propanedinitrile. After the mixture was stirred with heating at 50° C. for 2 hours, the product was separated by filtration and washed with ethanol. The product was purified by silica gel column chromatography to give 279 mg of a black crystal (yield: 76.2%; mp: 161-162° C.)

$^1$H-NMR (600 MHz, CDCl$_3$) δ: 0.98 (6H, t, J=7.7 Hz), 1.35-1.41 (4H, m), 1.58-1.64 (4H, m), 1.91 (3H, s), 3.33 (4H, t, J=7.7 Hz), 3.87 (3H, s), 6.10 (1H, d, J=2.2 Hz), 6.27 (1H, dd, J=2.2 Hz, 8.8 Hz), 6.43 (1H, d, J=14.8 Hz), 6.64 (1H, d, J=14.8 Hz), 6.84 (1H, dd, J=14.8 Hz, 11.0 Hz), 7.00 (1H, d, J=3.8 Hz), 7.09 (1H, dd, J=14.8 Hz, 11.0 Hz), 7.14 (1H, d, J=15.4 Hz), 7.36 (1H, d, J=8.8 Hz), 7.43 (1H, d, J=3.8 Hz), 8.13 (1H, d, J=14.8 Hz)

$^{13}$C-NMR (150 MHz, CDCl$_3$) δ: 14.0, 19.2, 20.3, 29.6, 50.9, 55.2, 57.8, 94.2, 104.9, 110.4, 110.7, 111.2, 113.3, 120.4, 121.1, 123.0, 123.3, 127.7, 128.9, 135.4, 138.3, 139.5, 139.8, 140.9, 150.6, 157.1, 159.4, 161.7, 175.3

Example 43

2-[4-[2-[5-[4-(4-dibutylamino-2-methoxyphenyl)-1,3-butadienyl]thiophene-2-yl]vinyl]-3-cyano-5-phenyl-5-trifluoromethyl-2(5H)-furanylidene]propanedinitrile

[Formula 221]

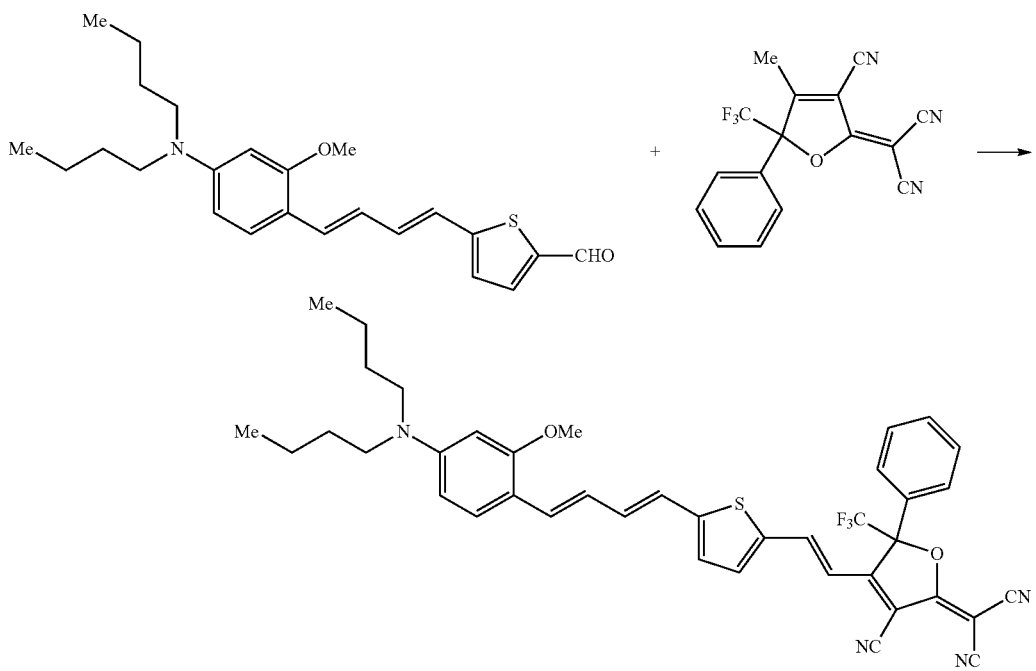

In 8 ml of ethanol were dissolved 220 mg (0.55 mmol) of 5-[4-(4-dibutylamino-2-methoxyphenyl)-1,3-butadienyl]thiophene-2-carboaldehyde and 192 mg (0.61 mmol) of 2-(3-cyano-4-methyl-5-phenyl-5-trifluoromethyl-2(5H)-furanylidene)propanedinitrile. After the mixture was stirred with heating at 50° C. for 2.5 hours, the product was separated by filtration and washed with ethanol. The product was purified by silica gel column chromatography to give 300 mg of a black crystal (yield: 78.1%; mp: 125-140° C.)

$^1$H-NMR (600 MHz, CDCl$_3$) δ: 0.97 (6H, t, J=7.7 Hz), 1.34-1.41 (4H, m), 1.58-1.63 (4H, m), 3.32 (4H, t, J=7.7 Hz), 3.87 (3H, s), 6.09 (1H, d, J=2.2 Hz), 6.25 (1H, dd, J=2.2 Hz, 8.8 Hz), 6.55 (1H, d, J=14.8 Hz), 6.61 (1H, d, J=14.8 Hz), 6.83 (1H, dd, J=14.8 Hz, 11.0 Hz), 6.95 (1H, d, J=4.4 Hz), 7.07 (1H, dd, J=14.8 Hz, 11.0 Hz), 7.13 (1H, d, J=15.4 Hz), 7.28 (1H, d, J=4.4 Hz), 7.34 (1H, d, J=8.8 Hz), 7.50-7.57 (5H, m), 7.79 (1H, d, J=14.8 Hz)

$^{13}$C-NMR (150 MHz, CDCl$_3$) δ: 14.0, 20.3, 29.6, 50.9, 55.2, 58.0, 94.2, 104.9, 110.7, 111.1, 111.2, 111.6, 113.4, 120.4, 121.1, 123.3, 126.8, 127.6, 128.9, 129.8, 131.5, 135.4, 138.4, 139.5, 139.7, 141.4, 150.5, 157.2, 159.4, 161.7, 175.4

Example 44

2-[4-[4-[5-[2-(4-dibutylamino-2-methoxyphenyl) vinyl] thiophene-2-yl]-1,3-butadienyl]-3-cyano-5,5-dimethyl-2(5H)-furanylidene]propanedinitrile (44-1) 3-[5-[2-(4-dibutylamino-2-methoxyphenyl) vinyl] thiophene-2-yl]acrylonitrile

[Formula 222]

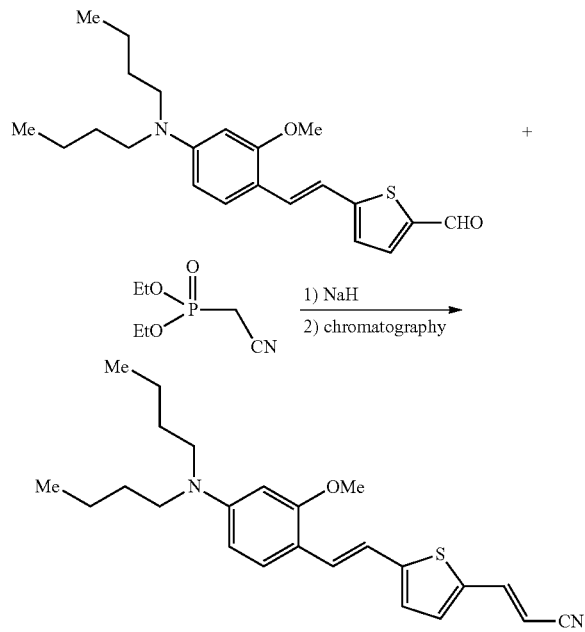

To 111 mg (4.63 mmol) of sodium hydride, 8 ml of tetrahydrofuran was added. To this mixture, 820 mg (4.63 mmol) of diethyl cyanomethylphosphonate was added dropwise under ice cooling, and the mixture was stirred for 30 minutes. Next, 860 mg (2.31 mmol) of 5-[2-(4-dibutylamino-2-methoxyphenyl)vinyl] thiophene-2-carboaldehyde in tetrahydrofuran was added dropwise, and the mixture was stirred for 1 hour. The reaction mixture was poured into water and subjected to extraction with ethyl acetate. The extract was washed with a saturated saline solution, dried over anhydrous sodium sulfate, and concentrated. The residue was purified by silica gel column chromatography to give 828 mg of a deep red oily matter (yield: 90.7%).

$^1$H-NMR (600 MHz, CDCl$_3$) δ: 0.97 (6H, t, J=7.7 Hz), 1.34-1.40 (4H, m), 1.57-1.62 (4H, m), 3.30 (4H, t, J=7.7 Hz), 3.87 (3H, s), 5.48 (1H, d, J=16.5 Hz), 6.12 (1H, d, J=2.2 Hz), 6.25 (1H, dd, J=2.2 Hz, 8.8 Hz), 6.87 (1H, d, J=3.8 Hz), 7.01 (1H, d, J=15.9 Hz), 7.07 (1H, d, J=3.8 Hz), 7.24 (1H, d, J=15.9 Hz) 7.33 (1H, d, J=8.8 Hz), 7.38 (1H, d, J=15.9 Hz)

$^{13}$C-NMR (150 MHz, CDCl$_3$) δ: 14.0, 20.3, 29.5, 50.9, 55.2, 91.8, 94.5, 104.6, 112.7, 116.2, 118.8, 124.8, 127.5, 128.3, 132.9, 134.9, 142.8, 149.8, 149.9, 158.8

(44-2) 3-[5-[2-(4-dibutylamino-2-methoxyphenyl) vinyl] thiophene-2-yl]propenal

[Formula 223]

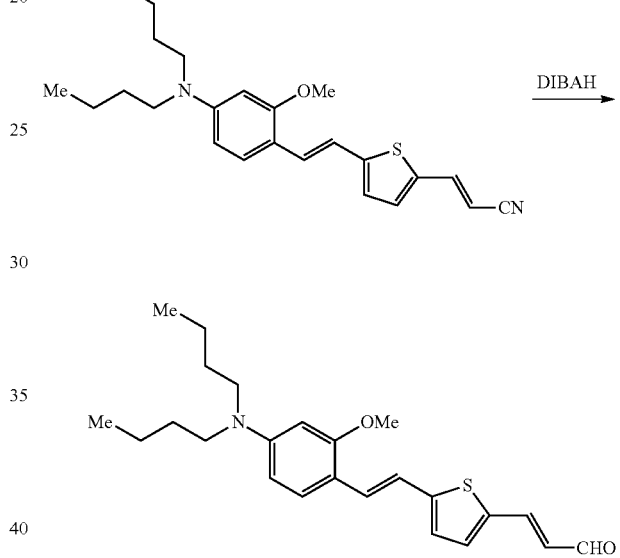

In 25 ml of toluene was dissolved 820 mg (2.08 mmol) of 3-[5-[2-(4-dibutylamino-2-methoxyphenyl)vinyl]thiophene-2-yl]acrylonitrile. To this mixture, 2.1 ml of diisobutylaluminiumhydride (1.5 mol solution in toluene) (3.15 mmol) was added dropwise under cooling at −75 to −76° C. under argon atmosphere. The reaction mixture was stirred for 75 minutes and the temperature was allowed to rise. To the mixture, 30 ml of a 5% ammonium chloride solution was added dropwise. The mixture was stirred for 30 minutes and filtrated. The phases were separated. The organic layer was washed with a saturated saline solution, dried over anhydrous sodium sulfate and concentrated. The residual liquid was purified by silica gel column chromatography to give 230 mg of a dark reddish brown oily matter (yield: 27.8%).

$^1$H-NMR (600 MHz, CDCl$_3$) δ: 0.97 (6H, t, J=7.7 Hz), 1.34-1.40 (4H, m), 1.57-1.63 (4H, m), 3.31 (4H, t, J=7.7 Hz), 3.88 (3H, s), 6.13 (1H, d, J=2.2 Hz), 6.25 (1H, dd, J=2.2 Hz, 8.8 Hz), 6.41 (1H, dd, J=15.4 Hz, 7.7 Hz), 6.93 (1H, d, J=3.3 Hz), 7.04 (1H, d, J=15.9 Hz), 7.21 (1H, d, J=3.3 Hz), 7.28 (1H, d, J=15.9 Hz), 7.35 (1H, d, J=8.8 Hz), 7.50 (1H, d, J=15.4 Hz), 9.59 (1H, d, J=7.7 Hz)

$^{13}$C-NMR (150 MHz, CDCl$_3$) δ: 14.0, 20.3, 29.5, 50.9, 55.3, 94.5, 104.6, 112.6, 116.4, 125.2, 125.7, 127.6, 128.4, 134.0, 135.9, 144.8, 149.8, 151.3, 158.9, 192.8

(44-3) 2-[4-[4-[5-[2-(4-dibutylamino-2-methoxyphenyl) vinyl]thiophene-2-yl]-1,3-dibutaenyl]-3-cyano-5,5-dimethyl-2(5H)-furanylidene]propanedinitrile

[Formula 224]

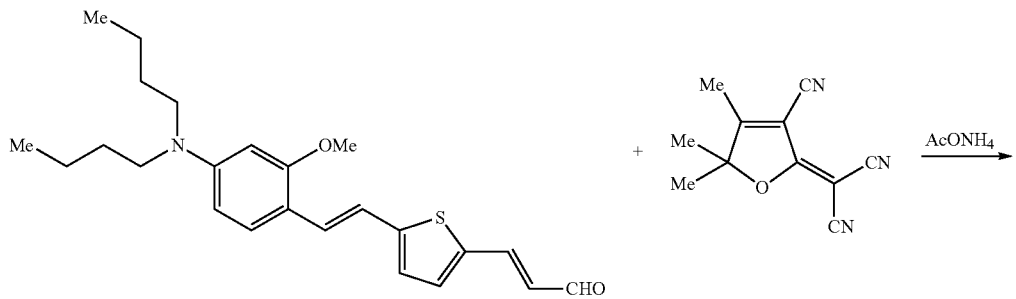

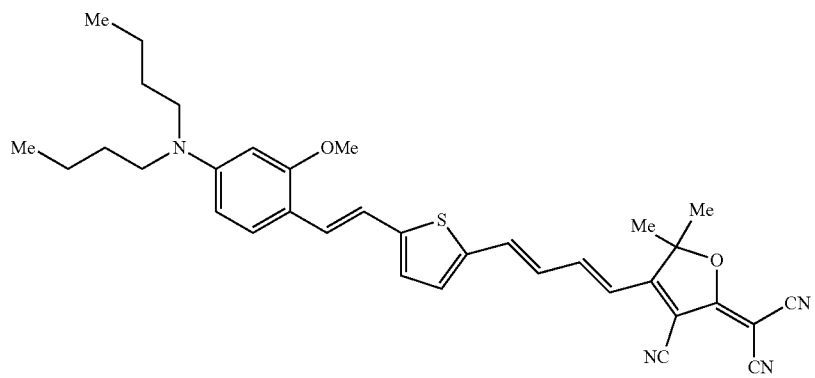

In 3 ml of ethanol and 1 ml of tetrahydrofuran were dissolved 130 mg (0.33 mmol) of 3-[5-[2-(4-dibutylamino-2-methoxyphenyl)vinyl]thiophene-2-yl]propenal and 72 mg (0.36 mmol) of 2-(3-cyano-4,5,5-trimethyl-2(5H)-furanylidene) propanedinitrile. To this mixture was added 26 mg of ammonium acetate, and the mixture was stirred at room temperature for 20 hours. The product was separated by filtration, washed with ethanol, and purified by silica gel column chromatography to give 87 mg of a black crystal (yield: 46.0%).

$^1$H-NMR (600 MHz, CDCl$_3$) δ: 0.98 (6H, t, J=7.7 Hz), 1.35-1.41 (4H, m), 1.58-1.63 (4H, m), 1.70 (6H, s), 3.32 (4H, t, J=7.7 Hz), 3.89 (3H, s), 6.12 (1H, d, J=2.2 Hz), 6.27 (1H, dd, J=2.2 Hz, 8.8 Hz), 6.37 (1H, d, J=14.8 Hz), 6.69 (1H, dd, J=14.8 Hz, 11.5 Hz), 6.94 (1H, d, J=3.8 Hz), 7.06 (1H, d, J=15.9 Hz), 7.16 (1H, d, J=3.8 Hz), 7.24 (1H, d, J=14.8 Hz), 7.32 (1H, d, J=15.9 Hz), 7.36 (1H, d, J=8.8 Hz), 7.55 (1H, dd, J=14.8 Hz, 11.5 Hz)

$^{13}$C-NMR (150 MHz, CDCl$_3$) δ: 14.0, 20.3, 26.4, 29.6, 50.9, 55.3, 55.8, 94.4, 95.8, 96.9, 104.8, 111.2, 111.5, 112.4, 112.7, 116.0, 116.3, 125.5, 126.1, 128.6, 134.4, 138.1, 139.4, 148.1, 150.2, 152.5, 159.1, 172.9, 175.9

Example 45

2-[4-[4-[5-[2-(4-dibutylamino-2-methoxyphenyl) vinyl] thiophene-2-yl]-1,3-butadienyl]-3-cyano-5-phenyl-5-trifluoromethyl-2(5H)-furanylidene]propanedinitrile

[Formula 225]

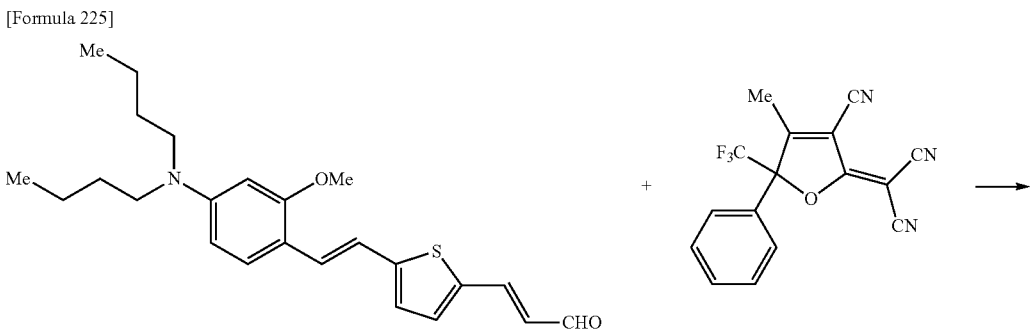

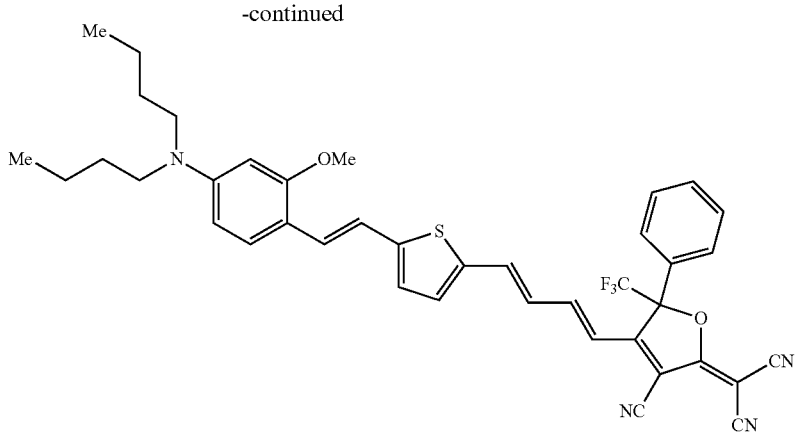

In 4 ml of ethanol were dissolved 100 mg (0.25 mmol) of 3-[5-[2-(4-dibutylamino-2-methoxyphenyl)vinyl]thiophene-2-yl]propenal and 87 mg (0.28 mmol) of 2-(3-cyano-4-methyl-5-phenyl-5-trifluoromethyl-2(5H)-furanylidene)propanedinitrile. After the mixture was stirred with heating at 50° C. for 4 hours, the product was separated by filtration and washed with ethanol. The product was purified by silica gel column chromatography to give 97 mg of a black crystal (yield: 55.5%).

$^1$H-NMR (600 MHz, CDCl$_3$) δ: 0.97 (6H, t, J=7.1 Hz), 1.35-1.41 (4H, m), 1.58-1.63 (4H, m), 3.32 (4H, t, J=7.7 Hz), 3.88 (3H, s), 6.10 (1H, s), 6.26 (1H, d, 8.8 Hz), 6.39 (1H, d, J=14.8 Hz), 6.65 (1H, dd, J=14.3 Hz, 11.5 Hz), 6.96 (1H, d, J=3.8 Hz), 7.07 (1H, d, J=15.9 Hz), 7.20 (1H, d, J=3.8 Hz), 7.21 (1H, d, J=14.8 Hz), 7.35 (1H, d, J=8.8 Hz), 7.36 (1H, d, J=15.9 Hz), 7.48-7.57 (5H, m), 7.69 (1H, bt)

$^{13}$C-NMR (150 MHz, CDCl$_3$) δ: 14.0, 20.3, 29.6, 50.9, 55.2, 58.0, 94.2, 96.0, 104.9, 110.7, 111.2, 112.7, 116.1, 121.1, 123.0, 126.0, 126.67, 126.76, 128.9, 129.69, 129.75, 129.9, 131.4, 136.3, 138.4, 141.6, 150.5, 150.8, 155.0, 159.4, 161.8, 175.5

Example 46

2-[4-[3-[3-[2-(4-dibutylamino-2-methoxyphenyl)vinyl]-5,5-dimethyl-2-cyclohexenylidene]-1-propenyl]-3-cyano-5,5-dimethyl-2(5H)-furanylidene]propanedinitrile (46-1) 3-[2-(4-dibutylamino-2-methoxyphenyl)vinyl]-5,5-dimethyl-2-cyclohexenone

[Formula 226]

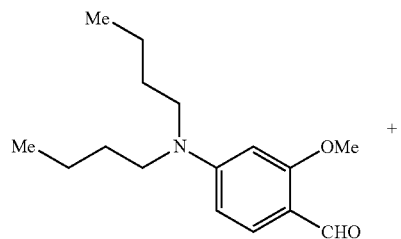

+

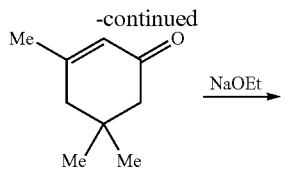

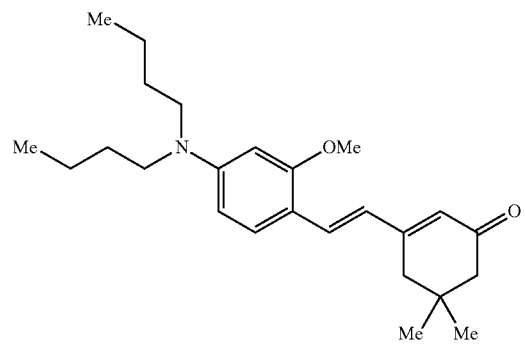

In 15 ml of tetrahydrofuran, 1.5 g (10.85 mmol) of isophorone was dissolved, and 3.4 g of sodium ethoxide (20% solution in ethanol) (10.0 mmol) was added thereto. To this mixture, 2.6 g (9.87 mmol) of 4-dibutylamino-2-methoxybenzaldehyde in tetrahydrofuran was added dropwise with heating at 50° C., and the mixture was stirred for 4.5 hours. To the mixture, 100 ml of ethyl acetate was added. Washing with a saturated saline solution, drying over anhydrous sodium sulfate, and concentration were performed. The residue was purified by silica gel column chromatography to give 1.7 g of a reddish orange oily matter (yield: 45.0%).

$^1$H-NMR (600 MHz, CDCl$_3$) δ: 0.97 (6H, t, J=7.1 Hz), 1.34-1.40 (4H, m), 1.57-1.62 (4H, m), 2.28 (2H, s), 2.49 (2H, s), 3.31 (4H, t, J=7.1 Hz), 3.87 (3H, s), 5.99 (1H, s), 6.10 (1H, d, J=2.2 Hz), 6.26 (1H, dd, J=2.2 Hz, 8.8 Hz), 6.75 (1H, d, J=15.9 Hz), 7.31 (1H, d, J=15.9 Hz), 7.42 (1H, d, J=8.8 Hz)

$^{13}$C-NMR (150 MHz, CDCl$_3$) δ: 14.0, 20.3, 28.6, 29.5, 33.3, 39.1, 50.8, 51.5, 55.2, 94.2, 104.7, 112.5, 124.2, 124.3, 128.3, 130.5, 150.4, 157.1, 159.2, 200.2

(46-2) [3-[2-(4-dibutylamino-2-methoxyphenyl)vinyl]-5,5-dimethyl-2-cyclohexenylidene]acetonitrile

[Formula 227]

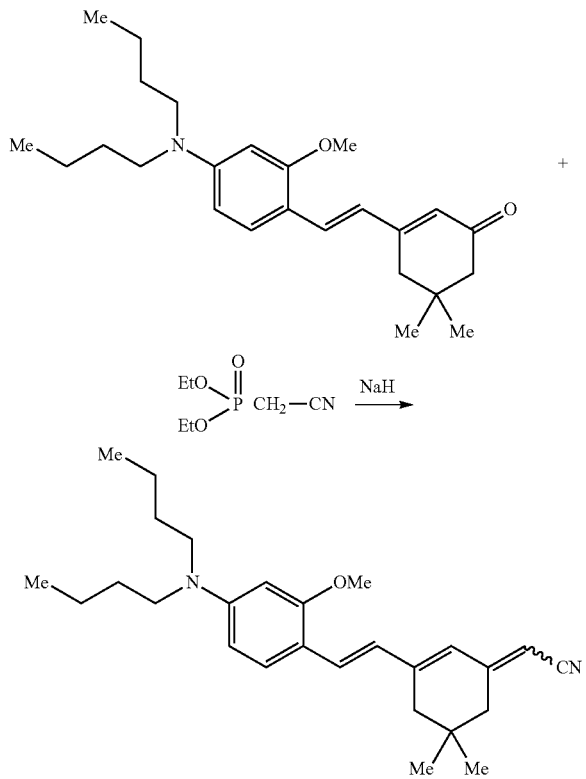

To 0.23 g (9.6 mmol) of sodium hydride, 20 ml of tetrahydrofuran was added. To this mixture, 1.39 g (7.85 mmol) of diethyl cyanomethylphosphonate was added dropwise under ice cooling. To the mixture, 1.21 g (3.15 mmol) of 3-[2-(4-dibutylamino-2-methoxyphenyl)vinyl]-5,5-dimethyl-2-cyclohexenone in tetrahydrofuran was added dropwise. After the reaction mixture was stirred at 50° C. overnight, water was added thereto and extraction with ethyl acetate was performed. The extract was washed with a saturated saline solution, dried over anhydrous sodium sulfate, and concentrated. The residue was purified by silica gel column chromatography to give 1.05 g of an orange oily matter (yield: 82.0%).

$^1$H-NMR (600 MHz, CDCl$_3$) δ: 0.96 and 0.97 (6H, t, J=7.7 Hz), 1.00 and 1.03 (6H, s), 1.34-1.40 (4H, m), 1.56-1.62 (4H, m), 2.21 and 2.33 (2H, s), 2.33 and 2.45 (2H, s), 3.28-3.31 (4H, m), 3.856 and 3.864 (3H, s), 4.85 and 5.03 (1H, s), 6.11 (1H, d, J=2.2 Hz), 6.19 and 6.64 (1H, s), 6.24 and 6.26 (1H, dd, J=2.2 Hz, 8.8 Hz), 6.69 and 6.81 (1H, d, J=16.5 Hz), 7.07 and 7.09 (1H, d, J=16.5 Hz), 7.36 and 7.37 (1H, d, J=8.8 Hz)

$^{13}$C-NMR (150 MHz, CDCl$_3$) δ: 14.0, 14.2, 20.3, 21.1, 28.159, 28.197, 29.6, 31.1, 31.3, 38.9, 42.2, 44.9, 50.9, 55.2, 60.4, 89.5, 91.1, 94.4, 104.67, 104.74, 113.1, 118.2, 119.0, 122.1, 124.2, 125.2, 125.6, 127.1, 127.4, 127.7, 128.0, 146.5, 146.9, 149.8, 158.4, 158.69, 158.73

(46-3) [3-[2-(4-dibutylamino-2-methoxyphenyl)vinyl]-5,5-dimethyl-2-cyclohexenylidene]acetaldehyde

[Formula 228]

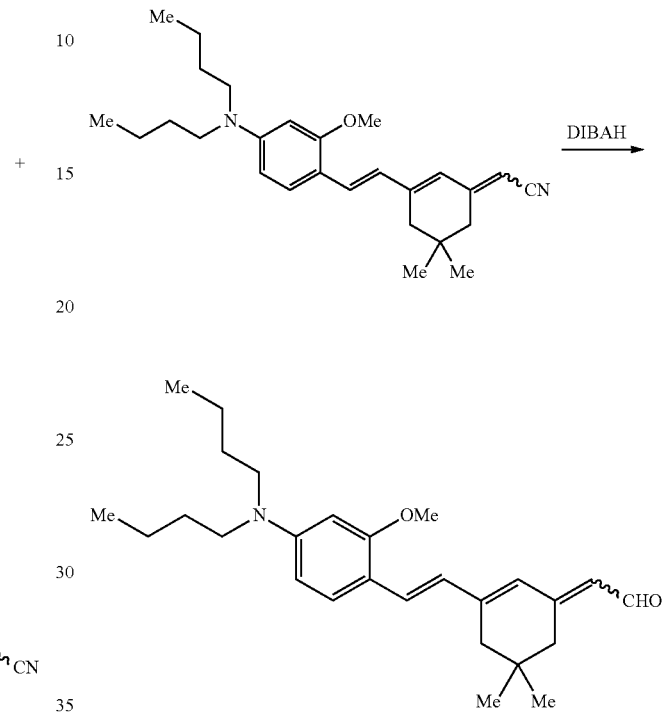

In 10 ml of toluene was dissolved 0.3 g (0.74 mmol) of [3-[2-(4-dibutylamino-2-methoxyphenyl)vinyl]-5,5-dimethyl-2-cyclohexenylidene]acetonitrile. To this mixture, 0.74 ml of diisobutylaluminium hydride (1.5 mol solution in toluene) was added dropwise under dry ice/acetone cooling. The reaction mixture was stirred for 2 hours and the temperature was allowed to rise. To the mixture, an ammonium chloride solution was added dropwise. The organic layer was separated, dried over anhydrous sodium sulfate, and concentrated. The residue was purified by silica gel column chromatography to give 0.21 g of a dark reddish brown oily matter (yield: 71.0%).

$^1$H-NMR (600 MHz, CDCl$_3$) δ: 0.97 (6H, t, J=7.7 Hz), 1.03 and 1.06 (6H, s), 1.34-1.40 (4H, m), 1.57-1.62 (4H, m), 2.27 and 2.39 (2H, s), 2.38 and 2.67 (2H, s), 3.30 (4H, m), 3.86 and 3.87 (3H, s), 5.67 and 5.89 (1H, d, J=8.2 Hz), 6.11 (1H, d, J=2.2 Hz), 6.24 and 7.15 (1H, s), 6.25-6.27 (1H, m), 6.76 and 6.80 (1H, d, J=16.5 Hz), 7.10 and 7.12 (1H, d, J=16.5 Hz), 7.38 and 7.40 (1H, d, J=8.8 Hz), 10.03 and 10.21 (1H, d, J=8.2 Hz)

$^{13}$C-NMR (150 MHz, CDCl$_3$) δ: 14.0, 20.3, 28.3, 28.4, 29.6, 31.1, 39.0, 39.2, 39.5, 46.5, 50.8, 55.2, 94.4, 104.8, 113.2, 120.0, 123.7, 125.69, 125.75, 125.9, 127.3, 127.4, 127.5, 127.91, 127.93, 147.7, 147.9, 150.0, 157.3, 157.6, 158.8, 158.9, 189.8, 190.6

(46-4) 2-[4-[3-[3-[2-(4-dibutylamino-2-methoxyphenyl)vinyl]-5,5-dimethyl-2-cyclohexenylidene]-1-propenyl]-3-cyano-5,5-dimethyl-2(5H)-furanylidene]propanedinitrile

[Formula 229]

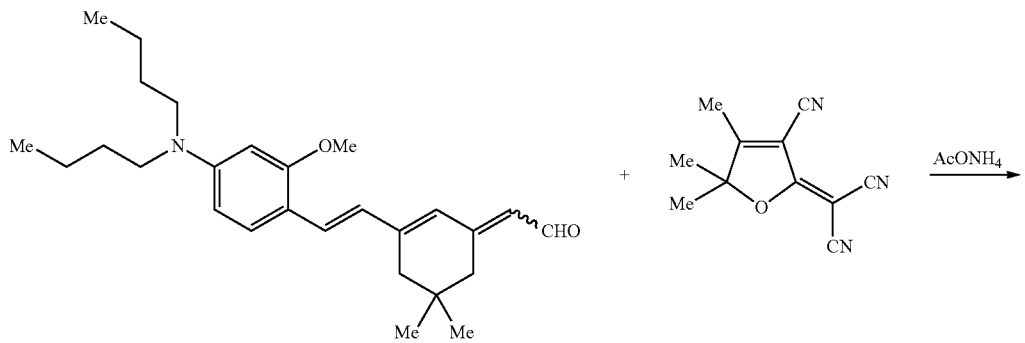

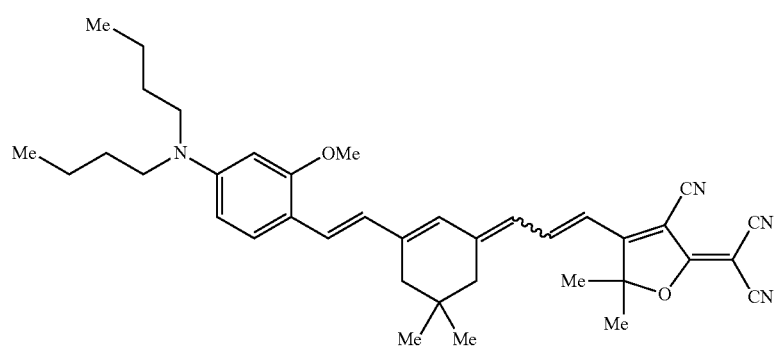

In 6 ml of ethanol were dissolved 173 mg (0.42 mmol) of [3-[2-(4-dibutylamino-2-methoxyphenyl)vinyl]-5,5-dimethyl-2-cyclohexenylidene]acetaldehyde and 95 mg (0.48 mmol) of 2-(3-cyano-4,5,5-trimethyl-2(5H)-furanylidene)propanedinitrile. To this mixture was added 34 mg of ammonium acetate, and the mixture was stirred with heating at 50° C. for 3.5 hours. The solvent was evaporated off and the residue was purified by silica gel column chromatography to give 229 mg of a dark brown crystal (yield: 91.8%; mp: 228-230° C.)

$^1$H-NMR (600 MHz, CDCl$_3$) δ: 0.98 (6H, t, J=7.7 Hz), 1.03 and 1.05 (6H, s), 1.35-1.41 (4H, m), 1.58-1.63 (4H, m), 1.69 and 1.74 (6H, s), 2.34 and 2.44 (2H, s), 2.42 (2H, s), 3.37 (4H, t, J=7.7 Hz), 3.88 (3H, s), 6.07 and 6.32 (1H, d, J=12.6 Hz), 6.09 (1H, s), 6.15 and 6.21 (1H, d, J=14.8 Hz), 6.27 (1H, d, J=8.8H), 6.36 and 6.78 (1H, s), 6.84 and 6.86 (1H, d, J=15.9 Hz), 7.24 and 7.25 (1H, d, J=15.9 Hz), 7.42 and 7.46 (1H, d, J=8.8 Hz), 8.00 and 8.30 (1H, b)

$^{13}$C-NMR (150 MHz, CDCl$_3$) δ: 14.0, 20.3, 26.6, 28.3, 28.5, 29.6, 31.5, 31.8, 39.5, 39.7, 40.0, 50.9, 54.3, 55.2, 94.1, 96.5, 105.0, 112.0, 112.2, 112.9, 113.3, 114.5, 125.5, 127.3, 128.3, 129.0, 129.8, 143.4, 144.1, 150.6, 150.8, 156.2, 159.4, 172.8, 176.4

Example 47

2-[4-[3-[3-[2-(4-dibutylamino-2-methoxyphenyl)vinyl]-5,5-dimethyl-2-cyclohexenylidene]-1-propenyl]-3-cyano-5-methyl-5-trifluoromethyl-2(5H)-furanylidene]propanedinitrile

[Formula 230]

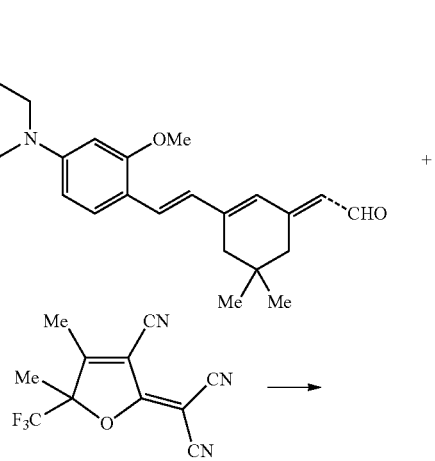

-continued

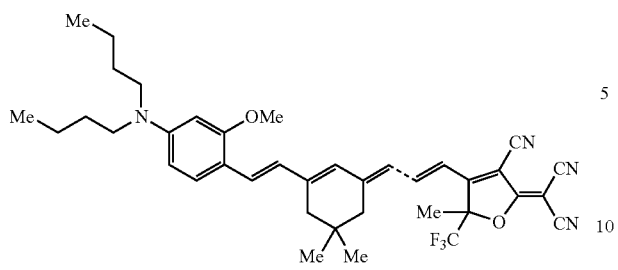

In 6 ml of ethanol were dissolved 200 mg (0.49 mmol) of [3-[2-(4-dibutylamino-2-methoxyphenyl) vinyl]-5,5-dimethyl-2-cyclohexenylidene]acetaldehyde and 136 mg (0.54 mmol) of 2-(3-cyano-4,5-dimethyl-5-trifluoromethyl-2(5H)-furanylidene)propanedinitrile. After the mixture was stirred with heating at 50° C. for 3.5 hours, the solvent was evaporated off. The residue was purified by silica gel column chromatography to give 224 mg of a dark brown crystal (yield: 71.2%; mp: 196-201° C.)

$^1$H-NMR (600 MHz, CDCl$_3$) δ: 0.98 (6H, t, J=7.1 Hz), 1.05 (6H, s), 1.35-1.41 (4H, m), 1.61-1.63 (4H, m), 1.82 (3H, s), 2.49 (4H, s), 3.35 (4H, t, J=7.1 Hz), 3.89 (3H, s), 6.08 (1H, s), 6.12 (1H, b), 6.29 (1H, d, J=8.2 Hz), 6.38 (1H, d, J=12.6 Hz), 6.43 (1H, s), 6.89 (1H, d, J=15.9 Hz), 7.42 (1H, d, J=15.9 Hz), 7.46 (1H, d, J=8.8 Hz), 8.39 (1H, b)

$^{13}$C-NMR (150 MHz, CDCl$_3$) δ: 14.0, 14.2, 19.4, 20.3, 28.4, 29.6, 31.8, 39.8, 40.1, 51.0, 55.3, 60.4, 93.9, 105.5, 111.5, 112.2, 113.2, 125.3, 128.6, 129.1, 129.7, 132.8, 145.8, 151.5, 160.1, 171.2, 176.0

Example 48

2-[4-[3-[3-[2-(4-dibutylamino-2-methoxyphenyl) vinyl]-5,5-dimethyl-2-cyclohexenylidene]-1-propenyl]-3-cyano-5-phenyl-5-trifluoromethyl-2(5H)-furanylidene]propanedinitrile

[Formula 231]

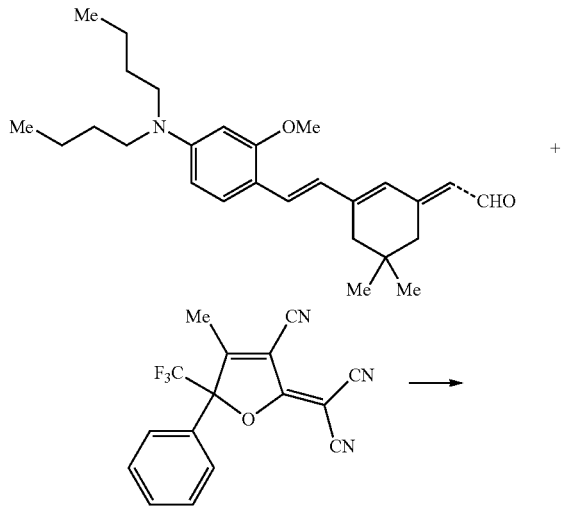

-continued

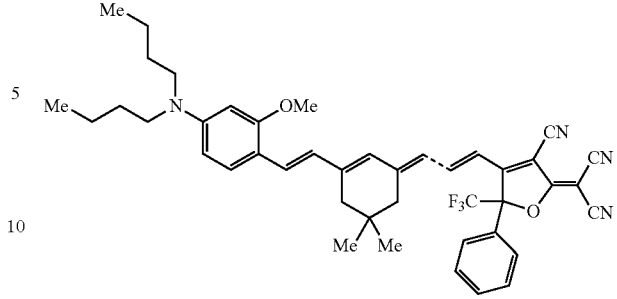

207 mg (0.51 mmol) of [3-[2-(4-dibutylamino-2-methoxyphenyl)vinyl]-5,5-dimethyl-2-cyclohexenylidene]acetaldehyde and 175 mg (0.56 mmol) of 2-(3-cyano-4-methyl-5-phenyl-5-trifluoromethyl-2(5H)-furanylidene)propanedinitrile were dissolved, and the mixture was stirred with heating at 50° C. for 3 hours. The precipitate was separated by filtration and washed with ethanol. The residue was purified by silica gel column chromatography to give 274 mg of a dark brown crystal (yield: 76.8%; mp: 164-166° C.)

$^1$H-NMR (600 MHz, CDCl$_3$) δ: 0.97 (3H, s), 0.98 (6H, t, J=7.7 Hz), 1.01 (3H, s), 1.35-1.41 (4H, m), 1.59-1.64 (4H, m), 2.26-2.34 (2H, b), 2.44 (2H, s), 3.35 (4H, t, J=7.7 Hz), 3.88 (3H, s), 6.07 (1H, d, J=2.2 Hz), 6.25 (2H, b), 6.29 (1H, d, J=8.8 Hz), 6.37 (1H, b), 6.85 (1H, d, J=15.4 Hz), 7.40 (1H, d, J=15.4 Hz), 7.45 (1H, d, J=8.8 Hz), 7.48-7.53 (5H, m), 8.08 (1H, b)

$^{13}$C-NMR (150 MHz, CDCl$_3$) δ: 13.9, 20.3, 28.1, 28.5, 29.6, 39.7, 39.8, 51.0, 55.2, 55.3, 93.9, 105.5, 111.6, 112.2, 113.6, 114.47, 114.52, 123.2, 125.3, 126.7, 128.5, 129.1, 129.5, 130.7, 131.0, 132.9, 151.5, 160.2, 176.2

Example 49

2-[4-[3-[3-[2-(4-dibutylamino-2-methoxyphenyl) vinyl]-2-methoxy-5,5-dimethyl-2-cyclohexenylidene]-1-propenyl]-3-cyano-5,5-dimethyl-2(5H)-furanylidene]propanedinitrile (49-1) 3-[2-(4-dibutylamino-2-methoxyphenyl)vinyl]-2-methoxy-5,5-dimethyl-2-cyclohexenone

[Formula 232]

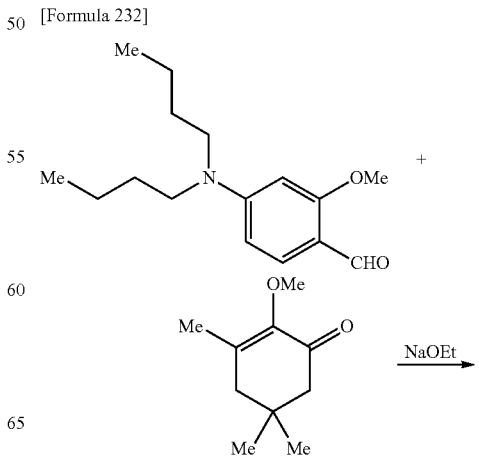

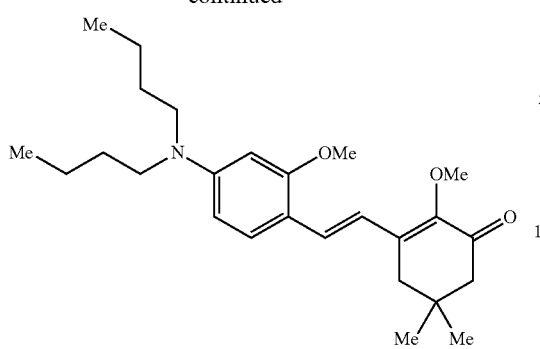

In 10 ml of ethanol, 0.32 g (13.9 mmol) of sodium was dissolved. Next, 2.36 g (8.96 mmol) of 4-dibutylamino-2-methoxybenzaldehyde and 1.58 g (9.39 mmol) of 2-methoxy-3,5,5-trimethyl-2-cyclohexenone were dissolved in ethanol and added to the mixture. The mixture was stirred with heating at 60° C. for 17 hours and concentrated. The residual liquid was purified by silica gel column chromatography to give 2.27 g of a dark red oily matter (yield: 61.2%).

$^1$H-NMR (600 MHz, CDCl$_3$) δ: 0.97 (6H, t, J=7.7 Hz), 1.11 (6H, s), 1.34-1.40 (4H, m), 1.58-1.63 (4H, m), 2.36 (2H, s), 2.56 (2H, s), 3.31 (4H, t, J=7.7 Hz), 3.73 (3H, s), 3.87 (3H, s), 6.11 (1H, d, J=2.2 Hz), 6.27 (1H, dd, J=2.2 Hz, 8.8 Hz), 7.23 (1H, d, J=16.5 Hz), 7.28 (1H, d, J=16.5 Hz), 7.53 (1H, d, J=8.8 Hz)

$^{13}$C-NMR (150 MHz, CDCl$_3$) δ: 14.0, 20.3, 28.5, 29.5, 32.7, 38.8, 50.9, 52.1, 55.3, 60.5, 94.2, 104.8, 113.3, 118.1, 128.0, 129.6, 141.2, 147.2, 150.2, 159.0, 194.5

(49-2) [3-[2-(4-dibutylamino-2-methoxyphenyl) vinyl]-2-methoxy-5,5-dimethyl-2-cyclohex-enylidene]acetonitrile

[Formula 233]

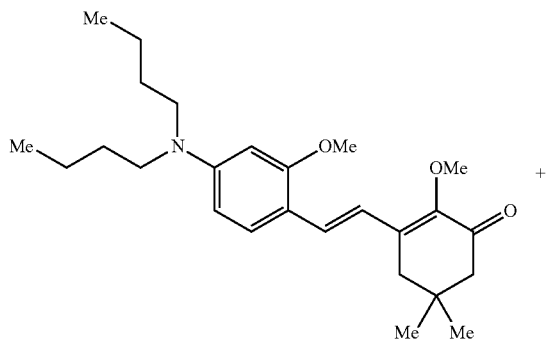

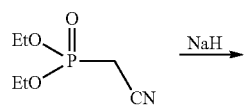

To 0.18 g (7.5 mmol) of sodium hydride, 12 ml of tetrahydrofuran was added. To this mixture, 0.98 g (5.5 mmol) of diethyl cyanomethylphosphonate was added dropwise under ice cooling. To the mixture, 0.915 g (2.2 mmol) of 3-[2-(4-dibutylamino-2-methoxyphenyl) vinyl]-2-methoxy-5,5-dimethyl-2-cyclohexenone in tetrahydrofuran was added dropwise. After the mixture was stirred at 60° C. for 24 hours, water was added to the mixture and extraction with ethyl acetate was performed. The extract was washed with a saturated saline solution, dried over anhydrous sodium sulfate, and concentrated. The residue was purified by silica gel column chromatography to give 0.51 g of an orange oily matter (yield: 52.9%).

$^1$H-NMR (600 MHz, CDCl$_3$) δ: 0.97 (6H, t, J=7.7 Hz), 1.04 (6H, s), 1.34-1.40 (4H, m), 1.57-1.62 (4H, m), 2.39 (2H, s), 2.53 (2H, s), 3.30 (4H, m), 3.63 (3H, s), 3.86 (3H, s), 5.44 (1H, s), 6.11 (1H, d, J=2.2 Hz), 6.26 (1H, dd, J=2.2 Hz, 8.8 Hz), 7.05 (1H, d, J=15.9 Hz), 7.15 (1H, d, J=16.5 Hz), 7.46 (1H, d, J=8.8 Hz)

$^{13}$C-NMR (150 MHz, CDCl$_3$) δ: 14.0, 20.3, 28.1, 29.6, 30.8, 39.0, 42.7, 50.9, 55.3, 60.8, 88.7, 94.4, 104.7, 113.6, 118.6, 119.1, 127.3, 127.7, 131.7, 148.0, 149.8, 153.2, 158.7

(49-3) [3-[2-(4-dibutylamino-2-methoxyphenyl) vinyl]-2-methoxy-5,5-dimethyl-2-cyclohex-enylidene]acetaldehyde

[Formula 234]

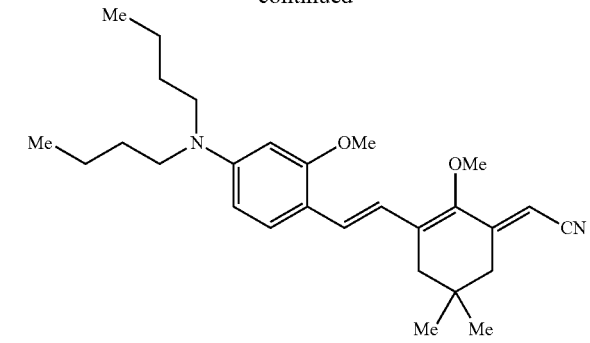

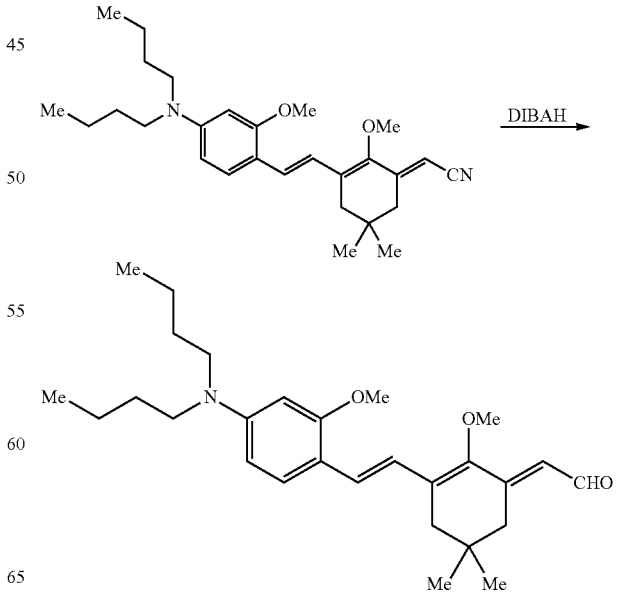

In 30 ml of toluene was dissolved 1.08 g (2.47 mmol) of [3-[2-(4-dibutylamino-2-methoxyphenyl)vinyl]-2-methoxy-5,5-dimethyl-2-cyclohexenylidene]acetonitrile. To this mixture, 3.6 ml of diisobutylaluminium hydride (1.5 mol solution in toluene) was added dropwise under dry ice/acetone cooling. The mixture was stirred for 2 hours and the temperature was allowed to rise. To the mixture, a 5% ammonium chloride solution was added dropwise. The organic layer was separated, dried over anhydrous sodium sulfate, and concentrated. The residue was purified by silica gel column chromatography to give 612 mg of a dark reddish brown crystal (yield: 56.3%).

$^1$H-NMR (600 MHz, CDCl$_3$) δ: 0.97 (6H, t, J=7.7 Hz), 1.07 (6H, s), 1.34-1.40 (4H, m), 1.57-1.62 (4H, m), 2.43 (2H, s), 2.73 (2H, s), 3.31 (4H, t, J=7.7 Hz), 3.64 (3H, s), 3.87 (3H, s), 6.12 (1H, d, J=2.2 Hz), 6.27 (1H, dd, J=2.2 Hz, 8.8 Hz), 6.30 (1H, d, J=8.2 Hz), 7.09 (1H, d, J=16.5 Hz), 7.24 (1H, d, J=16.5 Hz), 7.48 (1H, d, J=8.8 Hz), 10.07 (1H, d, J=8.2 Hz)

$^{13}$C-NMR (150 MHz, CDCl$_3$) δ: 14.0, 20.3, 28.3, 29.6, 30.7, 38.8, 39.2, 50.9, 55.3, 60.9, 94.4, 104.8, 113.7, 119.2, 121.2, 127.4, 127.7, 133.8, 149.0, 149.9, 151.6, 158.8, 191.1

(49-4) 2-[4-[3-[3-[2-(4-dibutylamino-2-methoxyphenyl) vinyl]-2-methoxy-5,5-dimethyl-2-cyclohexenylidene]-1-propenyl]-3-cyano-5,5-dimethyl-2 (5H)-furanylidene] propanedinitrile In 6 ml of ethanol and 2 ml of tetrahydrofuran were dissolved 239 mg (0.54 mmol) of [3-[2-(4-dibutylamino-2-methoxyphenyl) vinyl]-2-methoxy-5,5-dimethyl-2-cyclohexenylidene] acetaldehyde and 120 mg (0.60 mmol) of 2-(3-cyano-4,5,5-trimethyl-2(5H)-furanylidene)propanedinitrile. To this mixture was added 42 mg of ammonium acetate, and the mixture was stirred with heating at 50° C. for 2.5 hours. The solvent was evaporated off and the residue was purified by silica gel column chromatography to give 279 mg of a dark brown crystal (yield: 82.7%; mp: 244-246° C.)

$^1$H-NMR (600 MHz, CDCl$_3$) δ: 0.98 (6H, t, J=7.7 Hz), 1.06 (6H, s), 1.35-1.41 (4H, m), 1.59-1.63 (4H, m), 1.69 (6H, s), 2.27 (2H, s), 2.48 (2H, s), 3.33 (4H, t, J=7.7 Hz), 3.69 (3H, s), 3.88 (3H, s), 6.10 (1H, d, J=2.2 Hz), 6.29 (1H, dd, J=2.2 Hz, 8.8 Hz), 6.33 (1H, d, J=14.9 Hz), 6.76 (1H, d, J=14.9 Hz), 7.21 (1H, d, J=14.9 Hz), 7.29 (1H, d, J=16.5 Hz), 7.51 (1H, d, J=8.8 Hz), 8.00 (1H, t, J=13.9 Hz)

$^{13}$C-NMR (150 MHz, CDCl$_3$) δ: 14.0, 20.3, 26.5, 28.3, 29.6, 31.0, 39.1, 40.1, 50.9, 54.7, 55.3, 61.3, 93.5, 94.2 96.6, 105.1, 111.9, 112.1, 112.8, 113.9, 115.8, 119.1, 122.4, 128.2, 129.6, 137.1, 144.2, 148.8, 150.5, 151.0, 159.3, 173.0, 176.3

[Formula 235]

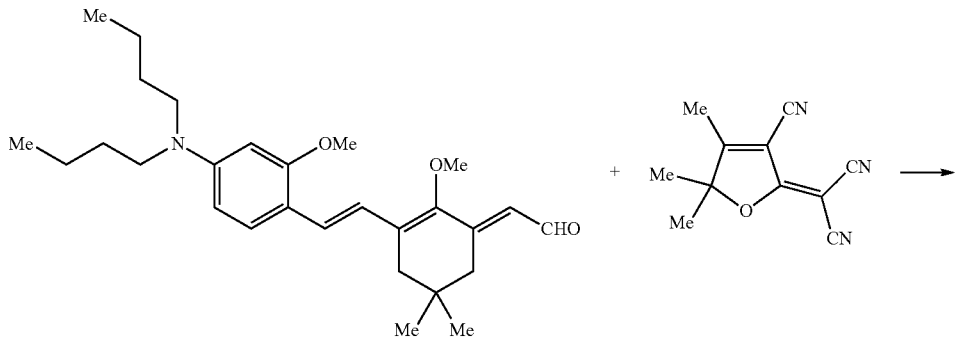

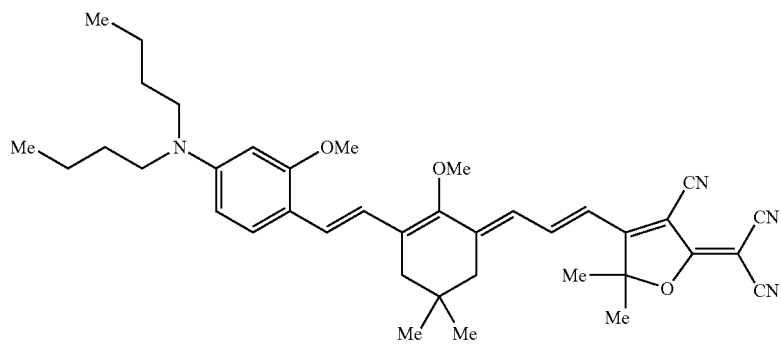

Example 50

2-[4-[3-[3-[2-(4-dibutylamino-2-methoxyphenyl)vinyl]-2-methoxy-5,5-dimethyl-2-cyclohexenylidene]-1-propenyl]-3-cyano-5-methyl-5-trifluoromethyl-2(5H)-furanylidene] propanedinitrile

[Formula 236]

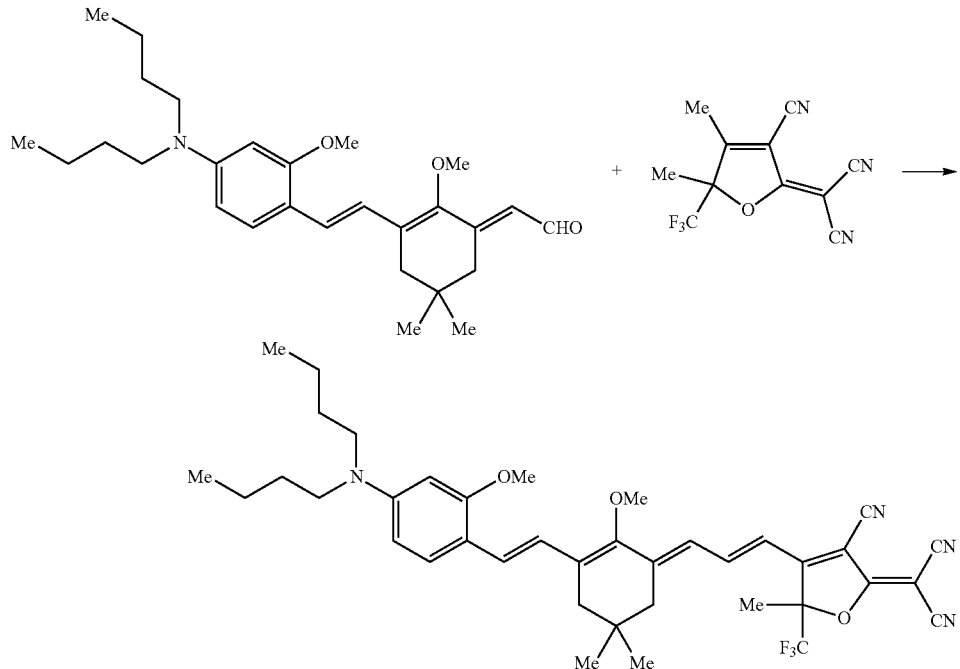

In 5 ml of ethanol were dissolved 200 mg (0.46 mmol) of [3-[2-(4-dibutylamino-2-methoxyphenyl)vinyl]-2-methoxy-5,5-dimethyl-2-cyclohexenylidene]acetaldehyde and 127 mg (0.50 mmol) of 2-(3-cyano-4,5-dimethyl-5-trifluoromethyl-2(5H)-furanylidene)propanedinitrile. After the mixture was stirred with heating at 60° C. for 2 hours, the solvent was evaporated off. The residue was purified by silica gel column chromatography to give 226 mg of a brown crystal (yield: 73.6%; mp: 141-151° C.)

$^1$H-NMR (600 MHz, CDCl$_3$) δ: 0.98 (6H, t, J=7.7 Hz), 1.06 (3H, s), 1.07 (3H, s), 1.36-1.42 (4H, m), 1.60-1.65 (4H, m), 1.84 (3H, s), 2.53 (4H, s), 3.36 (4H, t, J=7.7 Hz), 3.71 (3H, s), 3.90 (3H, s), 6.09 (1H, d, J=2.2 Hz), 6.26 (1H, d, J=13.7 Hz), 6.31 (1H, dd, J=2.2 Hz, 8.8 Hz), 6.81 (1H, d, J=12.6 Hz), 7.33 (1H, d, J=15.9 Hz), 7.38 (1H, d, J=16.5 Hz), 7.55 (1H, d, J=8.8 Hz), 8.37 (1H, b)

$^{13}$C-NMR (150 MHz, CDCl$_3$) δ: 14.0, 19.3, 20.3, 28.2, 29.6, 31.2, 39.4, 40.2, 51.0, 55.3, 55.7, 61.5, 92.9, 93.9, 105.5, 111.4, 112.0, 112.6, 114.1, 114.5, 119.0, 123.3, 128.9, 132.4, 141.7, 146.0, 151.3, 151.7, 151.9, 160.1, 161.1, 175.9

Example 51

2-[4-[3-[3-[2-(4-dibutylamino-2-methoxyphenyl)vinyl]-2-methoxy-5,5-dimethyl-2-cyclohexenylidene]-1-propenyl]-3-cyano-5-phenyl-5-trifluoromethyl-2(5H)-furanylidene] propanedinitrile

[Formula 237]

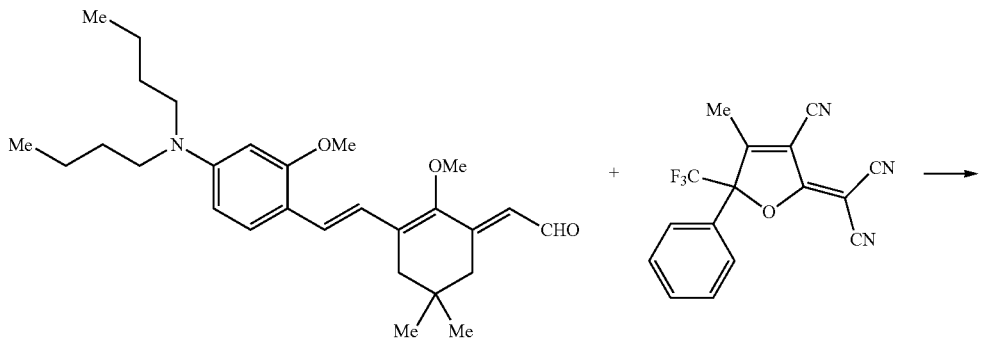

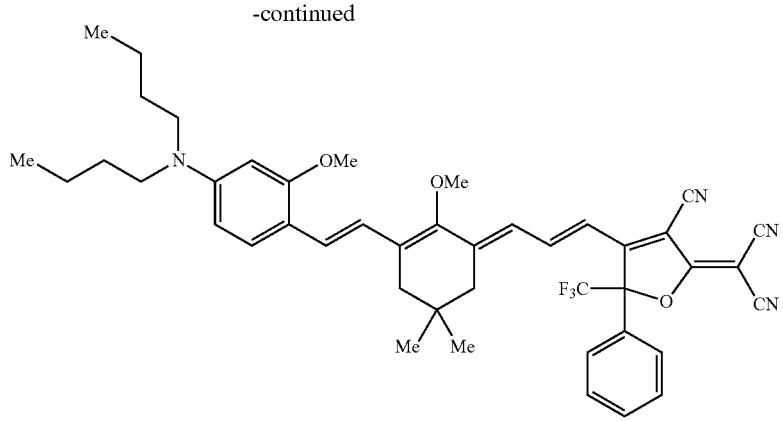

185 mg (0.42 mmol) of 3-[2-(4-dibutylamino-2-methoxyphenyl)vinyl]-2-methoxy-5,5-dimethyl-2-cyclohexenylidene]acetaldehyde and 146 mg (0.46 mmol) of 2-(3-cyano-4-methyl-5-phenyl-5-trifluoromethyl-2(5H)-furanylidene)propanedinitrile were dissolved, and the mixture was stirred with heating at 60° C. for 2 hours. The precipitate was separated by filtration and washed with ethanol. The residue was purified by silica gel column chromatography to give 172 mg of a brown crystal (yield: 55.5%; mp: 153-158° C.)

$^1$H-NMR (600 MHz, CDCl$_3$) δ: 0.97 (3H, s), 0.98 (6H, t, J=7.7 Hz), 1.02 (3H, s), 1.35-1.41 (4H, m), 1.59-1.64 (4H, m), 2.27 (1H, d, J=15.9 Hz), 2.36 (1H, d, J=15.9 Hz), 2.49 (2H, s), 3.35 (4H, t, J=7.7 Hz), 3.66 (3H, s), 3.89 (3H, s), 6.08 (1H, d, J=2.2 Hz), 6.30 (1H, dd, J=2.2 Hz, 8.8 Hz), 6.37 (1H, d, J=13.8 Hz), 6.72 (1H, d, J=12.6 Hz), 7.30 (1H, d, J=15.9 Hz), 7.36 (1H, d, J=15.9 Hz), 7.50-7.54 (6H, m), 8.02 (1H, b)

$^{13}$C-NMR (150 MHz, CDCl$_3$) δ: 14.0, 20.3, 28.0, 28.4, 29.6, 31.2, 39.3, 51.0, 55.3, 55.9, 61.5, 91.9, 105.5, 111.4, 111.9, 114.2, 115.8, 119.0, 121.2, 123.2, 123.3, 126.8, 128.9, 129.5, 130.6, 131.1, 132.5, 141.7, 146.4, 151.4, 151.7, 151.8, 160.1, 161.2, 176.0

Example 52

2-[3-cyano-5-phenyl-5-trifluoromethyl-4-[2-[5-[2-(2,4,6-trimethoxyphenyl)vinyl]-2-thienyl]vinyl]-2(5H)-furanylidene]propanedinitrile (52-1) 2-[2-(2,4,6-trimethoxyphenyl)vinyl]thiophene

[Formula 238]

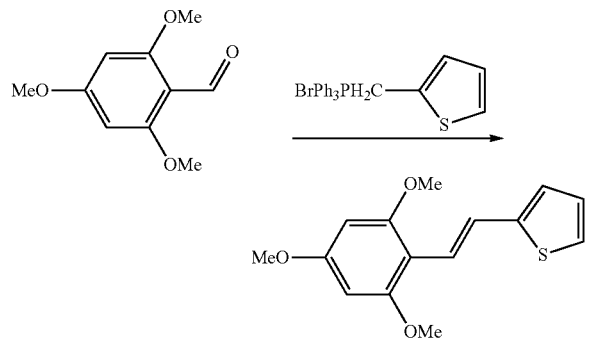

In a stream of argon, to 30 ml of tetrahydrofuran was added 0.95 g of phenyllithium (19% solution in dibutylether) (2.15 mmol). To this mixture, 0.78 g (1.98 mmol) of thiophene-2-ylmethyltriphenylphosphonium bromide was added under cooling. After the mixture was well-stirred, 0.38 g (1.98 mmol) of 2,4,6-trimethoxybenzaldehyde dissolved in 3 ml of tetrahydrofuran was added dropwise. The mixture was reacted with stirring for 1.5 hours. After the reaction mixture was poured into 70 ml of ice water, extraction with 200 ml of chloroform, washing with a saturated saline solution, drying over anhydrous magnesium sulfate, and concentration were performed. The residue was purified by silica gel chromatography to give 508 mg (yield: 92%) of 2-[2-(2,4,6-trimethoxyphenyl)vinyl]thiophene as a colorless crystal.

$^1$H-NMR (600 MHz, CDCl$_3$) δ: 3.80 (3H, s), 3.85 (6H, s), 6.13 (2H, s), 6.98 (1H, d, J=6 Hz), 7.29 (1H, s), 7.10 (1H, d, J=6 Hz), 7.25 (1H, d, J=18 Hz), 7.58 (1H, d, J=18 Hz)

$^{13}$C-NMR (150 MHz, CDCl$_3$) δ: 55.2, 55.7, 90.7, 107.6, 119.6, 122.9, 123.0, 124.3, 127.3, 145.6, 159.4, 160.1

(52-2) 5-[2-(2,4,6-trimethoxyphenyl)vinyl]thiophene-2-carbaldehyde

[Formula 239]

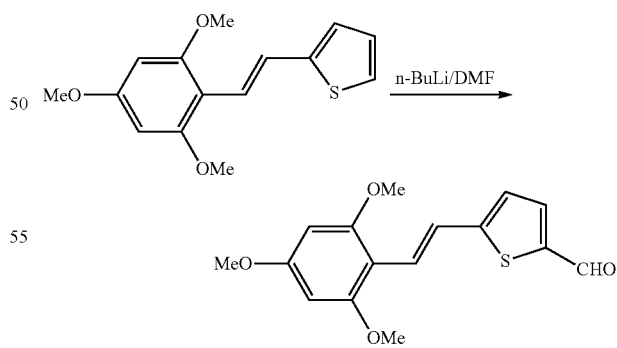

In a stream of argon, in 10 ml of tetrahydrofuran was dissolved 500 mg (1.80 mmol) of 2-[2-(2,4,6-trimethoxyphenyl) vinyl]thiophene, and 1.27 ml of n-butyllithium (1.6 M solution in hexane) (2.03 mmol) was added dropwise thereto under cooling. The mixture was stirred for 1 hour. To this mixture, 0.16 ml (2.00 mmol) of N,N-dimethylformamide was added dropwise and reacted. After reacted at gradually increasing temperature, the reaction mixture was stirred at room temperature for 12 hours. The mixture was poured into 50 ml of ice water and subjected to 3 times of extraction with 200 ml of chloroform. The extract was washed with a saturated saline solution, dried over anhydrous magnesium sulfate, and concentrated. The residue was purified by silica gel chromatography to give 380 mg (yield: 69%) of 5-[2-(2,4,6-trimethoxyphenyl)vinyl] thiophene-2-carbaldehyde as a light yellow crystal.

$^1$H-NMR (600 MHz, CDCl$_3$) δ: 3.74 (3H, s), 3.79 (6H, s), 6.03 (2H, s), 6.98 (1H, d, J=3.8 Hz), 7.51 (2H, s), 7.54 (1H, d, J=3.8 Hz), 9.70 (1H, s)

(52-3) 2-[3-cyano-5-phenyl-5-trifluoromethyl-4-[2-[5-[2-(2,4,6-trimethoxyphenyl)vinyl]-2-thienyl]vinyl]-2(5H)-furanylidene]propanedinitrile

[Formula 240]

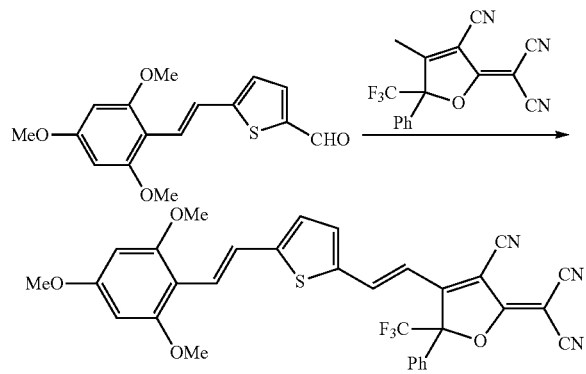

To 20 ml of acetonitrile were added 304 mg (1.00 mmol) of 5-[2-(2,4,6-trimethoxyphenyl)vinyl]thiophene-2-carbaldehyde, 315 mg (1.00 mmol) of 2-(3-cyano-4-methyl-5-phenyl-5-trifluoromethyl-2(5H)-furanylidene)propanedinitrile, and a catalytic amount of ammonium acetate. The mixture was stirred overnight. After the reaction, the mixture was concentrated and the residue was purified by silica gel column chromatography to give 490 mg (yield: 82%) of the target compound 2-[3-cyano-5-phenyl-5-trifluoromethyl-4-[2-[5-[2-(2,4,6-trimethoxyphenyl)vinyl]thiophene-2-yl]vinyl]-2(5H)-furanylidene]propanedinitrile as a yellow crystal.

$^1$H-NMR (600 MHz, CDCl$_3$) δ: 3.86 (3H, s), 3.89 (6H, s), 6.14 (2H, s), 6.65 (1H, d, J=12 Hz), 7.04 (1H, d, J=4 Hz), 7.26 (1H, s), 7.29 (1H, d, J=4 Hz), 7.49-7.56 (5H, m), 7.61 (1H, s), 7.75 (1H, d, J=12 Hz)

Example 53

2-[3-cyano-5,5-dimethyl-4-[2-[5-[2-(4-dibutylamino-2,6-dimethoxyphenyl)vinyl]-2-thienyl]vinyl]-2(5H)-furanylidene] propanedinitrile

[Formula 241]

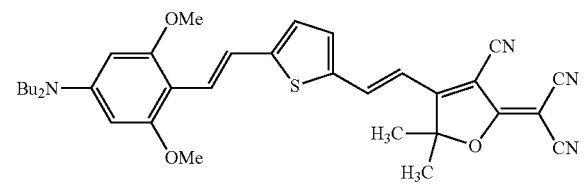

(53-1) 4-dibutylamino-3,5-dimethoxybenzene

[Formula 242]

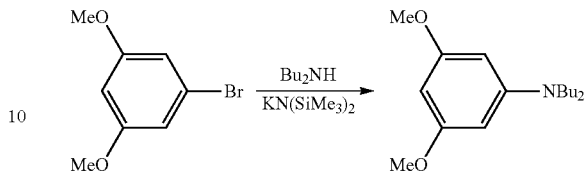

In a stream of argon, to 300 ml of dioxane were added 21.7 g (100 mmol) of 3,5-dimethoxybromobenzene and 13.0 g (100 mmol) of dibutylamine, and 22.0 g (110 mmol) of potassium bistrimethylsilylamide was added thereto with stirring. After well-stirred, the mixture was heated under reflux with stirring overnight. The reactant was poured into 2 L of ice water and subjected to 3 times of extraction with 200 ml of chloroform. Washing with a saturated saline solution, drying over anhydrous magnesium sulfate, and concentration were performed. The residue was purified by silica gel chromatography to give 23.4 g (yield: 88%) of 4-dibutylamino-3,5-dimethoxybenzene as a colorless transparent oily matter.

$^1$H-NMR (600 MHz, CDCl$_3$) δ: 0.946 (6H, t, J=8 Hz), 1.40 (4H, m), 1.56 (4H, m), 3.22 (4H, t, J=7 Hz), 3.75 (6H, s), 5.83 (3H, s)

$^{13}$C-NMR (150 MHz, CDCl$_3$) δ: 13.8, 20.2, 29.4, 50.7, 54.8, 87.0, 91.0, 149.8, 161.6

(53-2) 4-dibutylamino-2,6-dimethoxybenzaldehyde

[Formula 243]

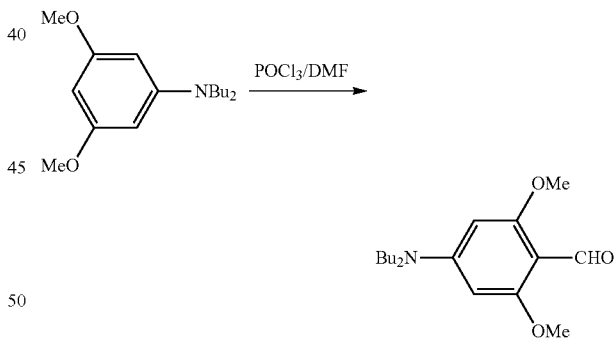

In a stream of argon, to 30 ml of N,N-dimethylformamide was added 16.0 g (104 mmol) of phosphorus oxychloride under cooling at 5 to 10° C. and stirring. After the mixture was well-stirred, 23.5 g (80.1 mmol) of 4-butylamino-2,6-dimethoxybenzene dissolved in 10 ml of N,N-dimethylformamide was added dropwise. The mixture was reacted with stirring for 1.5 hours. After the mixture was poured into 70 ml of ice water, extraction with 200 ml of chloroform, washing with a saturated saline solution, drying over anhydrous magnesium sulfate, and concentration were performed. The residue was purified by silica gel chromatography to give 18.8 g (yield: 80%) of 4-dibutylamino-2,6-dimethoxybenzaldehyde as a dark purple crystal (mp: 55-56° C.).

¹H-NMR (600 MHz, CDCl₃) δ: 0.99 (6H, t, J=8 Hz), 1.39 (4H, m), 1.62 (4H, m), 3.34 (4H, t, J=7 Hz), 3.85 (6H, s), 5.71 (2H, s), 9.98 (1H, s)

¹³C-NMR (150 MHz, CDCl₃) δ: 13.9, 20.2, 29.4, 50.8, 55.5, 86.8, 104.7, 153.8, 164.2, 186.2

(53-3) 2-[2-(4-dibutylamino-2,6-dimethoxyphenyl)vinyl]thiophene

[Formula 244]

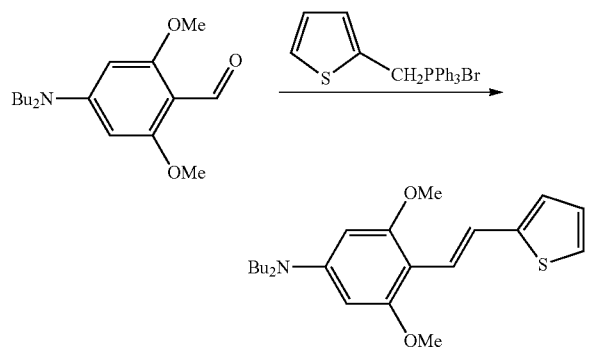

In a stream of argon, to 30 ml of tetrahydrofuran was added 3.76 g of a 19% phenyllithium solution (8.5 mmol), and 0.78 g (1.98 mmol) of thiophene-2-ylmethyltriphenylphosphonium bromide was added thereto under cooling. After the mixture was well-stirred, 0.58 g (1.98 mmol) of 4-dibutylamino-2,6-dimethoxybenzaldehyde dissolved in 3 ml of tetrahydrofuran was added dropwise. The mixture was stirred for 1.5 hours. After the mixture was poured into 70 ml of ice water, extraction with 200 ml of chloroform, washing with a saturated saline solution, drying over anhydrous magnesium sulfate, and concentration were performed. The residue was purified by silica gel chromatography to give 463 mg (yield: 62%) of 2-[2-(4-dibutylamino-2,6-dimethoxyphenyl)vinyl]thiophene as a dark purple crystal (mp: 90° C.).

¹H-NMR (600 MHz, CDCl₃) δ: 0.96 (6H, t, J=8 Hz), 1.35 (4H, m), 1.57 (4H, m), 3.27 (4H, t, J=7 Hz), 3.86 (6H, s), 5.84 (2H, s), 6.92 (2H, d, J=2 Hz), 7.03 (1H, d, J=2 Hz), 7.26 (1H, d, J=16 Hz), 7.48 (1H, d, J=16 Hz)

¹³C-NMR (150 MHz, CDCl₃) δ: 13.9, 20.3, 29.5, 50.7, 54.4, 88.5, 103.1, 120.3, 121.9, 123.2, 127.2, 146.5, 148.5, 159.7

(53-4) 5-[2-(4-dibutylamino-2,6-dimethoxyphenyl)vinyl]thiophene-2-carbaldehyde

[Formula 245]

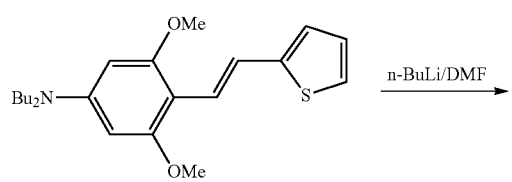

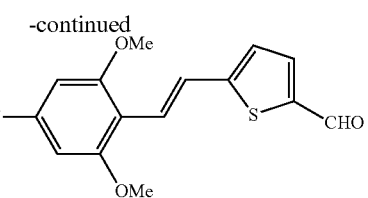

In a stream of argon, in 10 ml of tetrahydrofuran was dissolved 0.75 g (2.00 mmol) of 2-[2-(4-dibutylamino-2,6-dimethoxyphenyl)vinyl]thiophene, and 1.27 ml of n-butyllithium (1.6 M solution in hexane) (2.03 mmol) was added dropwise thereto under cooling. The mixture was stirred for 1 hour. To this mixture, 0.20 ml (1.20 mmol) of N,N-dimethylformamide was added dropwise and reacted. The temperature was then allowed to rise gradually, and the mixture was allowed to react at room temperature for 12 hours. After the mixture was poured into 100 ml of ice water, extraction with 200 ml of chloroform, washing with a saturated saline solution, drying over anhydrous magnesium sulfate, and concentration were performed. The residue was purified by silica gel chromatography to give 482 mg (yield: 60%) of 5-[2-(4-dibutylamino-2,6-dimethoxyphenyl)vinyl]thiophene-2-carboaldehyde as a dark purple crystal (mp: 105-106° C.)

¹H-NMR (600 MHz, CDCl₃) δ: 0.96 (6H, t, J=8 Hz), 1.36 (4H, m), 1.59 (4H, m), 3.26 (4H, t, J=7 Hz), 3.84 (6H, s), 5.79 (2H, s), 6.97 (1H, d, J=4 Hz), 7.46 (1H, d, J=16 Hz), 7.55 (1H, d, J=4 Hz), 7.60 (1H, d, J=16 Hz), 9.73 (1H, s)

¹³C-NMR (150 MHz, CDCl₃) δ: 13.9, 20.3, 29.6, 50.8, 55.4, 88.1, 101.6, 102.0, 118.4, 123.8, 125.6, 137.8, 139.0, 149.6, 157.7, 160.5, 182.1

(53-5) 2-[3-cyano-5,5-dimethyl-4-[2-[5-[2-(4-dibutylamino-2,6-dimethoxyphenyl)vinyl]-2-thienyl]vinyl]-2(5H)-furanylidene]propanedinitrile

[Formula 246]

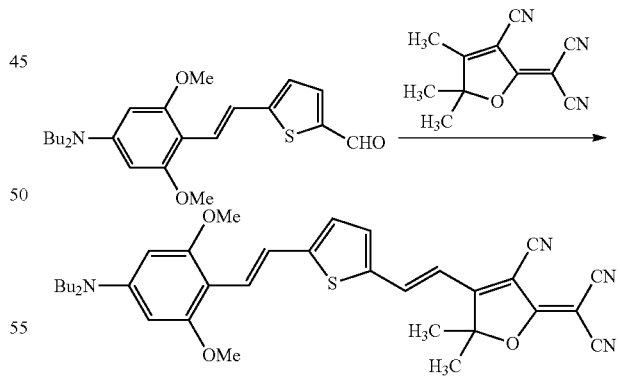

To 20 ml of acetonitrile were added 401 mg (1.00 mmol) of 5-[2-(4-dibutylamino-2,6-dimethoxyphenyl)vinyl]thiophene-2-carbaldehyde, 199 mg (1.00 mmol) of 2-(3-cyano-4,5,5-trimethyl-2(5H)-furanylidene)propanedinitrile, and a catalytic amount of ammonium acetate. The mixture was stirred overnight. After the reaction, the mixture was concentrated. The residue was purified by silica gel column chromatography to give 280 mg (yield: 48%) of the target compound 2-[3-cyano-5,5-dimethyl-4-(2-{5-[2-(4-dibutylamino-2,6-dimethoxyphenyl)vinyl]-2-thienyl}vinyl)-2 (5H)-furanylidene] propanedinitrile as a dark red crystal (mp: 230° C.)

$^1$H-NMR (600 MHz, CDCl$_3$) δ: 0.99 (6H, t, J=8 Hz), 1.39 (4H, m), 1.63 (4H, m), 1.72 (6H, s), 3.35 (4H, t, J=7 Hz), 3.91 (6H, s), 5.80 (2H, s), 6.48 (1H, d, J=17 Hz), 6.96 (1H, d, J=4 Hz), 7.31 (1H, d, J=4 Hz), 7.49 (1H, d, J=16 Hz), 7.62 (2H, d, J=16 Hz), 7.70 (1H, d, J=17 Hz)

$^{13}$C-NMR (150 MHz, CDCl$_3$) δ: 13.9, 19.2, 20.3, 29.7, 51.0, 54.8, 88.0, 92.7, 103.2, 109.1, 111.2, 111.9, 118.0, 121.3, 123.2, 127.1, 129.7, 137.4, 140.6, 151.1, 161.1, 161.8, 162.8, 175.5

Example 54

2-[3-cyano-5-methyl-5-trifluoromethyl-4-(2-{5-[2-(4-dibutylamino-2,6-dimethoxyphenyl)vinyl]-2-thienyl}vinyl)-2(5H)-furanylidene]propanedinitrile (a black crystal; 280 mg; yield: 40%; mp: 203° C.) was synthesized in the same manner as in Example 53.

[Formula 247]

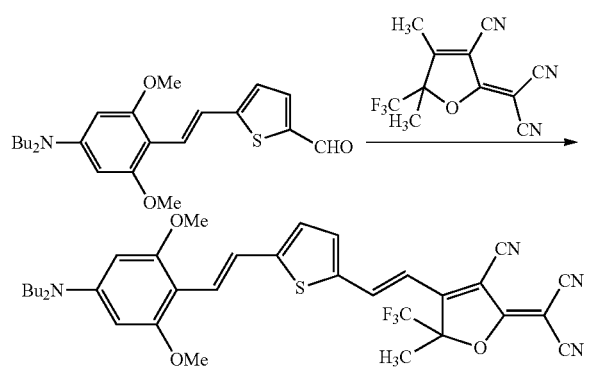

$^1$H-NMR (600 MHz, CDCl$_3$) δ: 0.92 (6H, t, J=8 Hz), 1.33 (4H, m), 1.57 (4H, m), 1.82 (3H, s), 3.30 (4H, t, J=7 Hz), 3.84 (6H, s), 5.77 (2H, s), 6.27 (1H, d, J=15 Hz), 6.96 (1H, d, J=4 Hz), 7.32 (1H, d, J=4 Hz), 7.47 (1H, d, J=15 Hz), 7.67 (1H, d, J=15 Hz), 7.99 (1H, d, J=15 Hz)

$^{13}$C-NMR (150 MHz, THF-d$_8$) δ: 14.3, 18.6, 21.0, 30.6, 51.4, 55.8, 89.1, 104.1, 110.3, 111.4, 112.0, 112.1, 119.0, 127.8, 129.5, 138.3, 141.7, 141.9, 152.0, 162.0, 162.2, 176.3

Example 55

2-[3-cyano-5-phenyl-5-trifluoromethyl-4-[2-[5-[2-(4-dibutylamino-2, 6-dimethoxyphenyl) vinyl]-2-thienyl]vinyl]-2 (5H)-furanylidene]propanedinitrile (a dark red crystal; 550 mg; yield: 77%; mp: 229-230° C.) was synthesized in the same manner as in Example 53.

[Formula 248]

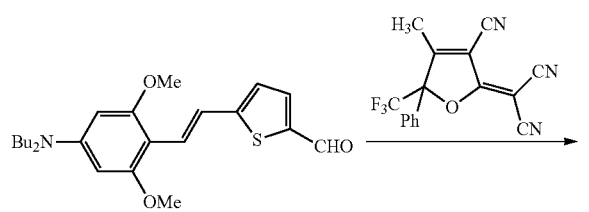

-continued

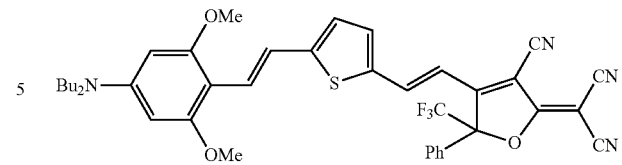

$^1$H-NMR (600 MHz, CDCl$_3$) δ: 0.99 (6H, t, J=8 Hz), 1.40 (4H, m), 1.63 (4H, m), 3.35 (4H, t, J=7 Hz), 3.93 (6H, s), 5.80 (2H, s), 6.52 (1H, d, J=15 Hz), 6.98 (1H, d, J=4 Hz), 7.26 (1H, d, J=4 Hz), 7.49-7.52 (6H, m), 7.72 (2H, d, J=15 Hz)

$^{13}$C-NMR (150 MHz, CDCl$_3$) δ: 14.1, 20.3, 29.8, 51.1, 55.6, 56.2, 88.0, 103.6, 110.5, 111.2, 111.5, 111.6, 118.2, 123.0, 127.2, 127.5, 129.8, 130.3, 130.5, 131.2, 137.0, 141.2, 151.2, 161.0, 161.3, 163.0, 175.4

Example 56

2-(4-{2-[5-(2-{2-benzyloxy-4-[(2-hydroxyethyl)-methylamino]-phenyl}-vinyl)-thiophene-2-yl]-vinyl}-3-cyano-5-phenyl-5-trifluoromethyl-5H-furan-2-ylidene)malononitrile (56-1) 2,2-dimethylpropionic acid 2-[(3-methoxyphenyl) methylamino]ethyl ester

[Formula 249]

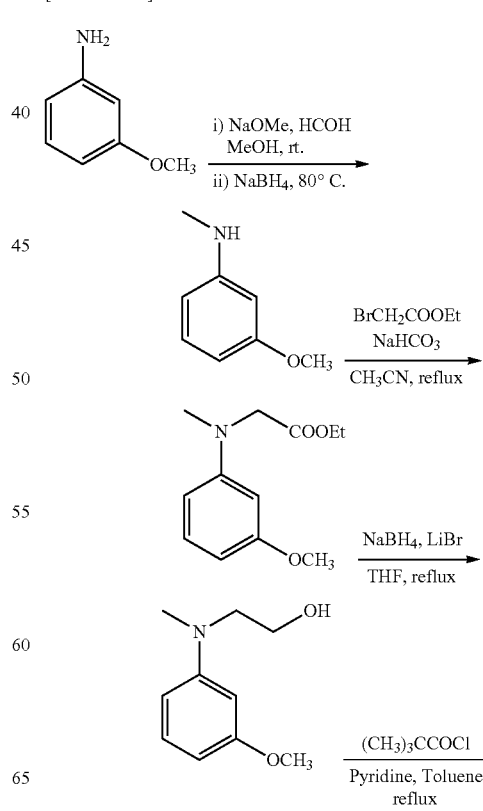

-continued

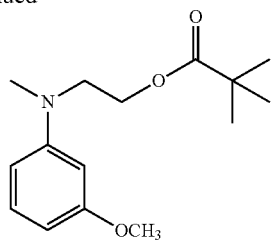

In a NaOMe (15.8 g, 0.29 mol)/methanol (70 ml) solution, 3-methoxyphenylamine (6.0 g, 48.7 mmol) was dissolved. The mixture was added to formaldehyde (2.2 g, 73.8 mmol)/methanol (25 ml) and stirred at room temperature for 12 hours. To this mixture, NaBH$_4$ (1.84 g, 48.6 mmol) was added. The mixture was stirred for 1 hour and reacted at 80° C. for 2 hours. After an aqueous KOH solution (1 M, 200 ml) was added dropwise, the produced oily matter was subjected to 3 times of extraction with 50 ml of dichloromethane. Drying over Na$_2$SO$_4$ and concentration gave crude (3-methoxyphenyl)methylamine (yield: 6.6 g (99.9%)).

Next, (3-methoxyphenyl)methylamine (6.6 g, 48.1 mmol) and ethyl bromoacetate (9.8 g, 58.4 mmol) were dissolved in acetonitrile (50 ml), and NaHCO$_3$ (6.1 g, 73 mmol) was added thereto. After the mixture was stirred at 90° C. for 2 hours, triethylamine (4 ml) was added thereto at room temperature. The mixture was stirred at room temperature for 16 hours. After the solvent was evaporated off, the crude product was dissolved in dichloromethane (100 ml) and washed with a saturated saline solution 3 times. The organic layer was dried over Na$_2$SO$_4$ and concentrated to give crude [(3-methoxyphenyl)methyl-amino] acetic acid ethyl ester (yield: 7.4 g (68.8%)).

Next, NaBH$_4$ (3.8 g, 100 mmol) and LiBr (8.7 g, 100 mmol) were added to THF (100 ml), and the mixture was stirred at 80° C. for 1 hour. To this mixture, [(3-methoxyphenyl)methylamino] acetic acid ethyl ester (7.4 g, 33.1 mmol) dissolved in THF (20 ml) was added dropwise at room temperature. The mixture was stirred at 80° C. for 5 hours and further at room temperature for 16 hours. After the reaction solvent was evaporated to about half, KH$_2$PO$_4$ (1 M, 200 ml) was slowly added dropwise thereto. The organic layer was extracted with dichloromethane (50 ml) times and dried over Na$_2$SO$_4$ to give crude 2-[(3-methoxyphenyl)methylamino]ethanol (yield: 8.1 g).

Next, in toluene (100 ml) were added 2-[(3-methoxyphenyl)methylamino]ethanol (8.1 g), pivaloyl chloride (10.8 g, 89.4 mmol), and pyridine (8.5 g, 107 mmol). The mixture was stirred at room temperature for 1 hour and further at 85° C. for 2 hours. After pyridine hydrochloride was removed by filtration, the filtrate was concentrated. The product was purified by silica gel chromatography to give 2,2-dimethylpropionic acid 2-[(3-methoxyphenyl)methylamino] ethyl ester as a colorless oily matter (yield: 10.4 g (78.4%)).

$^1$H NMR (396 MHz, CDCl$_3$): δ 7.14 (m, 1H, benzene ring), 6.36 (d, 1H, benzene ring), 6.29-6.28 (m, 2H, benzene ring), 4.23 (t, 2H, CH$_2$), 3.78 (s, 3H, OCH$_3$), 3.60 (t, 2H, CH$_2$), 2.97 (s, 3H, CH$_3$), 1.20 (m, 9H, t-Bu)

(56-2) 2,2-dimethylpropionic acid 2-[(4-formyl-3-methoxyphenyl)methylamino]ethyl ester

[Formula 250]

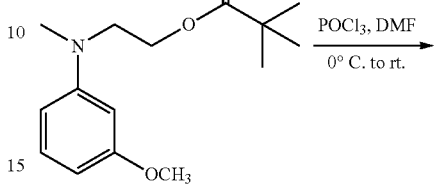

POCl$_3$ (5.8 g, 37.7 mmol) was added to 20 ml of DMF in an ice bath. After 40 minutes, 2,2-dimethylpropionic acid 2-[(3-methoxyphenyl)methylamino]ethyl ester (10 g, 37.7 mmol) dissolved in DMF (10 ml) was added dropwise. After the mixture was stirred for 16 hours, an aqueous sodium acetate solution (20%, 100 ml) was added dropwise thereto and the oily matter was subjected to extraction with ethyl acetate. Washing was performed with a saturated aqueous NaHCO$_3$ solution (100 ml) and then with a saturated saline solution (100 ml). After drying over Na$_2$SO$_4$ and concentration, the residue was purified by silica gel chromatography to give a light yellow crystal (yield: 8.7 g (78.9%)).

$^1$H NMR (396 MHz, CDCl$_3$): δ 10.16 (s, 1H, CHO), 7.71 (m, 1H, benzene ring), 6.34 (m, 1H, benzene ring), 6.13 (d, 1H, benzene ring), 4.26 (t, 2H, CH$_2$), 3.91 (s, 3H, OCH$_3$), 3.70 (t, 2H, CH$_2$), 3.10 (s, 3H, CH$_3$), 1.16 (m, 9H, t-Bu)

(56-3) 2,2-dimethylpropionic acid 2-{[3-methoxy-4-(2-thiophene-2-ylvinyl)phenyl]methylamino}ethyl ester

[Formula 251]

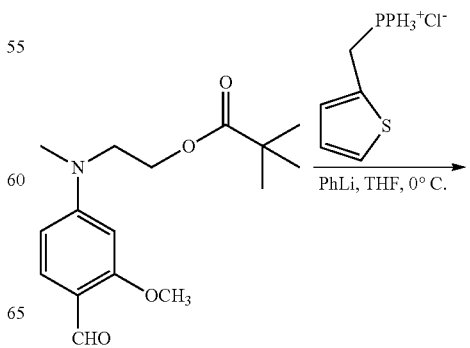

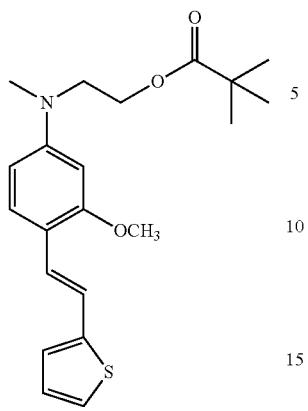

Thiophene-2-ylmethyl triphenylphosphonium chloride (4.4 g, 16.3 mmol) was added to THF (50 ml), and PhLi (8.6 g of 19% solution in hexane, 19.6 mmol) was added dropwise thereto in an ice bath. After 20 minutes, 2,2-dimethylpropionic acid 2-[(4-formyl-3-methoxyphenyl)methylamino]ethyl ester (4.0 g, 13.6 mmol) dissolved in THF (15 ml) was added dropwise. The mixture was reacted for 2 hours. The reaction mixture was added to 300 ml of ice water, and the oily matter was subjected to 3 times of extraction with dichloromethane (50 ml). Washing with a saturated saline solution, drying over Na$_2$SO$_4$, and concentration were performed. The residue was purified by silica gel chromatography to give a yellow oily matter (yield: 4.0 g (79.3%)).

$^1$H NMR (396 MHz, CDCl$_3$): δ 7.38-6.85 (m, 5H, thiophene, CH=CH, benzene ring), 6.56 (dd, 1H, CH=CH), 6.34-6.24 (m, 2H, benzene ring), 4.22 (t, 2H, CH$_2$), 3.82 (d, 3H, OCH$_3$), 3.59 (t, 2H, CH$_2$), 2.99 (s, 3H, CH$_3$), 1.14 (m, 9H, t-Bu)

(56-4) 2-{[3-methoxy-4-(2-thiophene-2-ylvinyl)phenyl] methylamino}ethanol

[Formula 252]

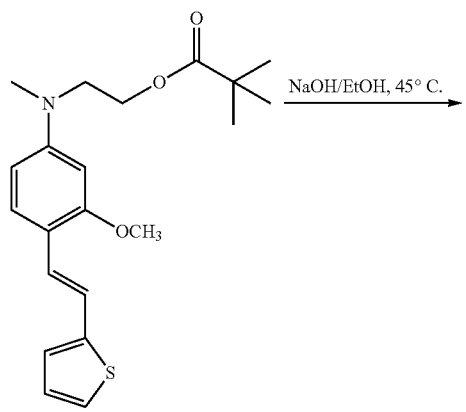

NaOH/EtOH, 45° C.

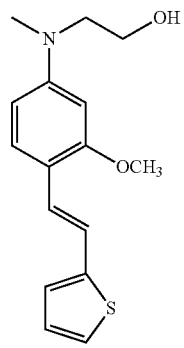

NaOH (4.3 g, 107 mmol) was dissolved in ethanol (25 ml), and water (7 ml) was added thereto. Next, 2,2-dimethylpropionic acid 2-{[3-methoxy-4-(2-thiophene-2-ylvinyl)phenyl]methylamino}ethyl ester (4.0 g, 10.7 mmol) was dissolved in ethanol (8 ml) and added dropwise to the mixture. The mixture was stirred at room temperature for 2 hours and further at 45° C. for 1 hour. After the solvent was evaporated off, water (100 ml) was added and the oily matter was subjected to extraction with ethyl acetate. After 2 times of washing with water, drying over Na$_2$SO$_4$ and concentration were performed. The residue was purified by silica gel chromatography to give a yellow oily matter (yield: 3.1 g (100%)).

$^1$H NMR (396 MHz, CDCl$_3$): δ 7.34-6.83 (m, 5H, thiophene, CH=CH, benzene ring), 6.54 (dd, 1H, CH=CH), 6.33-6.23 (m, 2H, benzene ring), 3.83-3.75 (m, 5H, CH$_2$, OCH$_3$), 3.45 (m, 2H, CH$_2$), 3.40 (d, 3H, CH$_3$)

(56-5) 5-(2-{4-[(2-hydroxyethyl)methylamino]-2-methoxyphenyl}vinyl)thiophene-2-carbaldehyde

[Formula 253]

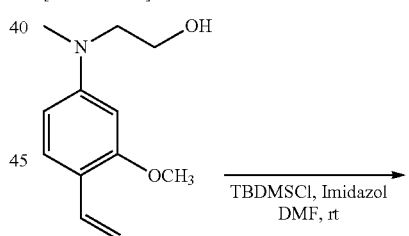

TBDMSCl, Imidazol
DMF, rt

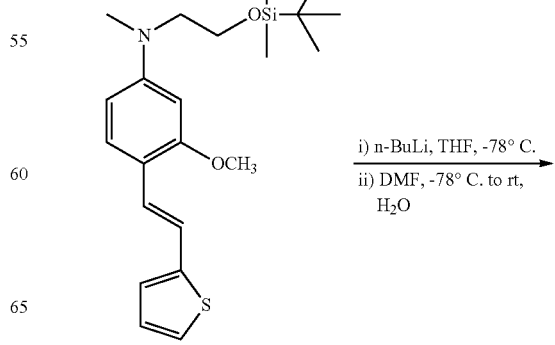

i) n-BuLi, THF, -78° C.
ii) DMF, -78° C. to rt, H$_2$O

-continued

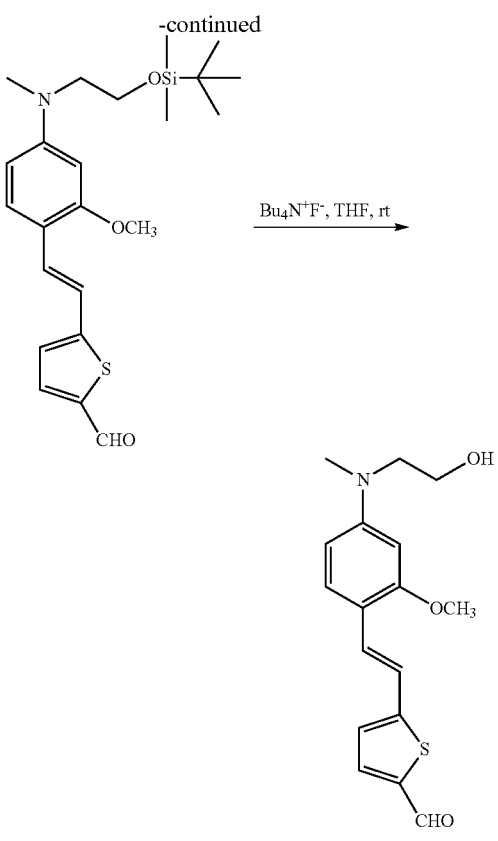

In DMF (8 ml) were dissolved 2-{[3-methoxy-4-(2-thiophene-2-ylvinyl)phenyl]methylamino}ethanol (3.1 g, 10.8 mmol) and imidazole (1.47 g, 21.6 mmol). Next, tert-butyldimethylsilyl chloride (2.4 g, 16.2 mmol) dissolved in DMF (5 ml) was added dropwise to the mixture at room temperature. After the mixture was stirred for 1 hour, 300 ml of water was added and the oily matter was subjected to extraction with dichloromethane. Washing with a saturated saline solution, drying over $Na_2SO_4$ and concentration were performed. The residue was purified by silica gel chromatography to give a yellow oily matter ([2-(tert-buthyldimethylsilanyloxy)ethyl][3-methoxy-4-(2-thiophene-2-ylvinyl)phenyl]methylamine) (yield: 4.3 g (98.6%)).

Next, in THF (30 ml) was dissolved [2-(tert-buthyldimethylsilanyloxy)ethyl][3-methoxy-4-(2-thiophene-2-ylvinyl)phenyl]methylamine (4.3 g, 10.7 mmol), and n-BuLi (1.57 mol/l, 10 ml, 15.7 mmol) was added dropwise thereto at −78° C. After the mixture was stirred for 1 hour, DMF (0.95 g, 12.3 mmol) was added dropwise thereto. The mixture was stirred for 1 hour. After the cooling bath was removed, water (10 ml) was added dropwise, and water (100 ml) was further added at 0° C. The organic layer was extracted with dichloromethane, washed with a saturated saline solution, dried over $Na_2SO_4$, and concentrated. The crude product was dissolved in 500 ml of toluene containing dissolved iodine (200 mg), and the mixture was stirred at room temperature for 30 minutes. Washing was performed with an aqueous sodium bisulfite solution (5%) and then with water. After drying over $Na_2SO_4$ and concentration, the residue was purified by silica gel chromatography to give a reddish brown crystal (5-[2-(4-{[2-(tert-buthyldimethylsilanyloxy)ethyl]methylamino}-2-methoxyphenyl)vinyl]thiophene-2-carbaldehyde) (yield: 4.0 g (87.4%)).

Next, in THF (100 ml) was dissolved 5-[2-(4-{[2-(tert-buthyldimethylsilanyloxy)ethyl]methylamino}-2-methoxyphenyl)vinyl]thiophene-2-carbaldehyde (4.0 g, 9.4 mmol), and 1 N $Bu_4N$ F (THF solution, 5 ml) was added dropwise thereto. After stirred at room temperature for 1 hour, the mixture was concentrated. The residue was purified by silica gel chromatography to give a reddish brown crystal (5-(2-{4-[(2-hydroxyethyl)methylamino]-2-methoxyphenyl}vinyl)thiophene-2-carbaldehyde) (yield: 2.25 g (75.5%)).

$^1$H NMR (396 MHz, $CDCl_3$): δ 9.80 (s, 1H, CHO), 7.62 (d, 1H, thiophene), 7.40 (t, 2H, thiophene, CH=CH), 7.08 (q, 2H, benzene ring, CH=CH), 6.39 (m, 1H, benzene ring), 6.27 (m, 1H, benzene ring), 3.90-3.84 (m, 5H, $CH_2$, $OCH_3$), 3.55 (t, 2H, $CH_2$), 3.06 (s, 3H, $CH_3$)

(56-6) 2-(3-cyano-4-{2-[5-(2-{4-[(2-hydroxyethyl)methylamino]-2-methoxyphenyl}vinyl)thiophene-2-yl]vinyl}-5-phenyl-5-trifluoromethyl-5H-furan-2-ylidene)malononitrile

[Formula 254]

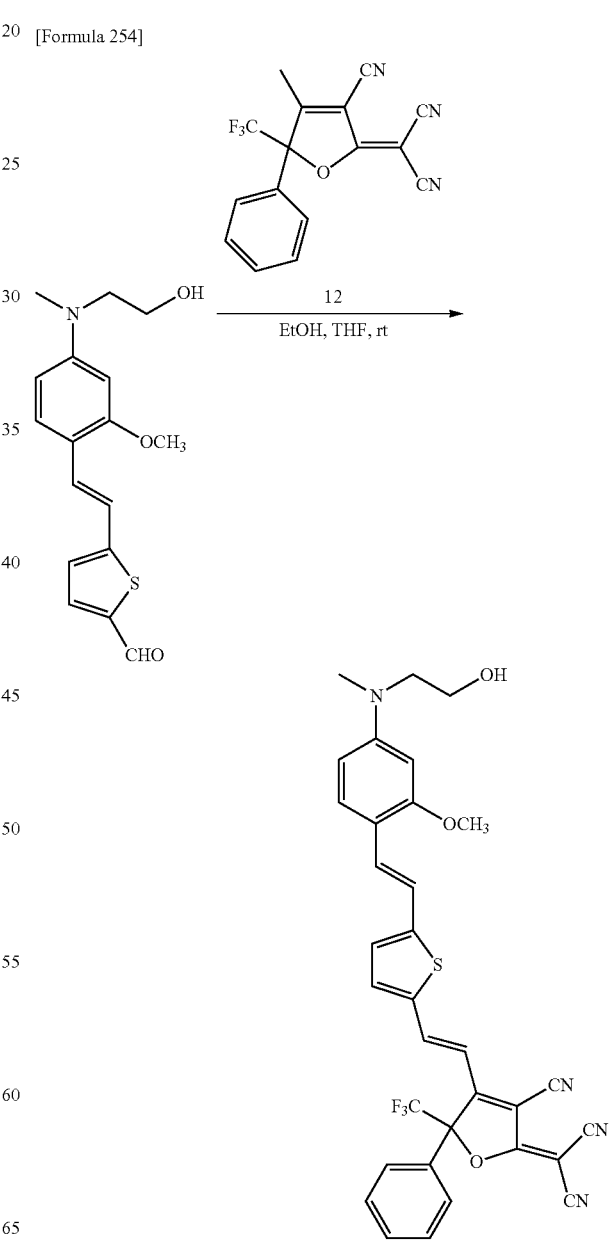

In a mixed solvent of ethanol (15 ml) and THF (5 ml) were dissolved 5-(2-{4-[(2-hydroxyethyl)methylamino]-2-methoxyphenyl}vinyl)thiophene-2-carbaldehyde (0.5 g, 1.58 mmol) and 2-(3-cyano-4-methyl-5-phenyl-5-trifluoromethyl-5H-furan-2-ylidene)malononitrile (0.50 g, 1.58 mmol). The mixture was stirred at room temperature for 18 hours and further at 50° C. for 3 hours. The mixture was cooled and the solid was collected. The solid was washed with cold ethanol (40 ml) 3 times to give a reddish brown crystal (yield: 0.91 g (93.8%)).

$^1$H NMR (270 MHz, DMSO-$d_6$): δ 7.75-7.61 (m, 7H, benzene ring, CH=CH), 7.51-7.26 (m, 4H, thiophene, benzene ring, CH=CH), 6.55-6.39 (m, 2H, CH=CH, benzene ring), 6.26 (s, 1H, benzene ring), 3.88 (s, 3H, OCH$_3$), 3.59-3.51 (m, 4H, CH$_2$), 3.06 (s, 3H, CH$_3$)

Example 57

2-(4-{2-[5-(2-{2-benzyloxy-4-[(2-hydroxyethyl)-methylamino]-phenyl}-vinyl)-thiophene-2-yl]-vinyl}-3-cyano-5-phenyl-5-trifluoromethyl-5H-furan-2-ylidene)malononitrile (57-1) 2,2-dimethylpropionic acid 2-[(3-benzyloxyphenyl) methylamino]ethyl ester

[Formula 255]

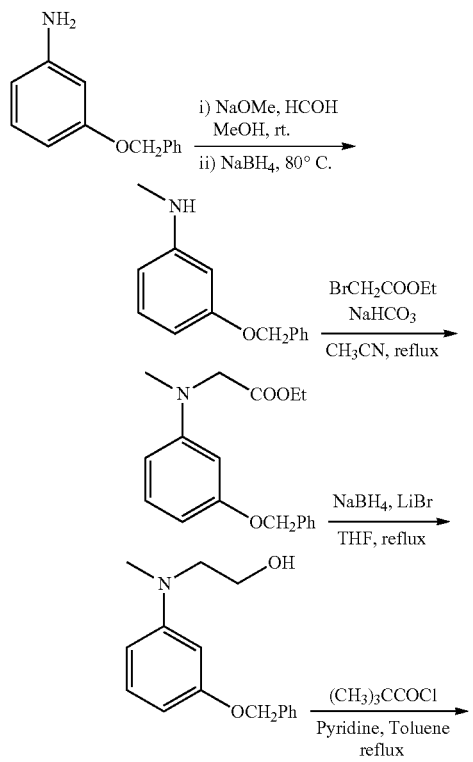

In a NaOMe (16 g, 0.96 mol)/methanol (150 ml) solution, 3-benzyloxyphenylamine (10.0 g, 50.2 mmol) was dissolved, and the mixture was added to formaldehyde (2.04 g, 68.4 mmol)/methanol (50 ml). The mixture was stirred at room temperature for 12 hours. To this mixture, NaBH$_4$ (2.08 g, 55 mmol) was added. The mixture was stirred for 1 hour and reacted at 80° C. for 2 hours. After an aqueous KOH solution (1 M, 200 ml) was added dropwise, the produced oily matter was subjected to 3 times of extraction with 50 ml of dichloromethane. Drying over Na$_2$SO$_4$ and concentration gave crude (3-benzyloxyphenyl)methylamine (yield: 9.6 g (89.7%)).

In acetonitrile (50 ml) were dissolved (3-benzyloxyphenyl)methylamine (9.6 g) and ethylbromoacetate (10.1 g, 60.2 mmol), and NaHCO$_3$ (6.3 g, 75.3 mmol) was added thereto. After the mixture was stirred at 90° C. for 2 hours, triethylamine (4 ml) was added thereto at room temperature. The mixture was stirred at room temperature for 16 hours. After the solvent was evaporated off, the crude product was dissolved in dichloromethane (100 ml) and washed with a saturated saline solution 3 times. The organic layer was dried over Na$_2$SO$_4$ and concentrated to give crude [(3-benzyloxyphenyl)methyl-amino] acetic acid ethyl ester (yield: 10.8 g (80.0%)).

Next, NaBH$_4$ (3.8 g, 100 mmol) and LiBr (8.7 g, 100 mmol) were added to THF (100 ml), and the mixture was stirred at 80° C. for 1 hour. To this mixture, [(3-benzyloxyphenyl)methylamino] acetic acid ethyl ester (10.8 g) dissolved in THF (20 ml) was added dropwise at room temperature. The mixture was stirred at 80° C. for 5 hours and further at room temperature for 16 hours. After the reaction solvent was evaporated to about half, KH$_2$PO$_4$ (1 M, 200 ml) was slowly added dropwise. The organic layer was extracted with dichloromethane (50 ml) 3 times, dried over Na$_2$SO$_4$ and concentrated to give crude 2-[(3-benzyloxyphenyl)methylamino]ethanol (yield: 10.3 g (90.4%)).

Next, to toluene (50 ml) were added 2-[(3-benzyloxyphenyl)methylamino]ethanol (10.3 g, 39.9 mmol), pivaloyl chloride (9.6 g, 79.8 mmol), and pyridine (7.6 g, 95.8 mmol). The mixture was stirred at room temperature for 1 hour and further at 85° C. for 2 hours. After pyridine hydrochloride was removed by filtration, the filtrate was concentrated. The product was purified by silica gel chromatography to give 2,2-dimethylpropionic acid 2-[(3-benzyloxyphenyl)methylamino]ethyl ester as a colorless oily matter (yield: 8.9 g (65.1%)).

$^1$H NMR (396 MHz, CDCl$_3$): δ 7.54 (d, 1H, benzene ring), 7.50 (d, 2H, benzene ring), 7.43 (dd, 2H, benzene ring), 7.24 (t, 1H, benzene ring), 6.49-6.47 (m, 3H, benzene ring), 5.13 (s, 2H, OCH$_2$Ph), 4.31 (m, 2H, CH$_2$), 3.64 (t, 2H, CH$_2$), 3.00 (s, 3H, CH$_3$), 1.30 (s, 9H, t-Bu)

(57-2) 2,2-dimethylpropionic acid 2-[(3-benzyloxy-4-formylphenyl)methylamino]ethyl ester

[Formula 256]

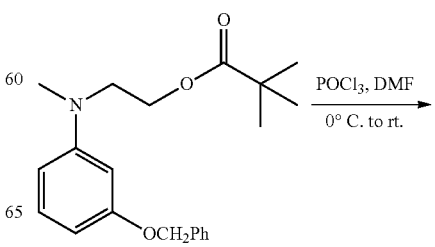

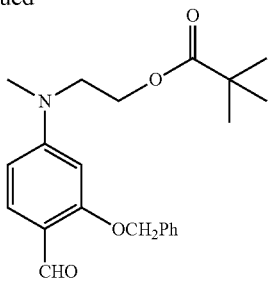

POCl₃ (3.6 g, 23.4 mmol) was added to 20 ml of DMF in an ice bath. After 40 minutes, 2,2-dimethylpropionic acid 2-[(3-benzyloxyphenyl)methylamino]ethyl ester (8.0 g, 23.4 mmol) dissolved in DMF (10 ml) was added dropwise. The mixture was stirred for 16 hours. After an aqueous sodium acetate solution (20%, 100 ml) was added dropwise, the oily matter was subjected to extraction with ethyl acetate. Washing was performed with a saturated aqueous NaHCO₃ solution (100 ml) and then with a saturated saline solution (100 ml). After drying over Na₂SO₄ and concentration, the residue was purified by silica gel chromatography to give a light yellow crystal (yield: 7.2 g (83.6%)).

¹H NMR (396 Hz, CDCl₃): δ 10.28 (s, 1H, CHO), 7.73 (d, 1H, benzene ring), 7.44 (d, 1H, benzene ring), 7.40 (d, 2H, benzene ring), 7.40-7.27 (m, 2H, benzene ring), 6.33 (d, 1H, benzene ring), 6.19 (s, 1H, benzene ring), 5.17 (s, 2H, CH₂Ph), 4.20 (t, 2H, CH₂), 3.62 (t, 2H, CH₂), 3.04 (s, 3H, CH₃), 1.16 (m, 9H, t-Bu)

(57-3) 2,2-dimethylpropionic acid 2-{[3-benzyloxy-4-(2-thiophene-2-ylvinyl)-phenyl]methylamino}ethyl ester

[Formula 257]

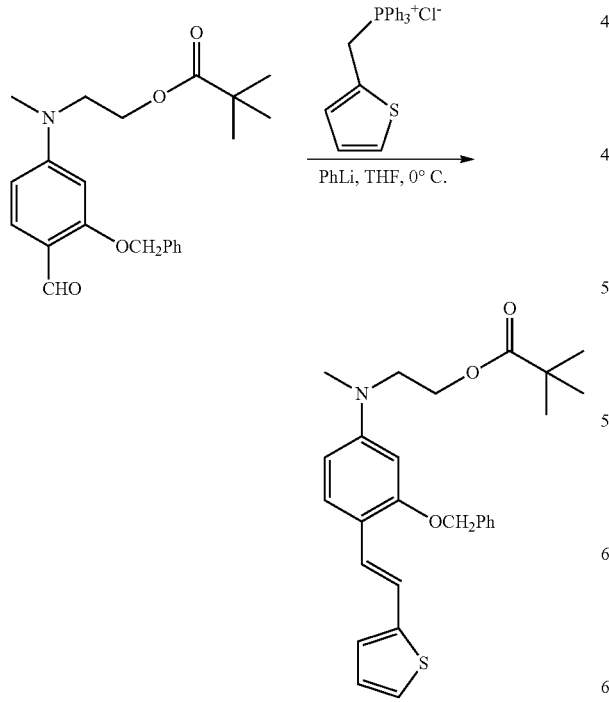

Thiophene-2-ylmethyl triphenylphosphonium chloride (9.0 g, 22.7 mmol) was added to THF (80 ml), and PhLi (12.0 g of 19% solution in hexane, 27.2 mmol) was added dropwise thereto in an ice bath. After 20 minutes, 2,2-dimethylpropionic acid 2-[(3-benzyloxy-4-formylphenyl)methylamino]ethyl ester (7.0 g, 18.9 mmol) dissolved in THF (20 ml) was added dropwise. The mixture was reacted for 2 hours. After the reaction mixture was added to 300 ml of ice water, the oily matter was subjected to 3 times of extraction with dichloromethane (50 ml). Washing with a saturated saline solution, drying over Na₂SO₄, and concentration were performed. The residue was purified by silica gel chromatography to give a yellow oily matter (yield: 7.15 g (84.5%)).

¹H NMR (396 MHz, CDCl₃): δ 7.48 (d, 1H, thiophene), 7.40-6.93 (m, 8H, thiophene, benzene ring, CH=CH), 6.88-6.86 (q, 1H, benzene ring), 6.59 (dd, 1H, CH=CH), 6.35-6.26 (m, 2H, benzene ring), 5.11 (d, 2H, CH₂Ph), 4.19 (m, 2H, CH₂), 3.55 (m, 2H, CH₂), 2.97 (s, 3H, CH₃), 1.17 (s, 9H, t-Bu)

(57-4) 2-{[3-benzyloxy-4-(2-thiophene-2-ylvinyl)-phenyl]-methylamino}ethanol

[Formula 258]

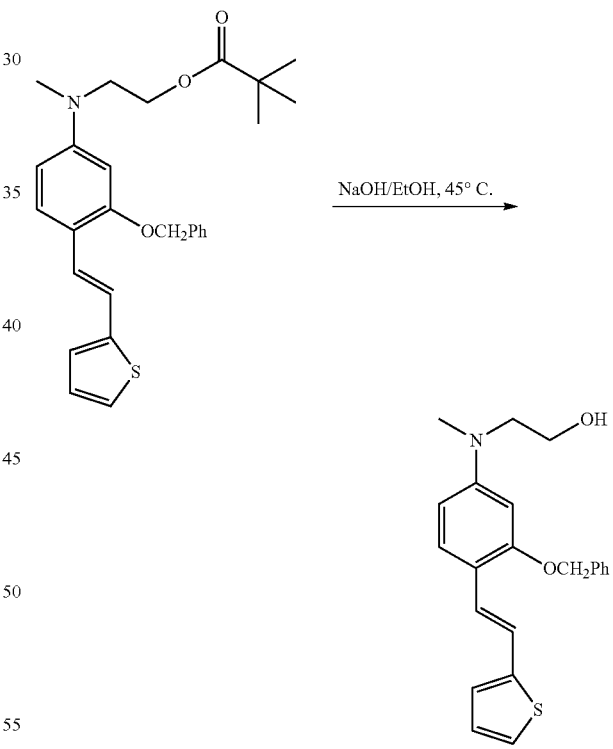

NaOH (6.2 g, 156 mmol) was dissolved in ethanol (45 ml), and water (10 ml) was added thereto. Next, 2,2-dimethylpropionic acid 2-{[3-benzyloxy-4-(2-thiophene-2-ylvinyl)-phenyl]methylamino}ethyl ester (7.0 g, 15.6 mmol) was dissolved in THF (20 ml) and added dropwise. The mixture was stirred at room temperature for 2 hours and further at 45° C. for 1 hour. After the solvent was evaporated off, water (100 ml) was added and the oily matter was subjected to extraction with ethyl acetate. After 2 times of washing with water, drying over Na₂SO₄ and concentration were performed. The residue was purified by silica gel chromatography to give a yellow oily matter (yield: 5.69 g (99.8%)).

¹H NMR (396 MHz, CDCl₃): δ 7.48 (d, 1H, thiophene), 7.42-6.94 (m, 8H, thiophene, benzene ring, CH=CH), 6.89 (q, 1H, benzene ring), 6.60 (dd, 1H, CH=CH), 6.41-6.33 (m, 2H, benzene ring), 5.12 (d, 2H, CH₂Ph), 3.77 (m, 2H, CH₂), 3.46 (t, 2H, CH₂), 2.97 (s, 3H, CH₃)

(57-5) [3-benzyloxy-4-(2-thiophene-2-ylvinyl)-phenyl]-[2-(tert-buthyldimethylsilanyloxy)ethyl]methylamine

[Formula 259]

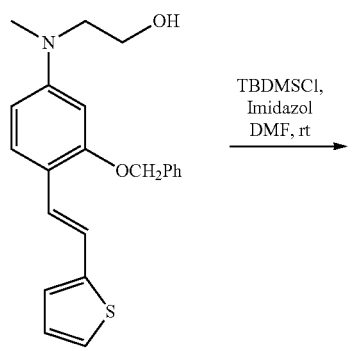

TBDMSCl, Imidazol DMF, rt

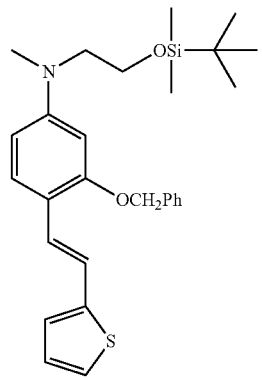

In DMF (15 ml) were dissolved 2-{[3-benzyloxy-4-(2-thiophene-2-ylvinyl)-phenyl]-methylamino}ethanol (5.5 g, 15 mmol) and imidazole (2.0 g, 30 mmol). Next, tert-butyldimethylsilyl chloride (3.4 g, 22.5 mmol) was dissolved in DMF (10 ml) and added dropwise at room temperature. The mixture was stirred for 1 hour. After 300 ml of water was added to the mixture, the oily matter was subjected to extraction with dichloromethane. Washing with a saturated saline solution, drying over Na₂SO₄, and concentration were performed. The residue was purified by silica gel chromatography to give a yellow oily matter (yield: 6.05 g (87.2%)).

¹H NMR (396 MHz, CDCl₃): δ 7.46 (d, 1H, thiophene), 7.39-6.84 (m, 9H, thiophene, benzene ring, CH=CH), 6.58 (dd, 1H, CH=CH), 6.30-6.22 (m, 2H, benzene ring), 5.08 (d, 2H, CH₂Ph), 3.71 (t, 2H, CH₂), 3.42 (t, 2H, CH₂), 2.95 (d, 3H, CH₃), 0.86 (s, 9H, t-Bu), 0.00 (d, 6H, Si—CH₃)

(57-6) 5-[2-(2-benzyloxy-4-{[2-(tert-buthyldimethylsilanyloxy)-ethyl]methylamino}phenyl)vinyl]thiophene-2-carbaldehyde

[Formula 260]

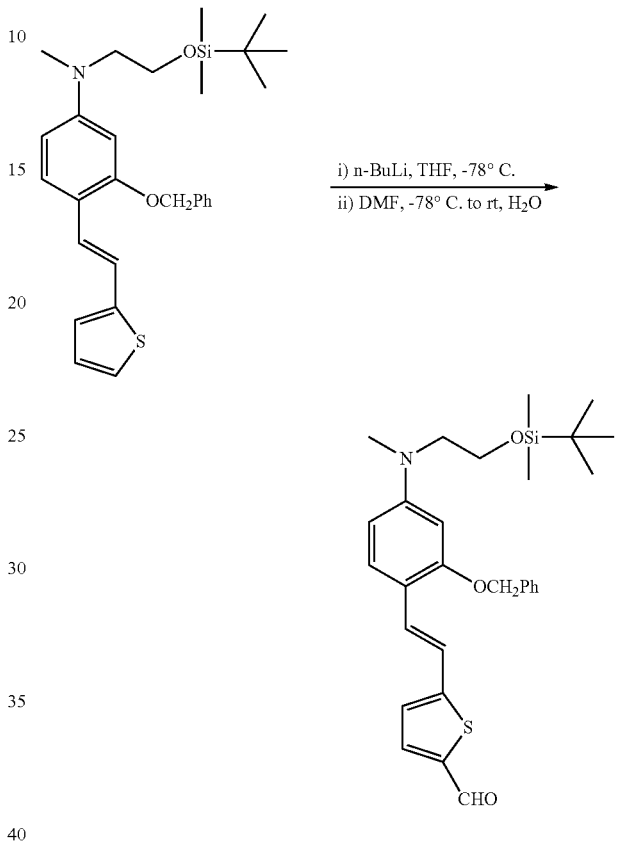

i) n-BuLi, THF, -78° C.
ii) DMF, -78° C. to rt, H₂O

In THF (50 ml) was dissolved [3-benzyloxy-4-(2-thiophene-2-ylvinyl)-phenyl]-[2-(tert-buthyldimethylsilanyloxy)ethyl]methylamine (5.9 g, 12.8 mmol), and n-BuLi (1.57 mol/l, 12 ml, 18.9 mmol) was added dropwise thereto at −78° C. After the mixture was stirred for 1 hour, DMF (1.1 g, 15.6 mmol) was added dropwise. The mixture was stirred for 1 hour. After the cooling bath was removed, water (10 ml) was added dropwise, and water (100 ml) was further added at 0° C. The organic layer was extracted with dichloromethane, washed with a saturated saline solution, dried over Na₂SO₄, and concentrated. The crude product was dissolved in 500 ml of toluene containing dissolved iodine (200 mg), and the mixture was stirred at room temperature for 30 minutes. Washing was performed with an aqueous sodium bisulfite solution (5%) and then with water. After drying over Na₂SO₄ and concentration, the residue was purified by silica gel chromatography to give a reddish brown crystal (yield: 5.0 g (79.8%)).

¹H NMR (396 MHz, CDCl₃): δ 9.77 (s, 1H, CHO), 7.58 (d, 1H, thiophene), 7.47-7.33 (m, 7H, benzene ring, CH=CH, thiophene), 7.40 (d, 1H, CH=CH), 6.96 (d, 1H, benzene ring), 6.31 (d, 1H, benzene ring), 6.21 (s, 1H, benzene ring), 5.13 (s, 2H, CH₂Ph), 3.72 (t, 2H, CH₂), 3.46 (t, 2H, CH₂), 3.00 (s, 3H, CH₃), 0.87 (t, 9H, t-Bu), 0.00 (m, 6H, Si—CH₃)

229

(57-7) 5-(2-{2-benzyloxy-4-[(2-hydroxyethyl)-methylamino]-phenyl}-vinyl)-thiophene-2-carbaldehyde

[Formula 261]

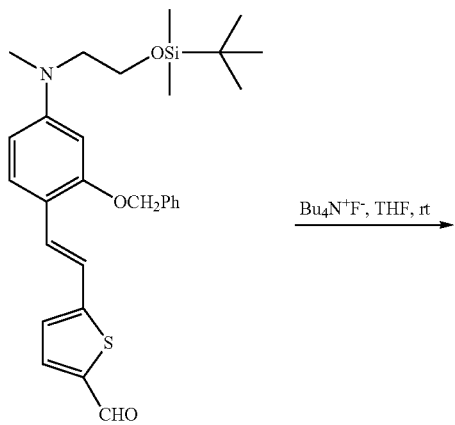

230

(57-8) 2-(4-{2-[5-(2-{2-benzyloxy-4-[(2-hydroxyethyl) methylamino]phenyl}vinyl)thiophene-2-yl]vinyl}-3-cyano-5-phenyl-5-trifluoromethyl-5H-furan-2-ylidene)malononitrile

[Formula 262]

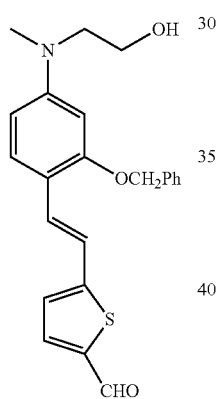

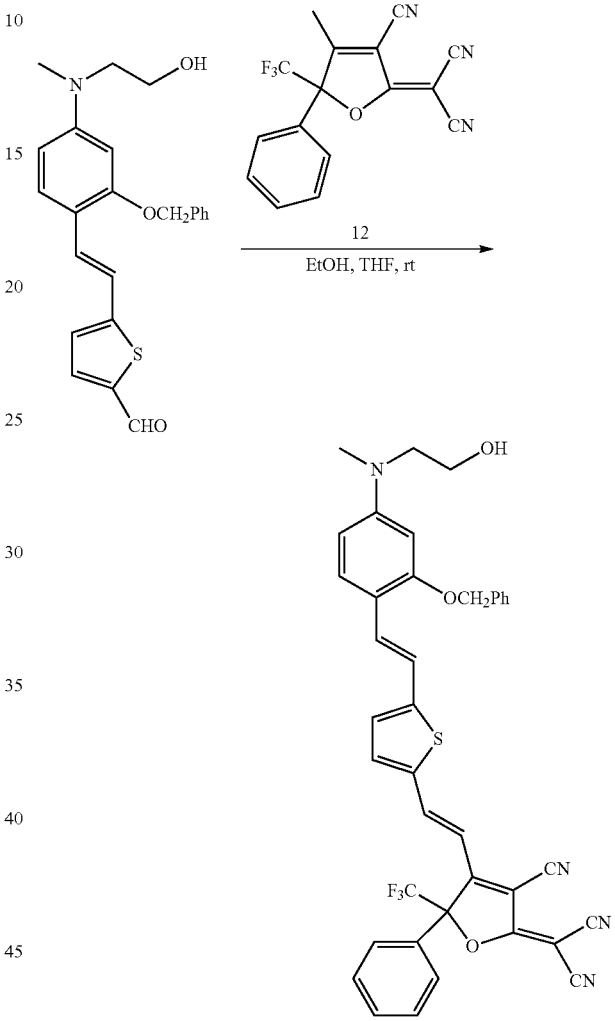

In THF (100 ml) was dissolved 5-[2-(2-benzyloxy-4-{[2-(tert-buthyldimethylsilanyloxy)ethyl]methylamino}phenyl)vinyl]thiophene-2-carbaldehyde (2.9 g, 5.9 mmol), and n-Bu₄NF (a THF solution, 5 ml) was added dropwise thereto. The mixture was stirred at room temperature for 1 hour and concentrated. The residue was purified by silica gel chromatography to give a reddish brown crystal (yield: 2.16 g (93.5%)).

$^1$H NMR (396 MHz, CDCl$_3$): δ 9.77 (s, 1H, CHO), 7.60 (d, 1H, thiophene), 7.46 (d, 2H, benzene ring), 7.43-7.39 (t, 3H, benzene ring, CH=CH), 7.37-7.32 (m, 2H, benzene ring), 7.13 (d, 1H, CH=CH), 6.98 (d, 1H, thiophene), 6.39-6.29 (m, 2H, benzene ring), 5.15 (s, 2H, CH$_2$Ph), 3.77 (t, 2H, CH$_2$), 3.49 (s, 2H, CH$_2$), 3.00 (s, 3H, CH$_3$)

In a mixed solvent of ethanol (40 ml) and THF (10 ml) were dissolved 5-(2-{2-benzyloxy-4-[(2-hydroxyethyl)-methylamino]-phenyl}-vinyl)-thiophene-2-carbaldehyde (2.16 g, 5.49 mmol) and 2-(3-cyano-4-methyl-5-phenyl-5-trifluoromethyl-5H-furan-2-ylidene)malononitrile (1.73 g, 5.49 mmol). The mixture was stirred at room temperature for 18 hours and further at 50° C. for 3 hours. The mixture was cooled and the solid was collected. The solid was washed with cold ethanol (40 ml) 3 times to give a reddish brown crystal (yield: 3.72 g (98.2%)).

$^1$H NMR (270 MHz, CDCl$_3$): δ 7.52-7.35 (m, 12H, benzene ring, thiophene, CH=CH), 7.47 (dd, 2H, CH=CH), 6.92 (d, 1H, thiophene), 6.58 (dd, 2H, CH=CH), 6.38 (d, 1H, benzene ring), 6.28 (m, 1H, benzene ring), 5.19 (s, 2H, CH$_2$Ph), 3.78 (t, 2H, CH$_2$), 3.52 (t, 2H, CH$_2$), 3.05 (s, 3H, CH$_3$)

Example 58

2-[3-cyano-4-[2-(8-methoxy-2,3,6,7-tetrahydro-1H, 5H-benzo [ij]quinolizine-9-yl)vinyl]-5,5-dimethyl-2 (5H)-furanylidene]propanedinitrile

[Formula 263]

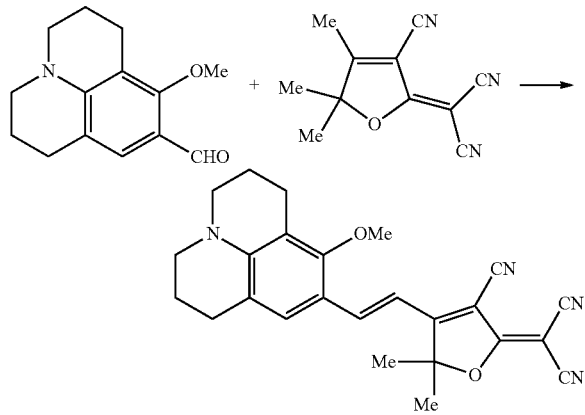

In 5 ml of ethanol were dissolved 150 mg (0.65 mmol) of 8-methoxy-2,3,6,7-tetrahydro-1H,5H-benzo[ij]quinolizine-9-carboaldehyde and 142 mg (0.71 mmol) of 2-(3-cyano-4, 5,5-trimethyl-2(5H)-furanylidene)propanedinitrile. The mixture was stirred at room temperature for 3 hours and further at 50° C. for 3 hours. The precipitate was separated by filtration and washed with methanol. The crystal was purified by silica gel column chromatography and washed with methanol to give 228 mg of a dark blue crystal having a mp of 250-252° C. (yield: 85.2%).

$^1$H-NMR (600 MHz, CDCl$_3$) δ: 1.74 (6H, s), 1.94-2.01 (4H, m), 2.74-2.77 (4H, m), 3.36-3.39 (4H, m), 3.76 (3H, s), 6.70 (1H, d, J=15.9 Hz), 7.24 (1H, s), 7.94 (1H, d, J=15.9 Hz)

$^{13}$C-NMR (150 MHz, CDCl$_3$) δ: 20.5, 21.0, 21.2, 24.4, 27.0, 27.4, 50.1, 50.5, 53.0, 61.9, 91.9, 96.3, 107.5, 112.1, 112.5, 113.3, 113.7, 114.8, 119.3, 126.5, 143.2, 149.7, 159.1, 174.4, 176.6

Example 59

2-[4-[2-[2-(tert-butyldiphenylsiloxy)-4-dibutylaminophenyl] vinyl]-3-cyano-5,5-dimethyl-2(5H)-furanylidene] propanedinitrile

[Formula 264]

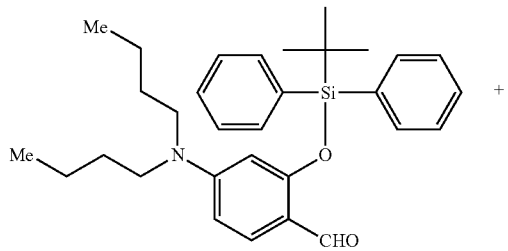

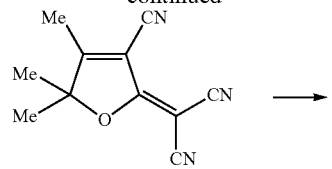

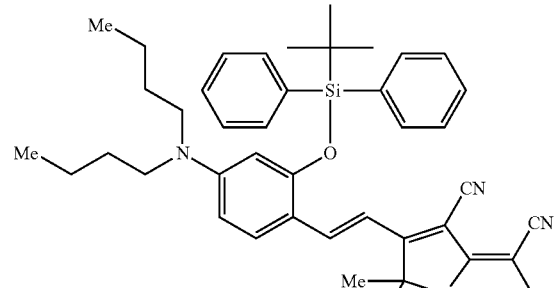

In 5 ml of ethanol were dissolved 200 mg (0.41 mmol) of 2-(tert-butyldiphenylsiloxy)-4-dibutylaminobenzaldehyde and mg (0.45 mmol) of 2-(3-cyano-4,5,5-trimethyl-2(5H)-furanylidene)propanedinitrile. After the mixture was stirred with heating at 60° C. for 3 hours, the precipitate was separated by filtration and washed with methanol. The crystal was purified by silica gel column chromatography and washed with methanol to give 199 mg of a dark brown crystal having a mp of 220-221° C. (yield: 72.6%).

$^1$H-NMR (600 MHz, CDCl$_3$) δ: 0.75 (6H, t, J=7.1 Hz), 0.99-1.03 (4H, m), 1.14 (13H, m), 1.79 (6H, s), 2.87 (4H, br), 5.64 (1H, s), 6.29 (1H, d, J=9.3 Hz), 6.88 (1H, d, J=15.9 Hz), 7.40-7.42 (4H, m), 7.46-7.49 (2H, m), 7.66 (1H, d, J=9.3 Hz), 7.71-7.73 (4H, m), 8.15 (1H, d, J=15.9 Hz)

$^{13}$C-NMR (150 MHz, CDCl$_3$) δ: 13.7, 19.5, 20.2, 26.5, 27.2, 29.2, 51.0, 53.4, 93.4, 96.2, 102.2, 107.6, 111.6, 112.4, 113.2, 113.7, 128.2, 129.3, 130.5, 131.4, 135.2, 142.0, 153.5, 158.7, 174.5, 176.4

Example 60

2-[5-[2-(2-benzyloxy-4-dibutylaminophenyl)vinyl] thiophene-2-yl]-3-cyano-2-butenedinitrile

[Formula 265]

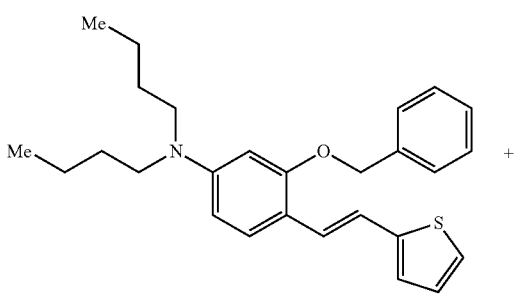

-continued

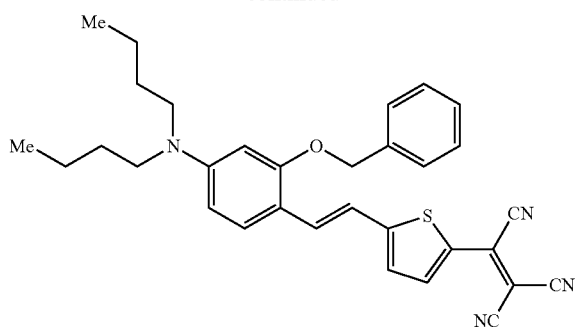

In 3 ml of N,N-dimethylformamide, 0.13 g (1.01 mmol) of tetracyanoethylene was dissolved. With stirring under ice cooling, 0.4 g (0.95 mmol) of [3-benzyloxy-4-[2-(thiophene-2-yl)vinyl]phenyl]dibutyl amine was dissolved in 1 ml of N,N-dimethylformamide and added dropwise. The mixture was stirred for 40 minutes and further stirred with heating at 40° C. overnight. After the reaction mixture was poured into 100 ml of water, extraction with chloroform, washing with a saturated saline solution, drying over anhydrous sodium sulfate, and concentration were performed. The residue was purified by silica gel column chromatography and washed with ethanol to give 157 mg of a black crystal having a mp of 125-130° C. (yield: 31.7%).

$^1$H-NMR (600 MHz, CDCl$_3$) δ: 0.95 (6H, t, J=7.7 Hz), 1.29-1.35 (4H, m), 1.50-1.55 (4H, m), 3.27 (4H, t, J=7.7 Hz), 5.21 (2H, s), 6.08 (1H, d, J=2.2 Hz), 6.29 (1H, dd, J=2.2 Hz, 8.8 Hz), 7.03 (1H, d, J=4.4 Hz), 7.18 (1H, d, J=15.9 Hz), 7.34-7.37 (1H, m), 7.36 (1H, d, J=8.8 Hz), 7.41-7.46 (4H, m), 7.60 (1H, d, J=15.9 Hz), 7.85 (1H, d, J=4.4 Hz)

$^{13}$C-NMR (150 MHz, CDCl$_3$) δ: 13.9, 20.3, 29.5, 51.0, 70.4, 75.4, 95.8, 105.6, 112.6, 113.3, 113.4, 113.8, 115.0, 126.1, 126.9, 128.2, 128.8, 129.4, 130.9, 131.3, 135.2, 136.7, 141.7, 151.6, 159.7, 162.7

Example 61

2-cyano-3-(4-dibutylamino-2-methoxyphenyl)-2-butenedinitrile (61-1) Dibutyl(3-methoxyphenyl)amine

[Formula 266]

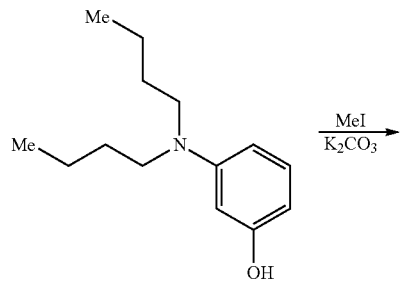

-continued

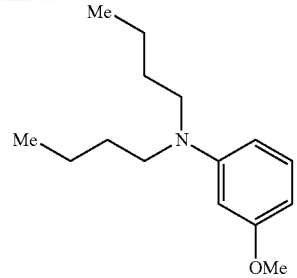

In 70 ml of 1-methyl-2-pyrrolidone were dissolved 10.0 g (45.18 mmol) of 3-(dibutylamino)phenol and 12.8 g (90.18 mmol) of methyl iodide. To this mixture was added 18.7 g (135.3 mmol) of anhydrous potassium carbonate and the mixture was stirred with heating at 60° C. for 6 hours. After the reaction mixture was poured into 350 ml of water, extraction with ethyl acetate, washing with a saturated saline solution, drying over anhydrous sodium sulfate, and concentration were performed. The residue was purified by silica gel column chromatography to give 5.2 g of a colorless oily matter (yield: 48.7%).

$^1$H-NMR (600 MHz, CDCl$_3$) δ: 0.94 (6H, t, J=7.1 Hz), 1.31-1.37 (4H, m), 1.55-1.59 (4H, m), 3.24 (4H, t, J=7.7 Hz), 3.78 (3H, s), 6.18-6.21 (2H, m), 6.27 (1H, dd, J=2.2 Hz, 8.8 Hz), 7.09-7.12 (1H, m)

$^{13}$C-NMR (150 MHz, CDCl$_3$) δ: 14.0, 20.3, 29.4, 50.8, 55.0, 98.3, 99.6, 105.0, 129.8, 149.6, 160.8

(61-2) 2-cyano-3-(4-dibutylamino-2-methoxyphenyl)-2-butenedinitrile

[Formula 267]

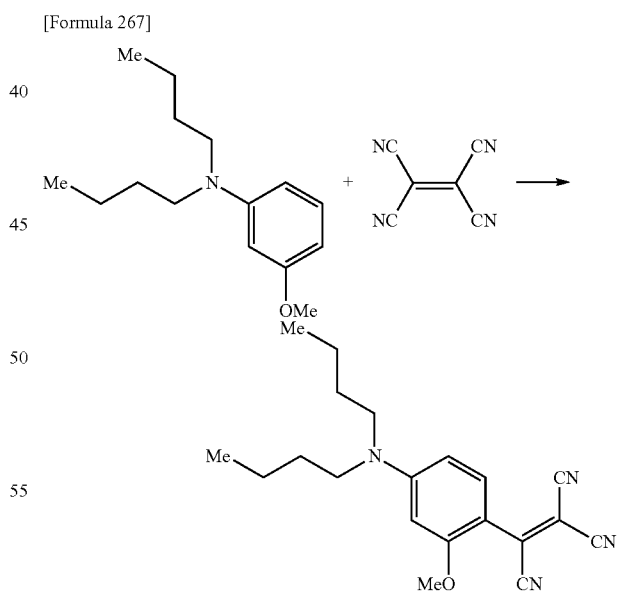

In 8 ml of N,N-dimethylformamide, 0.5 g (3.9 mmol) of tetracyanoethylene was dissolved. With stirring under ice cooling, 0.8 g (3.4 mmol) of dibutyl(3-methoxyphenyl)amine was dissolved in 2 ml of N,N-dimethylformamide and added dropwise. The mixture was stirred for 35 minutes. After the ice bath was removed, the mixture was further stirred for 2 hours. After the reaction mixture was poured into 100 ml of water, extraction with chloroform, washing with a saturated saline solution, drying over anhydrous sodium sulfate, and concentration were performed. The residue was purified by silica gel column chromatography and washed with hexane to give 0.88 g of a black crystal having a mp of 86° C. (yield: 77.2%).

$^1$H-NMR (600 MHz, CDCl$_3$) δ: 0.99 (6H, t, J=7.1 Hz), 1.37-1.43 (4H, m), 1.61-1.66 (4H, m), 3.40 (4H, t, J=7.7 Hz), 3.94 (3H, s), 6.04 (1H, d, J=2.2 Hz), 6.34 (1H, dd, J=2.2 Hz, 9.3 Hz), 7.61 (1H, d, J=9.3 Hz)

$^{13}$C-NMR (150 MHz, CDCl$_3$) δ: 13.9, 20.3, 29.6, 51.4, 55.0, 81.7, 93.4, 106.2, 108.3, 113.8, 114.1, 115.0, 133.6, 135.4, 155.3, 161.4

Example 62

2-cyano-3-[5-[2-(4-dibutylamino-2-methoxyphenyl)vinyl] thiophene-2-yl]-2-butenedinitrile

[Formula 268]

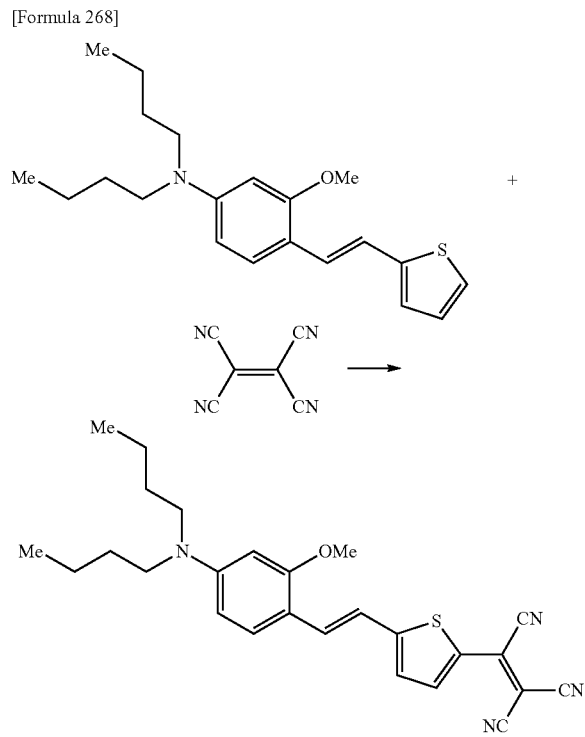

In 7 ml of N,N-dimethylformamide, 235 mg (1.83 mmol) of tetracyanoethylene was dissolved. With stirring under ice cooling, 600 mg (1.75 mmol) of dibutyl[3-methoxy-4-[2-(thiophene-2-yl)vinyl]phenyl]amine was dissolved in 2 ml of N,N-dimethylformamide and added dropwise. The mixture was stirred for 1.5 hours. After the ice bath was removed, the mixture was stirred at room temperature for 1 hour and further stirred with heating at 50° C. overnight. After the reaction mixture was poured into 80 ml of water, extraction with chloroform, washing with a saturated saline solution, drying over anhydrous sodium sulfate, and concentration were performed. The residue was purified by silica gel column chromatography and washed with methanol to give 324 mg of a dark reddish crystal having a mp of 189-192° C. (yield: 41.8%).

$^1$H-NMR (600 MHz, CDCl$_3$) δ: 0.99 (6H, t, J=7.7 Hz), 1.36-1.42 (4H, m), 1.60-1.66 (4H, m), 3.36 (4H, t, J=7.7 Hz), 3.92 (3H, s), 6.09 (1H, d, J=2.2 Hz), 6.29 (1H, dd, J=2.2 Hz, 8.8 Hz), 7.11 (1H, d, J=4.4 Hz), 7.12 (1H, d, J=15.9 Hz), 7.36 (1H, d, J=8.8 Hz), 7.55 (1H, d, J=15.4 Hz), 7.44 (1H, d, J=4.4 Hz)

$^{13}$C-NMR (150 MHz, CDCl$_3$) δ: 13.9, 20.3, 29.6, 51.0, 55.2, 76.8, 93.8, 105.4, 112.3, 113.3, 113.5, 113.9, 114.6, 126.0, 129.2, 130.6, 131.4, 135.0, 141.6, 151.9, 160.6, 162.7

Example 63

2-[4-[cyano-(4-dibutylamino-2-methoxyphenyl)methylene]-2,5-cyclohexadienylidene]malonnitrile

[Formula 269]

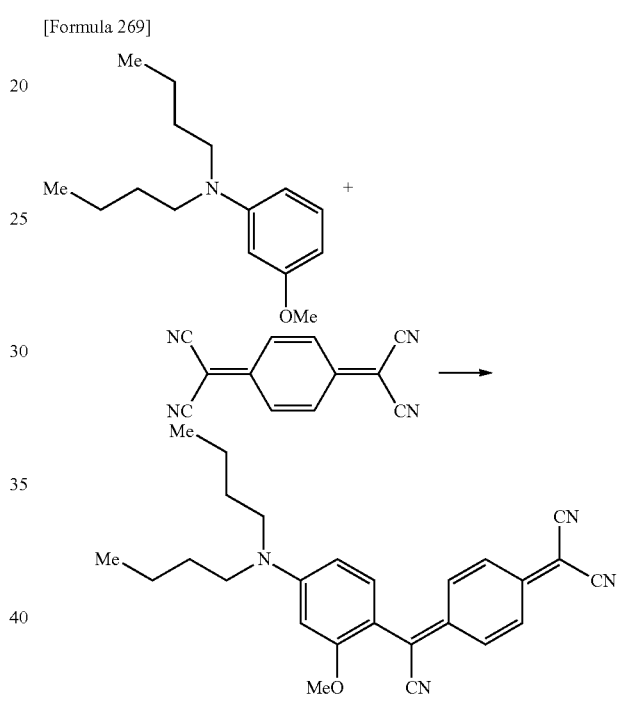

In 8 ml of N,N-dimethylformamide, 460 mg (2.25 mmol) of 7,7,8,8-tetracyanoquinodimethane was dissolved. With stirring under ice cooling, 500 mg (2.12 mmol) of dibutyl(3-methoxyphenyl)amine was dissolved in 2 ml of N,N-dimethylformamide and added dropwise. The mixture was stirred for 1.5 hours. After the ice bath was removed, the mixture was further stirred for 3.5 hours. After the reaction mixture was poured into 100 ml of water, extraction with ethyl acetate, washing with a saturated saline solution, drying over anhydrous sodium sulfate, and concentration were performed. The residue was purified by silica gel column chromatography and washed with chloroform to give 226 mg of an off-white crystal having a mp of 215-238° C. (yield: 25.6%).

$^1$H-NMR (600 MHz, acetone-d$_6$) δ: 0.95 (6H, t, J=7.7 Hz), 1.34-1.41 (4H, m), 1.57-1.62 (4H, m), 3.36 (4H, t, J=7.7 Hz), 3.86 (3H, s), 6.24 (1H, dd, J=2.2 Hz, 8.8 Hz), 6.36 (1H, d, J=2.2 Hz), 6.71 (1H, d, J=8.8 Hz), 6.96 (2H, d, J=8.2 Hz), 7.15 (2H, d, J=8.2 Hz)

$^{13}$C-NMR (150 MHz, acetone-d$_6$) δ: 14.2, 20.8, 43.0, 51.3, 56.0, 96.7, 104.6, 109.2, 116.9, 119.4, 120.2, 126.1, 127.5, 129.4, 145.8, 151.9, 158.8

Example 64

2-[4-[cyano-[5-[2-(4-dibutylamino-2-methoxyphenyl)vinyl] thiophene-2-yl]methylene]-2,5-cyclohexadienylidene] malonnitrile

[Formula 270]

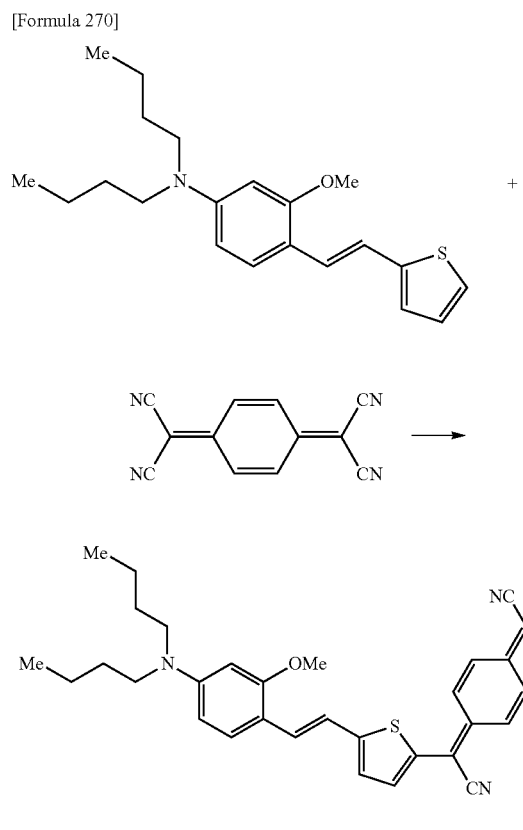

In 8 ml of N,N-dimethylformamide, 375 mg (1.84 mmol) of 7,7,8,8-tetracyanoquinodimethane was dissolved. With stirring under ice cooling, 600 mg (1.75 mmol) of dibutyl [3-methoxy-4-[2-(thiophene-2-yl)vinyl]phenyl]amine was dissolved in 2 ml of N,N-dimethylformamide and added dropwise. The mixture was stirred for 1 hour and further stirred with heating at 50° C. overnight. After the reaction mixture was poured into 80 ml of water, extraction with ethyl acetate, washing with a saturated saline solution, drying over anhydrous sodium sulfate and concentration were performed. The residue was purified by silica gel column chromatography and washed with chloroform to give 132 mg of a yellowish white crystal having a mp of 211-214° C. (yield: 14.5%).

$^1$H-NMR (600 MHz, acetone-$d_6$) δ: 0.96 (6H, t, J=7.7 Hz), 1.37-1.42 (4H, m), 1.58-1.63 (4H, m), 3.37 (4H, t, J=7.7 Hz), 3.85 (3H, s), 6.24 (1H, d, J=2.2 Hz), 6.30 (1H, dd, J=2.2 Hz, 8.8 Hz), 6.94 (1H, d, J=3.8 Hz), 7.11 (2H, d, J=8.8 Hz), 7.10 (1H, d, J=16.5 Hz), 7.14 (1H, d, J=16.5 Hz), 7.19 (1H, d, J=3.8 Hz), 7.25 (2H, d, J=8.8 Hz), 7.38 (1H, d, J=8.8 Hz)

$^{13}$C-NMR (150 MHz, acetone-$d_6$) δ: 14.3, 20.9, 43.2, 51.3, 55.5, 95.5, 105.4, 111.3, 115.9, 116.7, 119.6, 119.7, 124.5, 125.5, 126.8, 127.0, 129.0, 129.5, 134.5, 147.3, 149.6, 150.7, 159.7

Example 65

2-[2-(4-dibutylamino-2-methoxybenzylidene)-3-dicyanomethyleneindan-1-ylidene]malonnitrile

[Formula 271]

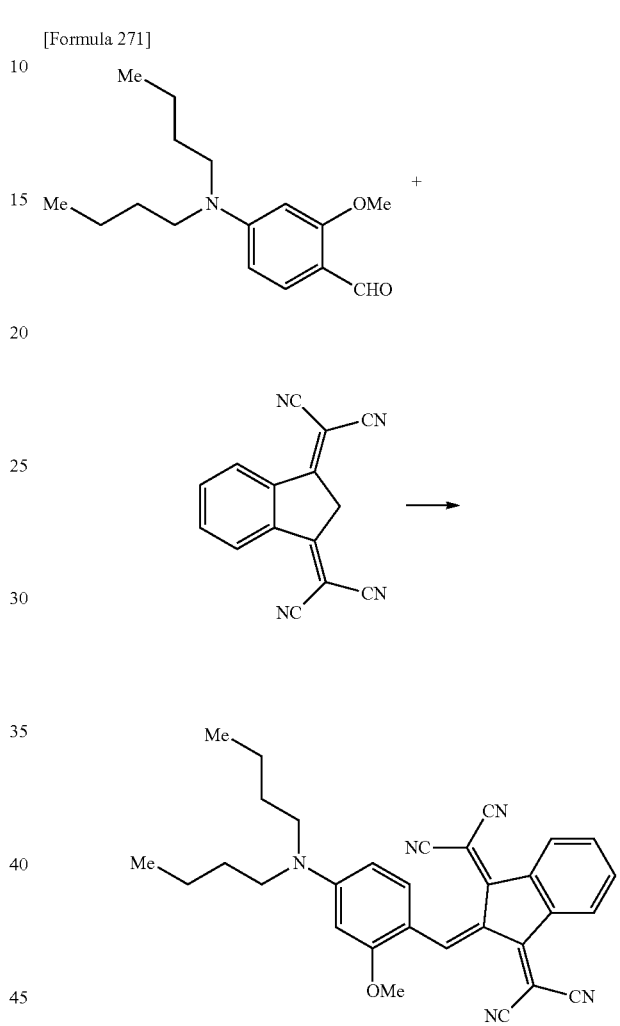

In 10 ml of anhydrous acetic acid were dissolved 0.8 g (3.04 mmol) of 4-(dibutylamino)-2-methoxybenzaldehyde and 0.73 g (3.01 mmol) of 1,3-bis(dicyanomethylidene) indan. The mixture was stirred with heating at 80° C. for 2 hours. The reaction mixture was poured into 200 ml of water and the precipitate was separated by filtration, washed with water, and dried. The crystal was purified by silica gel column chromatography and washed with methanol to give 1.27 g of a black crystal having a mp of 195-198° C. (yield: 86.4%).

$^1$H-NMR (600 MHz, CDCl$_3$) δ: 1.01 (6H, t, J=7.7 Hz), 1.39-1.45 (4H, m), 1.65-1.71 (4H, m), 3.45 (4H, t, J=7.7 Hz), 3.97 (3H, s), 6.02 (1H, d, J=1.6 Hz), 6.40 (1H, d, J=8.8 Hz), 7.40 (1H, d, J=8.8 Hz), 7.63-7.65 (2H, m), 8.54-8.56 (2H, m), 9.13 1H, b)

$^{13}$C-NMR (150 MHz, CDCl$_3$) δ: 13.8, 20.3, 29.7, 51.6, 55.9, 67.4, 92.9, 107.9, 114.8, 115.5, 115.8, 120.5, 124.8, 133.2, 137.9, 142.2, 156.5, 161.1, 164.4

Example 66

2-[4-[2-[5-[2-[2-benzyloxy-4-[butyl(4-hydroxybutyl)amino]phenyl]vinyl]thiophene-2-yl]vinyl]-3-cyano-5,5-dimethyl-2(5H)-furanylidene]propanedinitrile (66-1) 4-[(3-benzyloxyphenyl)butylamino]-1-butanol

[Formula 272]

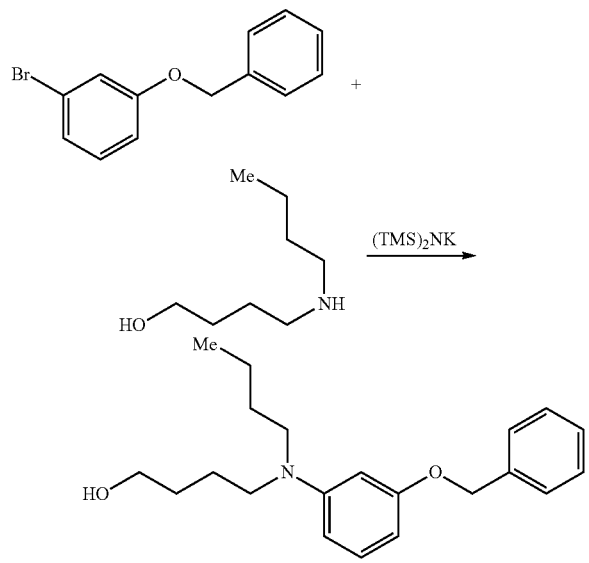

In 75 ml of dioxane were dissolved 5.19 g (19.7 mmol) of 3-benzyloxybromobenzene and 3.72 g (25.6 mmol) of 4-butylamino-1-butanol. To this mixture was added 5.89 g (29.5 mmol) of potassium hexamethyldisilazide and the mixture was stirred with heating at 100° C. for 22 hours. After the reaction mixture was poured into 200 ml of water, extraction with chloroform, washing with a saturated saline solution, drying over anhydrous sodium sulfate, and concentration were performed. The residue was purified by silica gel column chromatography to give 2.22 g of a light brown oily matter (yield: 34.4%).

$^1$H-NMR (600 MHz, CDCl$_3$) δ: 0.93 (3H, t, J=7.7 Hz), 1.29-1.35 (2H, m), 1.51-1.66 (6H, m), 3.22 (2H, t, J=7.7 Hz), 3.26 (2H, t, J=7.7 Hz), 3.66 (2H, t, J=6.9 Hz), 5.05 (2H, s), 6.27-6.31 (3H, m), 7.11 (1H, t, J=8.2 Hz), 7.30-7.33 (1H, m), 7.37-7.39 (2H, m), 7.43-7.45 (2H, m)

(66-2) 4-[(3-benzyloxyphenyl)butylamino]butyl acetate

[Formula 273]

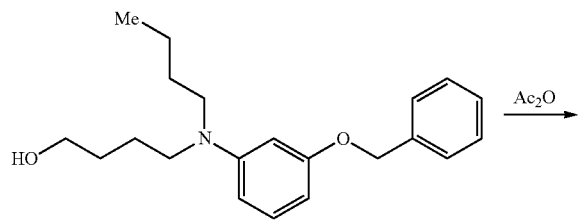

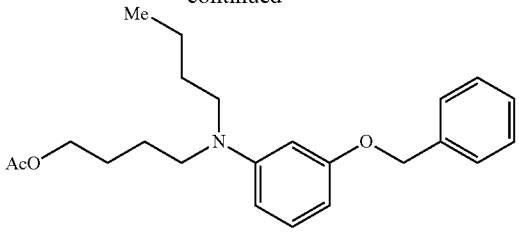

To 10 ml of anhydrous acetic acid was added 2.7 g (8.2 mmol) of 4-[(3-benzyloxyphenyl)butylamino]-1-butanol and the mixture was stirred with heating at 80° C. for 1 hour. The reaction mixture was poured into 150 ml of water and subjected to extraction with ethyl acetate. Washing was performed with a saturated sodium bicarbonate solution and then with a saturated saline solution. Drying over anhydrous sodium sulfate and concentration were performed. The residue was purified by silica gel column chromatography to give 2.68 g of a colorless oily matter (yield: 88.0%).

$^1$H-NMR (600 MHz, CDCl$_3$) δ: 0.93 (3H, t, J=7.1 Hz), 1.29-1.35 (2H, m), 1.51-1.56 (2H, m), 1.62-1.63 (4H, m), 2.04 (3H, s), 3.22 (2H, t, J=7.7 Hz), 3.25 (2H, t, J=7.1 Hz), 4.07 (2H, t, J=6.0 Hz), 5.04 (2H, s), 6.25-6.30 (3H, m), 7.10 (1H, dt, J=1.1 Hz, 8.2 Hz), 7.30-7.32 (1H, m), 7.36-7.39 (2H, m), 7.43-7.44 (2H, m)

$^{13}$C-NMR (150 MHz, CDCl$_3$) δ: 14.01, 20.3, 21.0, 23.8, 26.2, 29.4, 50.6, 50.9, 64.3, 69.9, 99.4, 101.1, 105.3, 127.5, 127.8, 128.6, 129.9, 137.5, 149.4, and 160.2, 171.2

(66-3) 4-[(3-benzyloxy-4-formylphenyl)butylamino]butyl acetate

[Formula 274]

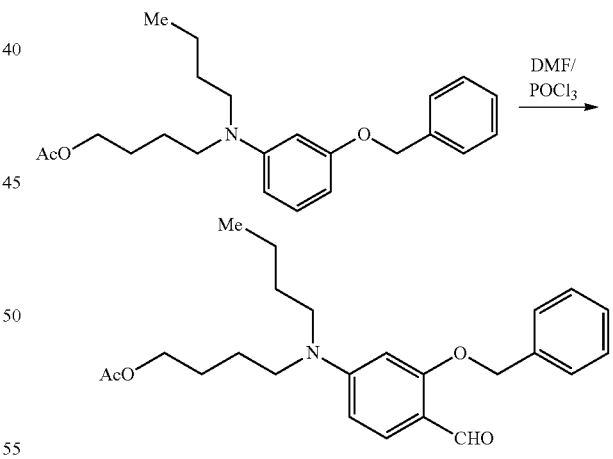

To 10 ml of N,N-dimethylformamide was added dropwise 1.11 g (7.24 mmol) of phosphoryl chloride over 8 minutes with stirring under ice cooling. After the mixture was stirred for 1 hour, 2.67 g (7.23 mmol) of 4-[(3-benzyloxyphenyl)butylamino]butyl acetate dissolved in 4 ml of N,N-dimethylformamide was added dropwise thereto. After stirred for 1 hour, the mixture was gradually heated and stirred at 50° C. for 3 hours and further at 70° C. for 0.5 hours. To this mixture, 20 ml of a 20% sodium acetate solution was added dropwise under cooling in an ice bath. The mixture was stirred for 1 hour and subjected to extraction with ethyl acetate. Washing was performed with a saturated sodium bicarbonate solution and then with a saturated saline solution. Drying over anhydrous sodium sulfate and concentration were performed. The residue was purified by silica gel column chromatography to give 2.14 g of a yellow oily matter (yield: 74.7%).

$^1$H-NMR (600 MHz, CDCl$_3$) δ: 0.94 (3H, t, J=7.7 Hz), 1.29-1.35 (2H, m), 1.49-1.54 (2H, m), 1.58-1.64 (4H, m), 2.05 (3H, s), 3.26 (2H, t, J=7.7 Hz), 3.31 (2H, t, J=7.7 Hz), 4.07 (2H, t, J=6.0 Hz), 5.18 (2H, s), 6.01 (1H, d, J=2.2 Hz), 6.25 (1H, dd, J=2.2 Hz, 8.8 Hz), 7.33 (1H, t, J=7.1 Hz), 7.38-7.44 (4H, m), 7.73 (1H, d, J=8.8 Hz), 10.25 (1H, s)

$^{13}$C-NMR (150 MHz, CDCl$_3$) δ: 13.7, 20.0, 20.7, 23.6, 25.9, 29.1, 50.4, 50.7, 63.7, 69.9, 94.3, 104.5, 114.4, 126.6, 127.8, 128.5, 130.1, 136.5, 153.6, 162.9, 170.8, 186.9

(66-4) 2-benzyloxy-4-[butyl(4-hydroxybutyl)amino]benzaldehyde

[Formula 275]

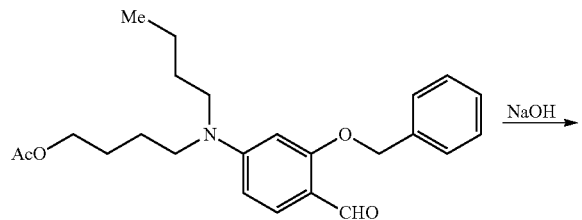

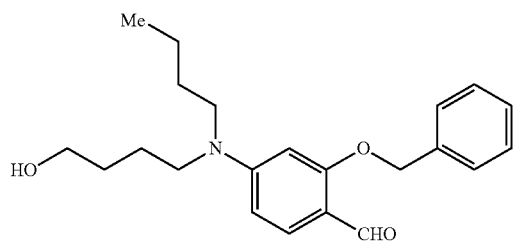

In 10 ml of ethanol was dissolved 2.14 g (5.38 mmol) of 4-[(3-benzyloxy-4-formylphenyl)butylamino]butyl acetate. To this mixture was added 8 ml of a 10% sodium hydroxide solution and the mixture was stirred at room temperature for 30 minutes. After the reaction mixture was poured into 100 ml of water, extraction with chloroform, washing with a saturated saline solution, drying over anhydrous sodium sulfate, and concentration were performed. The residual liquid was purified by silica gel column chromatography to give 1.63 g of a yellow liquid (yield: 85.2%).

$^1$H-NMR (600 MHz, CDCl$_3$) δ: 0.94 (3H, t, J=7.7 Hz), 1.29-1.35 (2H, m), 1.50-1.66 (6H, m), 3.27 (2H, t, J=7.7 Hz), 3.32 (2H, t, J=7.7 Hz), 3.66 (2H, t, J=6.0 Hz), 5.18 (2H, s), 6.03 (1H, d, J=2.2 Hz), 6.26 (1H, dd, J=2.2 Hz, 8.8 Hz), 7.31-7.43 (6H, m), 7.72 (1H, d, J=8.8 Hz), 10.24 (1H, s)

$^{13}$C-NMR (150 MHz, CDCl$_3$) δ: 14.0, 20.3, 23.8, 29.5, 30.0, 51.0, 51.1, 62.5, 70.2, 94.6, 104.8, 114.6, 127.0, 128.1, 128.8, 130.4, 136.9, 154.16, 163.3, 187.2

(66-5) 2-benzyloxy-4-[butyl[4-(tert-butyldiphenylsiloxy)butyl]amino]benzaldehyde

[Formula 276]

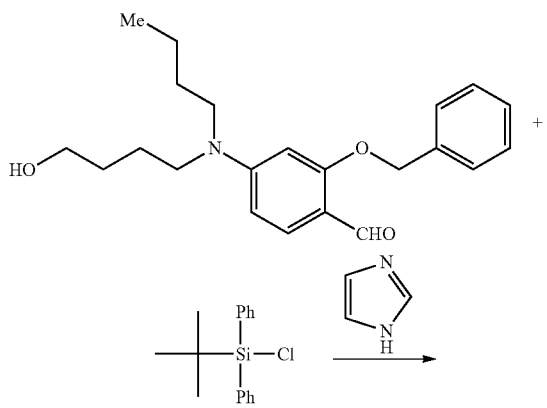

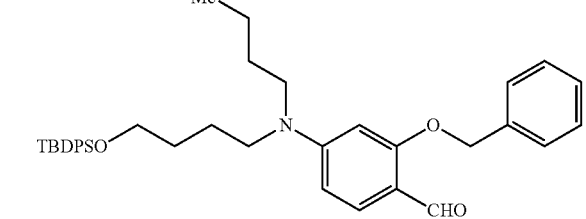

In 20 ml of N,N-dimethylformamide were dissolved 1.63 g (4.59 mmol) of 2-benzyloxy-4-[butyl(4-hydroxybutyl)amino] benzaldehyde and 1.2 g (17.63 mmol) of imidazole. To this mixture, 1.27 g (4.62 mmol) of tert-butylchlorodiphenylsilane was added dropwise with stirring at room temperature. The mixture was stirred for 2 hours. After the reaction mixture was poured into water, extraction with ethyl acetate, washing with a saturated saline solution, and drying over anhydrous sodium sulfate were performed. The residue was purified by silica gel column chromatography to give 2.08 g of a colorless oily matter (yield: 76.5%).

(66-6) [3-benzyloxy-4-(2-thiophene-2-ylvinyl)phenyl]butyl [4-(tert-butyldiphenylsiloxy)butyl]amine

[Formula 277]

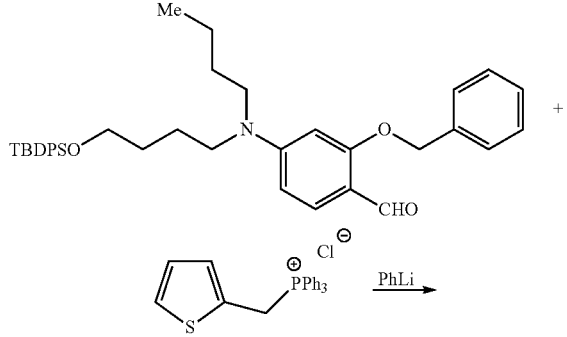

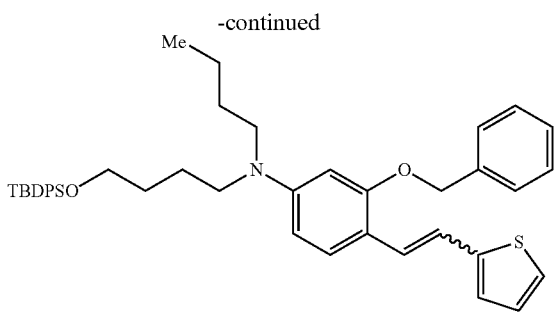

In a stream of argon, to 20 ml of tetrahydrofuran was added 1.7 g of phenyllithium (19% solution in dibutylether) (3.83 mmol), and 1.38 g (3.49 mmol) of 2-thenyl triphenylphosphonium chloride was added thereto under ice cooling over 5 minutes. After the mixture was stirred for 10 minutes, 2.07 g (3.49 mmol) of 2-benzyloxy-4-[butyl[4-(tert-butyldiphenylsiloxy)butyl] amino]benzaldehyde dissolved in 50 ml of tetrahydrofuran was added dropwise thereto over 8 minutes. The mixture was stirred under ice cooling for 2 hours. After the reaction mixture was poured into water, extraction with ethyl acetate, washing with a saturated saline solution, drying over anhydrous sodium sulfate, and concentration were performed. The residue was purified by silica gel column chromatography to give 2.03 g of a light brown oily matter (yield: 86.4%).

(66-7) 5-[2-[2-benzyloxy-4-[butyl[4-(tert-butyldiphenylsiloxy) butyl]amino]phenyl]vinyl]thiophene-2-carboaldehyde

[Formula 278]

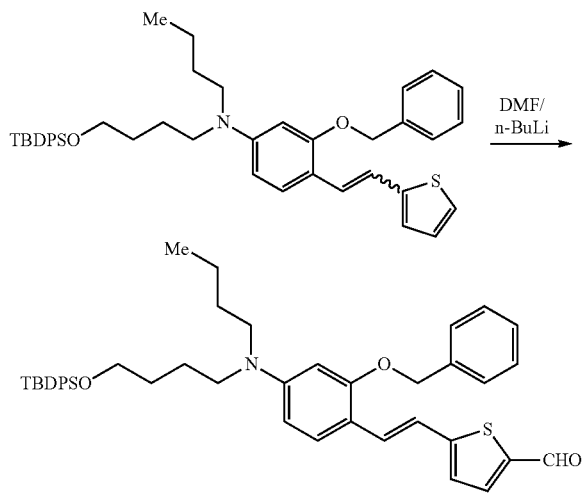

In a stream of argon, in 20 ml of tetrahydrofuran was dissolved 2.02 g (3.0 mmol) of [3-benzyloxy-4-(2-thiophene-2-ylvinyl)phenyl]butyl[4-(tert-butyldiphenylsiloxy) butyl]amine, and 2.8 ml of n-butyllithium (1.6 mol solution in hexane) (4.48 mmol) was added dropwise thereto under cooling at −66 to −72° C. After the mixture was stirred for 35 minutes, 0.3 ml (3.9 mmol) of N,N-dimethylformamide was added dropwise thereto. After the mixture was stirred for 1.5 hours, the bath was removed and the temperature was allowed to rise. At −10° C., 10 ml of water was added dropwise. After the reaction mixture was poured into 100 ml of water, extraction with ethyl acetate, washing with a saturated saline solution, drying over anhydrous sodium sulfate, and concentration were performed. The residual liquid was purified by silica gel column chromatography to give a reddish orange oily matter. Next, 1.43 g of the oily matter was dissolved in 150 ml of ether and 50 mg of iodine was added thereto. After stirred at room temperature for 30 minutes, the mixture was washed with a 5% sodium bisulfite solution and then with a saturated saline solution. Drying over anhydrous magnesium sulfate and concentration were performed. The residue was purified by silica gel column chromatography to give 1.21 g of a red oily matter (yield: 57.6%).

$^1$H-NMR (600 MHz, CDCl$_3$) δ: 0.93 (3H, t, J=7.7 Hz), 1.04 (9H, s), 1.26-1.31 (2H, m), 1.47-1.55 (4H, m), 1.60-1.64 (2H, m), 3.21 (2H, t, J=7.7 Hz), 3.24 (2H, t, J=7.7 Hz), 3.67 (2H, t, J=6.0 Hz), 5.13 (2H, s), 6.10 (1H, d, J=2.2 Hz), 6.25 (1H, dd, J=2.2 Hz, 8.8 Hz), 6.98 (1H, d, J=3.8 Hz), 7.10 (1H, d, J=15.9 Hz), 7.29-7.43 (12H, m), 7.46 (1H, d, J=15.9 Hz), 7.60 (1H, d, J=3.8 Hz), 7.65-7.66 (4H, m), 9.79 (1H, s)

$^{13}$C-NMR (150 MHz, CDCl$_3$) δ: 14.0, 19.2, 20.3, 23.9, 26.9, 29.5, 30.0, 50.9, 51.0, 63.6, 70.4, 96.5, 105.0, 112.8, 116.3, 124.4, 127.0, 127.7, 127.9, 128.7, 128.9, 129.3, 129.6, 133.9, 135.6, 137.2, 137.7, 139.7, 149.8, 155.7, 158.3, 182.3

(66-8) 5-[2-[2-benzyloxy-4-[butyl(4-hydroxybutyl) amino]phenyl] vinyl]thiophene-2-carboaldehyde

[Formula 279]

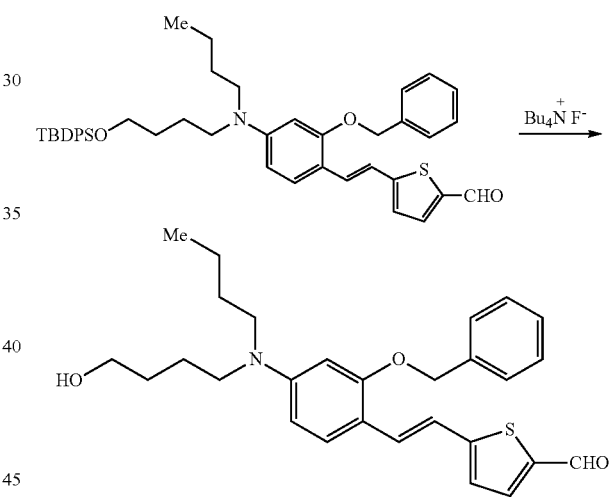

In 10 ml of tetrahydrofuran was dissolved 1.2 g (1.71 mmol) of 5-[2-[2-benzyloxy-4-[butyl[4-(tert-butyldiphenylsiloxy) butyl]amino]phenyl]vinyl]thiophene-2-carboaldehyde. To this mixture, 7.6 ml of tetrabutylammonium fluoride (1 mol/L solution in tetrahydrofuran) (7.6 mmol) was added dropwise with stirring at room temperature. The mixture was stirred for 1.5 hours. After the reaction mixture was poured into water, extraction with ethyl acetate, washing with a saturated saline solution, drying over anhydrous sodium sulfate, and concentration were performed. The residual liquid was purified by silica gel column chromatography to give 554 mg of a red crystal (yield: 70.1%).

$^1$H-NMR (600 MHz, CDCl$_3$) δ: 0.93 (3H, t, J=7.7 Hz), 1.28-1.34 (2H, m), 1.48-1.63 (6H, m), 3.24 (2H, t, J=7.7 Hz), 3.28 (2H, t, J=7.7 Hz), 3.65 (2H, t, J=6.0 Hz), 5.17 (2H, s), 6.13 (1H, d, J=2.2 Hz), 6.27 (1H, dd, J=2.2 Hz, 8.8 Hz), 6.98 (1H, d, J=3.8 Hz), 7.12 (1H, d, J=15.9 Hz), 7.32-7.48 (7H, m), 7.60 (1H, d, J=3.8 Hz), 9.79 (1H, s)

$^{13}$C-NMR (150 MHz, CDCl$_3$) δ: 14.0, 20.3, 23.8, 29.5, 30.1, 50.9, 51.0, 62.6, 70.4, 96.6, 105.1, 113.0, 116.4, 124.5, 127.0, 127.9, 128.7, 128.9, 129.2, 137.2, 137.7, 139.7, 149.8, 155.7, 158.3, 182.3

(66-9) 2-[4-[2-[5-[2-[2-benzyloxy-4-[butyl(4-hydroxybutyl)amino] phenyl]vinyl]thiophene-2-yl]vinyl]-3-cyano-5,5-dimethyl-2(5H)-furanylidene]propanedinitrile

[Formula 280]

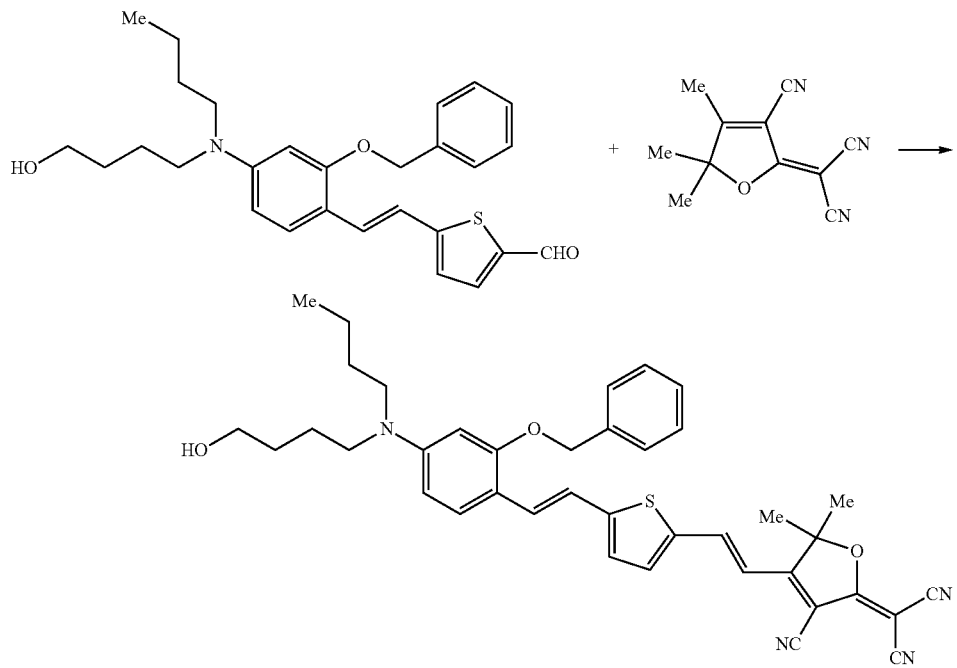

In 7 ml of ethanol and 2 ml of tetrahydrofuran were dissolved 218 mg (0.47 mmol) of 5-[2-[2-benzyloxy-4-[butyl(4-hydroxybutyl)amino]phenyl]vinyl]thiophene-2-carboaldehyde and 103 mg (0.52 mmol) of 2-(3-cyano-4,5,5-trimethyl-2(5H)-furanylidene)propanedinitrile. To this mixture was added 40 mg (0.52 mmol) of ammonium acetate, and the mixture was stirred at room temperature for 90 minutes. The precipitate was separated by filtration, purified by silica gel column chromatography and washed with methanol to give 171 mg of a dark brown crystal having a mp of 216-217° C. (yield: 56.4%).

$^1$H-NMR (600 MHz, CDCl$_3$) δ: 0.94 (3H, t, J=7.7 Hz), 1.28-1.34 (2H, m), 1.48-1.64 (6H, m), 1.73 (6H, s), 3.26 (2H, t, J=7.7 Hz), 3.30 (2H, t, J=7.7 Hz), 3.66 (2H, t, J=6.0 Hz), 5.21 (2H, s), 6.12 (1H, d, J=2.2 Hz), 6.29 (1H, dd, J=2.2 Hz, 8.8 Hz), 6.50 (1H, d, J=15.4 Hz), 6.94 (1H, d, J=4.4 Hz), 7.14 (1H, d, J=15.9 Hz), 7.31 (1H, d, J=4.4 Hz), 7.34-7.49 (7H, m), 7.75 (1H, d, J=15.4 Hz)

$^{13}$C-NMR (150 MHz, CDCl$_3$) δ: 14.0, 20.3, 23.8, 26.6, 29.5, 30.0, 50.9, 51.0, 55.3, 62.6, 70.4, 95.2, 96.4, 96.8, 105.3, 111.1, 111.3, 111.7, 112.5, 112.9, 116.2, 126.6, 126.9, 128.0, 128.7, 129.4, 130.9, 137.0, 137.1, 138.0, 139.4, 150.4, 156.4, 158.7, 172.8, 175.9

Example 67

2-[4-[2-[5-[2-[2-benzyloxy-4-[butyl(4-hydroxybutyl)amino] phenyl]vinyl]thiophene-2-yl]vinyl]-3-cyano-5-methyl-5-trifluoromethyl-2(5H)-furanylidene]propanedinitrile

[Formula 281]

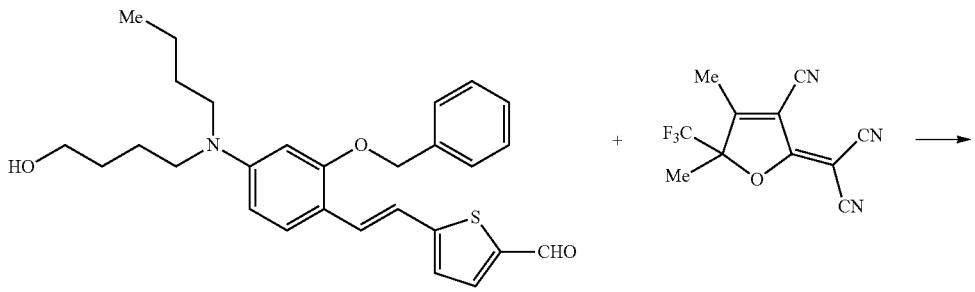

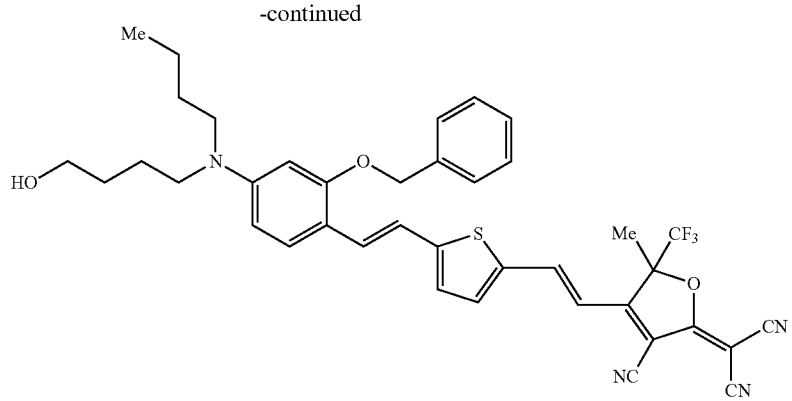

In 8 ml of ethanol were dissolved 180 mg (0.39 mmol) of 5-[2-[2-benzyloxy-4-[butyl(4-hydroxybutyl)amino]phenyl]vinyl]thiophene-2-carboaldehyde and 108 mg (0.43 mmol) of 2-(3-cyano-4,5-dimethyl-5-trifluoromethyl-2(5H)-furanylidene)propanedinitrile. The mixture was stirred with heating at 50° C. for 3 hours. The precipitate was separated by filtration, purified by silica gel column chromatography and washed with methanol to give 200 mg of a dark brown crystal having a mp of 176-178° C. (yield: 73.8%).

$^1$H-NMR (600 MHz, CDCl$_3$) δ: 0.94 (3H, t, J=7.1 Hz), 1.28-1.34 (2H, m), 1.49-1.66 (6H, m), 1.88 (3H, s), 3.27 (2H, t, J=7.7 Hz), 3.32 (2H, t, J=7.1 Hz), 3.66 (2H, t, J=6.0 Hz), 5.22 (2H, s), 6.12 (1H, s), 6.30 (1H, d, J=8.8 Hz), 6.40 (1H, d, J=15.4 Hz), 6.99 (1H, d, J=3.8 Hz), 7.17 (1H, d, J=15.4 Hz), 7.35-7.47 (7H, m), 7.54 (1H, d, J=15.4 Hz), 8.12 (1H, d, J=15.4 Hz)

$^{13}$C-NMR (150 MHz, CDCl$_3$) δ: 13.9, 19.3, 20.3, 23.9, 29.5, 30.0, 50.99, 51.04, 57.2, 62.5, 70.4, 93.3, 93.5, 94.6, 96.2, 105.5, 109.9, 110.9, 111.4, 112.9, 116.1, 122.1, 127.0, 127.4, 128.1, 128.7, 130.0, 132.6, 137.0, 137.8, 140.3, 141.1, 150.9, 159.2, 159.4, 161.6, 175.4

Example 68

2-[4-[2-[5-[2-[2-benzyloxy-4-[butyl(4-hydroxybutyl)amino] phenyl]vinyl]thiophene-2-yl]vinyl]-3-cyano-5-phenyl-5-trifluoromethyl-2(5H)-furanylidene]propanedinitrile

[Formula 282]

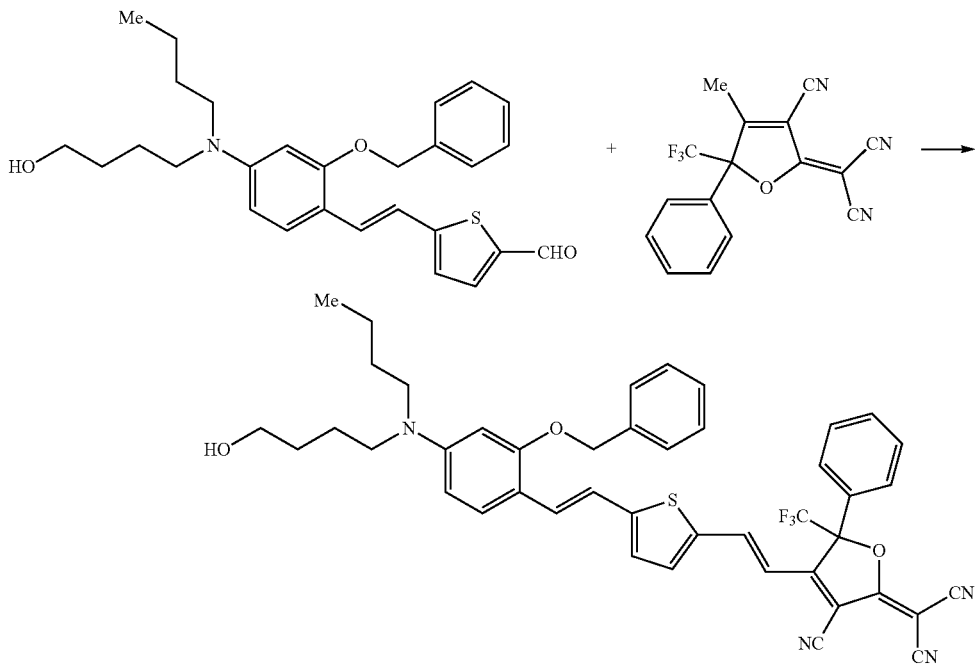

In 8 ml of ethanol were dissolved 155 mg (0.33 mmol) of 5-[2-[2-benzyloxy-4-[butyl(4-hydroxybutyl)amino]phenyl]vinyl]thiophene-2-carboaldehyde and 116 mg (0.37 mmol) of 2-(3-cyano-4-methyl-5-phenyl-5-trifluoromethyl-2(5H)-furanylidene)propanedinitrile. The mixture was stirred with heating at 65° C. for 1 hour. The tar-like matter was separated by decantation, purified by silica gel column chromatography, crystallized in methanol, and separated by filtration to give 153 mg of a dark brown crystal having a mp of 181-183° C. (yield: 60.2%).

$^1$H-NMR (600 MHz, CDCl$_3$) δ: 0.93 (3H, t, J=7.1 Hz), 1.29-1.34 (2H, m), 1.48-1.64 (6H, m), 3.26 (2H, t, J=7.7 Hz), 3.31 (2H, t, J=7.1 Hz), 3.66 (2H, t, J=6.0 Hz), 5.21 (2H, s), 6.11 (1H, s), 6.28 (1H, d, J=8.8 Hz), 6.55 (1H, d, J=14.9 Hz), 6.94 (1H, d, J=3.8 Hz), 7.14 (1H, d, J=15.9 Hz), 7.20 (1H, d, J=3.8 Hz), 7.33-7.56 (12H, m), 7.78 (1H, d, J=14.9 Hz)

$^{13}$C-NMR (150 MHz, CDCl$_3$) δ: 13.9, 20.3, 23.8, 29.5, 30.0, 51.0, 57.5, 62.5, 70.4, 96.2, 105.5, 110.9, 111.1, 111.2, 111.3, 113.0, 116.2, 122.3, 126.8, 126.9, 127.4, 128.1, 128.7, 129.7, 129.8, 129.9, 131.5, 132.6, 137.0, 137.8, 140.1, 141.6150.8, 159.2, 159.5, 161.7, 175.5

Example 69

2-[4-[3-[2-butyl-3-[2-(4-dibutylamino-2-methoxyphenyl) vinyl]-5,5-dimethyl-2-cyclohexenylidene]-1-propenyl]-3-cyano-5-phenyl-5-trifluoromethyl-2(5H)-furanylidene] propanedinitrile (69-1) 2-butyl-3,5,5-trimethyl-2-cyclohexenone

[Formula 283]

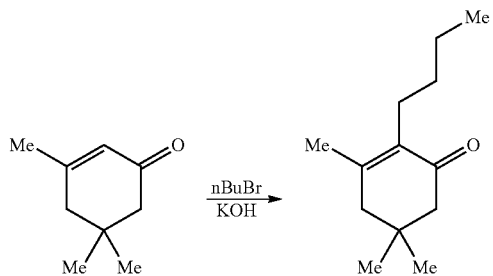

In 60 ml of 1-methyl-2-pyrrolidone were dissolved 10.0 g (72.36 mmol) of isophorone and 14.9 g (95.6 mmol) of 1-bromobutane. To this mixture was added 8.1 g (144.4 mmol) of powdered potassium hydroxide and the mixture was stirred with heating at 70° C. for 6 hours. After the reaction mixture was added to water, extraction with ethyl acetate, washing with a saturated saline solution, drying over anhydrous sodium sulfate, and concentration were performed. The residual liquid was purified by silica gel column chromatography to give 6.31 g of a yellow oily matter (yield: 44.9%).

$^1$H-NMR (600 MHz, CDCl$_3$) δ: 0.90 (3H, t, J=7.1 Hz), 1.00 (6H, s), 1.25-1.35 (4H, m), 1.91 (3H, s), 2.21 (2H, s), 2.23 (2H, s), 2.28 (2H, t, J=7.7 Hz)

$^{13}$C-NMR (150 MHz, CDCl$_3$) δ: 14.0, 21.3, 22.9, 24.8, 28.2, 31.4, 32.7, 47.0, 51.4, 134.8, 152.3, 199.0

(69-2) 3-[2-(4-dibutylamino-2-methoxyphenyl)vinyl]-2-butyl-5,5-dimethyl-2-cyclohexenone

[Formula 284]

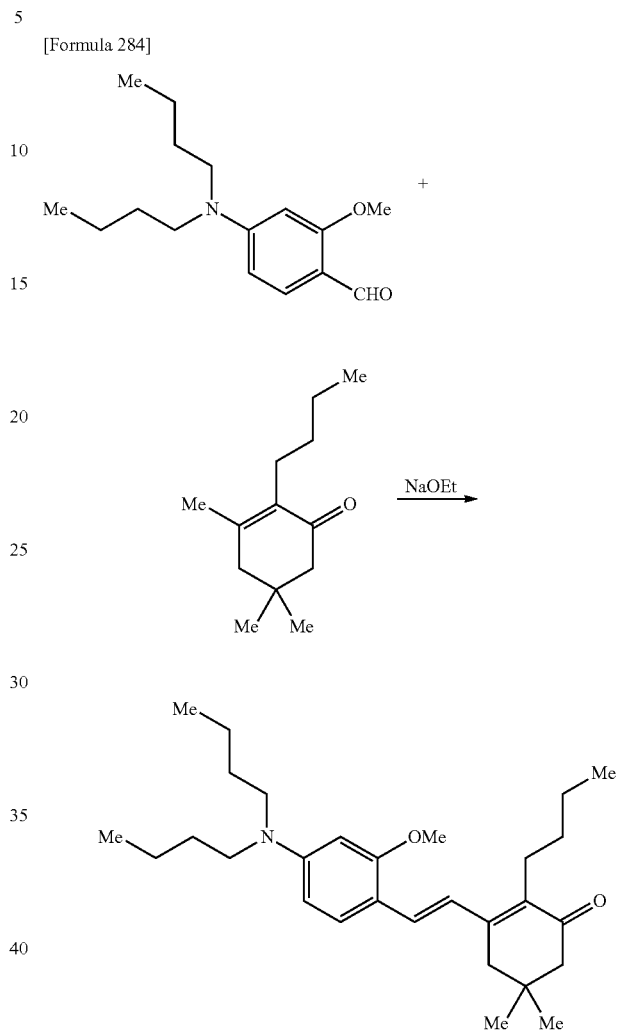

0.3 g (13.0 mmol) of sodium was dissolved in 15 ml of ethanol. Next, 2.63 g (10.0 mmol) of 4-dibutylamino-2-methoxybenzaldehyde and 2.22 g (11.0 mmol) of 2-butyl-3,5,5-trimethyl-2-cyclohexenone were dissolved in 5 ml of ethanol and added to the mixture. To this mixture, 0.36 g of ammonium acetate was added and the mixture was stirred with heating at 60° C. for 22 hours. To the mixture, 100 ml of ethyl acetate was added. Washing with a saturated saline solution, drying over anhydrous sodium sulfate, and concentration were performed. The residual liquid was purified by silica gel column chromatography to give 465 mg of a dark red oily matter (yield: 10.6%).

$^1$H-NMR (600 MHz, CDCl$_3$) δ: 0.93 (3H, t, J=6.6 Hz), 0.97 (6H, t, J=7.7 Hz), 1.05 (6H, s), 1.33-1.40 (8H, m), 1.58-1.63 (4H, m), 2.29 (2H, s), 2.51 (2H, s), 2.51-2.53 (2H, m), 3.31 (4H, t, J=7.7 Hz), 3.87 (3H, s), 6.13 (1H, d, J=2.2 Hz), 6.28 (1H, dd, J=2.2 Hz, 8.8 Hz), 7.20 (1H, d, J=15.9 Hz), 7.24 (1H, d, J=15.9 Hz), 7.41 (1H, d, J=8.8 Hz)

$^{13}$C-NMR (150 MHz, CDCl$_3$) δ: 14.0, 14.1, 20.4, 23.0, 24.3, 28.5, 29.5, 32.2, 32.4, 39.9, 50.8, 51.6, 55.3, 94.4, 104.7, 113.4, 122.0, 128.3, 129.6, 133.7, 149.0, 150.0, 159.0, 199.3

251

(69-3) [2-butyl-3-[2-(4-dibutylamino-2-methoxyphenyl) vinyl]-5,5-dimethyl-2-cyclohexenylidene]acetonitrile

[Formula 285]

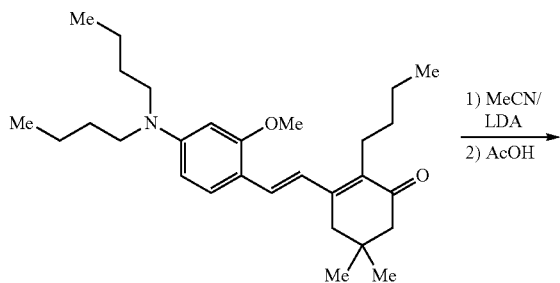

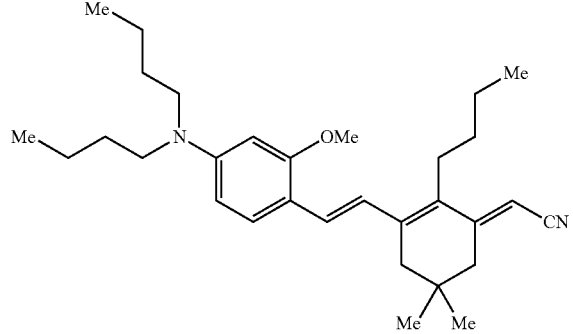

In a stream of argon, 3.8 ml of lithium diisopropylamide (2 mol/L solution) was added to 2 ml of tetrahydrofuran and cooled in a dry ice/acetone bath. To this mixture, 0.31 g (7.55 mmol) of acetonitrile in 4 ml of tetrahydrofuran was added dropwise. To this mixture was added dropwise 3-[2-(4-dibutylamino-2-methoxyphenyl)vinyl]-2-butyl-5,5-dimethyl-2-cyclohexenone in 5 ml of tetrahydrofuran. The mixture was stirred for 30 minutes and the temperature was allowed to rise slowly. At 0° C., 10 ml of water was added dropwise. The organic solvent was evaporated off in a reduced pressure. Extraction with ethyl acetate, washing with a saturated saline solution, drying over anhydrous sodium sulfate, and concentration gave a reddish orange oily matter. This oily matter was dissolved in 4 ml of acetic acid and stirred with heating at 75° C. for 2 hours. After the mixture was cooled, 100 ml of dichloromethane was added thereto and neutralized with a saturated sodium bicarbonate solution. The organic layer was separated, dried over anhydrous magnesium sulfate, and concentrated. The residue was purified by silica gel column chromatography to give 158 mg of an orange crystal (yield: 39.3%).

$^{1}$H-NMR (600 MHz, CDCl$_3$) δ: 0.96 (3H, t, J=6.6 Hz), 0.97 (6H, t, J=7.7 Hz), 1.00 (6H, s), 1.33-1.43 (8H, m), 1.55-1.62 (4H, m), 2.38 (2H, s), 2.44 (2H, t, J=7.7 Hz), 2.50 (2H, s), 3.30 (4H, t, J=7.7 Hz), 3.86 (3H, s), 6.13 (1H, d, J=2.2 Hz), 6.27 (1H, dd, J=2.2 Hz, 8.8 Hz), 7.09 (1H, d, J=15.9 Hz), 7.15 (1H, d, J=15.9 Hz), 7.36 (1H, d, J=8.8 Hz)

$^{13}$C-NMR (150 MHz, CDCl$_3$) δ: 14.0, 20.4, 23.1, 26.9, 27.7, 28.1, 29.5, 30.4, 31.7, 40.4, 43.6, 50.9, 55.3, 89.5, 94.6, 104.7, 113.8, 119.7, 122.2, 127.7, 128.0, 130.6, 140.4, 149.7, 158.7, 159.3

252

(69-4) [2-butyl-3-[2-(4-dibutylamino-2-methoxyphenyl) vinyl]-5,5-dimethyl-2-cyclohexenylidene]acetaldehyde

[Formula 286]

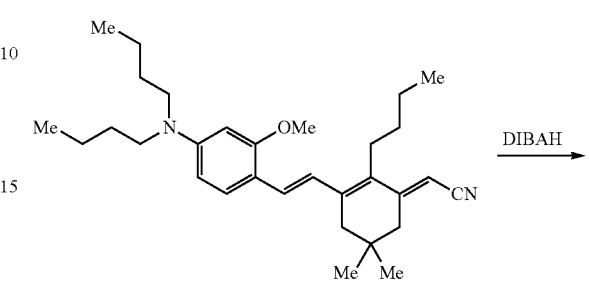

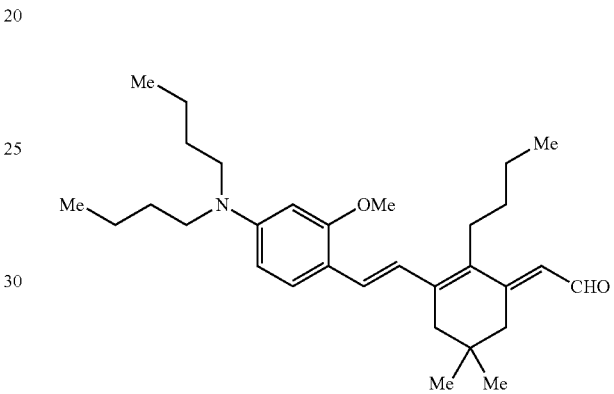

In 5 ml of toluene was dissolved 158 mg (0.34 mmol) of [2-butyl-3-[2-(4-dibutylamino-2-methoxyphenyl)vinyl]-5,5-dimethyl-2-cyclohexenylidene]acetonitrile. The mixture was cooled in a dry ice/acetone bath in a stream of argon. To this mixture, 0.46 ml of diisobutylaluminum hydride (1.5 mol solution in toluene) (0.69 mmol) was added dropwise. The mixture was stirred for 1.5 hours and the temperature was allowed to rise. At 0° C., 5 ml of a 5% ammonium chloride solution was added dropwise. After the mixture was stirred for 30 minutes, the phases were separated and the water phase was washed with ethyl acetate. The organic layer was washed with a saturated saline solution, dried over anhydrous sodium sulfate, and concentrated. The residual liquid was purified by silica gel column chromatography to give 119 mg of a red oily matter (yield: 74.8%).

$^{1}$H-NMR (600 MHz, CDCl$_3$) δ: 0.95 (3H, t, J=7.1 Hz), 0.97 (6H, t, J=7.7 Hz), 1.02 (6H, s), 1.34-1.44 (8H, m), 1.56-1.63 (4H, m), 2.42 (2H, s), 2.51 (2H, t, J=7.4 Hz), 2.69 (2H, s), 3.31 (4H, t, J=7.7 Hz), 3.87 (3H, s), 6.13 (1H, d, J=2.2 Hz), 6.19 (1H, d, J=8.2 Hz), 6.28 (1H, dd, J=2.2 Hz, 8.8 Hz), 7.11 (1H, d, J=15.9 Hz), 7.23 (1H, d, J=15.9 Hz), 7.38 (1H, d, J=8.8 Hz), 10.13 (1H, d, J=8.2 Hz)

$^{13}$C-NMR (150 MHz, CDCl$_3$) δ: 14.0, 20.4, 23.2, 27.2, 28.3, 29.6, 30.3, 32.0, 39.6, 40.4, 50.9, 55.3, 60.4, 94.5, 104.7, 113.9, 122.7, 123.2, 127.9, 128.1, 132.6, 141.9, 149.7, 158.1, 158.8, 191.8

(69-5) 2-[4-[3-[2-butyl-3-[2-(4-dibutylamino-2-methoxyphenyl) vinyl]-5,5-dimethyl-2-cyclohexenylidene]-1-propenyl]-3-cyano-5-phenyl-5-trifluoromethyl-2(5H)-furanylidene] propanedinitrile

[Formula 287]

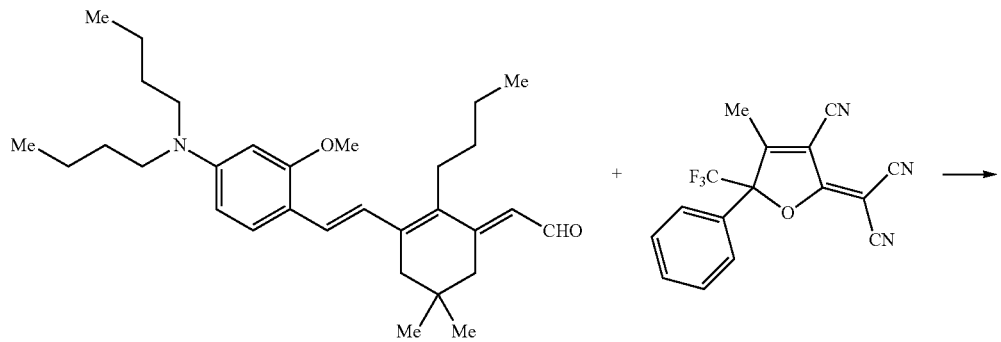

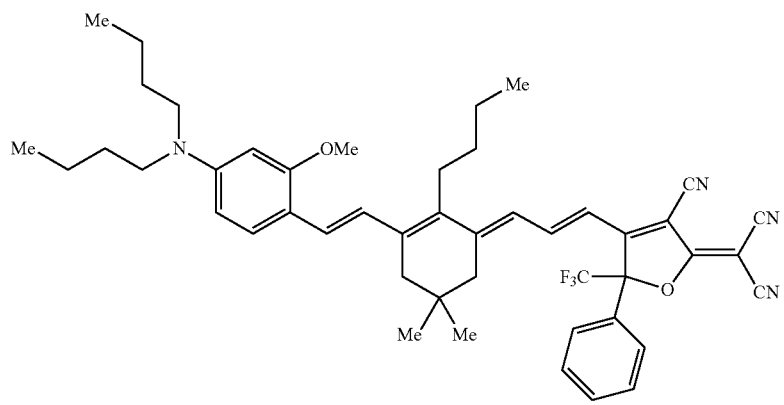

118 mg (0.25 mmol) of [2-butyl-3-[2-(4-dibutylamino-2-methoxyphenyl)vinyl]-5,5-dimethyl-2-cyclohexenylidene] acetaldehyde and 90 mg (0.29 mmol) of 2-(3-cyano-4-methyl-5-phenyl-5-trifluoromethyl-2(5H)-furanylidene] propanedinitrile were dissolved, and the mixture was stirred with heating at 50° C. for 40 minutes. The solvent was evaporated off. The residue was purified by silica gel column chromatography and washed with methanol to give 133 mg of a black crystal having a mp of 109-113° C. (yield: 68.9%).

$^1$H-NMR (600 MHz, CDCl$_3$) δ: 0.88 (3H, s), 0.97-1.00 (12H, m), 1.34-1.47 (8H, m), 1.59-1.64 (4H, m), 2.17 (1H, d, J=15.4 Hz), 2.28 (1H, d, J=15.9 Hz), 2.47 (2H, s), 2.25 (2H, b), 3.35 (4H, t, J=7.7 Hz), 3.89 (3H, s), 6.09 (1H, d, J=2.2 Hz), 6.30 (1H, dd, J=2.2 Hz, 8.8 Hz), 6.37 (1H, d, J=13.7 Hz), 6.58 (1H, d, J=12.6 Hz), 7.32 (1H, d, J=15.9 Hz), 7.40 (1H, d, J=15.9 Hz), 7.41 (1H, d, J=8.8 Hz), 7.51-7.54 (5H, m), 8.00 (1H, b)

$^{13}$C-NMR (150 MHz, CDCl$_3$) δ: 14.0 14.1, 20.3, 23.2, 27.0, 27.8, 28.5, 29.6, 30.7, 32.2, 40.6, 40.8, 55.3, 94.0, 95.2, 105.4, 111.6, 112.1, 114.1, 115.1, 121.3, 122.2, 123.2, 124.9, 126.9, 129.5, 130.8, 131.0, 133.5, 135.6, 147.5, 150.7, 151.3, 159.5, 160.2, 161.3, 176.0

Example 70

2-{3-cyano-4-[2-(4-dibutylamino-2,6-dimethoxyphenyl)vinyl]-5-methyl-5-trifluoromethyl-2(5H)-furanylidene}propanedinitrile

[Formula 288]

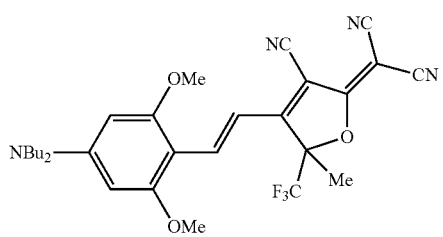

The compound was synthesized in the same procedure as in Example 30.

$^1$H-NMR (600 MHz, CDCl$_3$) δ: 1.00 (6H, t, J=7.7 Hz), 1.42 (4H, m), 1.68 (4H, m), 1.86 (3H, s), 3.44 (4H, m), 3.92 (6H, s), 5.76 (2H, s), 7.17 (1H, d, J=10.4 Hz), 8.70 (1H, d, J=10.4 Hz)

$^{13}$C-NMR (150 MHz, CDCl$_3$) δ: 13.8, 20.2, 27.2, 29.6, 51.2, 55.7, 87.8, 96.1, 104.0, 110.0, 112.1, 113.2, 114.1, 131.6, 14.07, 154.5, 163.4, 176.6, 176.9

Example 71

2-{3-cyano-4-[2-(4-dibutylamino-2,6-dimethoxyphenyl)vinyl]-5-phenyl-5-trifluoromethyl-2(5H)-furanylidene}propanedinitrile

[Formula 289]

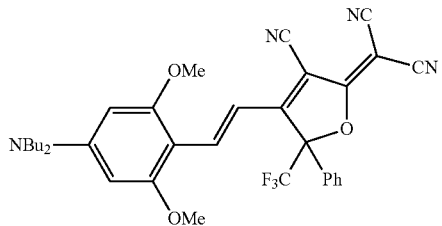

The compound was synthesized in the same procedure as in Example 30.

$^1$H-NMR (600 MHz, CDCl$_3$) δ: 0.98 (6H, t, J=7.7 Hz), 1.39 (4H, m), 1.64 (4H, m), 3.41 (4H, t, 7.7 Hz), 3.83 (6H, s), 5.69 (2H, s), 7.31 (1H, b), 7.46-7.48 (3H, m), 7.52-7.53 (2H, m), 8.42 (1H, b)

$^{13}$C-NMR (150 MHz, CDCl$_3$) δ: 13.8, 20.1, 29.7, 51.4, 55.7, 88.0, 105.3, 106.4, 110.8, 112.1, 113.0, 126.7, 129.1, 130.6, 131.5, 144.0, 155.9, 164.3, 177.0, 183.6

Comparative Example 1

2-[4-[2-[5-[2-(4-dibutylaminophenyl)vinyl]thiophene-2-yl] vinyl]-3-cyano-5,5-dimethyl-2(5H)-furanylidene] propanedinitrile

[Formula 290]

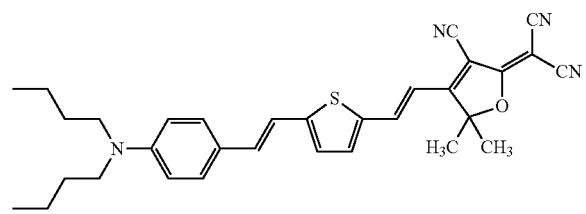

(1-1) Dibutyl[4-[2-(thiophene-2-yl)vinyl]phenyl]amine

[Formula 291]

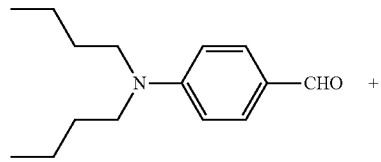

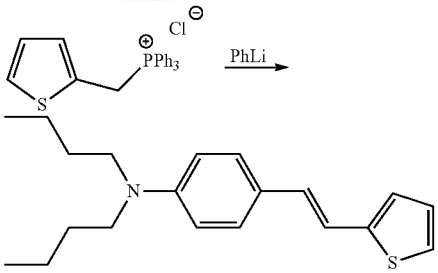

In a stream of argon, to 70 ml of tetrahydrofuran was added 10.45 g of phenyllithium (19% solution in dibutylether) (23.6 mmol), and 8.09 g (20.5 mmol) of 2-thenyl triphenylphosphonium chloride was added thereto under cooling. To this mixture was added dropwise 4.92 g (21.0 mmol) of 4-(dibutylamino)benzaldehyde. The mixture was stirred at the same temperature for 1 hour. After the reaction mixture was poured into water, extraction with toluene, washing with a saturated saline solution, drying over anhydrous sodium sulfate, and concentration were performed. The residue was purified by silica gel column chromatography to give an orange liquid. This liquid was dissolved in 200 ml of toluene and 200 mg of iodine was added thereto. After stirred at room temperature for 15 minutes, the mixture was added to water and the phases were separated. The organic layer was dried over anhydrous sodium sulfate and concentrated. The residue was purified by silica gel column chromatography to give 6.09 g of an orange oily matter (yield: 94.8%).

$^1$H-NMR (600 MHz, CDCl$_3$) δ: 0.96 (6H, t, J=7.7 Hz), 1.32-1.39 (4H, m), 1.55-1.60 (4H, m), 3.28 (4H, t, J=7.7 Hz), 6.60 (2H, d, J=8.8 Hz), 6.84 (1H, d, J=15.9 Hz), 6.95 (1H, d, J=3.9 Hz), 6.96 (1H, d, J=3.9 Hz), 6.99 (1H, d, J=15.9 Hz), 7.09 (1H, t, J=3.0 Hz), 7.31 (2H, d, J=8.8 Hz)

$^{13}$C-NMR (150 MHz, CDCl$_3$) δ: 14.0, 20.3, 29.5, 50.8, 116.9, 128.8, 111.7, 122.7, 124.1, 124.2, 127.4 127.6, 128.8, 144.2, 147.8

(1-2) 5-[2-[4-(dibutylamino)phenyl]vinyl]thiophene-2-carboaldehyde

[Formula 292]

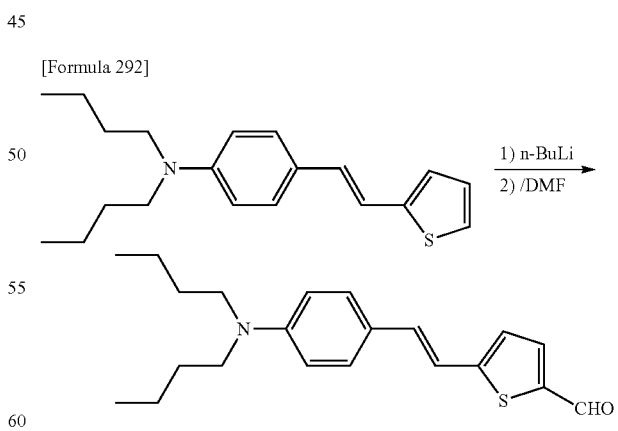

In a stream of argon, in tetrahydrofuran was dissolved 3.0 g (0.97 mmol) of dibutyl[4-[2-(thiophene-2-yl)vinyl] phenyl]amine. To this mixture, 9.0 ml of n-butyllithium (1.6 M solution in hexane) (14.4 mmol) was added dropwise under cooling. After the mixture was stirred for 1 hour, 0.87 g (11.9 mmol) of N,N-dimethylformamide was added dropwise thereto. After 20 minutes, the temperature was allowed to rise and 30 ml of water was added dropwise. Tetrahydrofuran was evaporated off. Extraction with chloroform, drying over anhydrous sodium sulfate, and concentration were performed. The residual liquid was purified by silica gel column chromatography to give 3.12 g of a reddish orange oily matter (yield: 95.5%).

$^1$H-NMR (600 MHz, CDCl$_3$) δ: 0.96 (6H, t, J=7.7 Hz), 1.33-1.39 (4H, m), 1.55-1.61 (4H, m), 3.30 (4H, t, J=7.7 Hz), 6.61 (2H, d, J=8.8 Hz), 6.96 (1H, d, J=15.9 Hz), 7.07 (1H, d, J=15.9 Hz), 7.03 (1H, d, J=4.2 Hz), 7.35 (2H, d, J=8.8 Hz), 7.61 (1H, t, J=4.2 Hz), 9.81 (1H, s)

$^{13}$C-NMR (150 MHz, CDCl$_3$) δ: 14.0, 20.3, 29.4, 50.7, 115.5, 133.7, 111.5, 122.8, 124.7, 128.5, 137.6, 140.0, 148.7, 154.5, 182.2

(1-3) 2-[4-[2-[5-[2-(4-dibutylaminophenyl)vinyl] thiophene-2-yl] vinyl]-3-cyano-5,5-dimethyl-2(5H)-furanylidene] propanedinitrile

[Formula 293]

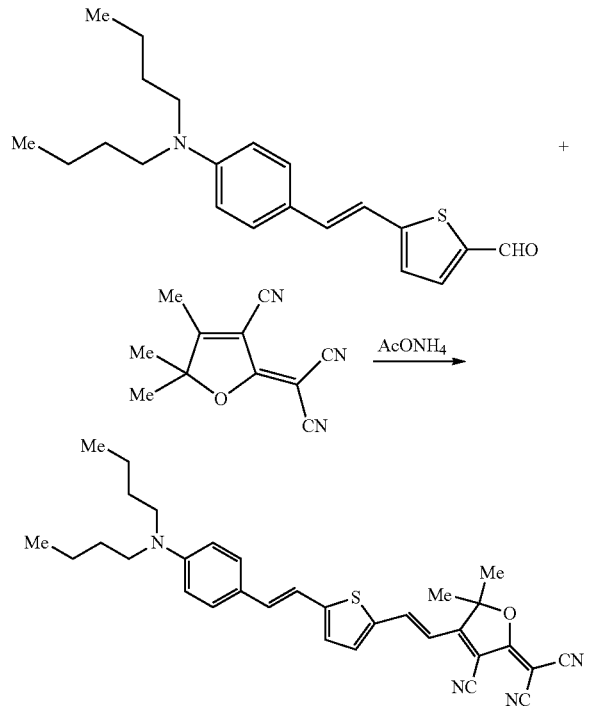

In an ethanol/tetrahydrofuran mixed solvent were dissolved 170 mg (0.50 mmol) of 5-[2-[4-(dibutylamino)phenyl]vinyl] thiophene-2-carboaldehyde and 110 mg (0.55 mmol) of 2-(3-cyano-4,5,5-trimethyl-2(5H)-furanylidene) propanedinitrile. To this mixture, 42 mg of ammonium acetate was added, and the mixture was stirred at room temperature. The solvent was evaporated off. The residue was purified by silica gel column chromatography and washed with ethanol to give 198 mg of a black crystal having a mp of 208-209° C. (yield: 76.1%).

$^1$H-NMR (600 MHz, CDCl$_3$) δ: 0.97 (6H, t, J=7.1 Hz), 1.34-1.40 (4H, m), 1.57-1.62 (4H, m), 1.75 (6H, s), 3.32 (4H, t, J=7.7 Hz), 6.55 (1H, d, J=15.9 Hz), 6.63 (2H, d, J=8.8 Hz), 6.98 (1H, d, J=15.9 Hz), 7.02 (1H, d, J=3.8 Hz), 7.08 (1H, d, J=15.9 Hz), 7.36 (1H, d, J=3.8 Hz), 7.37 (2H, d, J=8.8 Hz), 7.77 (1H, d, J=15.9 Hz)

$^{13}$C-NMR (150 MHz, CDCl$_3$) δ: 14.0, 20.3, 26.6, 29.5, 50.8, 55.8, 95.8, 96.9, 111.1, 111.5, 111.7, 112.3, 115.3, 122.7, 126.7, 129.0, 135.1, 137.2, 137.8, 139.4, 149.2, 154.8, 172.9, 175.8

Comparative Example 2

2-[4-[2-[4-[2-(4-dibutylaminophenyl)vinyl]phenyl] vinyl]-3-cyano-5,5-dimethyl-2(5H)-furanylidene] propanedinitrile

[Formula 294]

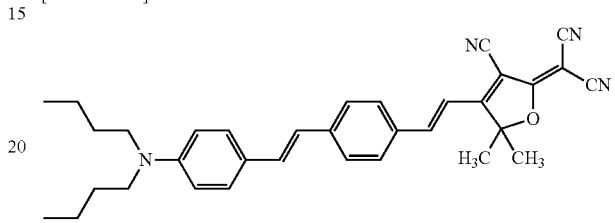

(2-1) 4-[2-[4-(dibutylamino)phenyl]vinyl]benzyl alcohol

[Formula 295]

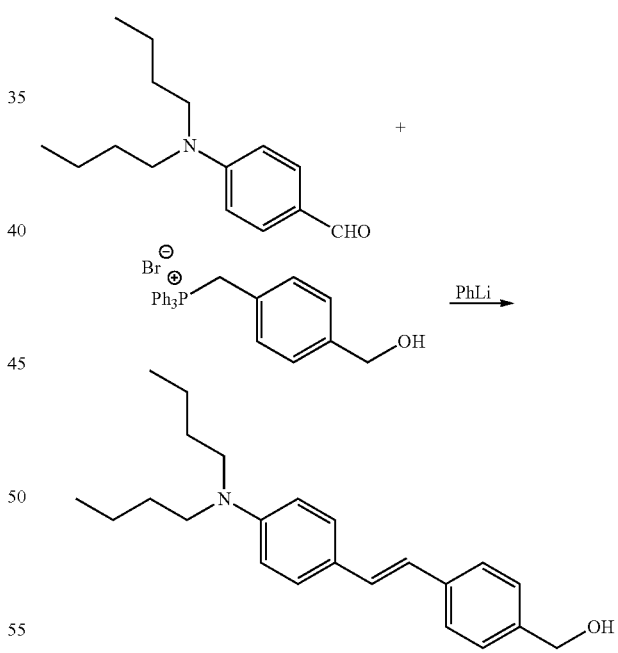

In a stream of argon, to 40 ml of tetrahydrofuran was added 8.0 g of phenyllithium (19% solution in dibutylether) (18.1 mmol). To this mixture, 3.81 g (8.2 mmol) of 4-(hydroxymethyl)benzyltriphenylphosphonium bromide was added under cooling. After the mixture was stirred at the same temperature, 2.0 g (8.6 mmol) of 4-(dibutylamino) benzaldehyde was added thereto. The mixture was stirred at the same temperature for 1 hour. After the reaction mixture was added to water, extraction with toluene, washing with a saturated saline solution, and drying over anhydrous sodium sulfate were performed. Toluene was evaporated off. The residue was purified by silica gel column chromatography to give 2.37 g of a yellow liquid (yield: 85.5%).

$^1$H-NMR (600 MHz, CDCl$_3$) δ: 0.96 (6H, t, J=7.7 Hz), 1.33-1.39 (4H, m), 1.55-1.60 (4H, m), 3.28 (4H, t, J=7.7 Hz), 4.66 (2H, d, J=4.9 Hz), 6.62 (2H, d, J=8.8 Hz), 6.86 (1H, d, J=16.5 Hz), 7.02 (1H, d, J=16.5 Hz), 7.31 (2H, d, J=8.3 Hz), 7.37 (2H, d, J=8.8 Hz), 7.45 (2H, d, J=8.3 Hz)

$^{13}$C-NMR (150 MHz, CDCl$_3$) δ: 14.0, 20.3, 29.5, 50.8, 65.3, 111.6, 123.2, 124.1, 126.1, 127.4, 127.7, 129.0, 138.0, 139.2, 148.0

(2-2) 4-[2-[4-(dibutylamino)phenyl]vinyl]benzaldehyde

[Formula 296]

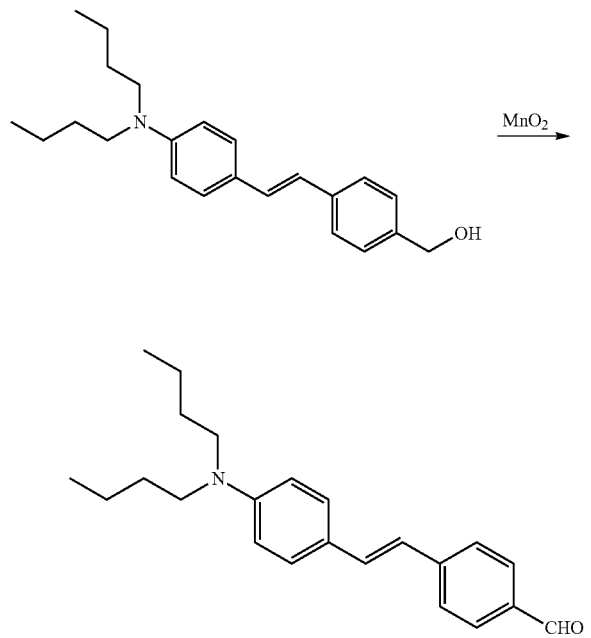

In 30 ml of dichloromethane was suspended 6.0 g (69.0 mmol) of active manganese dioxide. Next, 1.17 g (3.45 mmol) of 4-[2-[4-(dibutylamino)phenyl]vinyl]benzyl alcohol was dissolved in dichloromethane and added to the suspension. After stirred at room temperature for 20 hours, the suspension was filtrated and the solvent was evaporated off. The residue was purified by silica gel column chromatography to give 0.74 g of a yellow crystal (yield: 64.1%).

$^1$H-NMR (600 MHz, CDCl$_3$) δ: 0.97 (6H, t, J=7.7 Hz), 1.34-1.40 (4H, m), 1.56-1.62 (4H, m), 3.30 (4H, t, J=7.7 Hz), 6.63 (2H, d, J=8.2 Hz), 6.89 (1H, d, J=15.9 Hz), 7.19 (1H, d, J=15.9 Hz), 7.40 (2H, d, J=8.8 Hz), 7.59 (2H, d, J=8.3 Hz), 7.82 (2H, d, J=8.3 Hz), 9.95 (1H, s)

$^{13}$C-NMR (150 MHz, CDCl$_3$) δ: 14.0, 20.3, 29.5, 50.8, 111.6, 122.0, 123.5, 126.1, 128.4, 130.2, 132.7, 134.4, 144.8, 148.5, 191.6

(2-3) 2-[4-[2-[4-[2-(4-dibutylaminophenyl)vinyl]phenyl] vinyl]-3-cyano-5,5-dimethyl-2(5H)-furanylidene] propanedinitrile

[Formula 297]

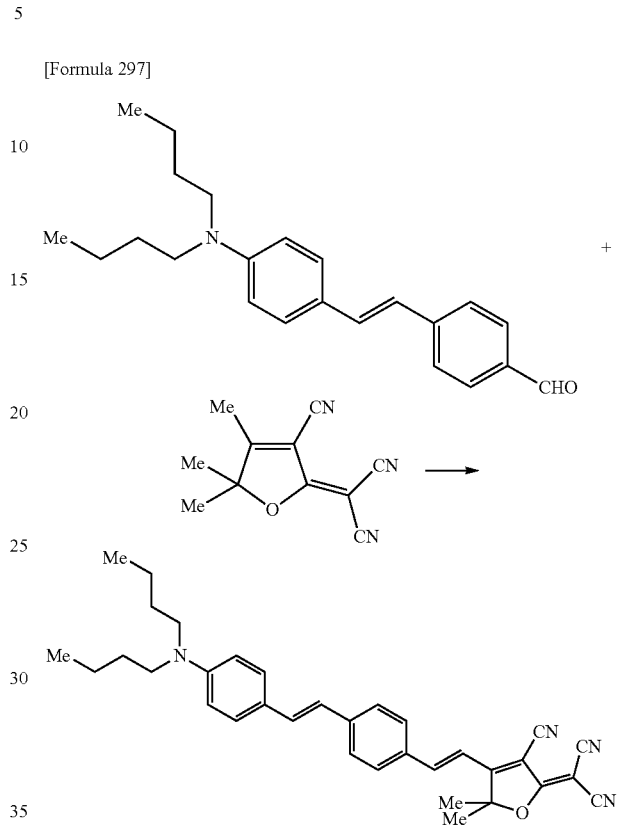

In an ethanol/tetrahydrofuran mixed solvent were dissolved 180 mg (0.54 mmol) of 4-[2-(4-dibutylaminophenyl) vinyl] benzaldehyde and 118 mg (0.59 mmol) of 2-(3-cyano-4,5,5-trimethyl-2(5H)-furanylidene]propanedinitrile. To this mixture, 46 mg (0.60 mmol) of ammonium acetate was added, and the mixture was stirred at room temperature. The solvent was evaporated off. The residue was purified by silica gel column chromatography and washed with ethanol to give 245 mg of a black crystal having a mp of 224-226° C. (yield: 88.4%).

$^1$H-NMR (600 MHz, CDCl$_3$) δ: 0.97 (6H, t, J=7.1 Hz), 1.34-1.41 (4H, m), 1.57-1.62 (4H, m), 1.80 (6H, s), 3.31 (4H, t, J=7.7 Hz), 6.63 (2H, d, J=8.8 Hz), 6.88 (1H, d, J=15.9 Hz), 7.00 (1H, d, J=16.5 Hz), 7.21 (1H, d, J=16.5 Hz), 7.41 (2H, d, J=8.8 Hz), 7.54 (2H, d, J=8.8 Hz), 7.59 (2H, d, J=8.8 Hz), 7.61 (1H, d, J=15.9 Hz)

$^{13}$C-NMR (150 MHz, CDCl$_3$) δ: 14.0, 20.3, 26.6, 29.5, 50.8, 57.2, 97.4, 98.7, 110.5, 111.1, 111.6, 111.9, 113.3, 121.7, 123.5, 126.7, 128.7, 129.8, 131.6, 132.9, 134.8, 147.1, 148.7, 173.7, 175.5

Test Example 1

The initial decomposition temperature (Td), maximum absorbance spectrum (λmax), and hyperpolarizability (β) of each of the compounds obtained in Examples 1 to 15 and Comparative Examples 1 and 2 were measured as described below. The results are shown in Tables 6 and 7.

Measurement of Initial Decomposition Temperature (Td)

The initial decomposition temperature (Td) was measured with a thermogravimetry-differential thermal analysis apparatus TG8120 (Rigaku Corporation) under the following conditions: test sample, 5 mg; standard sample, $Al_2O_3$; nitrogen atmosphere; and heating rate, 10° C./min.

Measurement of Hyperpolarizability (β)

The hyperpolarizability (β) was measured in the same manner as the method described in the following reference: "Intermolecular Coupling Enhancement of the Molecular Hyperpolarizability in Multichromophoric Dipolar Dendrons", Shiyoshi Yokoyama, Tatsuo Nakahama, Akira Otomo, and Shinro Mashiko, Journal of the American Chemical Society, vol. 122, pages 3174-3181 (2000). The laser light source was an erbium-doped fiber laser (Aisin Seiki Co., Ltd.) (Femtolite C-40-SP, BS-60; wavelength: 1.56 μm; pulse duration: 100 fsec; repetition rate: 50 MHz; and output: 60 mW). The photodetector was a photomultiplier tube (R3896) (Hamamatsu Photonics K.K.). Each of the nonlinear optical compounds was adjusted to a concentration of 5 μmol/l in 1,4-dioxane and used as the test sample. The hyperpolarizability (βr) of the nonlinear optical compound was determined by irradiating a laser beam, detecting the generated second harmonic wave intensity with the photomultiplier tube, and comparing the hyperpolarizability with that of a reference sample, according to the method described in the reference. The hyperpolarizability of the reference sample was the hyperpolarizability of chloroform ($-0.49 \times 10^{-30}$ esu) as the solvent or the hyperpolarizability of the nonlinear optical compound (No. 5b) described in the following reference: "Pyrroline Chromophores for Electro-Optics", Sei-Hum Jang, Jingdong Luo, Neil M. Tucker, Amalia Leclercq, Egbert Zojer, Marnie A. Haller, Tae-Dong Kim, Jae-Wook Kang, Kimberly Firestone, Denise Bale, David Lao, Jason B. Benedict, Dawn Cohen, Werner Kaminsky, Bart Kahr, Jean-Juc Brédas, Philip Reid, Larry R. Dalton, and Alex K.-Y. Jen, Chemistry of Materials, 18(13), pages 2982-2988 (2006).

Measurement of Maximum Absorption Wavelength (λmax)

Each of the nonlinear optical compounds was adjusted to a concentration of 5 μmol/l in 1,4-dioxane, and the maximum absorption wavelength (λmax) of the nonlinear optical compound was measured with a ultraviolet-visible spectroscopy (UVmini-1240) (Shimadzu Corporation).

TABLE 6

| | $T_d$ (° C.) | $\lambda_{max}$ (nm) | β ×$10^{-30}$ (esu) | $\beta_r$ |
|---|---|---|---|---|
| Comparative Example 1 | 257.7 | 610 | 2179 | 1 |
| Example 1 | 247.0 | 643 | 7256 | 3.3 |
| Example 2 | 199.2 | 710 | 11309 | 5.2 |
| Example 3 | 206.5 | 726 | 12181 | 5.6 |
| Example 4 | 252.6 | 644 | 7539 | 3.5 |
| Example 5 | 193.7 | 713 | 11876 | 5.5 |
| Example 6 | 219.8 | 727 | 10916 | 4.8 |
| Example 13 | 283.3 | 648 | 8389 | 3.9 |
| Example 14 | 261.2 | 716 | 11875 | 5.5 |
| Example 15 | 230.3 | 731 | 10437 | 4.8 |

($\beta_r$ is the ratio to the hyperpolarizability of Comparative Example 1.)

TABLE 7

| | $T_d$ (° C.) | $\lambda_{max}$ (nm) | β ×$10^{-30}$ (esu) | $\beta_r$ |
|---|---|---|---|---|
| Comparative Example 2 | 258.4 | 550 | 653 | 1 |
| Example 7 | 271.1 | 573 | 1216 | 1.9 |
| Example 8 | 255.7 | 629 | 2694 | 4.1 |
| Example 9 | 235.9 | 637 | 2609 | 4.0 |
| Example 10 | 261.1 | 576 | 1654 | 2.5 |
| Example 11 | 256.5 | 637 | 3656 | 5.6 |
| Example 12 | 232.3 | 644 | 3394 | 5.2 |

($\beta_r$ is the ratio to the hyperpolarizability of Comparative Example 2.)

As is apparent from Tables 6 and 7, the initial decomposition temperatures (Td) of the nonlinear optical compounds (Examples 1 to 15) of the present invention are not significantly different from those of the nonlinear optical compounds of Comparative Examples 1 and 2. However, it was shown that the nonlinear optical compounds (Examples 1 to 15) of the present invention have a markedly improved hyperpolarizability (β) in comparison with the nonlinear optical compounds of Comparative Examples 1 and 2.

These test results revealed that, in comparison with the nonlinear optical compounds of Comparative Examples 1 and 2, the nonlinear optical compounds of the present invention have a far superior nonlinear optical property that has been improved without significantly deterioration of the heat resistance.

Test Example 2

The initial decomposition temperature (Td), maximum absorbance spectrum (λmax), and hyperpolarizability (β) of each of the compounds obtained in Examples 1 to 6, 13 to 18, 27-1 to 27-28, 28 to 30, and 35 to 57 and Comparative Example 1 were measured as described below. The results are shown in Table 8.

Measurement of Initial Decomposition Temperature (Td)

The initial decomposition temperature (Td) was measured with a thermogravimetry-differential thermal analysis apparatus TG8120 (Rigaku Corporation) under the following conditions: test sample, 5 mg; standard sample, $Al_2O_3$; nitrogen atmosphere; and heating rate, 10° C./min.

Measurement of Hyperpolarizabilities (β)

Measurement of the hyperpolarizability (β) and calculation of the nonresonant hyperpolarizability ($\beta_0$) were performed in the same manner as the method described in the following reference: "Intermolecular Coupling Enhancement of the Molecular Hyperpolarizability in Multichromophoric Dipolar Dendron", Shiyoshi Yokoyama, Tatsuo Nakahama, Akira Otomo, and Shinro Mashiko, Journal of the American Chemical Society, vol. 122, pages 3174-3181 (2000). The laser light source was a Nd: YAG laser OPO system (Spectra-Physics K.K.) (Quanta Ray Nd: YAG laser, OPO versaScan; wavelength: 1.90 μm; pulse width: 20 nsec; repetition rate: 10 Hz; and output: 90 mW). The photodetector was a photomultiplier tube (R2658) (Hamamatsu Photonics K.K.). Each of the nonlinear optical compounds was adjusted to a concentration of 5 μmol/l in chloroform and used as the test sample. The hyperpolarizability (β) of the nonlinear optical compound was determined by irradiating a laser beam, detecting the generated second harmonic wave intensity with the photomultiplier tube, and comparing the hyperpolarizability with that of a reference sample, according to the method described in the reference. The hyperpolarizability of the reference sample was the hyperpolarizability of chloroform ($-0.49 \times 10^{-30}$ esu) as the solvent or the hyperpolarizability of the nonlinear optical compound (No. 5b) described in the following reference: "Pyrroline Chromophores for Electro-Optics", Sei-Hum Jang, Jingdong Luo, Neil M. Tucker, Amalia Leclercq, Egbert Zojer, Marnie A. Haller, Tae-Dong Kim, Jae-Wook Kang, Kimberly Firestone, Denise Bale, David Lao, Jason B. Benedict, Dawn Cohen, Werner Kaminsky, Bart Kahr, Jean-Juc Brédas, Philip Reid, Larry R. Dalton, and Alex K.-Y. Jen, Chemistry Materials, vol. 28, pages 2982-2988 (2006).

Measurement of Maximum Absorption Wavelength ($\lambda$max)

Each of the nonlinear optical compounds was adjusted to a concentration of 10 µmol/l in chloroform, and the maximum absorption wavelength ($\lambda$max) of the nonlinear optical compound was measured with a ultraviolet-visible spectroscopy (U-4000) (Hitachi, Ltd.).

TABLE 8

| | $T_d$ (°C.) | $\lambda_{max}$ (nm) | $\beta \times 10^{-30}$ (esu) | $\beta_r$ | $\beta_0 \times 10^{-30}$ (esu) | $\beta_{0r}$ |
|---|---|---|---|---|---|---|
| Comparative Example 1 | 257.7 | 685 | 1498 | 1 | 627 | 1 |
| Example 1 | 247.0 | 719 | 2666 | 1.8 | 976 | 1.6 |
| Example 2 | 199.2 | 814 | 9551 | 6.4 | 2073 | 3.3 |
| Example 3 | 206.5 | 819 | 10856 | 7.2 | 2270 | 3.6 |
| Example 4 | 252.6 | 715 | 3161 | 2.1 | 1176 | 1.9 |
| Example 5 | 193.7 | 812 | 9491 | 6.3 | 2090 | 3.3 |
| Example 6 | 219.8 | 823 | 10203 | 6.8 | 2068 | 3.3 |
| Example 13 | 283.3 | 724 | 4434 | 3.0 | 1589 | 2.5 |
| Example 14 | 261.2 | 826 | 11864 | 7.9 | 2348 | 3.7 |
| Example 15 | 230.3 | 839 | 12911 | 8.6 | 2287 | 3.6 |
| Example 16 | 187.6 | 716 | 2913 | 1.9 | 1080 | 1.7 |
| Example 17 | 256.1 | 824 | 11535 | 7.7 | 2320 | 3.7 |
| Example 18 | 231.4 | 836 | 12538 | 8.4 | 2281 | 3.6 |
| Example 27-1 | 261.8 | 717 | 3490 | 2.3 | 1288 | 2.1 |
| Example 27-2 | 200.6 | 818 | 9906 | 6.6 | 2087 | 3.3 |
| Example 27-3 | 215.2 | 829 | 10856 | 7.2 | 2096 | 3.3 |
| Example 27-4 | 279.0 | 706 | 2589 | 1.7 | 999 | 1.6 |
| Example 27-5 | 237.1 | 810 | 8988 | 6.0 | 2008 | 3.2 |
| Example 27-6 | 226.4 | 818 | 10461 | 7.0 | 2204 | 3.5 |
| Example 27-7 | 259.9 | 710 | 3127 | 2.1 | 1188 | 1.9 |
| Example 27-8 | 251.3 | 812 | 8498 | 5.7 | 1871 | 3.0 |
| Example 27-9 | 231.1 | 816 | 7700 | 5.1 | 1647 | 2.6 |
| Example 27-10 | 251.3 | 713 | 2943 | 2.0 | 1104 | 1.8 |
| Example 27-11 | 224.1 | 813 | 8409 | 5.6 | 1838 | 2.9 |
| Example 27-12 | 202.4 | 821 | 8732 | 5.8 | 1798 | 2.9 |
| Example 27-13 | 250.4 | 713 | 2262 | 1.5 | 849 | 1.4 |
| Example 27-14 | 248.4 | 809 | 7830 | 5.2 | 1762 | 2.8 |
| Example 27-15 | 230.9 | 816 | 9432 | 6.3 | 2017 | 3.2 |
| Example 27-16 | 247.0 | 712 | 2506 | 1.7 | 944 | 1.5 |
| Example 27-17 | 183.1 | 814 | 6776 | 4.5 | 1470 | 2.3 |
| Example 27-18 | 187.6 | 823 | 8248 | 5.5 | 1672 | 2.7 |
| Example 27-19 | 296.5 | 701 | 3259 | 2.2 | 1282 | 2.0 |
| Example 27-20 | 258.0 | 806 | 6510 | 4.3 | 1496 | 2.4 |
| Example 27-21 | 253.3 | 808 | 7041 | 4.7 | 1595 | 2.5 |
| Example 27-22 | 267.6 | 676 | 2046 | 1.4 | 882 | 1.4 |
| Example 27-23 | 257.5 | 774 | 4743 | 3.2 | 1330 | 2.1 |
| Example 27-24 | 246.1 | 781 | 5865 | 3.9 | 1580 | 2.5 |
| Example 27-25 | 276.1 | 662 | 1459 | 1.0 | 659 | 1.1 |
| Example 27-26 | 235.4 | 742 | 4313 | 2.9 | 1425 | 2.3 |
| Example 27-27 | 208.7 | 756 | 5112 | 3.4 | 1578 | 2.5 |
| Example 27-28 | 191.6 | 826 | 7935 | 5.3 | 1570 | 2.5 |
| Example 28 | 261.3 | 592 | 1321 | 0.9 | 730 | 1.2 |
| Example 29 | 223.8 | 629 | 2658 | 1.8 | 1329 | 2.1 |
| Example 30 | 216.5 | 632 | 3435 | 2.3 | 1702 | 2.7 |
| Example 35 | 238.9 | 675 | 3356 | 2.2 | 1452 | 2.3 |
| Example 36 | 210.6 | 731 | 2786 | 1.9 | 968 | 1.5 |
| Example 37 | 211.0 | 737 | 3445 | 2.3 | 1165 | 1.9 |
| Example 38 | 216.8 | 696 | 1962 | 1.3 | 787 | 1.3 |
| Example 39 | 259.2 | 826 | 4810 | 3.2 | 952 | 1.5 |
| Example 40 | 205.4 | 833 | 6375 | 4.3 | 1190 | 1.9 |
| Example 41 | 265.3 | 721 | 3507 | 2.3 | 1273 | 2.0 |
| Example 42 | 257.5 | 819 | 4778 | 3.2 | 999 | 1.6 |
| Example 43 | 235.9 | 830 | 4366 | 2.9 | 836 | 1.3 |
| Example 44 | 251.5 | 717 | 4546 | 3.0 | 1678 | 2.7 |
| Example 45 | 245.9 | 830 | 4926 | 3.3 | 943 | 1.5 |
| Example 46 | 238.8 | 747 | 4299 | 2.9 | 1387 | 2.2 |
| Example 47 | 204.4 | 919 | 17572 | 11.7 | — | — |
| Example 48 | 216.4 | 927 | 21311 | 14.2 | — | — |
| Example 49 | 262.2 | 750 | 5254 | 3.5 | 1670 | 2.7 |
| Example 50 | 188.5 | 928 | 11432 | 7.6 | — | — |
| Example 51 | 211.8 | 933 | 11386 | 7.6 | — | — |
| Example 52 | 257.9 | 678 | 2362 | 1.6 | 1011 | 1.6 |
| Example 53 | 251.3 | 749 | 4360 | 3.2 | 1553 | 2.5 |
| Example 54 | 233.6 | 840 | 10124 | 6.8 | 1777 | 2.8 |
| Example 55 | 233.7 | 846 | 10718 | 7.2 | 1778 | 2.8 |
| Example 56 | 307 | 767 | 4374 | 2.9 | 1275 | 2.0 |
| Example 57 | 301 | 767 | 4603 | 3.1 | 1341 | 2.1 |

($\beta_r$ and $\beta_{0r}$ are the ratios to the hyperpolarizability and to the nonresonant hyperpolarizability of Comparative Example 1, respectively.)

As is apparent from Table 8, the initial decomposition temperatures (Td) of the nonlinear optical compounds (Examples 1 to 6, 13 to 18, 27-1 to 27-28, 28 to 30, and 35 to 57) of the present invention are not significantly different from that of the nonlinear optical compound of Comparative Example 1. However, it was shown that the nonlinear optical compounds (Examples 1 to 6, 13 to 18, 27-1 to 27-28, 28 to 30, and 35 to 57) of the present invention have a markedly improved hyperpolarizabilities ($\beta$) in comparison with the nonlinear optical compound of Comparative Example 1.

These test results revealed that, in comparison with the nonlinear optical compound of Comparative Example 1, the nonlinear optical compounds of the present invention have a far superior nonlinear optical property that has been improved without significantly deterioration of the heat resistance.

INDUSTRIAL APPLICABILITY

By employing an aryl group substituted with a substituted oxy group in the donor structure D, the nonlinear optical property of the nonlinear optical compound of the present invention is improved without significant deterioration of the heat resistance. A material containing such a nonlinear optical compound exhibiting a larger nonlinear optical effect can give a nonlinear optical element that can change the intensity and phase of light in response to even a weaker external field applied thereto.

When such a nonlinear optical element is used in, for example, an optical modulator utilizing the electrooptic effect, the optical modulator can be driven by lower electric power, which makes possible energy saving and miniaturization. In addition, since the element has a larger nonlinear optical effect, which can change the intensity and phase of light in response to even a weaker electric field applied thereto, the element can be used for an electric field sensor that measures a leaked electric field of an electronic integrated circuit or for a sensor for terahertz electromagnetic waves. Further, the element in combination with an electronic circuit can be used for, for example, optical signal transmission between electronic circuits.

REFERENCE SIGNS LIST

1. Substrate, 2. Lower Electrode, 3. First Clad Layer, 4. Core Layer, 6. Second Clad Layer, 8. Upper Electrode, 9. Optical Waveguide Core, 10. Optical Waveguide (Nonlinear Optical Element)

The invention claimed is:
1. A chromophore represented by formula D-B-A, wherein B is represented by the formula B-I:

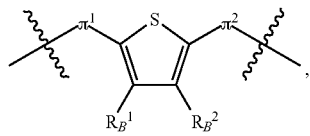

(B-I)

wherein
$\pi^1$ and $\pi^2$ independently represent the same or different carbon-carbon conjugated π-bonds, and $\pi^1$ and $\pi^2$ each may have the same or different substituents; and
$R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$ and $R_B^2$ each may have the same or different substituents and
D is represented by the formula D-1-1:

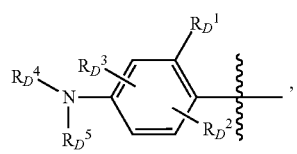

(D-1-1)

wherein
$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent selected from the group consisting of an alkyl group, a haloalkyl group, an aryl group, a heteroaryl group, an aralkyl group, a silyl group, an alkenyl group, an alkynyl group, an acyl group, and an alkenylcarbonyl group;
$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents selected from the group consisting of an alkyl group, a haloalkyl group, an aryl group, a heteroaryl group, an aralkyl group, a silyl group, an alkenyl group, an alkynyl group, an acyl group, and an alkenylcarbonyl group
when $R_D^2$ and $R_D^3$ are each attached to adjacent carbon atoms of the aryl of D,
$R_D^2$ and $R_D^3$ may form, together with the two adjacent carbon atoms, a ring optionally having a substituent selected from the group consisting of an alkyl group, a haloalkyl group, an aryl group, a heteroaryl group, an aralkyl group, a silyl group, an alkenyl group, an alkynyl group, an acyl group, and an alkenylcarbonyl group; and
$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, or $R_D^4$ and $R_D^5$ form, together with the nitrogen atom to which they are attached, a heterocyclic ring; or
(a) $R_D^2$ and $-NR_D^4R_D^5$ and (b) $R_D^3$ and $-NR_D^4R_D^5$ independently form, together with the carbon atoms to which they are attached, a heterocyclic ring,
A is represented by the formula

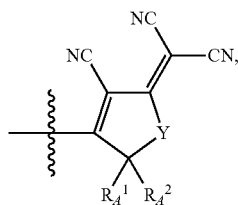

wherein
Y represents $-CR_A^1R_A^2-$, $-O-$, $-S-$, $-SO-$, $-SiR_A^1R_A^2-$, $-NR-$ wherein R represents a hydrogen atom or an alkyl group, or $-C(=CH_2)-$; and
$R_A^1$ and $R_A^2$ independently represent a hydrogen atom, an alkyl group, an alkenyl group, a cycloalkyl group, a cycloalkenyl group, an alkoxy group, a haloalkyl group, or an aryl group, or
$R_A^1$ and $R_A^2$ form, together with the carbon atom to which they are attached, a structure that is represented by the following formula:

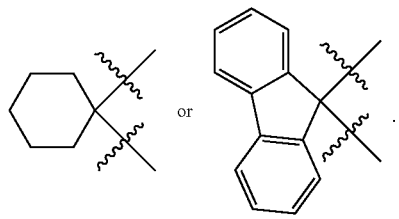 [SMILES: *C1(*)CCCCC1 ; *C1(*)c2ccccc2-c2ccccc21]

2. The chromophore according to claim 1, wherein the chromophore is represented by the formula I-1-1:

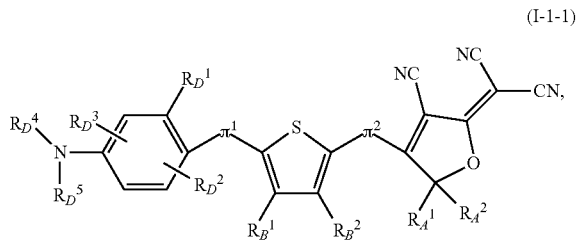

(I-1-1)

wherein
$\pi^1$ and $\pi^2$ independently represent the same or different carbon-carbon conjugated π-bonds, and $\pi^1$ and $\pi^2$ each may have the same or different substituents;
$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent as defined in claim 1;
$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents as defined in claim 1 when $R_D^2$ and $R_D^3$ are each attached to adjacent carbon atoms of the aryl of D, $R_D^2$ and $R_D^3$ may form, together with the two adjacent carbon atoms, a ring optionally having a substituent as defined in claim 1;

$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, or $R_D^4$ and $R_D^5$ form, together with the nitrogen atom to which they are attached, a heterocyclic ring containing the nitrogen atom as a hetero atom; or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom;

$R_B^1$ and $R_B^2$ independently represent a hydrogen atom, an alkyl group, an alkoxy group, an aryl group, an aralkyl group, an aryloxy group, or an aralkyloxy group, and $R_B^1$ and $R_B^2$ each may have the same or different substituents; and $R_A^1$ and $R_A^2$ independently represent a hydrogen atom, an alkyl group, a haloalkyl group, or an aryl group.

3. A chromophore represented by formula D-B-A, wherein B is represented by the formula B-III:

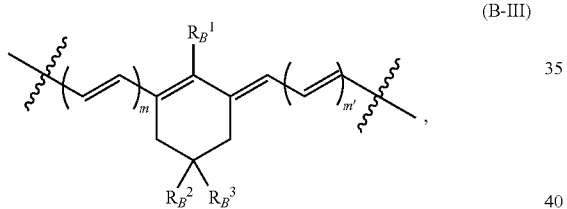

(B-III)

wherein m and m' independently represent an integer of 0 to 3; and $R_B^1$, $R_B^2$, and $R_B^3$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, or an aralkyloxy group, and $R_B^1$, $R_B^2$, and $R_B^3$ each may have the same or different substituents and D is represented by the formula D-1-1:

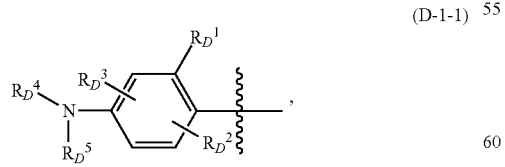

(D-1-1)

wherein $R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent selected from the group consisting of an alkyl group, a haloalkyl group, an aryl group, a heteroaryl group, an aralkyl group, a silyl group, an alkenyl group, an alkynyl group, an acyl group, and an alkenylcarbonyl group;

$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents selected from the group consisting of an alkyl group, a haloalkyl group, an aryl group, a heteroaryl group, an aralkyl group, a silyl group, an alkenyl group, an alkynyl group, an acyl group, and an alkenylcarbonyl group when $R_D^2$ and $R_D^3$ are each attached to adjacent carbon atoms of the aryl of D, $R_D^2$ and $R_D^3$ may form, together with the two adjacent carbon atoms, a ring optionally having a substituent selected from the group consisting of an alkyl group, a haloalkyl group, an aryl group, a heteroaryl group, an aralkyl group, a silyl group, an alkenyl group, an alkynyl group, an acyl group, and an alkenylcarbonyl group; and $R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, or $R_D^4$ and $R_D^5$ form, together with the nitrogen atom to which they are attached, a heterocyclic ring; or (a) $R_D^2$ and —$NR_D^4R_D^5$ and (b) $R_D^3$ and —$NR_D^4R_D^5$ independently form, together with the carbon atoms to which they are attached, a heterocyclic ring, A is represented by the formula

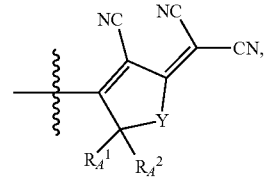

wherein

Y represents —$CR_A^1R_A^2$—, —O—, —S—, —SO—, —$SiR_A^1R_A^2$—, —NR— wherein R represents a hydrogen atom or an alkyl group, or —$C(=CH_2)$—; and $R_A^1$ and $R_A^2$ independently represent a hydrogen atom, an alkyl group, an alkenyl group, a cycloalkyl group, a cycloalkenyl group, an alkoxy group, a haloalkyl group, or an aryl group, or $R_A^1$ and $R_A^2$ form, together with the carbon atom to which they are attached, a structure that is represented by the following formula:

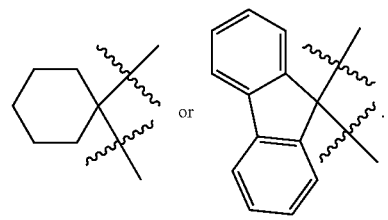 [SMILES: *C1(*)CCCCC1 ; *C1(*)c2ccccc2-c2ccccc21]

4. The chromophore according to claim 3, wherein the chromophore is represented by the formula III-1-1:

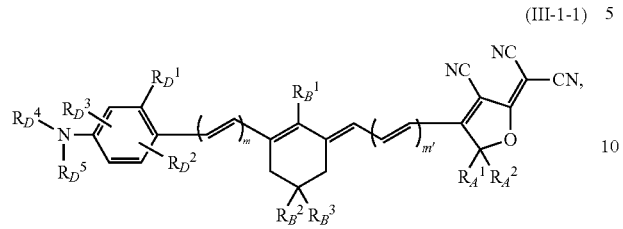

(III-1-1)

wherein
m and m' independently represent an integer of 0 to 3;
$R_D^1$ represents an alkoxy group, an aryloxy group, an aralkyloxy group, a silyloxy group, an alkenyloxy group, an alkenylcarbonyloxy group, an alkynyloxy group, or a hydroxy group; $R_D^2$, and $R_D^3$ independently represent a hydrogen atom or an alkyl group; and $R_D^1$, $R_D^2$, and $R_D^3$ each may have the same or different substituents as defined in claim 3,
when $R_D^2$ and $R_D^3$ are each attached to adjacent carbon atoms of the aryl of D,
(1) $R_D^2$ and $R_D^3$ may form, together with the two adjacent carbon atoms, a ring optionally having a substituent as defined in claim 3;
(2) $R_D^2$ and $R_D^3$ may form, together with the two adjacent carbon atoms, a heterocyclic ring containing an oxygen atom as a hetero atom and optionally having a substituent as defined in claim 3;
$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, or
$R_D^4$ and $R_D^5$ form, together with the nitrogen atom to which they are attached, a heterocyclic ring containing the nitrogen atom as a hetero atom; or
(a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom;
$R_B^1$, $R_B^2$, and $R_B^3$ independently represent a hydrogen atom, an alkyl group, an alkoxy group, an aryl group, an aralkyl group, an aryloxy group, or an aralkyloxy group, and $R_B^1$, $R_B^2$, and $R_B^3$ each may have the same or different substituents; and
$R_A^1$ and $R_A^2$ independently represent a hydrogen atom, an alkyl group, a haloalkyl group, or an aryl group.

5. The chromophore according to claim 3, wherein the chromophore is represented by the formula III-1-1:

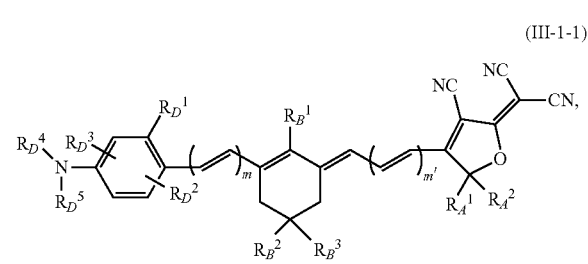

(III-1-1)

wherein
m and m' independently represent an integer of 0 to 3;
$R_D^1$ represents an alkoxy group, an aryloxy group, an aralkyloxy group, a silyloxy group, an alkenyloxy group, an alkenylcarbonyloxy group, an alkynyloxy group, or a hydroxy group, and $R_D^1$ may have a substituent as defined in claim 3;
$R_D^2$ and $R_D^3$ independently represent a hydrogen atom, an alkyl group, an alkoxy group, an aryloxy group, an aralkyloxy group, a silyloxy group, an alkenyloxy group, an alkenylcarbonyloxy group, an alkynyloxy group, or a hydroxy group, and $R_D^2$ and $R_D^3$ each may have the same or different substituents as defined in claim 3
when $R_D^2$ and $R_D^3$ are each attached to adjacent carbon atoms of the aryl of D,
$R_D^2$ and $R_D^3$ may form, together with the two adjacent carbon atoms, a ring optionally having a substituent as defined in claim 3;
$R_D^4$ and $R_D^5$ independently represent a hydrogen atom, an alkyl group, a haloalkyl group, a hydroxyalkyl group, an acyloxyalkyl group, a silyloxyalkyl group, an aminoalkyl group, or an aryl group, or
$R_D^4$ and $R_D^5$ form, together with the nitrogen atom to which they are attached, a heterocyclic ring containing the nitrogen atom as a hetero atom; or
(a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom;
$R_B^1$, $R_B^2$, and $R_B^3$ independently represent a hydrogen atom, an alkyl group, an alkoxy group, an aryl group, an aralkyl group, an aryloxy group, or an aralkyloxy group, and $R_B^1$, $R_B^2$, and $R_B^3$ each may have the same or different substituents; and
$R_A^1$ and $R_A^2$ independently represent a hydrogen atom, an alkyl group, a haloalkyl group, or an aryl group.

6. The chromophore according to claim 1, wherein the chromophore is represented by the formula selected from the group consisting of:

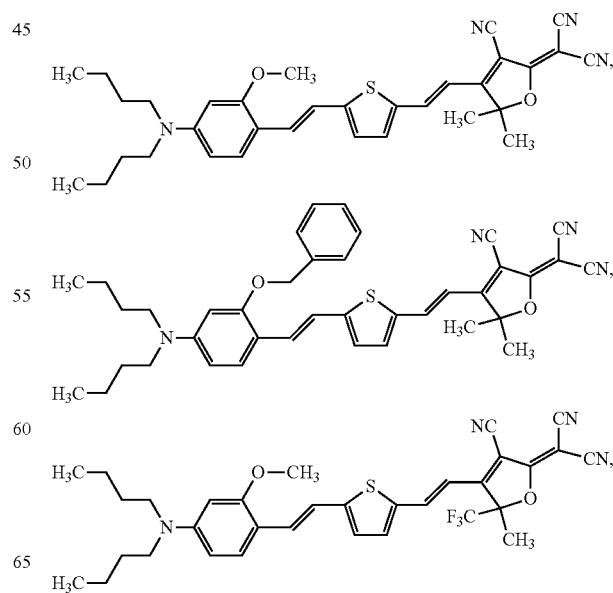

271
-continued
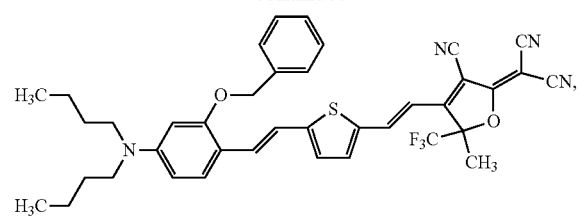
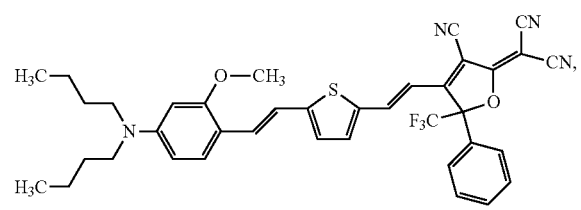
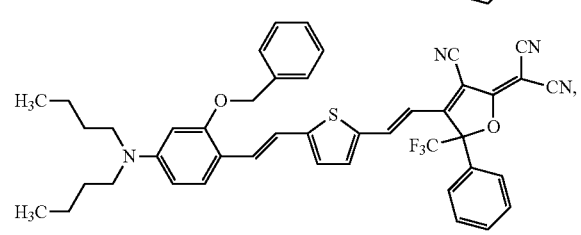
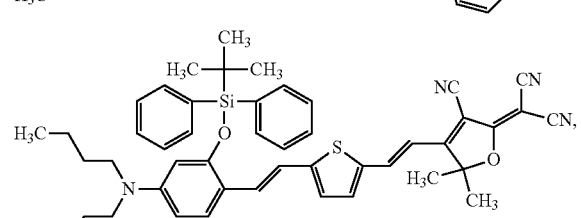
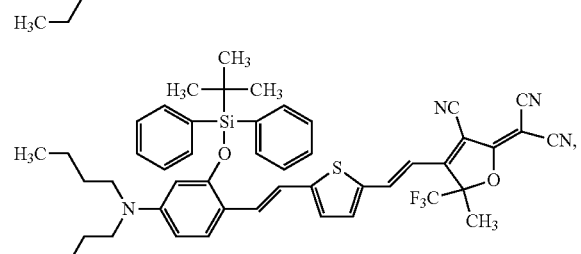
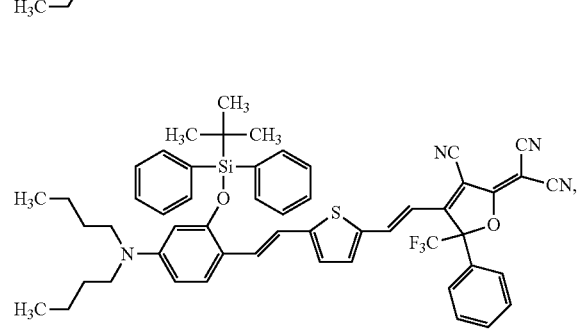
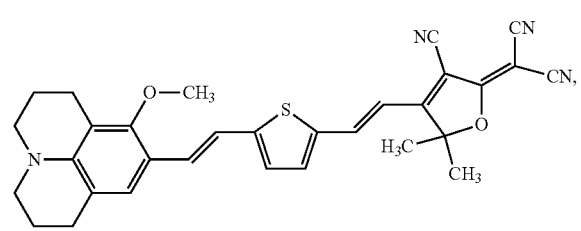
272
-continued
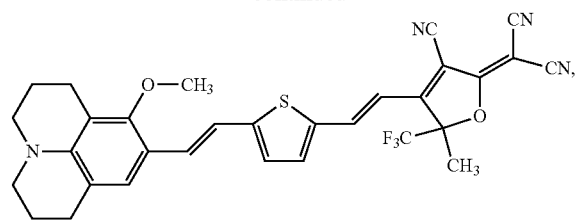
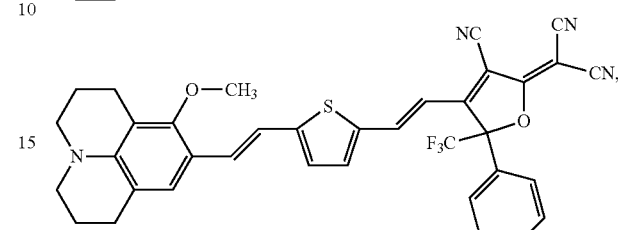
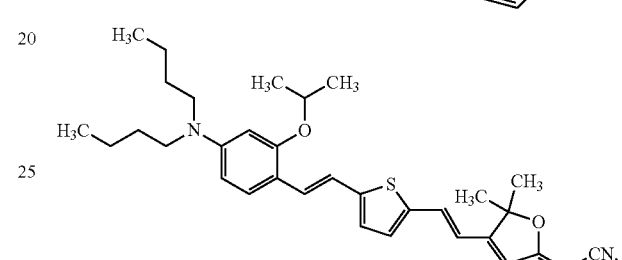
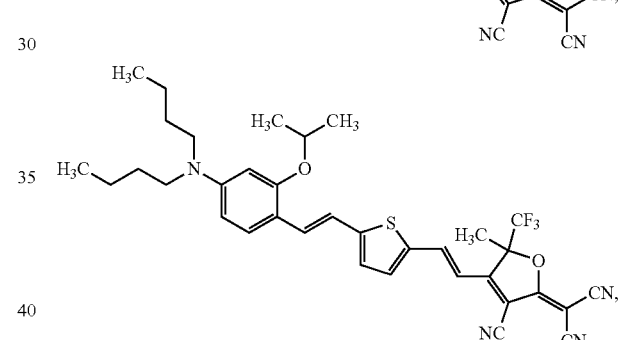
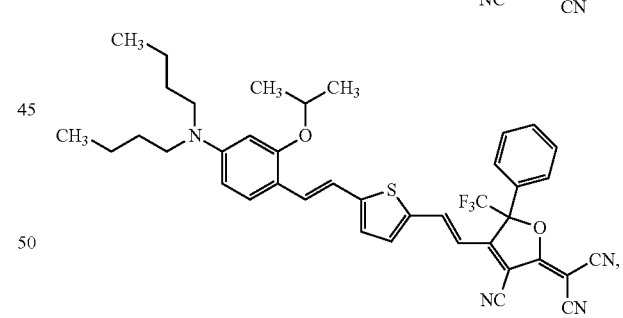
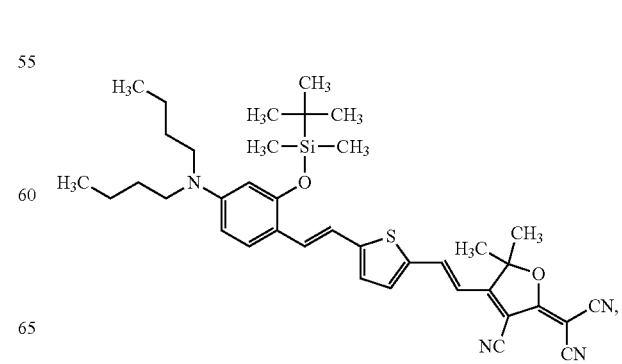

273
-continued
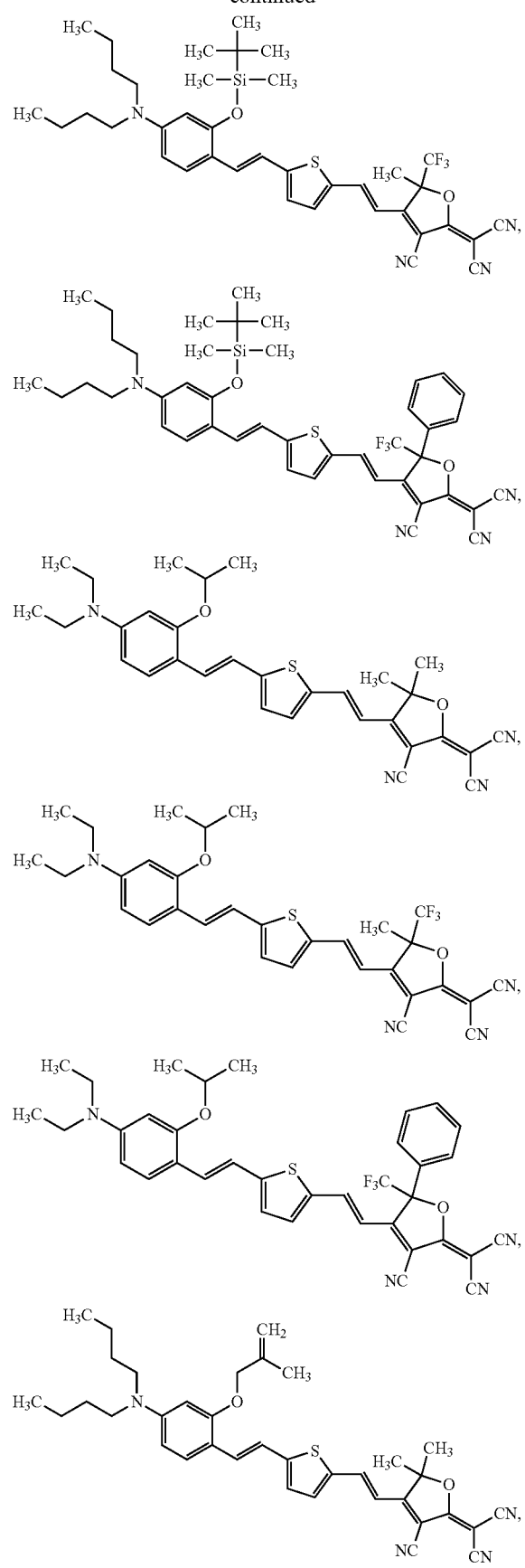
274
-continued
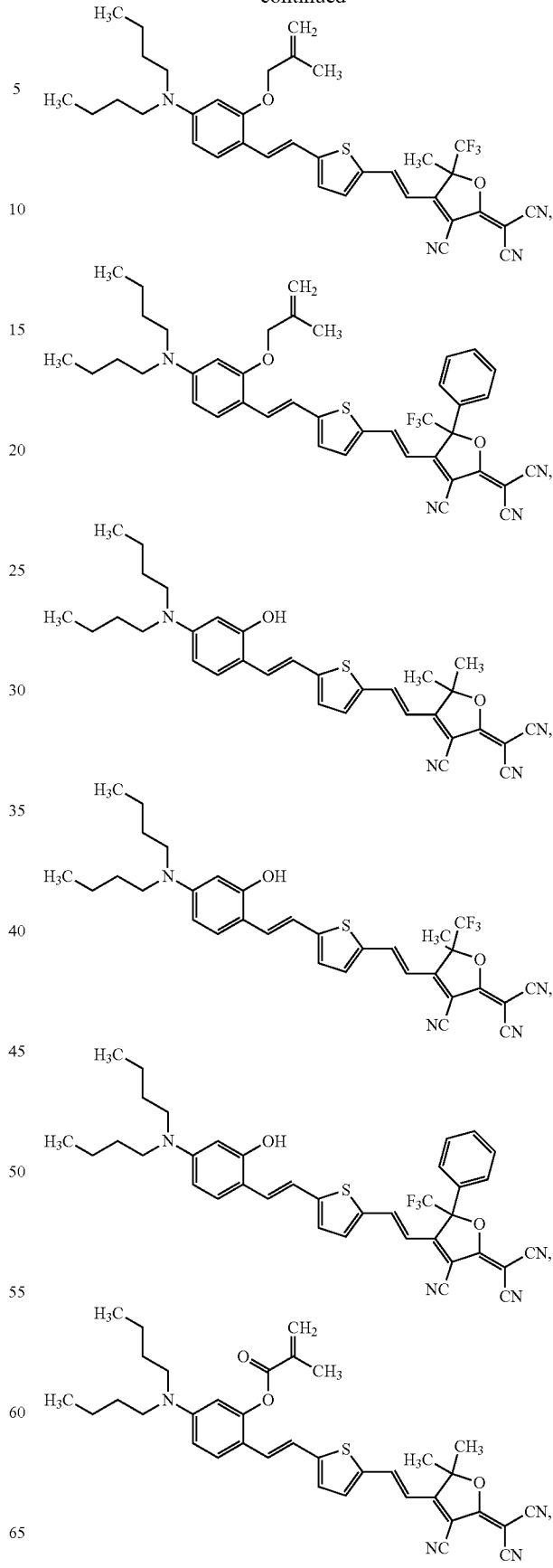

275
-continued
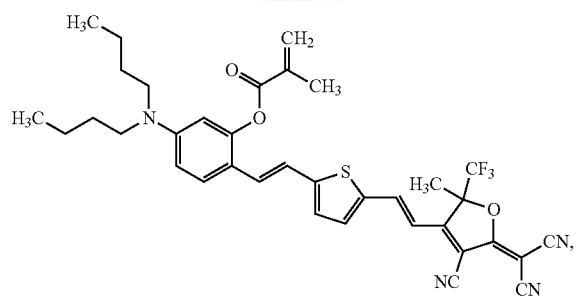 [SMILES: C=C(C)C(=O)Oc1cc(N(CCCC)CCCC)ccc1/C=C/c1ccc(/C=C/C2=C(C#N)C(=C(C#N)C#N)OC2(C)C)s1]
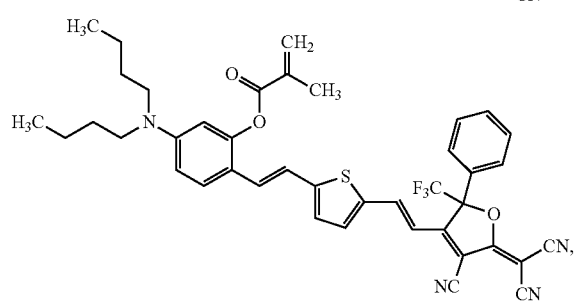
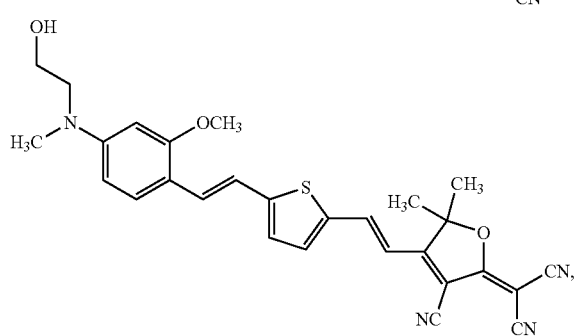
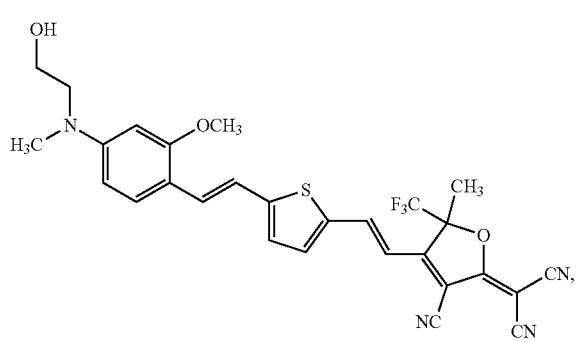
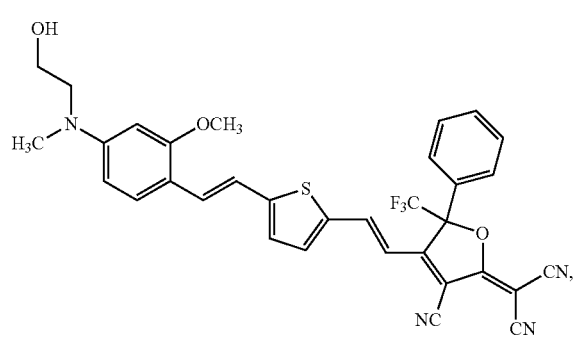
276
-continued
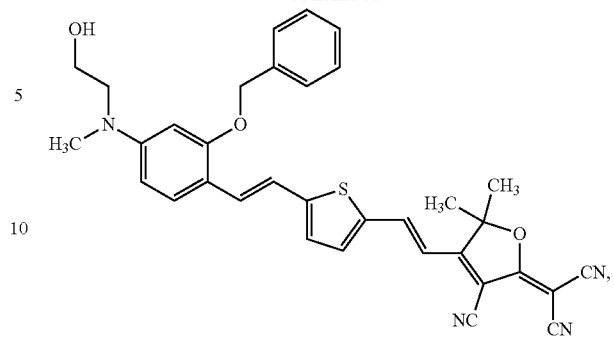
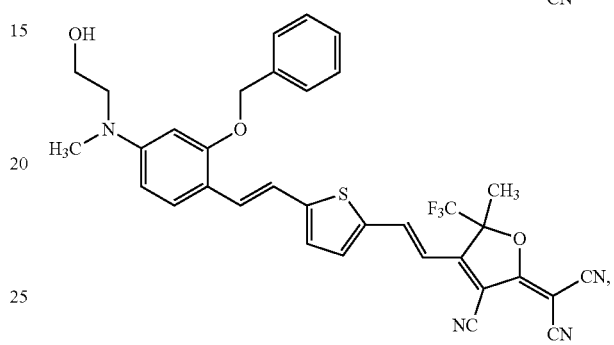
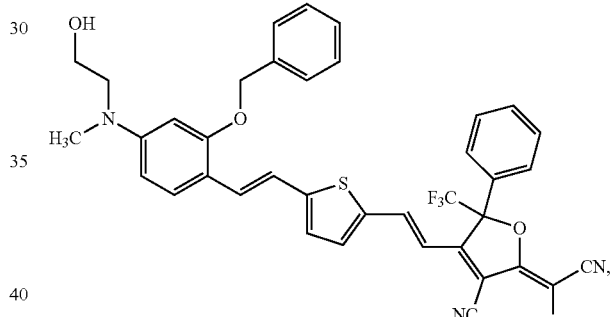
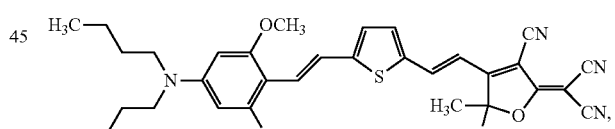
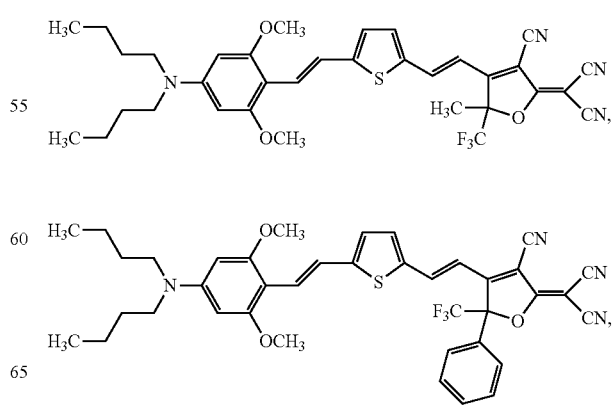

277
-continued
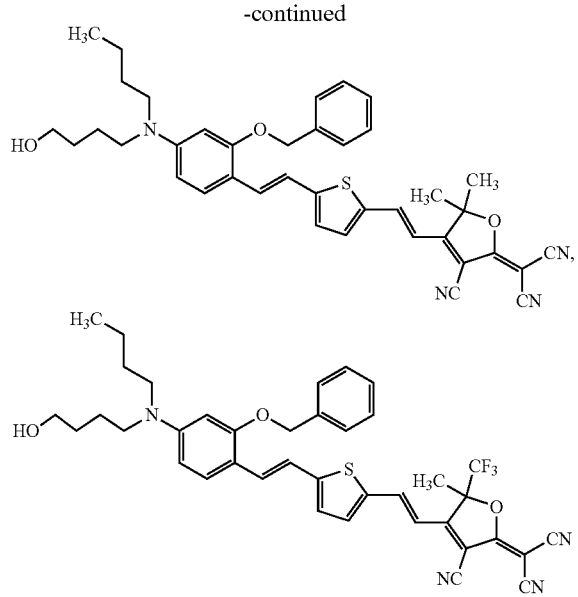
278
-continued
and
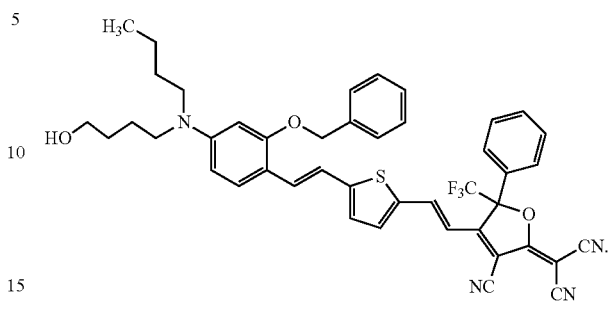
7. The chromophore according to claim 3, wherein the chromophore is represented by the formula selected from the group consisting of:
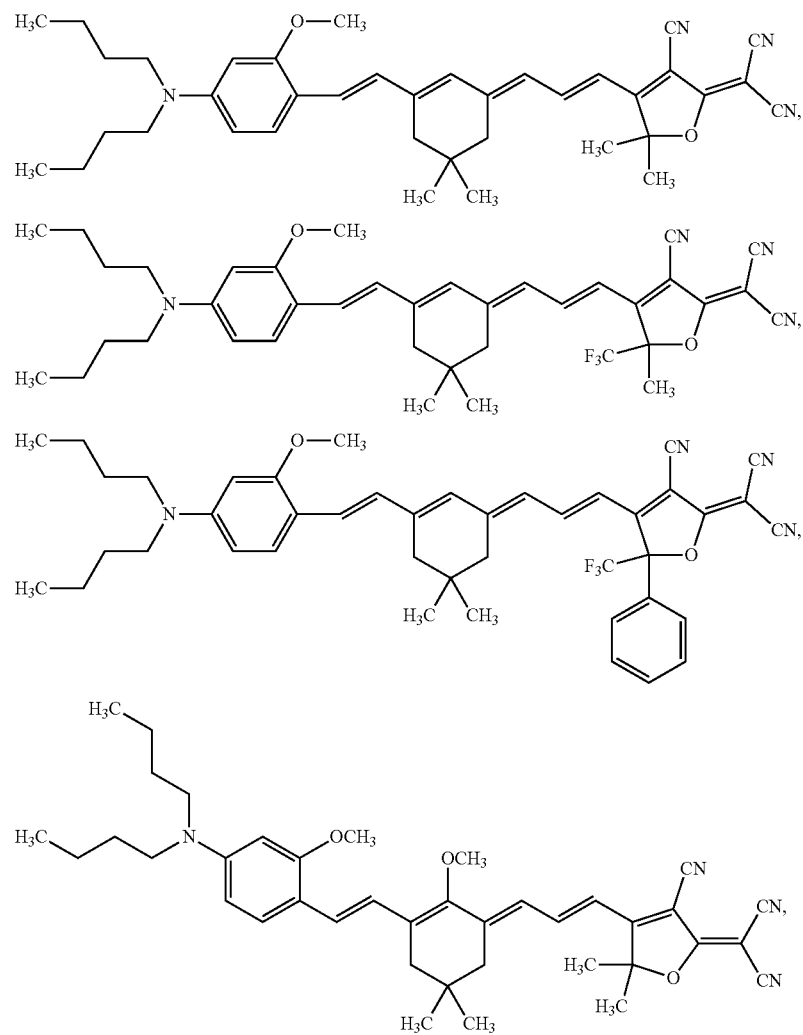

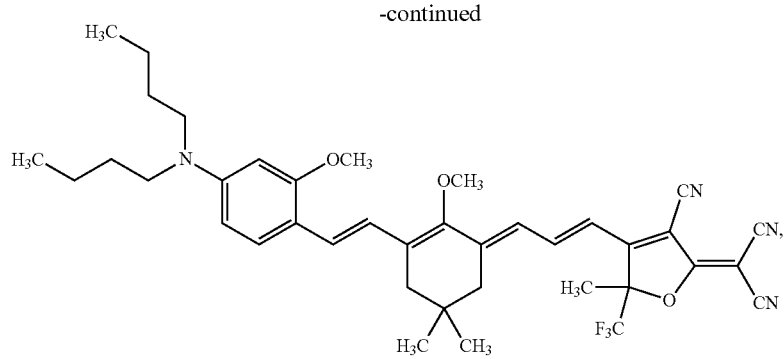
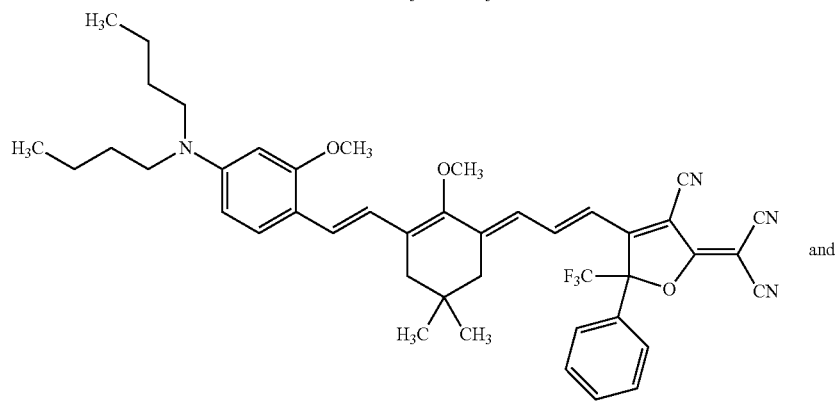
and
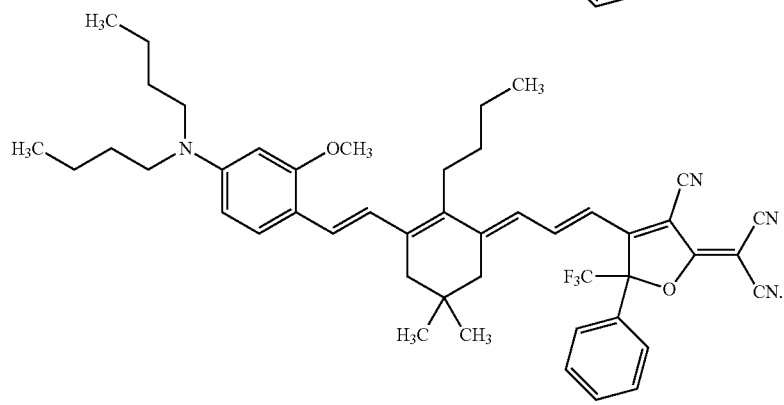
8. The chromophore according to claim 1, wherein the chromophore is represented by the formula selected from the group consisting of:
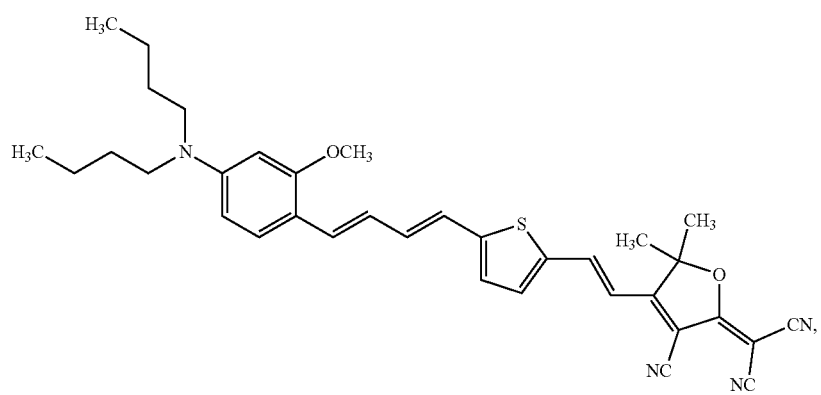

-continued
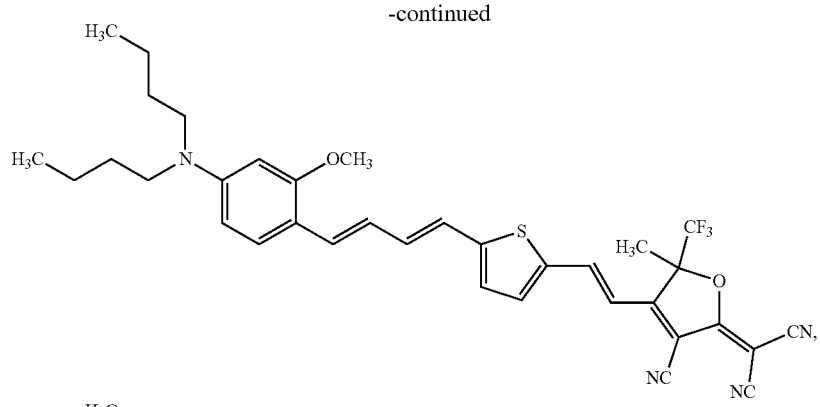
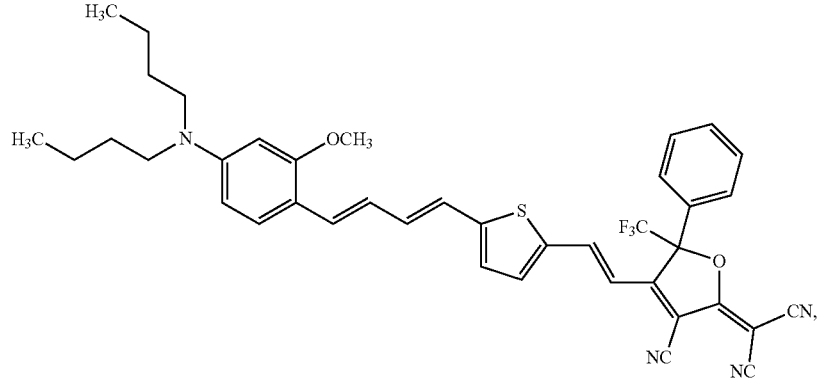
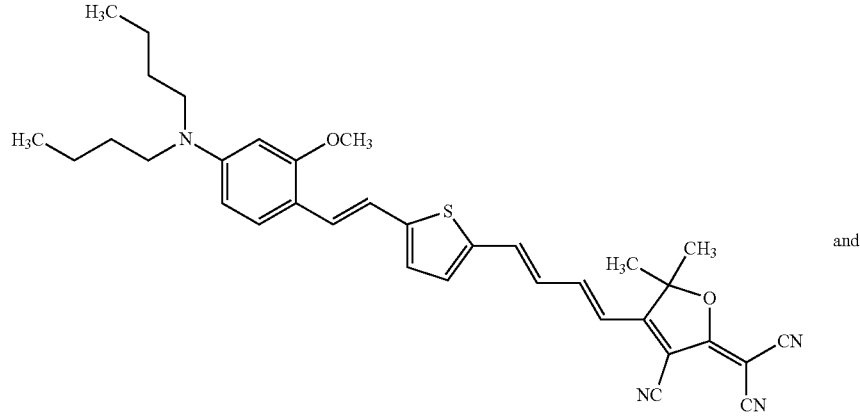
and
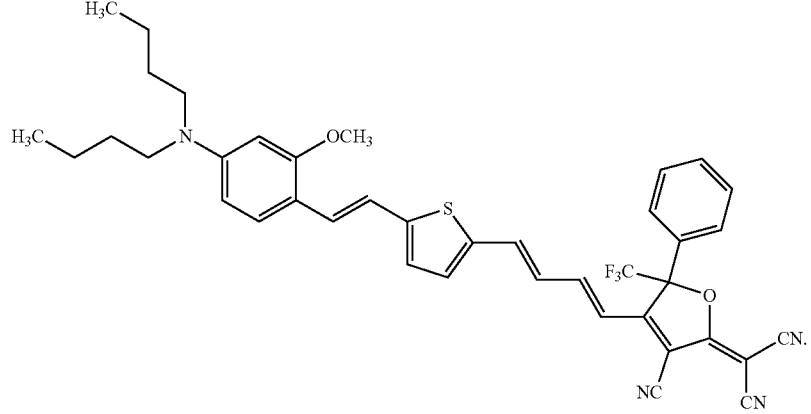 [SMILES: CCCCN(CCCC)c1ccc(/C=C/c2ccc(/C=C/C=C/C3=C(C#N)C(=C(C#N)C#N)OC3(c3ccccc3)C(F)(F)F)s2)c(OC)c1]
* * * * *